United States Patent
Ilan et al.

(10) Patent No.: US 9,943,597 B2
(45) Date of Patent: *Apr. 17, 2018

(54) ANTI-LPS ENRICHED IMMUNOGLOBULIN PREPARATION FOR USE IN TREATMENT AND/OR PROPHYLAXIS OF A PATHOLOGIC DISORDER

(75) Inventors: Yaron Ilan, Jerusalem (IL); Gadi Lalazar, Mevasseret Zion (IL); Tomer Adar, Modi'in (IL); Meir Mizrahi, Modi'in (IL); Ami Ben-Ya'acov, Jerusalem (IL)

(73) Assignee: Immuron Limited, Blackburn Nortth, VIC (AU)

( * ) Notice: Subject to any disclaimer, the term of this patent is extended or adjusted under 35 U.S.C. 154(b) by 43 days.

This patent is subject to a terminal disclaimer.

(21) Appl. No.: 13/817,414

(22) PCT Filed: Aug. 17, 2011

(86) PCT No.: PCT/IB2011/002596
§ 371 (c)(1),
(2), (4) Date: May 9, 2013

(87) PCT Pub. No.: WO2012/023051
PCT Pub. Date: Feb. 23, 2012

(65) Prior Publication Data
US 2013/0224216 A1   Aug. 29, 2013

Related U.S. Application Data

(60) Provisional application No. 61/374,328, filed on Aug. 17, 2010.

(51) Int. Cl.
*A61K 39/395* (2006.01)
*A61K 39/40* (2006.01)
*C07K 16/12* (2006.01)
*A61K 39/00* (2006.01)

(52) U.S. Cl.
CPC .......... *A61K 39/40* (2013.01); *C07K 16/1203* (2013.01); *A61K 2039/505* (2013.01); *C07K 2317/12* (2013.01)

(58) Field of Classification Search
None
See application file for complete search history.

(56) References Cited

U.S. PATENT DOCUMENTS

| 4,550,019 | A | 10/1985 | Polson |
| 4,748,018 | A | 5/1988 | Stolle et al. |
| 6,537,500 | B1 | 3/2003 | Brenner et al. |
| 2004/0161427 | A1 | 8/2004 | Nash et al. |

FOREIGN PATENT DOCUMENTS

| CA | 1101333 | 5/1981 |
| EP | 1795204 | 10/2009 |
| JP | 53-130411 | 11/1978 |
| JP | 58-154513 | 9/1983 |
| JP | 6-505867 | 7/1994 |
| JP | 7-206462 | 8/1995 |
| WO | 1992/016624 | 10/1992 |
| WO | 1995/08562 | 3/1995 |
| WO | 1999/61468 | 2/1999 |
| WO | 2003/080082 | 10/2003 |
| WO | 2003/097094 | 11/2003 |
| WO | 2004/078209 | 9/2004 |
| WO | 2006/035979 | 4/2006 |
| WO | 2006/053383 | 5/2006 |
| WO | 2008/025099 | 3/2008 |
| WO | 2009/113065 | 9/2009 |
| WO | 2010/125565 | 11/2010 |

OTHER PUBLICATIONS

Ruiz et al. ( Obesity Surgery vol. 17, pp. 1374-1380, 2007).*
Adams et al., "Nonalcoholic fatty liver disease," Can. Med. Assoc. J. 172:899-905 (2005).
Admyre et al., "Exosomes with Immune Modulatory Features are Present in Human Breast Mil," J. Immunol., 179:1969-1978 (2007).
Akita and Nakai, "Production and purification of Fab' fragments from chicken egg yolk immunoglobulin Y (IgY)," J. Immunol. Methods, 162(2):155-164 (1993).
Akita and Nakai, "Comparison of four purification methods for the production of immunoglobulins from eggs laid by hens immunized with an enterotoxigenic *E. coli* strain," J. Immunol. Methods, 160(2):207-214 (1993).
Amaral et al., "In vitro reactivity and growth inhibition of EPEC serotype O111 and STEC serotypes O111 and O157 by homologous and heterologous chicken egg yolk antibody," Vet. Res. Commun., 32:281-290 (2008).
Bedogni et al., "Natural Course of Chronic HCV and HBV Infection and Role of Alcohol in the General Population: The Dionysos Study," American Journal of Gastroenterology, 103:2248-2253 (2008).
Bluestone et al., "Therapeutic vaccination using CD4+CD25+ antigen-specific regulatory T cells," PNAS, 101 (2):14622-14626 (2004).
Brandon et al., "The Mechanism of Transfer of Immunoglobulin Into Mammary Secretion of Cows," Aust. J. Exp. Biol. Med. Sci., 49:613-623 (1971).
Clark et al., "Nonalcoholic Fatty Liver Disease: an Underrecognized Cause of Cryptogenic Cirrhosis," J. Am. Med. Assoc. 289:3000-3004 (2003).
Cohen et al., "Antibiotic prophylaxis for spontaneous bacterial peritonitis in cirrhotic patients with ascites, without gastro-intestinal bleeding (Review), Cochrane Database of Systematic Reviews," Issue 2, Art. No. CD004791, John Wiley & Sons, Ltd. (2009).

(Continued)

*Primary Examiner* — J. Hines
*Assistant Examiner* — Khatol Shahnan Shah
(74) *Attorney, Agent, or Firm* — Fish & Richardson P.C.

(57) ABSTRACT

Methods and compositions for treating conditions including liver dysfunction, e.g., associated with fatty liver; glucose intolerance; and others, by administering compositions comprising anti-LPS immunoglobulin enriched colostrum preparations.

10 Claims, 45 Drawing Sheets

(56) References Cited

OTHER PUBLICATIONS

Czaja et al., "Lipopolysaccharide-neutralizing Antibody Reduces Hepatocyte Injury from Acute Hepatotoxin Administration," Hepatology, 19:1282-1289 (1994).

Dos Santos et al., "Serum laminin, type IV collagen and hyaluronan as fibrosis markers in non-alcoholic fatty liver disease," Braz. J. Med. Biol. Res. 38:747-753 (2005).

DuPont et al., "Pathogenesis of *Escherichia coli* diarrhea," New England J. of Medicine, 285: 1-9 (1971).

El-Naggar et al., "Bacterial DNA and its consequences in patients with cirrhosis and culture-negative, non-neutrocytic ascites," Journal of Medical Microbiology, 57:1533-1538 (2008).

Evans et al., "Three characteristics associated with enterotoxigenic *Escherichia coli* isolated from man," Infect. Immunity, 8: 322-328 (1973).

Faria et al., "Oral tolerance: Therapeutic implications for autoimmune diseases," Clinical & Developmental Immunology, 13(2-4):143-157 (Jun.-Dec. 2006).

Feingold et al., "Endotoxin rapidly induces changes in lipid metabolism that produce hypertriglyceridemia: low doses stimulate hepatic triglyceride production while high doses inhibit clearance," J. Lipid Res., 33:1765-1776 (1992).

Freedman et al., "Milk Immunoglobulin with Specific Activity against Purified Colonization Factor Antigens Can Protect against Oral Challenge with Enterotoxigenic *Escherichia coli*," The Journal of Infectious Diseases, 177:662-667 (1998).

Godfrey et al., "Control points in NKT-cell development," Immunology, 7:505-518 (2007).

Homann et al., "Autoreactive CD4+ T Cells Protect from Autoimmune Diabetes via Bystander Suppression Using the IL-4/Stat6 Pathway," Immunity, 11:463-472 (1999).

Homann et al., "Insulin in Oral Immune 'Tolerance': A One-Amino Acid Change in the B Chain Makes the Difference," J. Immunol., 163:1833-1838 (1999).

Ilan et al., "Induction of regulatory T cells decreases adipose inflammation and alleviates insulin resistance in ob/ob mice," Proc Natl Acad Sci USA 107:9765-9770 (2010).

International Search Report issued in PCT/IB2011/002596 dated Mar. 7, 2012.

International Search Report issued in PCT/ IL2010/000339 dated Nov. 29, 2010.

Jones et al., "Enhanced pepsin digestion: a novel process for purifying antibody F(ab')2 fragments in high yield from serum," Journal of Immunological Methods, 263:57-74 (2002).

Kahn et al., "Mechanisms linking obesity to insulin resistance and type 2 diabetes," Nature, 444:840-846 (2006).

Larche et al., "Peptide-based therapeutic vaccines for allergic and autoimmune diseases," Nature Medicine Supplement, 11(4):S69-S76 (2005).

Machida et al., "Toll-like receptor 4 mediates synergism between alcohol and HCV in hepatic oncogenesis involving stem cell marker Nanog," PNAS, 106(5):1548-1553 (2009).

Maghraby et al., "Anti-schistosomal activity of colostral and mature camel milk on *Schistosoma mansoni* infected mice," Asia Pacific Journal of Clinical Nutrition, 14(4):432-438 (2005).

Margalit et al., "Glucocerebroside Ameliorates the Metabolic Syndrome in OB/OB Mice," The Journal of Pharmacology and Experimental Therapeutics, 319(1):105-110 (2006).

Margalit et al., "Induction of immune tolerance: a role for Natural killer T lymphocytes?" Liver International, 25:501-504 (2005).

Martin et al., "Bovine Milk Gangliosides: Changes in Ceramide Moiety with Stage of Lactation," Lipids, 36:291-298 (2001).

Martin-Blondel et al., "Low interleukin-10 production by monocytes of patients with a self-limiting hepatitis C virus infection," Journal of Viral Hepatitis, 16:485-491 (2009).

McConnell et al., "Characterization of a new putative colonization factor (CS17) from a human enterotoxigenic *Escherichia coli* of serotype 0114:H21 which produces only heat-labile enterotoxin," J. Infect. Dis., 161(2): 343-347 (1990).

Nagao et al., "Elevated Levels and Different Repertoire Profile of Colostral Anti-LPS Antibodies May Have a Significant Role in Compensating Newborn Immunity," Scand. J. Immunol., 53:602-609 (2001).

Nagatomo et al., "Microarray analysis of human milk cells: persistent high expression of osteopontin during the lactation period," Clin. Exp. Immunol., 138:47-53 (2004).

Neuschwander-Tetri et al., "Nonalcoholic Steatohepatitis: Summary of an AASLD Single Topic Conference," Hepatology37:1202-1219 (2003).

Nikoopour et al., "Therapeutic Benefits of Regulating Inflammation in Autoimmunity," Inflammation & Allergy—Drug Targets, 7:203-210 (2008).

Novak et al., "Regulation of Type 1 Diabetes by NKT Cells," International Reviews of Immunology, 26:49-72 (2007).

Nowak, Michael, "Invariant NKT Cells and Tolerance," International Reviews of Immunology, 26:95-119 (2007).

Oppenheim et al., "Alarmins Initiate Host Defense, Immune-Mediated Diseases: From Theory to Therapy," pp. 185-194, Springer (2007).

Oppenheim et al., "Alarmins: chemotactic activators of immune responses," Current Opinion in Immunology, 17:359-365 (2005).

Palmeira et al., "Passive immunity acquisition of maternal anti-enterohemorrhagic *Escherichia coli* (EHEC) O157:H7 IgG antibodies by the newborn," Eur. J. Pediatr., 166:413-419 (2007).

Poggi et al., "The inflammatory receptor CD40 is expressed on human adipocytes: contribution to crosstalk between lymphocytes and adipocytes," Diabetologia, 52:1152-1163(2009).

Putnam et al., "CD4+CD25high regulatory T cells in human autoimmune diabetes," Journal of Autoimmunity, 24:55-62 (2005).

Ramos-Casals et al., "Systemic autoimmune diseases co-existing with chronic hepatitis C virus infection (the HISPAMEC Registry): patterns of clinical and immunological expression in 180 cases," Journal of Internal Medicine, 257:549-557 (2005).

Ryan et al., "Associations between liver histology and severity of the metabolic syndrome in subjects with nonalcoholic fatty liver disease," Diabetes Care, 28:1222-1224 (2005).

Safadi et al., "Treatment of Chronic Hepatitis B Virus Infection via Oral Immune Regulation Toward Hepatitis B Virus Proteins," The American Journal of Gastroenterology, 98(11):2505-2515 (2003).

Sala-Vila et al., "Lipid composition in human breast milk from Granada (Spain): Changes during lactation," Nutrition, 21:467-473 (2005).

Skyler et al., "Effects of oral insulin in relatives of patients with type 1 diabetes: The Diabetes Prevention Trial—Type 1," Diabetes Care 28: 1068-76 (2005).

Song et al., "Clinical outcomes of spontaneous bacterial peritonitis due to extended-spectrum beta-lactamase-producing *Escherichia coli* and *Klebsiella* species: A retrospective matched case-control study," BMC Infectious Diseases, 9:41-46 (2009).

Struff et al., "Bovine colostrum as a biologic in clinical medicine: a review—Part II: clinical studies," International Journal of Clinical Pharmacology and Therapeutics, Dustri-Verlag, Deisenhofen-Muenchen, De, 46(5):211-225(2008).

Tacket et al., "Protection by Milk Immunoglobulin Concentrate Against Oral Challenge with Enterotoxigenic *Escherichia coli*," The New England Journal of Medicine, 318:1240-1243 (1988).

Tarbell et al., "CD25+CD4+ T Cells, Expanded with Dendritic Cells Presenting a Single Autoantigenic Peptide, Suppress Autoimmune Diabetes," J. Exp. Med., 199(11):1467-1477 (2004).

Turkenkopf et al., "Regional and Genotypic Differences in Stromal-Vascular Cells from Obese and Lean Zucker Rats," International Journal of Obesity, 12:515-524 (1988).

Van Dissel et al., "Bovine antibody-enriched whey to aid in the prevention of a relapse of *Clostridium difficile*-associated diarrhoea: preclinical and preliminary clinical data," Journal of Medical Microbiology, 54:197-205 (2005).

Van et al., "All-trans Retinoic Acid Inhibits Type 1 Diabetes by T Regulatory (Treg)-Dependent Suppression of Interferon-gamma-Producing T-cells Without Affecting Th17 Cells," Diabetes, 58:146-155 (2009).

Vignali et al., "How regulatory T cells work," Nat. Rev. Immunol., 8(7):523-532 (2008).

(56) References Cited

OTHER PUBLICATIONS

Wershil et al., "Gastrointestinal mucosal immunity," J. Allergy Clinical Immunol., 121:S380-383 (2008).
Yang et al., "Human Ribonuclease a Superfamily Members, Eosinophil-Derived Neurotoxin and Pancreatic Ribonuclease, Induce Dendritic Cell Maturation and Activation," J. Immunol., 173(10):6134-6142 (2004).
Yokoyama et al., "Oral passive immunization against experimental salmonellosis in mice using chicken egg yolk antibodies specific for *Salmonella enteritidis* and *S. typhimurium*," Vaccine, 16(4):388-393 (1998).
Office Action issued in Mexican Patent Application MS/a/2011/011376 dated May 22, 2015 with English translation (6 pages).
Yeh et al., "Pathology of Nonalcoholic Steatohepatitis," found at http://emedicine.medscape.com/article/2038493-overview (5 pages).
Mehta et al., "Drug-Induced Hepatotoxicity," found at http://emedicine.medscape.com/article/169814-overview (11 pages).
Golay et al., "Cholesterol-Lowering Effect of Skim Milk from Immunized Cows in Hypercholesterolemic Patients," The American Journal of Clinical Nutrition, 52(6):1014-1019 (Jan. 1, 1990).
Office Action issued in European Patent Application 10721856.2 dated Oct. 15, 2015 (7 pages).
Yang et al., "Obesity increases sensitivity to endotoxin liver injury: Implications for the pathogenesis of steatohepatitis," Proc. Natl. Acad. Sci. USA 94:2557-2562, 1997.
Office Action issued in Israeli Patent Application 215924 dated Feb. 22, 2016 (2 pages).
Office Action issued in Canadian Patent Application 2,760,096 dated Feb. 17, 2016 (5 pages).
Oral Hearing issued in EP11793860.5 dated Mar. 29, 2016 (7 pages).
"Nonalcoholic Steatohepatitis National Digestive Diseases Information Clearinghouse", Nov. 1, 2009 (Nov. 1, 2009), Retrieved from the Internet: URL:http://www.niddk.nih.gov/health-information/health-topics/liver-disease/nonalcoholic-steatohepatitis/Documents/NASH_508.pdf (6 pages).
"NAFLD & NASH 1 World Gastroenterology Organisation", Jun. 2012 (Jun. 2012), Retrieved from the Internet: URL:http://www.worldgastroenterology.org/guidelines/global-guidelines/nafld-nash (29 pages).
"Alanin-Aminotransferase—DocCheck Flexikon", Retrieved from the Internet: URL:http://flexikon.doccheck.com/de/Alanin-Aminotransferase [retrieved on Jul. 12, 2016] with machine translation (2 pages).
"Aspartat-Aminotransferase—DocCheck Flexikon", Retrieved from the Internet: URL:http://flexikon.doccheck.com/de/Aspartat—Aminotransferase [retrieved on Jul. 12, 2016] with machine translation (4 pages).

"Gamma-Glutamyltransferase—DocCheck Flexikon", Retrieved from the Internet: URL:http://flexikon.doccheck.com/de/Gamma-Glutamyltransferase [retrieved on Jul. 12, 2016] with machine translation (4 pages).
"Alkalische Phosphatase—DocCheck Flexikon", EPO Form Retrieved from the Internet: URL:http://flexikon.doccheck.com/de/Alkalische_Phosphatase [retrieved on Jul. 12, 2016] with machine translation (4 pages).
Communication re Summons to attend oral proceedings issued in EP11793860.5 dated May 27, 2016.
World Gastroenterology Organisation, "Nonalcoholic Fatty Liver Disease—A Growing Public Health Problem," Jul. 15, 2016, Retrieved from the Internet: URL:http://www.worldgastroenterology.org/publications/e-wgn/e-wgn-expert-point-of-view-articles-collection/nonalcoholic-fatty-liver-disease-a-growing-public-health-problem (4 pages).
Office Action in Canadian Application No. 2,808,361, dated Jun. 20, 2017, 5 pages.
Rawal et al, "Role of Colostrum in Gastrointestinal Infections", Indian Journal of Pediatrics, Sep. 2008, 75(9): 917-921.
Gao et al., "Effects of Traditional Chinese Medicine on Endotoxin and Its Receptors in Rats with Non-Alcoholic Steatohepatitis", Inflammation, Apr. 2008, 31: 121-132.
Office Action in European Application No. 10721856, dated Dec. 23, 2016, 6 pages.
Maier, "Medikamentose Therapie in der Hepatologie", Praxis : schweizer. Rundschau tor Medizin,, Nov. 2005, 94: 1907-1912 (with English summary).
Office Action in Korean Application No. 10-2011-7027634, dated Aug. 19, 2016, 13 pages.
Office Action in Korean Application No. 10-2011-7027634, dated Mar. 24, 2017, 6 pages.
Office Action in Israeli Application No. 215924, dated Jan. 17, 2017, 16 pages.
Office Action issued in Australian Application No. 2010243205 dated Aug. 26, 2013 (3 pages).
Office Action issued in Australian Application No. 2011290478 dated Oct. 14, 2013 (3 pages).
Office Action issued in Eurasian Application No. 201171304/28 dated Oct. 16, 2013 (3 pages).
Office Action issued in European Patent Application 10721856.2 dated Jul. 28, 2014.
Office Action issued in Japanese Patent Application 2012-507877 dated May 27, 2014.
Office Action issued in Mexican Patent Application MS/a/2011/011376 dated Apr. 1, 2014.
Office Action issued in European Patent Application 11793806.5 dated Oct. 7, 2014.
Office Action issued in Mexican Patent Application MS/a/2011/011376 dated Dec. 2, 2014 with English translation (7 pages).
Office Action issued in Eurasian Application No. 201171304/28 dated Jun. 27, 2014 with English Translation (3 pages).
U.S. Appl. No. 13/265,252, filed Oct. 19, 2011, Yaron Ilan.

\* cited by examiner

Liver: CD4+CD25+LAP-

Liver: CD4+CD25+LAP+

P<0.04

P<0.01

P<0.001

P<0.03

P<0.04

P<0.001

P<0.01

P<0.05

P<0.004

P<0.004

ANTI-LPS ENRICHED IMMUNOGLOBULIN PREPARATION FOR USE IN TREATMENT AND/OR PROPHYLAXIS OF A PATHOLOGIC DISORDER

CLAIM OF PRIORITY

This application is the U.S. national stage under 35 USC § 371 of International Application Number PCT/IB2011/002596, filed on Aug. 17, 2011, which claims priority to U.S. Application No. 61/374,328, filed on Aug. 17, 2010. The entire contents of the foregoing applications are hereby incorporated by reference.

FIELD OF THE INVENTION

The invention relates to the use of preparations enriched with anti LPS antibodies, such as those derived from mammalian colostrum or avian eggs, and optionally further antibodies against disease-associated antigens, colostrums, milk or milk product component/s and any adjuvants for treating, delaying or preventing the progression of a pathologic disorder such as chronic liver disease, cirrhosis and any complication or disorder associated therewith. The invention further relates to combined compositions comprising a combination of anti-LPS enriched antibody preparations and antibodies recognizing at least one antigen specific for a pathologic disorder and uses thereof in the treatment of immune-related disorders.

BACKGROUND OF THE INVENTION

All publications mentioned throughout this application are fully incorporated herein by reference, including all references cited therein.

Chronic hepatitis is inflammation of the liver that lasts at least six months. Chronic hepatitis, although much less common than acute hepatitis, can persist for years, even decades. In most people, it is quite mild and does not cause significant liver damage. However, in some people, continued inflammation slowly damages the liver, eventually resulting in cirrhosis (severe scarring of the liver), liver failure, and sometimes liver cancer. Chronic hepatitis is usually caused by Hepatitis B virus (HBV) Hepatitis C virus (HCV) and drugs.

Chronic Hepatitis C virus (HCV) infection is characterized by the inability of the host to establish an effective immune response. At the same time chronic HCV infection is associated with persistent, abnormally high levels of immune activation. This activation contributes to liver damage and disease progression. Patients with chronic HCV infection have widely varying clinical courses, while some develop cirrhosis, others do not show progression of liver disease.

Several risk factors including concomitant ethanol consumption have been associated with accelerated liver damage and progression to cirrhosis. Patients with both chronic HCV and ethanol consumption have been found to have accelerated progression of liver disease. This has been associated with increased levels of LPS (Bedogni, G. Am. J. Gastroenterol. 103(9): 2248-53 (2008)). Interestingly, a recent study has shown that the HCV nonstructural protein NS5A activates Toll-like receptor (TLR) 4 which is also activated by LPS (Machida, K. et al. Proc. Natl. Acad. Sci. USA, 106(5):1548-53 (2009).

LPS may not only be connected with progression of liver disease, but also with the perpetuation of chronic infection. When compared with patients with self limiting infection, monocytes from patients with chronic HCV produce significantly more IL-10 and TNF alpha in response to the HCV core protein or LPS (Martin-Blondel, G. et al. J. Viral. Hepatitis (Mar. 11, 2009)). Thus, although translocation of gut microbial products, immune activation and progression of liver disease appear to be closely linked, proof of causality is lacking. Additionally, there appears to be a connection between LPS levels and viral clearance, though this needs to be elucidated. Thus, studies designed at clarifying these relationships are needed. If microbial translocation is driving immune activation and progression of liver disease, strategies that reduce or prevent microbial translocation may therefore have a significant impact on immune activation, and thus on the natural history of chronic HCV infection.

Spontaneous bacterial peritonitis (SBP) is a common and severe complication of chronic liver diseases, such as liver cirrhosis, portal hypertension and ascites. SBP occurs in up to 30% of patients, and is associated with an in-hospital mortality rate of up to 25%. Bacterial translocation into the stagnant and immune depleted peritoneal fluid is considered to be the main pathogenic mechanism of SBP. While paracentesis and broad spectrum antibiotic therapy constitute an effective treatment for acute infection, many patients suffer from recurrent episodes of SBP with pathogens which become increasingly resistant to antibiotic therapy (Song, K. H. et al. BMC Infect Dis. 9(1): 41 (2009)). Methods for SBP prophylaxis using chronic antibiotics are controversial and associated with immergence of antibiotic resistant species (Cohen, M. J. et al. Cochrane Database Syst Rev. 2: CD004791 (2009)).

Recently, an increasing association has been found between bacterial translocation and the incidence of complications of cirrhosis. The levels of either bacterial products (ribosomal 16s RNA) in the serum or endotoxemia (LPS or LBP) have been correlated with variceal bleeding, hepatorenal syndrome and the hyperdynamic circulatory state found in cirrhotic patients (El-Naggar, M. M. et al. J. Med. Microbiol. 57(Pt 12):1533-8 (2008)).

For decades, various attempts have been made to obtain increased secretion of immunogen-specific antibodies via the mammary gland of farm animals. Such attempts are aimed at production of large quantities of immunogen-specific antibodies via milk. The antibody levels in mature milk, however, still remain low (approximately an order of magnitude) when compared to those that can be achieved in colostrum.

Colostrum (also known as first milk) is a form of milk produced by the mammary glands in late pregnancy and the few days after birth. In humans it has high concentrations of nutrients and antibodies, but it is small in quantity. Colostrum is high in carbohydrates, protein, mineral salts, vitamins and immunoglobulin. It also contains various floating cells such as granular and stromal cells, neutrophils, monocyte/macrophages and lymphocytes and includes growth factors, hormones and cytokines.

Leukocytes are also present in colostrum in large numbers which enable protection against viruses and bacteria. Colostral leukocytes enhance passive immunity of neonatal calf, especially in regard to antibodies and immunoglobulin classes which are essential for intestinal immunity.

The large numbers of secretory antibodies found in the colostrum help protect the mucous membranes in the throat, lungs, and intestines of the newborn. Bovine colostrum (BC) contains three major classes of immunoglobulins: IgG, IgM and IgA.

As indicated above, colostrum is quite a unique product that arises from a distinct physiological and functional state of the mammary gland. In ruminants, the principal compositional difference between colostrum and mature milk is the very high content of bioactive components such as lactoferrin and immunoglobulins (Tarbell, K. V. et al. J. Exp. Med. 199:1467-77 (2004); Bluestone, J. A. and Tang, Q. J. Autoimmun 24:55-62 (2005); Putnam, A.l. et al J. Autoimmun. 24:55-62 (2005)), of which IgG class makes up 80-90%.

The immunization of an animal such as a cow with specific antigens enables the production and harvest of specific antibodies that may be used for modulation of an immune response and thereby in the treatment of immune-related disorders. Accordingly, this method serves as an easy and safe means for generating antigen-specific antibodies and immune adjuvants.

Several previous patents and patent applications by some of the present inventors, described the use of specific bacterial pathogens antibodies, obtained from bovine colostrum for the passive treatment of infectious diseases. For example, WO 04/078209 by some of the present inventors describes compounds and compositions for the treatment or prophylaxis of gastrointestinal disorders prepared by immunizing a host animal with a vaccine comprising one or more cell wall antigens of enteric bacteria, specifically, gram negative bacteria. The hyper immune material produced is in the form of tablets for oral administration. WO 03/097094 describes the use of a hyper immune colostrum in the production of antibodies (whole IgG), or F(ab')2 antibodies fragments, conjugated with mammalian colostrum and colostrum extracts, for intranasal administration aimed at the prevention of symptoms arising from the presence of air-borne pathogenic bacteria.

Mucosal tolerance is considered as an attractive approach for the treatment of autoimmune and inflammatory diseases due to the lack of toxicity, ease of administration, and antigen-specific mechanism of action (Wershil, B. K. and Furuta, G. T. J. Allergy Clin. Immunol. 121:S380-3; quiz S415 (2008); Faria, A. M. and Weiner, H. L. Clin. Dev. Immunol. 13:143-57 (2006)). Hence, major attempts were made to generate stable colostrum-derived products suitable for oral and nasal administration. For Example, WO 95/08562 by some of the inventors, describes the method of obtaining high purity immunoglobulins from antibody rich colostrum and the possibility of compressing these colostral-antibodies into a tablet form without substantial loss of activity. Specific antibodies may be obtained by immunization of a mammal with specific antigens against enterotoxic bacteria such as *E. coli, Salmonela* and *Shigella*. WO 06/053383 by some of the inventors, describes a carboxylic acid and alkalizing moieties which confer upon a bioactive agent composition of a hyper immune colostrum, lactoferrin or lactoferracin, stability under a wide variety of gastric pH values. Finally, WO 03/080082 by some of the inventors describes a method of improving the viability of a labile bioactive substance, preferably immunoglobulins or fragments thereof or enzymes, in a gastric environment, comprising forming a mixture of the bioactive substance and mammalian colostrum and colostrums extracts. This conjugation protects the antibodies or antibodies fragments from the proteolysis occasioned by enzyme or low pH conditions and preserves their function in the stomach or rumen or other hostile environment.

The bowel mucosa is the largest lymphoid organ of the body. It deals with the dual role of nutrient absorption, while maintaining a physical and immunological barrier to the gut content. Despite constant antigenic stimulation, suppression of inflammation is the rule. Two key concepts pertain to the treatment of viral disease and its complications with colostrums: mucosal microbial translocation and enhanced immune regulation by oral feeding of disease antigens, termed "oral tolerance".

Increased mucosal microbial translocation: this is an immerging concept in disease pathogenesis. The higher levels of microbial translocation, quantified by the presence of LPS and bacterial DNA are central to a state of chronic immune activation accounting for immune exhaustion and autoimmune damage.

Stimulation through the bowel mucosa tends to elicit a tolerogenic immune response. This feature may be used advantageously to induce tolerance towards auto-antigens and in this way to suppress autoimmunity. Indeed, "oral tolerance" has been shown to effectively diminish the immune response towards orally fed antigens in different disease models (Safadi, R. et al. Am. J. Gastroenterol. 98(11): 2505-15 (2003)).

It has been previously shown that bovine-derived colostrum preparations can be used in treating toxin-mediated intestinal conditions. In a study of 10 volunteers challenged orally with a concentrate of enterotoxigenic *E. coli*, administration of a bovine antibody concentrate obtained by immunizing cows with the corresponding *E. coli* strains prevented the development of diarrhea in all 10 participants who received the product; by contrast, 9/10 controls developed diarrhea (Tacket, C. O. et al. N. Engl. J. Med. 318(19): 1240-3 (1988)). In another study, the administration of milk-derived antibodies against the enterotoxigenic *E. coli* colonization factor protected 14/15 subjects from diarrhea, compared to 7/10 subjects given placebo (Freedman, D. J. et al. J. Infect. Dis. 177(3): 662-7 (1998)).

Another disease with a similar pathogenesis is pseudomembranous colitis. A study evaluated to effect of immune whey protein, obtained by immunizing cows with *C. difficile* inactivated toxins and whole-cell killed *C. difficile* shown as preventing relapse of *C. difficile* disease. Sixteen patients received the product after standard treatment for a confirmed episode of *C. difficile* colitis for two weeks. In all but one case, *C. difficile* toxin disappeared from the stool, and there were no recurrences after a median follow-up of 333 days (van Dissel, J. T. et al. J. Med. Microbiol. 54(2): 197-205 (2005)).

Collectively, these observations suggest that bovine-derived colostrum preparations deliver biologically active concentrations of specific antibodies to the intestinal lumen when taken orally, and might be capable of blocking various forms of bacterial toxins in the gut by that mechanism.

Since microbial translocation is driving immune activation and progression of liver disease, strategies that reduce or prevent microbial translocation may have a significant impact on immune activation, and thus on the natural history of chronic HCV infection. The present invention now demonstrates the use of bovine colostrum powder (BPC) preparations from immunized cows, containing high levels of antibodies, as immuno-modulators capable of reducing immune activation in response to microbial products such as LPS. Without being bound to any theory, the inventors hypothesize that the attachment of the BPC antibodies to the microbial antigens may prevent their translocation onto the blood stream, thereby restricting the immune response. These effects upon the immune system enable the use of such colostrum preparations for the treatment of infectious disease, which involve the immune system. More specifically, the present invention provides the use of a colostrum-derived preparation, comprising high concentrations of anti-LPS antibodies, in the treatment and amelioration of chronic liver diseases.

Microbial translocation is also associated with alteration of the liver inflammation in different liver disorders, including viral mediated, drug mediated, non-alcoholic steatohepatitis and any other hepatic disorder. Microbial translocation may also be associated with insulin resistance, diabetes type 2, obesity and overweight. As shown by the invention, prevention of such translocation may be achieved using the anti-LPS enriched colostrum of the invention, optionally along with regulation of regulatory T cells, or any other component of the immune system, using a combination of the anti-LPS enriched colostrum with colostrum preparations enriched with antibodies recognizing disease-specific antigens, for example, anti-insulin enriched colostrum. Thus, the invention further provides compositions, combined compositions and methods for the treatment of any acute or chronic liver disease, diabetes and any complication associated therewith, fatty liver, non-alcoholic steatohepatitis, and obesity.

It is therefore an object of the invention to provide the use of colostrum- or avian egg derived anti-LPS enriched immunoglobulin preparations in compositions and methods of treating, delaying or preventing the progression of chronic liver disease, cirrhosis and any complication or disorder associated therewith.

Another object of the invention is to provide combined compositions comprising a combination of anti-LPS antibodies enriched colostrum and antibodies recognizing at least one antigen specific for a pathologic disorder and uses thereof in the treatment of immune-related disorders.

These and other objects of the invention will become clearer as the description proceeds.

SUMMARY OF THE INVENTION

The present invention is based, at least in part, on the discovery that subjects who suffer from advanced disease, e.g., severely impaired liver function, severe insulin resistance, or high levels of serum cholesterol, can be treated using an anti-LPS immunoglobulin-enriched colostrum preparation. Thus, provided herein are compositions for use in treating such subjects, methods for treating such subjects, and methods for selecting treatment for such subjects.

In a first aspect, the invention provides compositions including an anti-LPS immunoglobulin-enriched colostrum preparation, e.g., a bovine colostrum preparation, as described herein for use in improving liver function in a subject who has one or more of: an ALT level above 50 IU/dL, an AST level above 50 IU/dL, an AP of greater than 70 U/L, and/or a GGT of greater than 60 U/L.

In a further aspect, the invention provides methods for selecting a treatment to improve liver function in a subject. The methods include detecting the presence in a sample from the subject of one or more of: an ALT level above 50 IU/dL, an AST level above 50 IU/dL, an AP of greater than 70 U/L, and/or a GGT of greater than 60 U/L; and selecting a treatment comprising administration of a composition comprising an anti-LPS immunoglobulin-enriched colostrum preparation for the subject. In some embodiments, the methods further include administering the treatment to the subject.

In some embodiments, the subject has metabolic syndrome or non-alcoholic steatohepatitis (NASH).

In yet another aspect, the invention provides compositions including an anti-LPS immunoglobulin-enriched colostrum preparation as described herein for use in improving insulin resistance in a subject who has one or more of a level of HbA1c above 7, and/or a level of insulin secretion above 300 pg/ml.

In another aspect, the invention provides methods for selecting a treatment to improve insulin resistance in a subject. The methods include detecting the presence in a sample from the subject of one or more of: a level of HbA1c above 7, and/or a level of insulin secretion above 300 pg/ml, and selecting a treatment comprising administration of a composition comprising an anti-LPS immunoglobulin-enriched colostrum preparation for the subject. In some embodiments, the methods further include administering the treatment to the subject.

In some embodiments, the subject has metabolic syndrome or diabetes. In some embodiments, the composition reduces serum insulin levels, increases serum insulin levels, improves fasting glucose levels, reduces HbA1c levels, or both.

In a further aspect, the invention provides compositions including an anti-LPS immunoglobulin enriched colostrum preparation as described herein for use in improving serum cholesterol levels in a subject who has one or more of a level of total serum cholesterol above 6 uM/dL; a level of serum LDL above 4 uM/dL; and/or a level of serum triglycerides above above 2 or 2.5 uM/dL.

In an additional aspect, the invention features methods for selecting a treatment to improve serum cholesterol levels in a subject. The methods include detecting the presence in a sample from the subject of one or more of: a level of total serum cholesterol above the upper limit of normal; a level of serum LDL above the upper limit of normal; a level of serum triglycerides above the upper limit of normal; and selecting a treatment comprising administration of a composition comprising an anti-LPS immunoglobulin-enriched colostrum preparation for the subject. In some embodiments, the methods further include administering the treatment to the subject.

Also provided herein are compositions including an anti-LPS immunoglobulin enriched colostrum preparation as described herein for use in increasing levels of GLP-1 or adiponectin in a subject.

Also provided herein are compositions including an anti-LPS immunoglobulin enriched colostrum preparation as described herein for use in treating sepsis in a subject.

Also provided herein are compositions including an anti-LPS immunoglobulin enriched colostrum preparation as described herein for use in treating inflammatory bowel disease in a subject.

In some embodiments, the anti-LPS immunoglobulin preparation is prepared by immunizing a cow with LPS comprising O6, O8, O15, O25, O27, O63, O78, O114, O115, O128, O148, O153, and O159.

In some embodiments, the composition is formulated for oral administration.

In some embodiments, the anti-LPS immunoglobulin preparation is administered at a dose of about 100 mg to about 2000 mg per day, e.g., at a dose of about 1800 mg per day.

Thus, the present invention provides a composition comprising an anti-LPS enriched immunoglobulin preparation, e.g., an anti-LPS immunoglobulin-enriched colostrum preparation, e.g., a bovine colostrum preparation, for use in treatment and/or prophylaxis of a pathologic disorder. The anti-LPS enriched immunoglobulin preparation may be derived from colostrum or from avian eggs.

In some embodiments, the anti-LPS enriched immunoglobulin preparation is an anti-LPS immunoglobulin-enriched colostrum preparation, e.g., a bovine colostrum preparation, produced by a method described herein.

In one embodiment, the pathologic disorder is acute or chronic liver disease, cirrhosis or any disease or complication associated therewith. In another embodiment, the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness. In another embodiment, the pathologic disorder is liver damage.

In another embodiment, the pathologic disorder is an immune-related disorder selected from the group consisting of autoimmune disease, non-alcoholic steatohepatitis (NASH), fatty liver, atherosclerosis, metabolic syndrome and any disorder associated therewith, infectious disease, and proliferative disorder.

Alternatively, the pathologic disorder may be selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

In another embodiment, the composition further comprises an immunoglobulin preparation comprising immunoglobulins that recognize and bind at least one antigen specific for said pathologic disorder. The further immunoglobulin preparation may be derived from colostrum.or from avian eggs.

In one embodiment, the composition modulates regulatory T cells leading to modulation of the Th1/Th2, Tr1/Th3 cell balance toward an anti-inflammatory Th2, Tr1/Th3 immune response or a pro-inflammatory Th1 immune response thereby inhibiting or activating an immune response specifically directed toward said disorder.

In another embodiment, the composition modulates the Th1/Th2, Tr1/Th3 cell balance toward an anti-inflammatory Th2, Tr1/Th3 immune response thereby inhibiting an immune response specifically directed toward said disorder, and wherein said composition is for the treatment of any one of an autoimmune disease, non-alcoholic steatohepatitis, fatty liver, atherosclerosis, metabolic syndrome and any disorder associated therewith selected from diabetes type 2, insulin resistance, obesity and overweight.

In another embodiment, the composition is for the treatment and/or prophylaxis of metabolic syndrome or non-alcoholic steatohepatitis or both. In another embodiment, the composition is for the treatment, and/or prophylaxis of diabetes, the treatment of impaired glucose tolerance, such as decreasing glucose tolerance. decreasing serum insulin levels, decreasing hepatic triglyceride levels, or decreasing cholesterol levels.

In one embodiment, the composition modulates the Th1/Th2, Tr1/Th3 cell balance toward a pro-inflammatory Th1/Th2 immune response thereby enhancing an immune response specifically directed toward said disorder, and wherein said composition is for the treatment of infectious diseases, and proliferative disorders.

The composition may further comprise a therapeutic agent, carrier or adjuvant and/or non-hyperimmune colostrum.

The composition may be formulated for administration orally, by inhalation as an aerosol, or by parenteral, intravaginal, intranasal, mucosal, sublingual, topical, or rectal administration, or any combination thereof.

In some embodiments, the colostrum preparation or any fractions thereof comprise immunoglobulins that recognize and bind LPS.

In some embodiments, the composition inhibits microbial translocation. In some embodiments the composition inhibits microbial translocation and thereby modulates immune activation.

In another aspect, the present invention provides a composition comprising a mammalian anti-LPS enriched colostrum-derived immunoglobulin preparation for modulating immune tolerance in a subject, or in another aspect, for modulating oral tolerance in a subject.

In another aspect, the present invention provides a composition comprising a mammalian anti-LPS immunoglobulin enriched colostrum-derived preparation for inducing CD4+ CD25+ T cells in the liver, inducing CD4+ CD25+ LAP− T cells in the liver, inducing CD45+ LAP+ T cells in the liver, inducing CD3+ LAP+ T cells in the liver, inducing CD45+ LAP+ T cells in the spleen, inducing CD8+ LAP+ T cells in the spleen, inducing CD3+ LAP+ T cells in the spleen, inducing CD8+ CD25+ T cells in the spleen, inducing CD4+ CD25+ T cells in adipose tissue, inducing CD3+ LAP+ T cells in adipose tissue, inducing CD4+ CD25+ T cells in stromal vascular cells, inducing CD4+ CD25+ LAP+ T cells in stromal vascular cells, decreasing CD3+ NK1.1+ cells in the liver, decreasing CD25+ LAP− T cells in the liver, increasing CD25+ LAP+ T cells in the liver, inducing CD4+ CD25+ LAP− T cells in the spleen, inducing CD4+ CD25+ LAP− T cells in adipose tissue.

The anti-LPS enriched immunoglobulin preparation described herein may be derived from colostrum or from avian eggs. In some embodiments, the preparation is an anti-LPS immunoglobulin-enriched colostrum preparation, e.g., a bovine colostrum preparation, produced by a method described herein.

In another aspect, the present invention provides a use of an anti-LPS enriched immunoglobulin preparation in the manufacture of a medicament for the treatment and/or prophylaxis of a pathologic disorder.

The anti-LPS enriched immunoglobulin preparation may be derived from colostrum or from avian eggs.

In one embodiment, the pathologic disorder is acute or chronic liver disease, cirrhosis or any disease or complication associated therewith.

In another embodiment, the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness.

In another embodiment, the medicament is for the treatment and/or prophylaxis of liver damage.

In another embodiment, the pathologic disorder is an immune-related disorder selected from the group consisting of autoimmune disease, non-alcoholic steatohepatitis, fatty liver, atherosclerosis, metabolic syndrome and any disorder associated therewith, infectious disease, and proliferative disorder. Alternatively, the pathologic disorder is selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

The medicament may further comprise an immunoglobulin preparation comprising immunoglobulins that recognize and bind at least one antigen specific for said pathologic disorder. The further immunoglobulin preparation may be derived from colostrum.or from avian eggs.

In one embodiment, the medicament modulates regulatory T cells leading to modulation of the Th1/Th2, Tr1/Th3 cell balance toward an anti-inflammatory Th2, Tr1/Th3 immune response or a pro-inflammatory Th1 immune response thereby inhibiting or activating an immune response specifically directed toward said disorder.

In another embodiment, the medicament modulates the Th1/Th2, Tr1/Th3 cell balance toward an anti-inflammatory Th2, Tr1/Th3 immune response thereby inhibiting an immune response specifically directed toward said disorder, and wherein said composition is for the treatment of any one of an autoimmune disease, non-alcoholic steatohepatitis, fatty liver, atherosclerosis, metabolic syndrome and any disorder associated therewith selected from diabetes type 2, insulin resistance, obesity and overweight.

In another embodiment, the medicament is for the treatment and/or prophylaxis of metabolic syndrome or non-alcoholic steatohepatitis or both, the treatment and/or prophylaxis of diabetes, the treatment impaired glucose tolerance, such as decreasing glucose tolerance, decreasing serum insulin levels, decreasing hepatic triglyceride levels, or decreasing cholesterol levels.

In one embodiment, the medicament modulates the Th1/Th2, Tr1/Th3 cell balance toward a pro-inflammatory Th1/Th2 immune response thereby enhancing an immune response specifically directed toward said disorder, and wherein said composition is for the treatment of infectious diseases, and proliferative disorders, The medicament may further comprise a therapeutic agent, carrier or adjuvant and/or non-hyperimmune colostrum.

In some embodiments, the medicament is formulated for administration orally, by inhalation as an aerosol, or by parenteral, intravaginal, intranasal, mucosal, sublingual, topical, or rectal administration, or any combination thereof.

In some embodiments, the immunoglobulin preparation or any fractions thereof recognizes and binds LPS or any fragments thereof.

In some embodiments, the composition reduces or inhibits mucosal microbial translocation and thereby modulates immune activation.

In another aspect, the present invention provided a use of a mammalian anti-LPS enriched colostrum-derived immunoglobulin preparation in the manufacture of a medicament for modulating immune tolerance in a subject, or in another embodiment, a medicament for modulating oral tolerance in a subject.

In another aspect, the present invention provides the use of a mammalian anti-LPS enriched colostrum-derived immunoglobulin preparation in the manufacture of a medicament for inducing CD4+ CD25+ T cells in the liver, inducing CD4+ CD25+ LAP− T cells in the liver, inducing CD45+ LAP+ T cells in the liver, inducing CD3+ LAP+ T cells in the liver, inducing CD45+ LAP+ T cells in the spleen, inducing CD8+ LAP+ T cells in the spleen, inducing CD3+ LAP+ T cells in the spleen, inducing CD8+ CD25+ T cells in the spleen, inducing CD4+ CD25+ T cells in adipose tissue, inducing CD3+ LAP+ T cells in adipose tissue, inducing CD4+ CD25+ T cells in stromal vascular cells, inducing CD4+ CD25+ LAP+ T cells in stromal vascular cells, decreasing CD3+ NK1.1+ cells in the liver, decreasing CD25+ LAP− T cells in the liver, increasing CD25+ LAP+ T cells in the liver, inducing CD4+ CD25+ LAP-T cells in the spleen, or inducing CD4+ CD25+ LAP− T cells in adipose tissue.

The anti-LPS enriched immunoglobulin preparation may be derived from colostrum or from avian eggs.

In one aspect, the present invention provides a method for the treatment and/or prophylaxis of a pathologic disorder comprising the step of administering to a subject in need thereof a therapeutically effective amount of a composition comprising an anti-LPS enriched immunoglobulin preparation. The anti-LPS enriched immunoglobulin preparation may be derived from colostrum or from avian eggs.

In one embodiment, the pathologic disorder is acute or chronic liver disease, cirrhosis or any disease or complication associated therewith.

In another embodiment the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness.

In another embodiment, the pathologic disorder is liver damage.

In another embodiment, the pathologic disorder is an immune-related disorder selected from the group consisting of autoimmune disease, non-alcoholic steatohepatitis, fatty liver, atherosclerosis, metabolic syndrome and any disorder associated therewith, infectious disease, and proliferative disorder. Alternatively, the pathologic disorder is selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

In another embodiment, the composition further comprises an immunoglobulin preparation comprising immunoglobulins that recognize and bind at least one antigen specific for said pathologic disorder. The further immunoglobulin preparation may be derived from colostrum.or from avian eggs.

In another embodiment, the composition modulates regulatory T cells leading to modulation of the Th1/Th2, Tr1/Th3 cell balance toward an anti-inflammatory Th2, Tr1/Th3 immune response or a pro-inflammatory Th1 immune response thereby inhibiting or activating an immune response specifically directed toward said disorder.

In another embodiment, the composition modulates the Th1/Th2, Tr1/Th3 cell balance toward an anti-inflammatory Th2, Tr1/Th3 immune response thereby inhibiting an immune response specifically directed toward said disorder, and wherein said composition is for the treatment of any one of an autoimmune disease, non-alcoholic steatohepatitis, fatty liver, atherosclerosis, metabolic syndrome and any disorder associated therewith selected from diabetes type 2, insulin resistance, obesity and overweight.

In another embodiment the pathologic disorder is metabolic syndrome or non-alcoholic steatohepatitis or both.

In another embodiment, the pathologic disorder is diabetes. In another embodiment, the pathologic disorder is impaired glucose tolerance.

In another embodiment, the method decreases glucose tolerance, decreases serum insulin levels, decreases hepatic triglyceride levels, or decreases cholesterol levels.

In another embodiment, the method modulates the Th1/Th2, Tr1/Th3 cell balance toward a pro-inflammatory Th1/Th2 immune response thereby enhancing an immune response specifically directed toward said disorder, and wherein said composition is for the treatment of infectious diseases, and proliferative disorders, In another embodiment, the composition further comprises non-hyperimmune colostrum and/or a therapeutic agent, carrier or adjuvant.

The composition may be administered orally, by inhalation as an aerosol, or by parenteral, intravaginal, intranasal, mucosal, sublingual, topical, or rectal administration, or any combination thereof.

In another embodiment, the immunoglobulin preparation or any fractions thereof recognizes and binds LPS or any fragments thereof.

In another embodiment, the method reduces or inhibits mucosal microbial translocation. In another embodiment, the method reduces or inhibits mucosal microbial translocation and thereby modulates immune activation.

In another aspect, the present invention provides a method for modulating immune tolerance in a subject comprising the step of administering to a subject in need thereof a therapeutically effective amount of a composition comprising a mammalian anti-LPS enriched colostrum-derived immunoglobulin preparation. Alternatively, the method may be for modulating oral tolerance.

A method for inducing CD4+ CD25+ T cells in the liver of a subject comprising the step of administering to a subject in need thereof a therapeutically effective amount of a composition comprising a mammalian anti-LPS enriched colostrum-derived immunoglobulin preparation. In another embodiment, the method may be for inducing CD4+ CD25+ LAP− T cells in the liver, inducing CD45+ LAP+ T cells in the liver, inducing CD3+ LAP+ T cells in the liver, inducing CD45+ LAP+ T cells in the spleen, inducing CD8+ LAP+ T cells in the spleen, inducing CD3+ LAP+ T cells in the spleen, inducing CD8+ CD25+ T cells in the spleen, inducing CD4+ CD25+ T cells in adipose tissue, inducing CD3+ LAP+ T cells in adipose tissue, inducing CD4+ CD25+ T cells in stromal vascular cells, inducing CD4+ CD25+ LAP+ T cells in stromal vascular cells, decreasing CD3+ NK1.1+ cells in the liver, decreasing CD25+ LAP− T cells in the liver, decreasing CD25+ LAP+ T cells in the liver, inducing CD4+ CD25+ LAP− T cells in the spleen, or inducing CD4+ CD25+ LAP− T cells in adipose tissue.

In another aspect, the present invention provides a composition for the treatment and prophylaxis of a pathologic disorder. The composition of the invention comprises as active ingredient a mammalian anti-lipopolysaccharide (anti-LPS) enriched colostrum-derived immunoglobulin preparation and optionally further colostrum, milk or milk product component/s, and any adjuvant/s. The immunoglobulin preparation or any fractions thereof, recognizes and binds LPS and any fragments thereof. According to an optional embodiment, the composition of the invention may further comprises colostrum-derived immunoglobulin preparation recognizing at least one antigen specific for said disorder, thereby activating or inhibiting an immune response specifically directed toward said disorder. Such combined composition may optionally further comprises an additional therapeutic agent or any carrier and adjuvant.

Thus, according to one specific embodiment, the invention provides a composition comprising as an active ingredient a mammalian anti-lipopolysaccharide (LPS) enriched colostrum-derived immunoglobulin preparation. Such composition wherein said composition is particularly applicable for the treatment, prevention and prophylaxis of acute or chronic liver disease, cirrhosis and any disease or complication associated therewith, optionally said composition further comprises an additional therapeutic agent or any carrier and adjuvant.

According to another optional embodiment, the invention provides combined compositions comprising a combination of anti-LPS enriched immunoglobulin preparation with at least one colostrum- or avian-derived immunoglobulin preparation comprising immunoglobulins that recognize and bind at least one antigen specific for said pathologic disorder. Such combined composition may optionally further comprises an additional therapeutic agent or any carrier and adjuvant. These combined compositions may be used for treating any one of an autoimmune disease, non-alcoholic steatohepatitis, fatty liver, atherosclerosis, metabolic syndrome and any disorder associated therewith such as diabetes type 2, insulin resistance, obesity and overweight.

In another aspect, the present invention provides the use of a mammalian anti-LPS enriched colostrum-derived immunoglobulin preparation and optionally of a colostrum-derived immunoglobulin preparation recognizing at least one antigen specific for a pathologic disorder in the manufacture of a composition for the treatment and prophylaxis of a pathologic disorder, It should be noted that the immunoglobulin preparation or any fractions thereof recognizes and binds LPS and any fragments thereof. According to an optional embodiment, the invention provides the use of the anti-LPS enriched immunoglobulin preparation of the invention furthering combination with at least one immunoglobulin preparation comprising immunoglobulins recognizing at least one antigen specific for said disorder. Such combined composition may be used as an immunomodulatory composition that activates or inhibits an immune response specifically directed toward said disorder.

In a further aspect, the present invention provides a method for the treatment and/or prophylaxis of a pathologic disorder. The method of the invention comprises the step of administering to a subject in need thereof a therapeutically effective amount of a mammalian colostrum-derived anti-LPS enriched immunoglobulin preparation or of a composition comprising the same. It should be noted that the immunoglobulin preparation or any fractions thereof recognizes and binds LPS and any fragments thereof. Such method may be used for the treatment, prevention and prophylaxis of acute or chronic liver disease, cirrhosis and any disease or complication associated therewith. According to an optional embodiment, the anti-LPS enriched immunoglobulin preparation of the invention may be further combined with at least one immunoglobulins recognizing at least one antigen specific for said disorder, thereby activating or inhibiting an immune response specifically directed toward said disorder. This method may be specifically applicable for treating immune-related disorders. It should be particularly appreciated that the compositions and combined compositions used by the methods of the invention may be also applicable for treating any one of non-alcoholic steatohepatitis, fatty liver, atherosclerosis, metabolic syndrome and any disorder associated therewith such as diabetes type 2, insulin resistance, obesity and overweight.

In another aspect the present invention provides a method for treating a human subject with a condition selected from the group consisting of hypertension, increase in body mass index (BMI), increase in waist circumference, dyslipidemia, insulin resistance, elevated liver enzymes, and fatty liver comprising administering to the subject an effective amount of a composition comprising an anti-LPS immunoglobulin preparation.

In another aspect the present invention provides a composition comprising an anti-LPS immunoglobulin preparation for use in treatment and/or prophylaxis of a human subject with a condition selected from the group consisting of hypertension, increase in body mass index (BMI), increase in waist circumference, dyslipidemia, insulin resistance, elevated liver enzymes, and fatty liver.

In another aspect the present invention provides a use of an anti-LPS immunoglobulin preparation in the manufacture of a medicament for the treatment and/or prophylaxis of a human subject with a condition selected from the group consisting of hypertension, increase in body mass index (BMI), increase in waist circumference, dyslipidemia, insulin resistance, elevated liver enzymes, and fatty liver.

The hypertension may characterized by a blood pressure of >120 mmHg/80 mmHg, a blood pressure of >130 mmHg/90 mmHg or a blood pressure of >140 mmHg/90 mmHg.

The fatty liver may be characterized by macrovesicular steatosis, macrovesicular steatosis and necroinflammatory activity, or a NAS score of at least 4.

The anti-LPS immunoglobulin preparation may be derived from colostrum or avian eggs.

The anti-LPS immunoglobulin preparation may be administered at a dose of about 5 mg to about 25000 mg per day, 10 mg to about 20000 mg per day, 25 mg to about 15000 mg per day, 100 mg to about 2000 mg per day, or about 1800 mg per day. In one embodiment, the anti-LPS immunoglobulin preparation is not administered at a dose of about 600 mg per day.

The anti-LPS immunoglobulin preparation may be formulated for administration at a dose of about 5 mg to about 25000 mg per day, about 10 mg to about 20000 mg per day, about 25 mg to about 15000 mg per day, about 100 mg to about 2000 mg per day or about 1800 mg per day. In one embodiment, the anti-LPS immunoglobulin preparation is not formulated for administration at a dose of about 600 mg per day The anti-LPS immunoglobulin preparation may be prepared by immunizing a mammal or avian with LPS from multiple E. coli strains. The mammal or avian may be immunized with LPS selected from the group consisting of O6, O8, O15, O25, O27, O63, O78, O114, O115, O128, O148, O153, O159, and other LPS associated with enterotoxigenic E. coli.

The mammal or avian may be immunized with LPS selected from the group consisting of O78, O6, O8, O129 and O153 LPS. The LPS may comprise O78 LPS.

In another embodiment, composition further comprises an anti-insulin immunoglobulin preparation.

The anti-insulin immunoglobulin preparation is administered at a dose of about 5 mg to about 25000 mg per day, about 10 mg to about 20000 mg per day, about 25 mg to about 15000 mg per day, about 50 mg to about 10000 mg per day, about 50 mg to about 4000 mg per day, about 500 mg to about 3000 mg per day, about 1000 mg to about 1400 mg per day, or about 1200 mg per day.

The anti-insulin immunoglobulin preparation may be formulated for administration at a dose of about 5 mg to about 25000 mg per day, about 10 mg to about 20000 mg per day, about 25 mg to about 15000 mg per day, about 50 mg to about 10000 mg per day, about 50 mg to about 4000 mg per day, about 500 mg to about 3000 mg per day, about 1000 mg to about 1400 mg per day or of about 1200 mg per day The anti-insulin immunoglobulin preparation may be prepared by immunizing a mammal or avian with insulin conjugated to keyhole limpet hemocyanin (KLH).

In another aspect, the present invention provides a method for reducing fasting glucose levels in a human patient in need thereof, comprising administering to said patient a therapeutically effective amount a composition comprising an anti-LPS immunoglobulin preparation.

In another aspect, the present invention provides a method for increasing the early peak of insulin secretion in a human patient in need thereof, comprising administering to said patient a therapeutically effective amount a composition comprising an anti-LPS immunoglobulin preparation.

In another aspect, the present invention provides a method for decreasing oral glucose tolerance in a human patient in need thereof, comprising administering to said patient a therapeutically effective amount a composition comprising an anti-LPS immunoglobulin preparation.

In another aspect, the present invention provides a method for increasing insulin secretion in a human patient in need thereof, comprising administering to said patient a therapeutically effective amount a composition comprising an anti-LPS immunoglobulin preparation.

In another aspect, the present invention provides a method for decreasing HBA1C levels in a human patient in need thereof, comprising administering to said patient a therapeutically effective amount a composition comprising an anti-LPS immunoglobulin preparation.

In another aspect, the present invention provides a method for decreasing triglyceride levels in a human patient in need thereof, comprising administering to said patient a therapeutically effective amount a composition comprising an anti-LPS immunoglobulin preparation.

In another aspect, the present invention provides a method for decreasing total cholesterol levels in a human patient in need thereof, comprising administering to said patient a therapeutically effective amount a composition comprising an anti-LPS immunoglobulin preparation.

In another aspect, the present invention provides a method for decreasing LDL cholesterol levels in a human patient in need thereof, comprising administering to said patient a therapeutically effective amount a composition comprising an anti-LPS immunoglobulin preparation.

In another aspect, the present invention provides a method for decreasing ALT levels in a human patient in need thereof, comprising administering to said patient a therapeutically effective amount a composition comprising an anti-LPS immunoglobulin preparation.

In another aspect, the present invention provides a method for decreasing AST levels in a human patient in need thereof, comprising administering to said patient a therapeutically effective amount a composition comprising an anti-LPS immunoglobulin preparation.

In another aspect, the present invention provides a method for decreasing ALP levels in a human patient in need thereof, comprising administering to said patient a therapeutically effective amount a composition comprising an anti-LPS immunoglobulin preparation.

In another aspect, the present invention provides a method for decreasing GGT levels in a human patient in need thereof, comprising administering to said patient a therapeutically effective amount a composition comprising an anti-LPS immunoglobulin preparation.

In another aspect, the present invention provides a method for increasing GLP-1 levels in a human patient in need thereof, comprising administering to said patient a therapeutically effective amount a composition comprising an anti-LPS immunoglobulin preparation.

In another aspect, the present invention provides a method for increasing Adiponectin levels in a human patient in need thereof, comprising administering to said patient a therapeutically effective amount a composition comprising an anti-LPS immunoglobulin preparation.

In another aspect, the present invention provides a method for increasing the Adiponectin/IL-6 ratio in a human patient in need thereof, comprising administering to said patient a therapeutically effective amount a composition comprising an anti-LPS immunoglobulin preparation.

In another aspect, the present invention provides a method for increasing the CD25+ T regulatory cells in a human patient in need thereof, comprising administering to said patient a therapeutically effective amount a composition comprising an anti-LPS immunoglobulin preparation.

In another aspect, the present invention provides a method for decreasing body weight in a human patient in need thereof, comprising administering to said patient a therapeutically effective amount a composition comprising an anti-LPS immunoglobulin preparation.

In another aspect, the present invention provides a method for decreasing waist circumference or arm circumference in a human patient in need thereof, comprising administering to said patient a therapeutically effective amount a composition comprising an anti-LPS immunoglobulin preparation.

In another aspect, the present invention provides a composition comprising an anti-LPS immunoglobulin preparation for use in reducing fasting glucose levels in a human patient in need thereof.

In another aspect, the present invention provides a composition comprising an anti-LPS immunoglobulin preparation for use in increasing the early peak of insulin secretion in a human patient in need thereof.

In another aspect, the present invention provides a composition comprising an anti-LPS immunoglobulin preparation for use in decreasing oral glucose tolerance in a human patient in need thereof.

In another aspect, the present invention provides a composition comprising an anti-LPS immunoglobulin preparation for use in increasing insulin secretion in a human patient in need thereof.

In another aspect, the present invention provides a composition comprising an anti-LPS immunoglobulin preparation for use in decreasing HBA1C levels in a human patient in need thereof.

In another aspect, the present invention provides a composition comprising an anti-LPS immunoglobulin preparation for use in decreasing triglyceride levels in a human patient in need thereof.

In another aspect, the present invention provides a composition comprising an anti-LPS immunoglobulin preparation for use in decreasing total cholesterol levels in a human patient in need thereof.

In another aspect, the present invention provides a composition comprising an anti-LPS immunoglobulin preparation for use in decreasing LDL cholesterol levels in a human patient in need thereof.

In another aspect, the present invention provides a composition comprising an anti-LPS immunoglobulin preparation for use in decreasing ALT levels in a human patient in need thereof.

In another aspect, the present invention provides a composition comprising an anti-LPS immunoglobulin preparation for use in decreasing AST levels in a human patient in need thereof.

In another aspect, the present invention provides a composition comprising an anti-LPS immunoglobulin preparation for use in decreasing ALP levels in a human patient in need thereof.

In another aspect, the present invention provides a composition comprising an anti-LPS immunoglobulin preparation for use in decreasing GGT levels in a human patient in need thereof.

In another aspect, the present invention provides a composition comprising an anti-LPS immunoglobulin preparation for use in increasing GLP-1 levels in a human patient in need thereof.

In another aspect, the present invention provides a composition comprising an anti-LPS immunoglobulin preparation for use in increasing Adiponectin levels in a human patient in need thereof.

In another aspect, the present invention provides a composition comprising an anti-LPS immunoglobulin preparation for use in increasing the Adiponectin/IL-6 ratio in a human patient in need thereof.

In another aspect, the present invention provides a composition comprising an anti-LPS immunoglobulin preparation for use in increasing the CD25+ T regulatory cells in a human patient in need thereof.

In another aspect, the present invention provides a composition comprising an anti-LPS immunoglobulin preparation for use in decreasing body weight in a human patient in need thereof.

In another aspect, the present invention provides a composition comprising an anti-LPS immunoglobulin preparation for use in decreasing waist circumference or arm circumference in a human patient in need thereof.

In another aspect, the present invention provides a use of an anti-LPS immunoglobulin preparation in the manufacture of a medicament for reducing fasting glucose levels in a human patient in need thereof.

In another aspect, the present invention provides a use of an anti-LPS immunoglobulin preparation in the manufacture of a medicament for increasing the early peak of insulin secretion in a human patient in need thereof.

In another aspect, the present invention provides a use of an anti-LPS immunoglobulin preparation in the manufacture of a medicament for decreasing oral glucose tolerance in a human patient in need thereof.

In another aspect, the present invention provides a use of an anti-LPS immunoglobulin preparation in the manufacture of a medicament for increasing insulin secretion in a human patient in need thereof.

In another aspect, the present invention provides a use of an anti-LPS immunoglobulin preparation in the manufacture of a medicament for decreasing HBA1C levels in a human patient in need thereof.

In another aspect, the present invention provides a use of an anti-LPS immunoglobulin preparation in the manufacture of a medicament for decreasing triglyceride levels in a human patient in need thereof.

In another aspect, the present invention provides a use of an anti-LPS immunoglobulin preparation in the manufacture of a medicament for decreasing total cholesterol levels in a human patient in need thereof.

In another aspect, the present invention provides a use of an anti-LPS immunoglobulin preparation in the manufacture of a medicament for decreasing LDL cholesterol levels in a human patient in need thereof.

In another aspect, the present invention provides a use of an anti-LPS immunoglobulin preparation in the manufacture of a medicament for decreasing ALT levels in a human patient in need thereof.

In another aspect, the present invention provides a use of an anti-LPS immunoglobulin preparation in the manufacture of a medicament for decreasing AST levels in a human patient in need thereof.

In another aspect, the present invention provides a use of an anti-LPS immunoglobulin preparation in the manufacture of a medicament for decreasing ALP levels in a human patient in need thereof.

In another aspect, the present invention provides a use of an anti-LPS immunoglobulin preparation in the manufacture of a medicament for decreasing GGT levels in a human patient in need thereof.

In another aspect, the present invention provides a use of an anti-LPS immunoglobulin preparation in the manufacture of a medicament for increasing GLP-1 levels in a human patient in need thereof.

In another aspect, the present invention provides a use of an anti-LPS immunoglobulin preparation in the manufacture of a medicament for increasing Adiponectin levels in a human patient in need thereof.

In another aspect, the present invention provides a use of an anti-LPS immunoglobulin preparation in the manufacture of a medicament for increasing the Adiponectin/IL-6 ratio in a human patient in need thereof.

In another aspect, the present invention provides a use of an anti-LPS immunoglobulin preparation in the manufacture of a medicament for increasing the CD25+ T regulatory cells in a human patient in need thereof.

In another aspect, the present invention provides a use of an anti-LPS immunoglobulin preparation in the manufacture of a medicament for decreasing body weight in a human patient in need thereof.

In another aspect, the present invention provides a use of an anti-LPS immunoglobulin preparation in the manufacture of a medicament for decreasing waist circumference or arm circumference in a human patient in need thereof.

In another aspect, the present invention provides a method of treating a human suffering a T-cell mediated disease comprising administering to the human an effective amount of a composition comprising an anti-LPS immunoglobulin preparation In another aspect, the present invention provides a composition comprising an anti-LPS immunoglobulin preparation for use in treating a human suffering a T-cell mediated disease In another aspect, the present invention provides a use of an anti-LPS immunoglobulin preparation in the manufacture of a medicament for the treatment and/or prophylaxis of a human subject suffering a T-cell mediated disease The T-cell mediated disease may be insulin resistance, impaired glucose tolerance, diabetes, metabolic syndrome, or a disease associated therewith, or non-alcoholic steatohepatitis (NASH).

In another aspect, the present invention provides a method of treatment of a human suffering a disease selected from insulin resistance or associated disorders comprising administering an effective amount of a composition comprising an anti-LPS immunoglobulin preparation.

In another aspect, the present invention provides a composition comprising an anti-LPS immunoglobulin preparation for use in treatment of a human suffering a disease selected from insulin resistance or associated disorders.

In another aspect, the present invention provides a use of an anti-LPS immunoglobulin preparation in the manufacture of a medicament treatment of a human suffering a disease selected from insulin resistance or associated disorders.

The insulin resistance or an associated disorder may be diabetes, metabolic syndrome or non-alcoholic steatohepatitis (NASH).

BRIEF DESCRIPTION OF THE DRAWINGS

The anti-LPS immunoglobulin enriched colostrum preparation used in some embodiments of the methods described herein is referred to in the figures variously as Imm124-E, Travelan, Anti-LPS, T-IgG (produced by vaccination with multiple strains), and HIBC (produced by vaccination with a single strain).

FIG. 42D shows an increase in CD4+CD62+ cells.

DETAILED DESCRIPTION OF THE INVENTION

Figure 1:
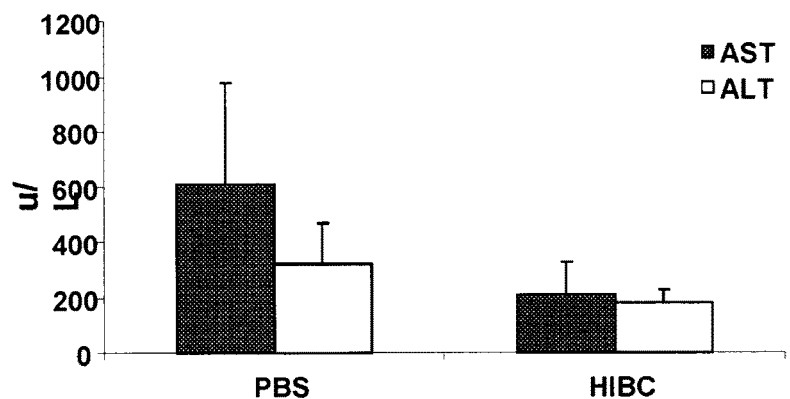
FIG. 1. Oral administration of anti-LPS enriched colostrum-derived immunoglobulin preparation decreases liver enzymes. Values are mean±SD. AST; aspartic transaminase, and ALT; alanine aminotransferase.

A productive immune response results from the effective integration of positive and negative signals that have an impact on both innate and adaptive immune cells. When positive signals dominate, cell activation and pro-inflammatory responses ensue, resulting in the elimination of pathogenic microorganisms, viruses as well a transformed cell. In the absence of such productive stimulation, cell activation is blocked and active anti-inflammatory responses can occur. Modulation of this binary system occurs through the action of cytokines, downstream signaling pathways and cell-cell contact. The perturbation of these thresholds can result in aberrant responses that are either insufficient to deal with pathogenic microorganisms or result in the loss of tolerance and the induction of autoimmune responses. The present invention shows an immunomodulatory effect of a colostrum-derived immunoglobulin preparation enriched in anti-lipopolysaccharide (LPS) antibodies that may act in an active manner for the treatment of immune-related disorders.

Regulatory T cells (Tregs) are increasingly recognized as an important immunomodulatory component of the adaptive immune system. Immune dysregulation may lead to chronic inflammation as a trigger for chronic insulin insensitivity. The present invention shows in a particular example, that oral administration of colostrum-derived anti-LPS antibodies promote Tregs in adipose tissue and in adipose tissue associated stromal vasculature. These alterations are associated with alleviation of the Metabolic Syndrome and liver injury in the ob/ob mice model. Therefore, the present invention provides as a novel therapeutic composition for the alleviation and treatment of the Metabolic Syndrome.

The present inventors have shown that orally administered anti-LPS antibodies promoted Tregs in the liver, spleen, adipose tissue and SV (stromal-vascular cells). CD25+ LAP+ T cells, CD4+ CD25+ T cells, CD4+ CD25+ LAP− T cells, CD45+ LAP+ T and CD3+ LAP+ T cells are induced in the liver. CD45+ LAP+ T cells, CD8+ LAP+ T cells, CD3+ LAP+ T, CD8+ CD25+ T cells are induced in the spleen. CD4+ CD25+ T cells, CD3+ LAP+ T cells, CD4+ CD25+ LAP− T cells are induced in adipose tissue. CD4+ CD25+ T cells and CD4+ CD25+ LAP+ T cells are induced in stromal vascular cells, CD3+ NK1.1+ cells in the liver, and CD25+ LAP− T cells are decreased in the liver.

Various constituents of the adipose tissue, such as mature adipocytes and stromal vascular cells, have distinct functions. They express and secrete different kinds of bioactive molecules collectively called adipokines. Altered adipokine secretion patterns characterize obesity and insulin resistance, which are major risk factors for type 2 diabetes mellitus. Regional and genotypic differences are present in stromal-vascular cells from obese and lean Zucker rats (Turkenkopf, I. J. et al. Int. J. Obes. 12:515-24 (1988)). Gene expression profiling using DNA microarrays showed differences between adipose tissue, adipocytes, and stromal vascular cells (Permana (2008) ibid.). The present invention further supports this notion, showing that the distribution of Tregs in these tissues is important in the metabolic syndrome and liver diseases.

The invention further shows that the promotion of Tregs in the adipose tissue and SV by administration of anti-LPS antibodies is associated with insulin resistance alleviation. This is demonstrated by glucose tolerance tests. In addition, the inflammatory liver damage is alleviated by the present invention, as manifested by a decrease in liver enzymes.

As described above, the invention shows that oral administration of colostrum-enriched with anti-LPS antibodies can serve as a mean to promote Tregs in the adipose tissue and the adipose tissue associated stromal vasculature.

The invention also presents synergy between colostrum-derived components and anti-LPS antibodies by the effect on the distribution of Tregs. Several proteins were identified in breast milk as involved in host defense (Kahn, S. E. et al. Nature 444:840-6 (2006)), including high concentrations mediators of the innate immune system (Poggi, M. et al. Diabetologia (2009)). Among these mediators are multiple defensin proteins, sphingolipids, osteopontin, exosomes, TLRs, cathelicidin, ˆ eosinophil-derived neurotoxin, and high-mobility group box protein 1, and LL-37 (Poggi (2009) ibid.; Nagatomo, T. et al. Clin. Exp. Immunol. 138:47-53 (2004); Admyre, C. et al. J. Immunol. 179:1969-78 (2007); Oppenheim, J. J. and Yang, D. Curr. Opin. Immunol. 17:359-65 (2005)). These can activate the innate and adaptive immune systems. Some of these proteins are also termed 'alarmins', in recognition of their role in mobilizing the immune system (Oppenheim (2005) ibid.). Alarmins have both chemotactic and activating effects on APCs, and can thus amplify innate and Ag-specific immune responses to danger signals (Yang, D. et al. J. Immunol. 173:6134-42 (2004); Oppenheim, J. J. et al. Adv. Exp. Med. Biol. 601:185-94 (2007)). BC (bovine colostrum) contains high levels of β-glycosphingolipids (BGS) (Martin, M. J. et al. Lipids 36:291-8 (2001); Sala-Vila, A. et al. Nutrition 21:467-73 (2005); Van, Y. H. et al. Diabetes 58:146-55 (2009); Nagatomo, T. et al. Clin. Exp. Immunol. 138:47-53 (2004)), the composition of which can determine the effect of APCs or other components of the gut-immune system (Novak, J. et al. Int. Kev. Immunol. 26:49-72 (2007); Nowak, M. and Stein-Streilein, J. Int. Rev. Immunol. 26:95-119 (2007); Nikoopour, E. and Schwartz, J. A. Inflamm. Allergy Drug Targets 7:203-10 (2008); Admyre, C. et al. J. Immunol. 179:1969-78 (2007); Oppenheim, J. J. and Yang, D. Curr. Opin. Immunol. 17:359-65 (2005); Yang, D. et al. J. Immunol. 173:6134-42 (2004); Oppenheim, J. J. et al. Adv. Exp. Med. Biol. 601:185-94 (2007)). Some of these mediators can serve as mucosal adjuvants, enhancing the cross talk between subsets of APCs and Tregs in the bowel mucosa (Vignali, D. A. et al. Nat. Rev. Immunol. 8:523-32 (2008); Margalit, M. et al. J. Pharmacol. Exp. Ther. 319:105-10 (2006); Godfrey, D. I. and Berzins, S. P. Immunol. 7:505-18 (2007; Margalit, M. and Ilan, Y. Liver Int. 25:501-4 (2005); Novak, J. et al. Int. Rev. Immunol. 26:49-72 (2007); Nowak, M. and Stein-Streilein, J. Int. Rev. Immunol. 26:95-119 (2007); Nikoopour, E. and Schwartz, J. A. Inflamm. Allergy Drug Targets 7:203-10 (2008)). Induction of Treg cells may result in a long-lasting tolerance to P3 cell antigens, mediated by local immune modulation in the pancreatic draining lymph nodes (PLNs) (Homann, D. et al. J. Immunol. 163:1833-8 (1999); Homann, D. et al. Immunity 11:463-72 (1999)). This intervention has shown great promise in animal models, but has had little efficacy in human trials. In the Diabetes Prevention Trial, only a sub-fraction of treated patients showed a beneficial effect with immunization with islet autoantigens (Skyler, J. S. et al. Diabetes Care 28:1068-76 (2005)). Prevention of type 1 diabetes was only seen when patients were immunized during the pre-diabetic phase, and immunization was incapable of reverting recent-onset diabetes (Larche, M. and Wraith, D. C. Nat. Med. 11:S69-76 (2005)). Therefore, antigen-specific interventions may require additional adjuvants in order to be used successfully in humans, especially in recent-onset diabetics (Harlan (2005) ibid.).

The present inventors have shown dose dependent effects on the immune system.

In summary, the invention clearly demonstrates that anti-LPS antibodies together with colostrum adjuvants can promote Treg cell accumulation, and thereby serve as a means for alleviating inflammatory response, improving liver damage and improving Metabolic Syndrome complications. Further, according to the invention, Regulatory T lymphocytes in the adipose tissue and the SV can serve as a new therapeutic target in Metabolic Syndrome patients. Moreover, the immunoglobulins in the colostrum may promote regulatory T cells or any other cell related to the immune system in an antigen specific and non-specific way, by targeting bystander antigens, or by being directed against non-associated antigens.

Thus, in a first aspect, the present invention provides a composition comprising an anti-LPS enriched immunoglobulin preparation for use in treatment and/or prophylaxis of a pathologic disorder. The anti-LPS enriched immunoglobulin preparation may be derived from colostrum or from avian eggs.

"Treatment" as used herein refers to the reduction or elimination of the severity of a symptom of the disease, the frequency with which such a symptom is exhibited, or both.

"Prophylaxis" as used herein refers to completely or partially preventing or inhibiting a symptom of the disease or the frequency with which such a symptom is exhibited.

In a one aspect, the present invention provides a composition for the treatment and prophylaxis of a pathologic disorder as described herein. The composition of the invention comprises as active ingredient a mammalian anti-lipopolysaccharide (anti-LPS) enriched colostrum-derived immunoglobulin preparation or anti-LPS immunoglobulin preparation and optionally further colostrum, milk or milk product component/s, and any adjuvant/s. The immunoglobulin preparation or any fractions thereof, recognizes and binds LPS and any fragments thereof. Optionally, the composition of the invention may comprise a combination of anti-LPS enriched colostrum-derived-immunoglobulin preparation with at least one immunoglobulin preparation comprising immunoglobulins recognizing at least one antigen specific for said disorder, thereby activating or inhibiting an immune response specifically directed towards said disorder. It should be further noted that the anti-LPS enriched colostrum-derived immunoglobulin preparations of the invention may be combined with any other immune modulatory drug, including but not limited to other colostrums derived antibodies, other antigen, other adjuvant, other cytokines or any type of molecule that can alter any component of the immune system. The combination can be administered as one product, or in two or more separate products. The combination may be administered together or separately from one another.

In some embodiments, the methods described herein can be used for selecting a treatment for a subject. The methods include detecting the presence in a sample from the subject of one or more of: an ALT level above 50 IU/dL (e.g., above 55, 60, 65, or 70, or alternatively above 40 or 45 IU/DL), an AST level above 50 IU/dL (e.g., above 55, 60, 65, or 70, or alternatively above 40 or 45 IU/DL), an AP of greater than 70 U/L (e.g., above 75, 80, 85, or 90, or alternatively above 60 or 65 IU/DL), a GGT of greater than 60 U/L (e.g., above 65, 70, 75, or 80, or alternatively above 50 or 55 IU/DL); a level of HbA1c above 7% (e.g., above 8, 9, 10, 11, 12, or 13%, or alternatively above 6.5%), a level of fasting insulin secretion above 300 pg/ml (i.e., a fasting level above about 40 uIU/ml, e.g., above 45, 50, 55, 60, 65, or 70 uIU/ml, or alternatively above 10, 20, 25, 30 or 35 uIU/ml); a level of total serum cholesterol above 6 uM/dL (230 mg/dl), (e.g., above 250, 300, 350, or 400); a level of serum LDL above 4 uM/dL (about 150 mg/dL), (e.g., above 100, 125, 175, 200, mg/dL); and/or a level of serum triglycerides above 2 or 2.5 uM/dL (about 175 or 200 mg/dl), (e.g., above about 225, 250, 275, or 300 uM/dL); optionally selecting the subject based on the presence of such levels, and selecting a treatment comprising administration of a composition comprising an anti-LPS immunoglobulin-enriched colostrum preparation for the subject. In some embodiments, the methods further include administering the treatment to the subject. In some embodiments, the methods include obtaining a sample from the subject, and detecting a level of an analyte listed above in the sample using known methods.

In some embodiments, the subject has metabolic syndrome or non-alcoholic steatohepatitis (NASH); metabolic syndrome or diabetes; or elevated cholesterol levels. In some embodiments, the composition reduces AST and/or ALT levels; reduces serum insulin levels, increases serum insulin levels, improves fasting glucose levels, and/or reduces HbA1c levels; reduces serum cholesterol levels, reduces levels of serum LDL, and/or reduces levels serum triglycerides.

According to one specific embodiment, the colostrum-derived anti-LPS enriched immunoglobulin preparation or anti-LPS immunoglobulin preparation may comprise monomeric, dimeric or multimeric immunoglobulin selected from the group consisting of IgG, IgA and IgM and any fragments thereof. As indicated above, in ruminants, the principal compositional difference between colostrum and mature milk is the very high content of colostral immunoglobulin, of which IgG class makes up 80-90%.

Thus, according to a specific embodiment, the colostrum-derived anti-LPS enriched immunoglobulin preparation or anti-LPS immunoglobulin preparation of the invention mainly comprises IgG, specifically, IgG1 and IgG2.

Immunoglobulin G (IgG) as used herein, is a multimeric immunoglobulin, built of two heavy chains and two light chains. Each complex has two antigen binding sites. This is the most abundant immunoglobulin and is approximately equally distributed in blood and in tissue liquids, constituting 75% of serum immunoglobulins in humans. In general, the number of IgG subclasses varied widely between different species, ranging from one subclass in rabbits to seven subclasses in horses, making it difficult to find orthologues. In humans, for example, IgG1 and IgG3 are the most pro-inflammatory IgG subclasses. In mice, however, IgG2a and IgG2b are the most pro-inflammatory IgG molecules showing a greater activity than mouse IgG1 and IgG3 in many in vivo model systems.

Optionally or additionally, the anti-LPS enriched immunoglobulin preparation or anti-LPS immunoglobulin preparation may comprise a secretory antibody, specifically, sIgA.

Dimeric and multimeric IgA and IgM are secreted by a number of exocrine tissues. IgA is the predominant secretory immunoglobulin present in colostrum, saliva, tears, bronchial secretions, nasal mucosa, prostatic fluid, vaginal secretions, and mucous secretions from the small intestine. IgA output exceeds that of all other immunoglobulins, making it the major antibody produced by the body daily and is the major immunoglobulin found in human milk, whey and colostrum. IgM secretion is less abundant but can increase to compensate for deficiencies in IgA secretion. J chain containing IgA is produced and secreted by plasma B immunocytes located in the lamina propria just beneath the basement membrane of exocrine cells. IgA has a typical immunoglobulin four-chain structure ($M_r$ 160,000) made up of two heavy chains ($M_r$ 55,000) and two light chains ($M_r$ 23,000). In humans, there are two subclasses of IgA. These are IgA1 and IgA2 that have one and two heavy chains, respectively. IgA can occur as monomers, dimers, trimers or multimers. In plasma, 10% of the total IgA is polymeric while the remaining 90% is monomeric. The secreted IgA binds to a $M_r$ 100,000 poly-Ig receptor positioned in the basolateral surface of most mucosal cells. The receptor-IgA complex is next translocated to the apical surface where IgA is secreted. The binding of dimeric IgA to the poly-Ig receptor is completely dependent upon the presence of a J chain. Monomeric IgA will not bind to the receptor.

The difference in function of IgG and IgA, follows the position where the molecules operate. IgA is found mainly on mucosal surfaces where there is little in the way of tissue fluid to carry immune cells and chemicals. Therefore, IgA (often as a dimer) would be preferably used for physical neutralisation of pathogens, and may be too effective at other immune functions. IgGs are present in the tissue fluid and blood where there is the full collection of leukocytes, complement system, macrophages etc. may physically neutralize a pathogen effectively and are also more effective in a communication/presentation role than IgA, i.e., they tend to induce better opsonisation by phagocytes (e.g., Killer T cells and macrophages) and switch on the complement system better.

More specifically, the anti-LPS enriched immunoglobulin preparations or anti-LPS immunoglobulin preparations of the invention may be obtained from any one of colostrum, colostrum serum, hyperimmunised milk or colostrum, colostrum whey (either cheese or casein), cheese or casein whey, directly from skim milk, whole milk, or a reconstituted form of such streams.

It should be appreciated that the anti-LPS enriched immunoglobulin preparation or anti-LPS immunoglobulin preparation comprised within the composition of the invention may be any fraction of colostrum. Thus, the term colostrum where used herein includes colostral milk, processed colostral-milk such as colostral milk processed to partly or completely removes one or more of fat, cellular debris, lactose and casein.

The colostrum, or milk, containing the anti-LPS antibodies and optionally, the antigen-specific antibodies may be preferably collected by milking the animal colostrum or milk thus collected can either be used directly, may be further processed, for instance to purify anti-LPS and optionally, antigen-specific antibodies. Methods for the (partial) purification of (LPS and optionally, antigen-specific) antibodies from colostrum or milk are present in the art.

It should be further appreciated that any adjuvants may be added to the compositions of the invention. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner.

Alternatively, the anti-LPS enriched immunoglobulin preparation or anti-LPS immunoglobulin preparation may be an affinity purified antibody or any fragment thereof. The term "antibody" is meant to include both intact molecules as well as fragments thereof, such as, for example, Fab and $F(ab')_2$, which are capable of binding antigen. Fab and $F(ab')_2$ fragments lack the Fc fragment of intact antibody, clear more rapidly from the circulation, and may have less non-specific tissue binding than an intact antibody. It will be appreciated that Fab and $F(ab')_2$ and other fragments of the antibodies useful in the present invention may be used for immuno-modulation, according to the methods disclosed herein for intact antibody molecules. Such fragments are typically produced by proteolytic cleavage, using enzymes such as papain (to produce Fab fragments) or pepsin (to produce $F(ab')_2$ fragments).

An antibody is said to be "capable of specifically recognizing" a certain antigen if it is capable of specifically reacting with an antigen which is in this particular example an antigen or a mixture of antigens specific for a certain immune-related disorder, to thereby bind the molecule to the antibody.

An "antigen" is a molecule or a portion of a molecule capable of being bound by an antibody, which is additionally capable of inducing an animal to produce antibody capable of binding to an epitope of that antigen. An antigen may have one or more than one epitope. The term "epitope" is meant to refer to that portion of any molecule capable of being bound by an antibody that can also be recognized by that antibody. Epitopes or "antigenic determinants" usually consist of chemically active surface groupings of molecules such as amino acids or sugar side chains, and have specific three-dimensional structural characteristics as well as specific charge characteristics.

In yet another embodiment, the anti-LPS enriched immunoglobulin preparation or anti-LPS immunoglobulin preparation used as an active ingredient for the composition of the invention may be obtained from a mammal immunized with LPS or any fragments thereof. Optionally, in addition to LPS, said mammal according to certain embodiments may be further immunized with at least one antigen or a mixture of at least two antigens specific for said disorder, as well as with a mixture of at least two different antibodies directed against at least two different antigens associated with the disease.

According to one embodiment, the LPS or any antigen used for immunizing said mammal, preferably, bovine or avian, may be provided as any one of an isolated and purified peptide, a purified recombinant protein, a fusion protein, cell lysate, membranal preparation, nuclear preparation, or cytosolic preparation of any one of tissue culture cells, primary cells or tissue samples obtained from a subject suffering from said disorder.

According to another embodiment, the composition of the invention may optionally further comprise colostrum component/s such as for example, alarmins, defenensins, colostrinin, and any other colostrum or milk derived carbohydrates, glycolipids or any other molecules or components that may further enhance or inhibit modulation of an immune response, or any preparations, mixtures or combinations thereof. Moreover, the composition of the invention may comprise any additional adjuvant. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner.

In some embodiments of the composition, the composition comprises a constituent of a bird's egg, wherein the bird's egg comprises IgY specific for LPS or a fragment thereof. Crude egg yolk may be used as an antibody source However, avian antibodies are usually purified or concentrated from the yolk prior to use. The constituent of the bird's egg may be concentrated or purified as necessary, as is understood by those skilled in the art In some embodiments of the composition, the composition comprises the yolk of the egg, or any IgY antibody-containing fraction thereof. The yolk is preferable to the white of the egg, as the yolk typically contains much higher concentrations of IgY than does the white. However, the white may contain concentrations of IgY sufficient for some applications.

In some embodiments of the antibody composition, the IgY is concentrated, isolated, or purified from the constituent of the bird egg This can be accomplished by a variety of methods In some embodiments the antibodies may be purified by the water dilution method. The precipitate may then be removed by any conventional method, including centrifugation. The supernatant can then be stored frozen, for example at −20° C. IgY can then be isolated by precipitation with ammonium sulfate and subsequent dialysis. If desired, the titer of IgY antibodies can be determined by immunoassay, for example ELISA. The water dilution method is more completely described in the well-known literature, for example by Akita and Nakai (1993), which is incorporated by reference to teach this method. Other useful methods are described for example is U.S. Pat. No. 4,550,019, U.S. Pat. No. 4,748,018, and U S Patent Publication 2004/0161427 which are hereby incorporated by reference for such teachings Commercial kits are available for example from the Promega Corporation (Madison, Wis.).

Some embodiments of the antibody composition are substantially isolated. In such embodiments a significant fraction of a non-antibody yolk component has been removed. The non-antibody yolk component may be for example the lipid component of the yolk, the carbohydrate component of the yolk, the yolk granules, the hydrophobic component of the yolk, the steroid component of the yolk, and the non-immunoglobulin protein component of the yolk. The fraction of the component removed is at least 50%. In some embodiments the removed fraction is at least 60%, 75%, 80%, 90%, 95%, 99%, or 99 9%. Greater removed fractions have the advantage of producing a more pure antibody composition. Smaller removed fractions have the advantage of requiring less processing.

Some embodiments of the antibody composition are substantially concentrated. In such embodiments the concentration of IgY will be greater in the composition than in the egg yolk. Substantially concentrated antibody compositions comprise IgY that is at least twice as concentrated as in the yolk. Some embodiments of the substantially concentrated antibody composition are concentrated by at least a factor of 3, 4, 5, 6, 7, 8, 9, 10, 100, 1000, or 10,000. More concentrated antibody compositions have the advantage of providing the same mass of antibodies in lower volume. Less concentrated antibody compositions have the advantage of requiring less processing.

The antibody compositions of the present disclosure may be processed so as to largely remove all isotypes except IgG and IgY. In some embodiments the immunoglobulin may be derived from numerous donors. Any number of donors may be used In some embodiments, the antibodies are derived from one donor. In further embodiments, the antibodies are derived from 1-10 donors. In further embodiments, the antibodies are derived from 10-100 donors. In further embodiments, the antibodies are derived from 100-1000 donors. In still further embodiments, the antibodies are derived from over 1000 donors.

In some embodiments of the antibody composition, the composition is made by the method comprising obtaining an egg laid by a fowl previously immunized against influenza and separating the antibody fraction from a yolk of the egg. In some embodiments of the composition the fowl has been actively immunized, for example by vaccination. The fowl is preferably a domesticated fowl The domesticated fowl may be chicken, duck, swan, goose, turkey, peacock, guinea hen, ostrich, pigeon, quail, pheasant, dove, or other domesticated fowl The domesticated fowl is preferably a chicken The domesticated fowl is more preferably a domesticated chicken raised primarily for egg or meat production. The fowl may be immunized against any strain of influenza, any subtype of influenza, any type of influenza, or combinations thereof.

Use of eggs from chickens raised for egg or meat production, and which are vaccinated pursuant to this purpose, has the great advantage of using as the feedstock for the process eggs that are widely available commercially in great volumes and at very low price. Previously, animals used for the production of antibodies have been raised solely or mainly for that purpose, and maintained in small numbers at very high expense.

In some embodiments of the antibody composition, the antibody composition is made by a method comprising actively immunizing a hen with antigen, collecting eggs from the hen after an immunization period, and separating the antibody fraction from a yolk of the egg. Optionally, collecting eggs from the hen can occur continuously after the immunization period. The immunization of the bird may occur by any means known in the art. For example, a vaccine may be administered to the bird that is known to effectively elicit an immune response in birds, or that is known to effectively elicit an immune response in mammals. Many such influenza vaccines are commercially available, and can be routinely developed by those of ordinary skill m the art without undue experimentation further methods of producing IgY with a specific target are known to those skilled in the art.

Such methods can be found for example in U.S. Pat. No. 4,550,019, U.S. Pat. No. 4,748,018, and U S Patent Publication 2004/0161427, and U.S. Pat. No. 6,537,500, which are incorporated by reference.

In one embodiment, the present invention provides a composition comprising an anti-LPS enriched immunoglobulin preparation or anti-LPS immunoglobulin preparation for use in treatment and/or prophylaxis of a pathologic disorder wherein the anti-LPS enriched immunoglobulin preparation is derived from avian eggs and further comprising non-hyperimmune colostrum.

In one embodiment, the pathologic disorder is acute or chronic liver disease, cirrhosis or any disease or complication associated therewith. In another embodiment, the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness. In another embodiment, the pathologic disorder is liver damage.

In another embodiment, the pathologic disorder is an immune-related disorder selected from the group consisting of autoimmune disease, non-alcoholic steatohepatitis, fatty liver, atherosclerosis, metabolic syndrome and any disorder associated therewith, infectious disease, and proliferative disorder.

Alternatively, the pathologic disorder may be selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

In one embodiment, the immuno-modulating composition of the invention is capable of reducing, eliminating or inhibiting mucosal microbial translocation, thereby modulating immune activation. It should be noted that chronic activation of the immune system is a hallmark of progressive viral infection and predicts disease outcome. It has been previously shown that circulating microbial products, likely derived from the gastrointestinal tract, in a process also known as "mucosal microbial translocation", are a primary cause of virus-related systemic immune activation. Thus, according to certain embodiments, the compositions of the invention may modulate immune function, or alternatively, reduce or change the number of bacteria or of bacteria related products not related to alteration of the immune system.

According to one embodiment, the invention provides a composition comprising as an active ingredient a mammalian anti-lipopolysaccharide (LPS) enriched colostrum-derived immunoglobulin preparation. Such composition wherein said composition is particularly applicable for the treatment, prevention and prophylaxis of acute or chronic liver disease, cirrhosis and any disease or complication associated therewith, optionally said composition further comprises an additional therapeutic agent or any carrier and adjuvant.

More specifically, according to the invention, acute or chronic liver disease, cirrhosis and any disease or complication associated therewith may be for example, at least one of hepatic encephalopathy, spontaneous bacterial peritonitis (SBP), ascites, variceal bleeding, cirrhosis associated hyperdynamic circulation, hepatorenal syndrome, hepatopulmonary syndrome, portopulmonary hypertension, variceal bleeding, adrenal insufficiency and altered level of consciousness.

In a further embodiment, the composition of the invention may be used for the treatment of pathologic disorders such as any type of viral disease including HCV, HBV, CMV, and EBV.

It should be noted that such colostrum-derived preparations may be therefore combined with any drug used for liver disease, as an additional therapeutic agent.

The term "cirrhosis" as used herein refers to the final common histological outcome of a wide verity of chronic liver diseases, characterized by the replacement of liver tissue by fibrous scar tissue and regeneration of nodules, leading to progressive loss of liver function. Cirrhosis is usually caused by Hepatitis B and C viruses, alcoholism and fatty liver disease.

The term "ascites", as used herein describes the condition of pathologic fluid accumulation within the abdominal cavity, most commonly due to cirrhosis and sever liver disease.

It should be noted that such colostrum-derived preparations may be therefore combined with any immunomodulatory therapeutic agent/s or any combination or mixture thereof, creating a combined immunomodulatory composition for the treatment and/or prevention of immune-related disorders, a non-alcoholic steatohepatitis, fatty liver, atherosclerosis, metabolic syndrome and any disorder associated therewith, infectious disease, malignant or infectious disorders.

It should be noted that the colostrum-derived composition of the invention may further comprises any added adjuvant.

It should be noted that since microbial translocation is also associated with alteration of the liver inflammation in many liver disorders, including viral-mediated, drug-mediated, non-alcoholic steatohepatitis and any other hepatic disorder, as well as with insulin resistance, diabetes type 2, obesity and overweight, prevention of this translocation by the composition of the invention may be applicable in the treatment of these disorders. Therefore, the invention further provides the use of the anti LPS compositions of the invention, optionally, combined with colostrum preparations enriched for antibodies directed against antigens associated with a disease, for example, anti-insulin antibodies, in the treatment of any acute or chronic liver disease, diabetes, and any complication of diabetes, fatty liver, non-alcoholic steatohepatitis, and obesity.

In another embodiment, the composition further comprises an immunoglobulin preparation comprising immunoglobulins that recognize and bind at least one antigen specific for said pathologic disorder. The further immunoglobulin preparation may be derived from colostrum or from avian eggs.

According to one optional embodiment, the invention provides combined compositions comprising a combination of anti-LPS enriched immunoglobulin preparation with at least one colostrum-derived immunoglobulin preparation comprising immunoglobulins that recognize and bind at least one antigen specific for said pathologic disorder and thereby modulate immune-regulatory cells, specifically, regulatory T cells. It should be noted that such modulation may results for example, in modulation of the Th1/Th2, Tr1/Th3 cell balance toward an anti-inflammatory Th2, Tr1/Th3 immune response thereby inhibiting an immune response specifically directed toward said disorder.

Immunoglobulins that recognize and bind at least one antigen specific for said pathologic disorder and thereby modulate immune-regulatory cells, specifically, regulatory T cells include the following:

Anti influenza antibodies for the treatment and/or prophylaxis of influenza; Anti HCV antibodies for the antibodies for the treatment and/or prophylaxis of any type of liver cancer or acute and chronic liver disorders associated with HCV infection; Anti HBV antibodies for the treatment and/or prophylaxis of any type of liver cancer or acute and chronic liver disorders associated with HBV infection; Anti CMV antibodies for the treatment and/or prophylaxis of acute and chronic disorders associated with CMV infection; anti amyloid antibodies for the treatment and/or prophylaxis of Alzheimer's disease, hepatic encephalopathy, any type of memory loss, attention deficit disorders (ADHA), any type of learning disability, effect of alcohol or drugs on the brain, antibodies against any viral, bacterial, spirochetal, preon, parasitic, spore or fungal antigen for the treatment and/or prophylaxis of acute and chronic disorders associated with the relevant infection; anti-insulin antibodies for the treatment and/or prophylaxis of any disorder associated with insulin resistance; antibodies against any type of cancer associated antigen for the treatment and/or prophylaxis of any malignant disorder including metastatic and non metastatic, solid and non solid that is associated to the target antigen; antibodies against disease specific and disease associated antigens for the treatment and/or prophylaxis of any type of immune mediated or autoimmune disease; anti-HSV, JC virus, Adenovirus. Parainfluenza virus and RSV antibodies for the treatment and/or prophylaxis of viral disease; anti Mycoplasma/*Legionella* antibodies for the treatment and/or prophylaxis of pneumonia; anti PTHrp, aldosteron, steroids, GH and prolactin antibodies for the treatment and/or prophylaxis of secreting tumors; anti IL-12, omp C antibodies for the treatment and/or prophylaxis of IBD; Anti Intrinsic Factor antibodies for the treatment and/or prophylaxis of Megaloblastic anemia; anti *H. pylori* antibodies or the treatment and/or prophylaxis of *H. pylori* infection; anti EBV antibodies for the treatment and/or prophylaxis of Burkitt's lymphoma; and antibodies specific for antigens associated with Autoimmune pancreatitis, Chronic lung diseases such as CF, Asthma etc, Liver Cirrhosis, liver fibrosis (CCL4), and Hyperclacemia.

According to another alternative embodiment, the anti-LPS enriched immunoglobulin preparation of the invention may further comprise immunoglobulins directed to antigens that are not specific to the treated disorder. Such antigens may be any target immune-related components having a modulatory effect on the immune-response. Thereby, recognition of such disease non-specific antigens by the immunoglobulin preparation of the invention may results in alteration of the immune-response. Such modulation may results for example, in modulation of the Th1/Th2, Tr1/Th3 cell balance toward an anti-inflammatory Th2, Tr1/Th3 immune response thereby inhibiting an immune response specifically directed toward said disorder. According to another embodiment, the combined composition of the invention may optionally further comprises an additional therapeutic agent or any carrier and adjuvant.

Alternatively or additionally, the combined colostrums-derived immunoglobulin preparation of the invention as well as the immuno-modulatory composition derived therefrom, may act in an indirect manner by activation or promotion of specific subsets of regulatory cells, or antigen presenting cells, or by any type of cell-cell contact. Such anti-LPS enriched combined composition may be directed towards different components of the immune-system. For example, activation of specific regulatory T cells, B cells or antigen presenting cells, or any other cells that associated with an effect on the immune system, or induces the secretion of cytokines or chemokines or affects the immune system in any other way. Alteration or promotion of immune cells may further involve induction of any type of regulatory cells, preferably, regulatory T cells, for example, Th3 cells, Tr1, T17 cells or any other type of regulatory, effector or suppressor cells. It should be noted that Th17 cells are a recently-identified subset of CD4 T helper cells. They are found at the interfaces between the external environment and the internal environment, e.g., skin and lining of the GI tract. More specifically, it should be noted that the colostrum-derived anti-LPS enriched immunoglobulin preparations of the invention may promote regulatory T cells or any other cell related to the immune system in an antigen specific and non specific manner, by targeting bystander antigens, or by being directed towards non associated antigens.

Thus, according to another embodiment, the invention provides a combination of an anti-LPS enriched immunoglobulin preparation of the invention with at least one additional immunoglobulin preparation comprising immunoglobulins directed against at least one antigen associated with said disorder, creating a combined composition for treating immune-related disorders. Such composition therefore may be antigen or disease specific or alternatively, may augment or induce specific cells or parts of the immune system in a non-antigen specific way, including an immune bystander effect.

In one embodiment, the composition modulates regulatory T cells leading to modulation of the Th1/Th2, Tr1/Th3 cell balance toward an anti-inflammatory Th2, Tr1/Th3 immune response or a pro-inflammatory Th1 immune response thereby inhibiting or activating an immune response specifically directed toward said disorder.

In another embodiment, the composition modulates the Th1/Th2, Tr1/Th3 cell balance toward an anti-inflammatory Th2, Tr1/Th3 immune response thereby inhibiting an immune response specifically directed toward said disorder, and wherein said composition is for the treatment of any one of an autoimmune disease, non-alcoholic steatohepatitis, fatty liver, atherosclerosis, metabolic syndrome and any disorder associated therewith selected from diabetes type 2, insulin resistance, obesity and overweight.

In another embodiment, the composition is for the treatment and/or prophylaxis of metabolic syndrome or non-alcoholic steatohepatitis or both. In another embodiment, the composition is for the treatment, and/or prophylaxis of diabetes, the treatment of impaired glucose tolerance, such as decreasing glucose tolerance. decreasing serum insulin levels, decreasing hepatic triglyceride levels, or decreasing cholesterol levels.

In one embodiment, the composition modulates the Th1/Th2, Tr1/Th3 cell balance toward a pro-inflammatory Th1/Th2 immune response thereby enhancing an immune response specifically directed toward said disorder, and wherein said composition is for the treatment of infectious diseases, and proliferative disorders.

The composition may further comprise a therapeutic agent, carrier or adjuvant and/or non-hyperimmune colostrum.

It should be further appreciated that the anti-LPS enriched immunoglobulin preparation of the invention may be used either for an active or a passive treatment.

In a further embodiment of the immuno-modulating composition of the invention, said immune-related disorder is any one of autoimmune disease, infectious disease, and proliferative disorder.

It should be noted that the composition of the invention may be applicable for treating acute complications, or prevention the development or the recurrence of these complications.

According to one embodiment, the combined composition of the invention leads to modulation of the Th1/Th2, Tr1/Th3 cell balance toward an anti-inflammatory Th2, Tr1/Th3 immune response thereby inhibiting an immune response specifically directed toward said disorder. Such regulation may involve regulatory T cells, antigen presenting cells, any type of T cell or B cell, the function of any cell associated directly or indirectly with the immune system, or any type of cytokine or chemokine, or adjuvant. According to this specific embodiment, such composition may be applicable in the treatment of an autoimmune disease. Examples of autoimmune disorders include, but are not limited to, Alopecia Areata, Lupus, Anlcylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The combined compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

In yet another embodiment, the combined compositions of the invention may be used for treating any one of non-alcoholic steatohepatitis, fatty liver, atherosclerosis, metabolic syndrome and any disorder associated therewith for example, diabetes type 2, insulin resistance, obesity and overweight.

Alternatively, the combined composition of the invention may lead to modulation of the Th1/Th2, Tr1/Th3 cell balance toward a pro-inflammatory Th1/Th2 immune response thereby enhancing an immune response specifically directed toward said disorder. Such regulation may involve regulatory T cells, antigen presenting cells, any type of T cell or B cell, the function of any cell associated directly or indirectly with the immune system, or any type of cytokine or chemokine, or adjuvant. According to this specific embodiment, such composition may be applicable in the treatment of infectious diseases, and proliferative disorders.

According to one specific embodiment, a malignant proliferative disorder may be a solid or non-solid tumor, for example, carcinoma, sarcoma, melanoma, leukemia, myeloma or lymphoma.

According to another specific embodiment, the composition of the invention is intended for preventing and/or treating carcinoma such as hepaotcellular carcinoma, prostate cancer, breast carcinoma, colon carcinoma. In yet another embodiment, the composition of the invention may be used for preventing and/or treating leukemia, more specifically, acute or chronic leukemia.

As used herein to describe the present invention, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods and compositions of the present invention may be used in the treatment of non-solid and solid tumors.

Malignancy, as contemplated in the present invention may be selected from the group consisting of carcinomas, melanomas, lymphomas and sarcomas. Malignancies that may find utility in the present invention can comprise but are not limited to hematological malignancies (including leukemia, lymphoma and myeloproliferative disorders), hypoplastic and aplastic anemia (both virally induced and idiopathic), myelodysplastic syndromes, all types of paraneoplastic syndromes (both immune mediated and idiopathic) and solid tumors (including lung, liver, breast, colon, prostate GI tract, pancreas and Karposi). More particularly, the malignant disorder may be hepaotcellular carcinoma, colon cancer, melanoma, myeloma and acute or chronic leukemia.

According to another embodiment, the immuno-modulating composition of the invention may be specifically applicable for treating infectious diseases, for example, conditions caused by viral pathogens such as HCV, HBV, CMV, and EBV.

According to one particular embodiment, the combined immunomodulatory composition of the invention may lead to a Th2, Tr1/Th3 anti-inflammatory response. More specifically, such anti-inflammatory response may be accompanied by a decrease or reduction in the amount or expression of pro-inflammatory cytokines such as IL-2, IL-17, IL-23, IFN-γ, IL-6. Such decrease or reduction according to the invention may be a reduction of about 5% to 99%, specifically, a reduction of about 5%, 10%, 15%, 20%, 25%, 30%, 35%, 40%, 45%, 50%, 55%, 60%, 65%, 70%, 75%, 80%, 85%, 90%, 95% or 99% as compared to untreated control. In yet another specific embodiment, the composition of the invention may elevate and increase the amount or expression of anti-inflammatory cytokines such as TGF-β, IL-10, IL-4, IL-5, IL-9 and IL-13. More specifically, the increase, induction or elevation of the anti-inflammatory cytokines may be an increase of about 5%, 10%, 15%, 20%, 25%, 30%, 35%, 40%, 45%, 50%, 55%, 60%, 65%, 70%, 75%, 80%, 85%, 90%, 95% or 99% as compared to untreated control.

It should be appreciated that the anti-inflammatory effect of the combined immuno-modulatory composition of the invention may be achieved by activation or promotion of specific subsets of regulatory cells, antigen presenting cells or any type of cell-cell contact, or via direct or indirect activation of cytokines and/or chemokines. It should be further noted that any type of regulatory or effector cell, specifically regulatory T cells, including Th3 and Tr1. cells may be involved. Thus, the colostrum-derived anti-LPS enriched immunoglobulin preparations of the invention may promote regulatory T cells or any other cell related to the immune system in an antigen specific and non specific way, by targeting bystander antigens, or by being directed against non associated antigens.

More specifically, an immune-related cell activated or promoted by the composition of the invention may be an APC (such as DC), Treg cell or any other cell associated directly on indirectly with the immune system including but not limited to platelets, macrophages, any type of B cell, T cell (including double negative cells), and any type of non-professional antigen presenting cell, adipocytes, endothelial cell, any type of cell that is part of an organ, specifically, an organ connected to the treated immune-related disorder and any type of cell having regulatory enhancing or suppressing properties. More particularly, the compositions of the invention demonstrate anti-inflammatory effect on immune-related cells such as specific T regulatory cells for example, adipocytes and Antigen Presenting Cells (APC), such as DC. Therefore, according to one embodiment, the composition of the invention may be used for inducing at least one of T regulatory (Treg) cells, or any cell having regulatory properties, either suppressive or inductive, adipocyte and Antigen Presenting Cells (APC) in a subject suffering from hepatic disorder.

As indicated above, the compositions or the optional combined compositions of the invention are intended for preventing and/or treating a pathologic disorder, specifically, hepatic disorders, or an immune-related disorder. As used herein, the term "disorder" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein. It should be further noted that an "immune-related disorder or disease" or "hepatic disorder" may be any disorder associated with, caused by, linked to, a non normal immune response. Such disorders may usually occur together with a disturbed immune response, or believed to have an impact on or by a non normal immune response.

The composition may be formulated for administration orally, by inhalation as an aerosol, or by parenteral, intravaginal, intranasal, mucosal, sublingual, topical, or rectal administration, or any combination thereof.

In one embodiment, the immunoglobulin preparation or any fractions thereof recognizes and binds LPS or any fragments thereof.

In another embodiment, the composition inhibits microbial translocation. In another embodiment, the composition inhibits microbial translocation and thereby modulates immune activation.

In another aspect, the present invention provides a composition comprising a mammalian anti-LPS enriched colostrum-derived immunoglobulin preparation for modulating immune tolerance in a subject, or in another aspect, for modulating oral tolerance in a subject According to one preferred embodiment, any of the compositions of the invention may be administered orally or by inhalation as an aerosol or by intravenous, intramuscular, subcutaneous, intraperitoneal, parenteral, transdermal, intravaginal, intranasal, mucosal, sublingual, topical, rectal or subcutaneous administration, or any combination thereof. Orally administrated antibodies would be expected to be degraded in the gastrointestinal tract, given the low gastric pH and the presence of gastric and intestinal proteases. However, bovine colostral IgG (BCIg) has been cited as particularly resistant to GI destruction, relative to other immunoglobulins. Early studies of BCIg cited remarkable "resistance to proteolytic digestion in the intestine of a heterologous host". There is also evidence that bovine IgG1 is somewhat more resistant to proteolysis by trypsin, chymotrypsin and pepsin than other Igs. These results drove much of the early development of oral antibody therapy. More specifically, the composition of the invention may be suitable for mucosal administration, for example, pulmonary, buccal, nasal, intranasal, sublingual, rectal, vaginal administration and any combination thereof.

As indicated above, although oral and nasal administration are preferred, it should be appreciated that any other route of administration may be applicable, for example, intravenous, intravenous, intramuscular, subcutaneous, intraperitoneal, parenteral, intravaginal, intranasal, mucosal, sublingual, topical, rectal or subcutaneous administration, or any combination thereof.

Moreover, the anti-LPS enriched immunoglobulin preparation used by the compositions and combined compositions of the invention may be prepared in preparations such as food additives, aqueous solutions, oily preparations, emulsions, gels, etc., and these preparations may be administered orally, topically, rectally, nasally, bucally, or vaginally. The preparations may be administered in dosage formulations containing conventional non-toxic acceptable carriers and may also include one or more acceptable additives, including acceptable salts, polymers, solvents, buffers, excipients, bulking agents, diluents, excipients, suspending agents, lubricating agents, adjuvants, vehicles, deliver systems, emulsifiers, dis-integrants, absorbents, preservatives, surfactants, colorants, flavorants or sweeteners. An optional dosage form of the present invention may be a powder for incorporation into beverages, pills, syrup, capsules, tablets, granules, beads, chewable lozenges or food additives, using techniques known in the art. Thus, immuno-modulating composition of the invention may be administered in a form selected from the group consisting of orally-active powders, pills, capsules, teas, extracts, dried extracts, subliguals, sprays, dispersions, solutions, suspensions, emulsions, foams, syrups, lotions, ointments, gels, pastes, dermal patches, injectables, vaginal creams and suppositories.

Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal or by inhalation) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein, fully incorporated herein by reference.

The pharmaceutical composition of the invention can be administered and dosed in accordance with good medical practice.

The composition of the invention may comprise the active substance in free form and be administered directly to the subject to be treated, Formulations typically comprise at least one active ingredient, as defined above, together with one or more acceptable carriers thereof. Each carrier should be both pharmaceutically and physiologically acceptable in the sense of being compatible with the other ingredients and not injurious to the patient.

Formulations include those suitable for oral, nasal, or parenteral (including subcutaneous (s.c.), intramuscular (i.m.), intraperitoneal (i.p.), intravenous (i.v.) and intradermal or by inhalation to the lung mucosa) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The pharmaceutical compositions of the invention generally comprise a buffering agent, an agent that adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

In instances in which oral administration is in the form of a tablet or capsule, the active drug components (anti-LPS enriched immunoglobulin preparation or a combination with other immunoglobulin preparation) can be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture. Stabilizing agents such as antioxidants, propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

In another aspect, the present invention provides the use of a mammalian anti-LPS enriched colostrum-derived immunoglobulin preparation and optionally of a colostrum-derived immunoglobulin preparation recognizing at least one antigen specific for a pathologic disorder in the manufacture of an immuno-modulating composition for the treatment and prophylaxis of a pathologic disorder. It should be noted that the anti-LPS enriched immunoglobulin preparation or any fractions thereof recognizes and binds LPS and any fragments thereof. Optionally, the composition prepared by the use of the invention may comprise a combination of the anti-LPS enriched immunoglobulin preparation of the invention and at least one immunoglobulin preparation comprising immunoglobulins recognizing at least one antigen specific for said disorder. Such recognition leads to alteration of regulatory T cells, and as a result, causes modulation of the Th1/Th2, Tr1/Th3 cell balance either toward an anti-inflammatory Th2, Tr1/Th3 immune response or toward a pro-inflammatory Th1 immune response. Thereby creating a combined immuno-modulating composition inhibiting or activating an immune response specifically directed toward said disorder.

It should be noted that any type of regulatory or effector cells, specifically regulatory T cells, including Th3 and Tr1 ($T_H3$, T cells are preferentially induced at mucosal surfaces and secrete transforming growth factor (TGF)-$\beta$) cells may be involved. Moreover, it should be noted that the colostrum-derived anti-LPS enriched immunoglobulin preparations of the invention may promote regulatory T cells or any other cell related to the immune system in an antigen specific and non specific way, by targeting bystander antigens, or by being directed against non associated antigens.

According to one embodiment, the anti-LPS enriched colostrum-derived immunoglobulin preparation used for the invention comprises monomeric, dimeric or multimeric immunoglobulin selected from the group consisting of IgG, IgA and IgM and any fragments, mixtures or combinations thereof.

In yet another embodiment, the use according to the invention of colostrum-derived, milk or milk products-derived anti-LPS enriched immunoglobulin preparation is for manufacturing a composition or combined composition that optionally may further comprises colostrum, milk or milk products component/s and any adjuvant/s, preferably, alarmins, defenensins, colostrinin and any preparation, mixture or combination thereof. It should be further appreciated that the composition of the invention may comprise any additional adjuvant. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner. It should be noted that according to certain embodiments the present invention further provides the use of colostrum or any colostrum-derived preparations in the combined compositions of the invention for enhancing an immunomodulatory effect of an immunomodulatory therapeutic agent.

The term alarmin, denotes an array of structurally diverse multifunctional host proteins that are rapidly released during infection or tissue damage, and that have mobilizing and activating effects on receptor-expressing cells engaged in host defence and tissue repair. Innate-immune mediators that have alarmin function include defensins, eosinophil-derived neurotoxin, cathelicidins and HMGB1.

Defensins are small (15-20 residue) cysteine-rich cationic proteins found in both vertebrates and invertebrates. They are active against bacteria, fungi and enveloped viruses. They consist of 15-20 amino acids including six to eight conserved cysteine residues. Cells of the immune system contain these peptides to assist in killing phagocytized bacteria, for example in neutrophil granulocytes and almost all epithelial cells. Most defensins function by penetrating the microbial's cell membrane by way of electrical attraction, and once embedded, forming a pore in the membrane which allows efflux.

The term "Colostrinin", as use herein refers to a polypeptide which, in its natural form, is obtained from mammalian colostrum. Colostrinin is sometimes known as "colostrinine", and has a molecular weight in the range 16,000 to 26,000 Daltons. Colostrinin may form a dimer or trimer of sub-units (each having a molecular weight in the range 5,000 to 10,000 Daltons, preferably 6,000 Daltons), and contains mostly praline (the amount of proline is greater than the amount of any other single amino acid).

Colostrinin is characterized in that it stimulates the production of cytokines, especially gamma interferon (IFN-$\gamma$), tumor necrosis factor TNF-$\alpha$), interleukins (e.g. IL-6 and IL-10) and various growth factors.

As indicated above, it should be noted that the anti-LPS enriched immunoglobulin preparation and any other optional immunoglobulin preparations used by the invention may be obtained from a mammal, immunized with LPS or any fragments thereof and optionally, in addition, with at least one antigen or a mixture of at least two antigens specific for the disorder to be treated. Means and methods of the invention are suited to obtain high and prolonged antigen-specific antibody production in the colostrum, milk or milk products of any lactating mammal. Preferably, said animal is a farm-animal. Farm animals are animals that are used on a commercial basis by man, be it for the production of milk, meat or even antibodies. Farm-animals already used for the commercial scale production of milk are preferred for the present invention since for these animals special lines and/or breeds exist that are optimized for milk production. Preferably, said farm-animal is a cow or a goat. More preferably said farm-animal is a cow.

In one embodiment of said use of the invention, the composition reduces or inhibits mucosal microbial translocation. In one embodiment of said use of the invention, the composition reduces or inhibits mucosal microbial translocation and thereby modulates immune activation.

According to one embodiment, the invention relates to the use of a mammalian anti-LPS enriched colostrum-derived immunoglobulin preparation for manufacturing a composition for the treatment, prevention and prophylaxis of acute or chronic liver disease, cirrhosis and any disease or complication associated therewith, optionally said composition further comprises an additional therapeutic agent or any carrier and adjuvant.

According to one embodiment of the use of the invention, this particular composition reduces or inhibits mucosal microbial translocation and thereby alters the direct effect of bacteria or any other infectious agent on the pathogenesis of complications of acute or chronic liver diseases-associated complications whether due to portal hypertension or any other cause.

More specifically, as used herein, acute or chronic liver disease, cirrhosis and any disease or complication associated therewith is at least one of hepatic encephalopathy, spontaneous bacterial peritonitis (SBP), ascites, cirrhosis associated hyperdynamic circulation, hepatorenal syndrome, hepatopulmonary syndrome, portopulmonary hypertension, variceal bleeding, adrenal insufficiency and altered level of consciousness.

It should be noted that these complications may results from chronic HCV infection, alcoholic hepatitis, chronic HBV, non-alcoholic steatoheaptitis, drug induced liver injury, or any other cause of acute or chronic liver disease.

According to an optional embodiment, the invention provides the use of a combination of anti-LPS enriched immunoglobulin preparation with at least one colostrum-derived immunoglobulin preparation comprising immunoglobulins that recognize and bind at least one antigen specific for said pathologic disorder. According to this particular embodiment, the use of such combination is for preparing an immuno-modulatory composition that modulates regulatory T cells leading to modulation of the Th1/Th2, Tr1/Th3 cell balance toward an anti-inflammatory Th2, Tr1/Th3 immune response or a pro-inflammatory Th1 immune response thereby inhibiting or activating an immune response specifically directed toward said disorder. Optionally such combined composition further comprises an additional therapeutic agent or any carrier and adjuvant. Such composition modulates regulatory T cells leading to modulation of the Th1/Th2, Tr1/Th3 cell balance toward an anti-inflammatory Th2, Tr1/Th3 immune response or a pro-inflammatory Th1 immune response, thereby inhibiting or activating an immune response specifically directed toward said disorder.

In a further embodiment, the immune-related disorder may be any one of autoimmune disease, non-alcoholic steatohepatitis, fatty liver, metabolic syndrome and any disorder associated therewith, infectious disease, and proliferative disorder.

According to one embodiment of the use of the invention, the composition of the invention may be used for treating acute complication, or for preventing the development or recurrence of these complications.

According to another embodiment, the combined composition of the invention leads to modulation of the Th1/Th2, Tr1/Th3 cell balance toward an anti-inflammatory Th2, Tr1/Th3 immune response thereby inhibiting an immune response specifically directed toward said disorder. According to this specific embodiment, such composition may be applicable in the treatment of an autoimmune disease.

Alternatively, the combined composition of the invention may lead to modulation of the Th1/Th2, Tr1/Th3 cell balance toward a pro-inflammatory Th1/Th2 immune response thereby enhancing an immune response specifically directed toward said disorder. According to this specific embodiment, such composition may be applicable in the treatment of infectious diseases, and proliferative disorders.

In an even further embodiment of said use of the present invention, the composition of the invention may be administerable orally or by inhalation as an aerosol, or via intravenous, intramuscular, subcutaneous, intraperitoneal, perenteral, transdermal, intravaginal, intranasal, mucosal, sublingual, topical, rectal or subcutaneous, or any combination thereof.

Tolerance has been defined as a lack of response to self, or any mechanism by which a potentially injurious immune response is prevented, suppressed, or shifted to a noninjurious class of immune response. Thus, tolerance is related to productive self-recognition, rather than blindness of the immune system to its own components. The present inventors have demonstrated that exposure to disease-associated antigens, whether self-antigens or not, can activate some parts of the immune system while suppressing unwanted immunity in an antigen-specific manner. Without wishing to be bound by theory, oral antigen administration, on one hand activates specific subsets of cells, suppressing specific cells and alleviating unwanted autoimmunity, and on the other hand promotes anti-viral or anti-tumor-associated antigen immune responses. For many immune-mediated diseases or disorders in which the immune system plays a role, the balance between different types of signals/cells that are promoted in the systemic immune system will determine the final immunological effect.

Oral tolerance is a natural immunologic process driven by the presence of an exogenous antigen that is thought to have evolved to treat external agents that gain access to the body via a natural route and then become part of the self. With the understanding that oral exposure to antigens in the gastrointestinal tract such as the bowel results in an active immune response, antigen-specific therapy seems an attractive approach for immunotherapy toward antigens present in the gut mucosa, where they can be dealt with in a noninjurious or noninflammatory immunologic environment. Accordingly, specific immune cells may be activated and, antigen-specific therapy can serve as an immunotherapeutic chronic hepatitis, infectious agents, metabolic syndrome and other pathologic disorders discussed herein.

The mechanisms responsible for gastrointestinal homeostasis involve a complex interplay between different types of T cells, including regulatory T cells, dendritic cells (DCs), natural killer T (NKT) cells, and the gut microenvironment.

The follicle-associated epithelium (FAE) plays key roles in antigen uptake and subsequent induction of mucosal immunity. FAE M cells, by targeting antigen (Ag) deliver, facilitate oral tolerance via the reduction in Ag-specific CD4+ T cells and increased levels of transforming growth factor (TGF)-$\beta$ and interleukin (IL)-10-producing CD25+ CD4+ T-regulatory cells (Tregs) in both systemic and mucosal lymphoid tissues.

Intestinal DCs are key regulators of pathogenic immunity, oral tolerance, and intestinal inflammation. The relevant DCs may be in the PP, MLNs, or LP of the villus mucosa. All of these tissues contain a number of distinctive DC subsets, including some that can preferentially induce the differentiation of Tregs.

NKT cells are a unique lineage of T cells that share properties with both NK cells and memory T cells. This subset of lymphocytes may be either CD4+ or double negative and is CD1d reactive. These cells are unique in their invariant Vα14-Jα18 TCR α-chain, and their T-cell receptor (TCR) β-chain is biased toward Vβ8.2, Vβ2, and Vβ7. NKT cells are unique in their glycolipid antigen reactivity and marked cytokine production. The ability of NKT cells to generate both Th1 and Th2 responses indicates their importance as immunoregulatory cells. The use of NKT ligands induces a profound immunomodulatory effect by altering the plasticity of these cells.

The present inventors have demonstrated a role for NKT cells in oral tolerance induction, and recent evidence have provided evidence for cross talk between Tregs and NKT cells. Without wishing to be bound by theory, it is thought that NKT cells produce cytokines immediately after exposure to activating signals and can determine the differentiation of Tregs.

The liver is considered to be important for oral tolerance. The liver is a site at which apoptotic CD8+ T cells accumulate during the clearance phase of peripheral immune responses. The normal mouse liver contains an unusual mixture of lymphocytes, in which natural killer (NK) and natural killer T (NKT) cells are abundant and apoptotic T cells are also present. These cells are relevant for intrahepatic T-cell trapping and killing. Continuous exposure of diverse liver cell types to LPS derived from intestinal bacteria is thought to promote expression of cytokines, antigen-presenting molecules, and costimulatory signals that impose T-cell inactivation. Other possible explanations for the tolerogenic environment in the liver involve clonal deletion, specific antigen presentation by endothelial cells or Kupffer cells, and the ability to induce regulatory T cells.

Different stimuli in the liver microenvironment are associated with T-cell priming and the generation of an effective immune response, whereas others result in tolerance. Antigen presentation in the liver by dendritic cells and their migration into the liver represent part of the interplay in the gut-liver axis. Liver-derived DCs are inherently tolerogenic when compared with skin DCs, produce IL-10, and express low levels of costimulatory molecules. Local secretion of IL-10 and TGF-β by Kupffer cells and hepatocytes can skew DC function toward the generation of regulatory as opposed to effector pathways. Liver sinusoidal endothelial cells (LSECs) are capable of trafficking antigens to an early endosomal compartment committed to presentation on MHC class I, explaining their ability to cross-present to CD8+ T cells. The outcome of antigen presentation by LSECs is usually tolerance, with apoptosis of CD8+ T cells and secretion of IL-4 and IL-10 by CD4+ T cells. Activated T cells are also trapped by intercellular adhesion molecule 1 (ICAM-1)-dependent mechanisms within the sinusoids as a mechanism for regulating apoptotic pathways during control of systemic CD8 responses. Hepatocytes themselves can function as APCs to activate naive T cells. In most cases, activation by hepatocytes leads to antigen-specific tolerance, but this process may also involve activation of Tregs. Peripheral Tregs are generated by activation of naive T cells by immature DCs or in the presence of IL-10 and TGF-β, both of which are present in the liver environment.

Tregs are important in the gut-liver immune axis. CD4+ CD25+ Tregs suppress the activation of CD4+ T cells by LSECs, Kupffer cells, or hepatocytes. Because this process can be overcome by TLR4 activation, the interaction among Tregs, pathogens, and other liver cells determines the outcome of immune activation in the liver. Tregs can curb unwanted immune responses and regulate responses to the microflora and can play a role in a number of chronic inflammatory diseases of the gut. Tregs can prevent detrimental inflammatory responses against commensal organisms in the lower gut, thus guarding against inflammatory bowel diseases. Various subsets of T lymphocytes have been suggested to exhibit regulatory functions, including natural Tregs, induced Tregs, Tr1, and Th3 cells. These cells may be activated by cytokines, and their inductive phase may be antigen driven. Most CD4+ regulatory T cells (Tr1, Th3, and CD4+CD25+) are thought to interact with dendritic cells. Other subsets of Tregs, such as CD8+ TrE cells, may recognize antigens that are presented by intestinal epithelial cells.

CD4+CD25+ Tregs are considered to be instrumental in regulating immune responses in the mucosa. TGF-β has emerged as one of the most important cytokines produced in the gut, and its interaction with CD4+CD25+ Tregs is key in maintaining a balance between T-cell immunity and tolerance. Expression of a stable form of β-catenin in CD4+ CD25+ Tregs results in a marked enhancement of the survival of these cells. The number of Tregs necessary for protection against inflammatory bowel disease could be substantially reduced when stable β-catenin-expressing CD4+CD25+ Tregs are used. IL-35 is an inhibitory cytokine produced by Treg cells and is required for maximal suppressive activity. As discussed below, the present inventors have demonstrated modulation of CD4+ CD25+ Treg cells with compositions according to the present invention, Foxp3+ Tregs are important for the establishment and maintenance of mucosal tolerance. Cytokine deprivation-induced apoptosis is a prominent mechanism by which Tregs inhibit effector TCR. As such, CD4+CD25+Foxp3+ Tregs induce apoptosis in effector CD4+ T cells.

TGF-β secretion by Th3 or other Treg cells is considered to be a key factor in oral tolerance. TGF-β-producing cells are crucial for oral tolerance and may be master regulators of most of the mechanisms triggered by antigen feeding. Latency-associated peptide (LAP) is the amino-terminal domain of the TGF-β precursor peptide, and remains non-covalently associated with the TGF-β peptide after cleavage and forms the latent complex. The presence of membrane-bound TGF-β or LAP on the surface of Tregs has linked TGF-β with the suppressive function of Tregs. TGF-β-secreting Th3 cells and CD8+ regulatory cells have been associated with oral tolerance and are dependent on TGF-β. As discussed below, the present inventors have demonstrated modulation of LAP+ and LAP− Treg cells with compositions according to the present invention, A membrane-bound form of TGF-β containing LAP has been described. LAP+CD4+ cells mediate suppression in the gut via a TGF-β-dependent mechanism. The present inventors have shown that TGF-β-dependent Tregs that express surface LAP are induced/promoted by oral administration of anti-LPS antibodies. TGF-β may induce the differentiation of IL-10-producing cells, indicating that cross-talk between different cytokine-producing Tregs may exist in oral tolerance induction, for example inducing CD4+CD25−LAP+ Tregs, which suppress autoimmunity.

Subsets of CD8+ lymphocytes are also involved in tolerance induction. Intestinal epithelial cells (IECs) can promote CD8+ Tregs to process and present antigen to T cells. T cells activated by IECs are suppressive in function, whereas IECs can induce the proliferation of a small fraction of CD8+ peripheral T cells. The CD8+CD28− subset of IEC-activated CD8+ T cells expresses CD101 and CD103, interacts with IECs through gp180, and possesses a regulatory function. CD8+ T cells with regulatory activity are present in the LP of normal, healthy individuals, but not in patients with inflammatory bowel disease (IBD), indicating that these cells play an active role in mucosal tolerance. "Antigen-cross-presentation," or the possibility that molecules presented by professional APCs can leak into the major histocompatibility complex class I (MHC-I) pathway and are presented to CD8+ T cells, is a possible mechanism. Alternatively, "cross-priming" of CD8+ by APCs associated with CD4+ T-cell activation may be a mechanism responsible for suppression. CD8+ T cells play a regulatory role via secretion of TGF-β. Antigen-primed CD8+ T-cell populations produce IL-4 or IL-10, and may be associated with tolerance induction.

Accordingly, in another aspect, the present invention provides a composition comprising a mammalian anti-LPS enriched colostrum-derived immunoglobulin preparation for inducing CD4+ CD25+ T cells in the liver, inducing CD4+ CD25+ LAP− T cells in the liver, inducing CD45+ LAP+ T cells in the liver, inducing CD3+ LAP+ T cells in the liver, inducing CD45+ LAP+ T cells in the spleen, inducing CD8+ LAP+ T cells in the spleen, inducing CD3+ LAP+ T cells in the spleen, inducing CD8+ CD25+ T cells in the spleen, inducing CD4+ CD25+ T cells in adipose tissue, inducing CD3+ LAP+ T cells in adipose tissue, inducing CD4+ CD25+ T cells in stromal vascular cells, inducing CD4+ CD25+ LAP+ T cells in stromal vascular cells, decreasing CD3+ NK1.1+ cells in the liver, decreasing CD25+ LAP− T cells in the liver, increasing CD25+ LAP+ T cells in the liver, inducing CD4+ CD25+ LAP− T cells in the spleen, inducing CD4+ CD25+ LAP− T cells in adipose tissue.

Adipocytes are the cells that primarily compose adipose tissue, specialized in storing energy as fat. There are two types of adipose tissue, white adipose tissue (WAT) and brown adipose tissue (BAT), which are also known as white fat and brown fat, respectively, and comprise the two types of fat cells. White fat cells or monovacuolar cells contain a large lipid droplet surrounded by a layer of cytoplasm. The nucleus is flattened and located on the periphery. A typical fat cell is 0.1 mm in diameter with some being twice that size and others half that size. The fat stored is in a semi-liquid state, and is composed primarily of triglycerides and cholesteryl ester. White fat cells secrete resistin, adiponectin, and leptin. Brown fat cells or pluri vacuolar cells are polygonal in shape. Unlike white fat cells, these cells have considerable cytoplasm, with lipid droplets scattered throughout. The nucleus is round, and, although eccentrically located, it is not in the periphery of the cell. The brown color comes from the large quantity of mitochondria.

As shown, by the Examples, the compositions of the invention, significantly decreased the serum levels of triglycerides, ALT, AST and glucose. Therefore, according to one embodiment, the pharmaceutical composition of the invention leads to at least one of a decrease in the serum levels of cholesterol, triglycerides, ALT, AST and glucose and a decrease in insulin resistance in a subject suffering of a liver disorder or an immune-related disorder, for example, Metabolic syndrome. Wherein indicated decease, reduction, inhibition, it is meant that the composition of the invention leads to a reduction of about 5% to 99% of the serum level of any one of triglycerides, ALT, AST and Glucose, in a subject suffering of an-immune-related disorder. More specifically, such reduction may be a reduction of about, 5%, 10%, 15%, 20%, 25%, 30%, 35%, 40%, 45%, 50%, 55%, 60%, 65%, 70%, 75%, 80%, 85%, 90%, 95% and over 99%, as compared to the levels prior to the treatment, or the levels of untreated control. Wherein indicated increase, elevation, enhancement, induction, it is meant that the composition of the invention leads to induction, or increase of about 5% to 99%. More specifically, such increase may be an. increase of about, 5%, 10%, 15%, 20%, 25%, 30%, 35%, 40%, 45%, 50%, 55%, 60%, 65%, 70%, 75%, 80%, 85%, 90%, 95% and over 99%, as compared to the levels prior to the treatment, or the levels of untreated control.

According to one specific embodiment the composition of the invention may be used for preventing and/or treating autoimmune disease for example, Metabolic Syndrome or any of the conditions comprising the same, any condition associated with, caused by, linked to or believed to have an impact on metabolic syndrome, for example, at least one of dyslipoproteinemia (hypertriglyceridemia, hypercholesterolemia, low HDL-cholesterol), obesity, NIDDM (non-insulin dependent diabetes mellitus), IGT (impaired glucose tolerance), blood coagulability, blood fibrinolysis defects and hypertension.

The Metabolic Syndrome is characterized by a group of metabolic risk factors in one person including:
  Abdominal obesity (excessive fat tissue in and around the abdomen);
  Atherogenic dyslipidemia (blood fat disorders—high triglycerides, low HDL cholesterol and high LDL cholesterol—that foster plaque buildups in artery walls); *Elevated blood pressure; *Insulin resistance or glucose intolerance; *Pro thrombotic state (e.g., high fibrinogen or plasminogen activator inhibitor-1 in the blood); and *Proinflammatory state (e.g., elevated C-reactive protein in the blood). People with the metabolic syndrome are at increased risk of coronary heart disease and other diseases related to plaque buildups in artery walls (e.g., stroke and peripheral vascular disease) and type 2 diabetes.

More particularly, the composition of the invention is intended for the treatment of dyslipoproteinemia, which may include hypertriglyceridemia, hypercholesterolemia and low HDL-cholesterol, obesity, NIDDM (non-insulin dependent diabetes mellitus type 2), IGT (impaired glucose tolerance), blood coagulability, blood fibronolysis defects and hypertension.

According to one specific embodiment, the immunomodulatory composition of the invention may be used for treating diabetes, particularly, Type 2 diabetes. Diabetes mellitus, often simply diabetes, is a syndrome characterized by disordered metabolism and inappropriately high, blood sugar (hyperglycaemia) resulting from either low levels of the hormone insulin or from abnormal resistance to insulin's effects coupled with inadequate levels of insulin secretion to compensate. The characteristic symptoms are excessive urine production (polyuria), excessive thirst and increased fluid intake (polydipsia), and blurred vision. These symptoms are likely absent if the blood sugar is only mildly elevated.

The World Health Orgnization recogizes three main forms of diabetes mellitus: Type 1, Type 2, and gestational diabetes (occurring during pregnancy), which have different causes and population distributions. While, ultimately, all forms are due to the beta cells of the pancreas being unable to produce sufficient insulin to prevent hyperglycemia, the causes are different. Type 1 diabetes is usually due to autoimmune destruction of the pancreatic beta cells. Type 2 diabetes is characterized by insulin resistance in target tissues, this causes a need for abnormally high amounts of insulin and diabetes develops when the beta cells cannot meet this demand. Gestational diabetes is similar to type 2 diabetes in that it involves insulin resistance, hormones in pregnancy may cause insulin resistance in women genetically predisposed to developing this condition.

Acute complication of diabetes (hypoglycemia, ketoacidosis or nonketotic hyperosmolar coma) may occur if the disease is not adequately controlled. Serious long-term complications include cardiovascular disease (doubled risk), chronic renal failure, retinal damage (which can lead to blindness), nerve damage (of several kinds), and microvascular damage, which may cause impotence and poor healing. Poor healing of wounds, particularly of the feet, can lead to gangrene, which may require amputation.

According to another embodiment, the immunomodulatory composition of the invention may be used for the treatment of Type 1 diabetes. Type 1 diabetes mellitus is characterized by loss of the insulin-producing beta cells of the islets of Langerhans in the pancreas, leading to a deficiency of insulin. The main cause of this beta cell loss is. a T-cell mediated autoimmune attack.

In yet another embodiment, the pharmaceutical composition of the invention may be used for the treatment of an autoimmune disorder. Examples of autoimmune disorders include, but are not limited to, Alopecia Areata, Lupus, Ankylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The oral compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

According to a specifically preferred embodiment, an autoimmune disease treated by the composition of the invention may be any one of rheumatoid arthritis, type 1 diabetes, type 2 diabetes, artherosclerosis, asthma, acute and chronic graft versus host disease, systemic lupus erythamatosus, scleroderma, multiple sclerosis, inflammatory bowel disease, psoriasis, uvietis, thyroiditis and immune mediated hepatitis.

According to another embodiment, the composition of the invention may be used for the treatment of MS. Multiple Sclerosis (MS) is typically characterized clinically by recurrent or chronically progressive necrologic dysfunction, caused by lesions in the CNS. Pathologically, the lesions include multiple areas of demyelination affecting the brain, optic nerves, and spinal cord. The underlying etiology is uncertain, but MS is widely believed to be at least partly an autoimmune or immune-mediated disease.

Thus, the invention includes compositions and methods of treating, delaying or preventing the onset of MS, by orally or mucosally administering the colostrum-derived immunoglobulin preparation of the invention. Included are methods wherein a subject who has or is at risk of having MS is orally administered with the composition of the invention.

According to another preferred embodiment, the composition of the invention may be used for the treatment of RA. Rheumatoid arthritis (RA) is the most common chronic inflammatory arthritis and affects about 1% of adults, it is two to three times more prevalent in women than in men. RA may begin as early as infancy, but onset typically occurs in the fifth or sixth decade.

Diagnosis may be made according to the American Rheumatism Association Criteria for the so Classification of Rheumatoid Arthritis. A therapeutically effective amount will cause an improvement in one or more of the following: the number of inflamed joints, the extent of swelling, and the range of joint motion. Laboratory measurements (e.g., ESR and hematocrit value) and assessments of subjective features (e.g., pain and morning stiffness) can also be made. The invention also includes methods of treating autoimmune arthritis, e.g., RA, in a subject by administering to the subject a therapeutically effective amount of composition of the invention comprising colostrum-derived immunoglobulin preparations.

The compositions of the invention described herein can also be used to treat or prevent graft rejection in a transplant recipient. For example, the compositions can be used in a wide variety of tissue and organ transplant procedures, e.g., the compositions can be used to induce central tolerance in a recipient of a graft of cells, e.g., stem cells such as bone marrow and/or of a tissue or organ such as pancreatic islets, liver, kidney, heart, lung, skin, muscle, neuronal tissue, stomach, and intestines. Thus, the new methods can be applied in treatments of diseases or conditions that entail cell, tissue or organ transplantation (e.g., liver transplantation to treat hypercholesterolemia, transplantation of muscle cells to treat muscular dystrophy, or transplantation of neuronal tissue to treat Huntington's disease or Parkinson's disease).

According to another embodiment, the composition of the invention may modulate the Th1/Th2, Th3 balance towards an anti-Th2, Tr1/Th3 response in a subject suffering from IBD. Therefore, according to this embodiment, the composition of the invention is intended for treating IBD. Inflammatory bowel diseases (IBD) are common gastrointestinal disorders that can be perceived as being the result of a dysbalance between Th1-pro-inflammatory, and Th2-anti-inflammatory subtypes of immune responses.

Patients with IBD have antibodies against components of colon cells and several different bacterial antigens. These antigens gain access to the immune system as a consequence of epithelial damage. Abnormalities of T cell-mediated immunity, including coetaneous anergy and diminished responsiveness to T cell stimuli, have also been described in these patients. In addition, changes in mucosal cell mediated immunity were identified, including increased concentrations of mucosal IgG cells and changes in T cells subsets, suggesting antigen stimulation.

In yet another preferred embodiment, the composition of the invention may be used for the treatment of atherosclerosis. Atherosclerosis is a slowly progressive disease characterized by the accumulation of cholesterol within the arterial wall. The atherosclerotic process begins when LDL-C becomes trapped within the vascular wall. Oxidation of the LDL-C results in the bonding of monocytes to the endothelial cells lining the vessel wall. These monocytes are activated and migrate into the endothelial space where they are transformed into macrophages, leading to further oxidation of LDL-C. The oxidized LDL-C is taken up through the scavenger receptor on the macrophage leading the formation of foam cells. A fibrous cap is generated through the proliferation and migration of arterial smooth muscle cells, thus creating an atherosclerotic plaque. Lipids depositing in atherosclerotic legions are derived primarily from plasma apo B containing lipoproteins. These include chylomicrons, LDL-C, IDL, and VLDL. This accumulation forms bulky plaques that inhibit the flow of blood until a clot eventually forms, obstructing an artery and causing a heart attack or stroke.

Alternatively, the immunoglobulin preparation used by the composition of the invention may recognize and bind at least one antigen specific for the treated disorder and may modulates immune-regulatory cells, specifically, regulatory T cells. Such modulation may results for example, in modulation of the Th1/Th2 cell balance toward a pro-inflammatory ThI immune response thereby activating an immune response specifically directed toward said disorder.

It should be appreciated that the pro-inflammatory effect of the immunomodulatory composition of the invention may be achieved by activation or promotion of specific subsets of regulatory cells, antigen presenting cells or any type of cell-cell contact via direct or indirect activation, of cytokines, and/or chemokines.

According to this specific embodiment, modulation of the Th1/Th2, Th3 balance towards a pro-inflammatory Th1 response may be particularly applicable in immune related disorders having an undesired unbalanced anti-inflammatory Th2, Tr1/Th3 response, for example, a malignant and non-malignant proliferative disorder, infectious disease, genetic disease and neurodegenerative disorders.

In another aspect, the present invention provides a use of an anti-LPS enriched immunoglobulin preparation in the manufacture of a medicament for the treatment and/or prophylaxis of a pathologic disorder. The anti-LPS enriched immunoglobulin preparation may be derived from colostrum or from avian eggs.

In one embodiment, the pathologic disorder is acute or chronic liver disease, cirrhosis or any disease or complication associated therewith.

In another embodiment, the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness.

In another embodiment, the medicament is for the treatment and/or prophylaxis of liver damage.

In another embodiment, the pathologic disorder is an immune-related disorder selected from the group consisting of autoimmune disease, non-alcoholic steatohepatitis, fatty liver, atherosclerosis, metabolic syndrome and any disorder associated therewith, infectious disease, and proliferative disorder. Alternatively, the pathologic disorder is selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

The medicament may further comprise an immunoglobulin preparation comprising immunoglobulins that recognize and bind at least one antigen specific for said pathologic disorder. The further immunoglobulin preparation may be derived from colostrum.or from avian eggs.

In one embodiment, the medicament modulates regulatory T cells leading to modulation of the Th1/Th2, Tr1/Th3 cell balance toward an anti-inflammatory Th2, Tr1/Th3 immune response or a pro-inflammatory Th1 immune response thereby inhibiting or activating an immune response specifically directed toward said disorder.

In another embodiment, the medicament modulates the Th1/Th2, Tr1/Th3 cell balance toward an anti-inflammatory Th2, Tr1/Th3 immune response thereby inhibiting an immune response specifically directed toward said disorder, and wherein said composition is for the treatment of any one of an autoimmune disease, non-alcoholic steatohepatitis, fatty liver, atherosclerosis, metabolic syndrome and any disorder associated therewith selected from diabetes type 2, insulin resistance, obesity and overweight.

In another embodiment, the medicament is for the treatment and/or prophylaxis of metabolic syndrome or non-alcoholic steatohepatitis or both, the treatment and/or prophylaxis of diabetes, the treatment impaired glucose tolerance, such as decreasing glucose tolerance, decreasing serum insulin levels, decreasing hepatic triglyceride levels, or decreasing cholesterol levels.

In one embodiment, the medicament modulates the Th1/Th2, Tr1/Th3 cell balance toward a pro-inflammatory Th1/Th2 immune response thereby enhancing an immune response specifically directed toward said disorder, and wherein said composition is for the treatment of infectious diseases, and proliferative disorders, The medicament may further comprise a therapeutic agent, carrier or adjuvant and/or non-hyperimmune colostrum.

In one embodiment, the medicament is formulated for administration orally, by inhalation as an aerosol, or by parenteral, intravaginal, intranasal, mucosal, sublingual, topical, or rectal administration, or any combination thereof.

In another embodiment, the immunoglobulin preparation or any fractions thereof recognizes and binds LPS or any fragments thereof.

In another embodiment the composition reduces or inhibits mucosal microbial translocation. In another embodiment the composition reduces or inhibits mucosal microbial translocation and thereby modulates immune activation.

In another aspect, the present invention provided a use of a mammalian anti-LPS enriched colostrum-derived immunoglobulin preparation in the manufacture of a medicament for modulating immune tolerance in a subject, or in another embodiment, a medicament for modulating oral tolerance in a subject.

In another aspect, the present invention provides the use of a mammalian anti-LPS enriched colostrum-derived immunoglobulin preparation in the manufacture of a medicament for inducing CD4+ CD25+ T cells in the liver, inducing CD4+ CD25+ LAP− T cells in the liver, inducing CD45+ LAP+ T cells in the liver, inducing CD3+ LAP+ T cells in the liver, inducing CD45+ LAP+ T cells in the spleen, inducing CD8+ LAP+ T cells in the spleen, inducing CD3+ LAP+ T cells in the spleen, inducing CD8+ CD25+ T cells in the spleen, inducing CD4+ CD25+ T cells in adipose tissue, inducing CD3+ LAP+ T cells in adipose tissue, inducing CD4+ CD25+ T cells in stromal vascular cells, inducing CD4+ CD25+ LAP+ T cells in stromal vascular cells, decreasing CD3+ NK1.1+ cells in the liver, decreasing CD25+ LAP− T cells in the liver, increasing CD25+ LAP+ T cells in the liver, inducing CD4+ CD25+ LAP-T cells in the spleen, or inducing CD4+ CD25+ LAP− T cells in adipose tissue.

The anti-LPS enriched immunoglobulin preparation may be derived from colostrum or from avian eggs.

In one aspect, the present invention provides a method for the treatment and/or prophylaxis of a pathologic disorder comprising the step of administering to a subject in need thereof a therapeutically effective amount of a composition comprising an anti-LPS enriched immunoglobulin preparation. The anti-LPS enriched immunoglobulin preparation may be derived from colostrum or from avian eggs.

In one embodiment, the pathologic disorder is acute or chronic liver disease, cirrhosis or any disease or complication associated therewith.

In another embodiment the acute or chronic liver disease, cirrhosis and any disease or complication associated therewith is selected from the group consisting of hepatic encephalopathy, spontaneous bacterial peritonitis (SBP), ascites, bleeding varices, cirrhosis associated hyperdynamic circulation, hepatorenal syndrome, hepatopulmonary syndrome, portopulmonary hypertension, variceal bleeding, adrenal insufficiency and altered level of consciousness.

In another embodiment, the pathologic disorder is liver damage.

In another embodiment, the pathologic disorder is an immune-related disorder selected from the group consisting of autoimmune disease, non-alcoholic steatohepatitis, fatty liver, atherosclerosis, metabolic syndrome and any disorder associated therewith, infectious disease, and proliferative disorder. Alternatively, the pathologic disorder is selected from the group consisting of secondary peritonitis and infection after surgery, hepatic cardiomyopathy and hypotension, hepatoadrenal syndrome, hepatocellular carcinoma, Alzheimer's disease, any type of memory loss, any type of dementia, attention deficit disorders (ADHA), any type of learning disability, effect of alcohol or drugs on the brain, any type of immune mediated disease including asthma, and peritonitis.

In another embodiment, the composition further comprises an immunoglobulin preparation comprising immunoglobulins that recognize and bind at least one antigen specific for said pathologic disorder. The further immunoglobulin preparation may be derived from colostrum.or from avian eggs.

In another embodiment, the composition modulates regulatory T cells leading to modulation of the Th1/Th2, Tr1/Th3 cell balance toward an anti-inflammatory Th2, Tr1/Th3 immune response or a pro-inflammatory Th1 immune response thereby inhibiting or activating an immune response specifically directed toward said disorder.

In another embodiment, the composition modulates the Th1/Th2, Tr1/Th3 cell balance toward an anti-inflammatory Th2, Tr1/Th3 immune response thereby inhibiting an immune response specifically directed toward said disorder, and wherein said composition is for the treatment of any one of an autoimmune disease, non-alcoholic steatohepatitis, fatty liver, atherosclerosis, metabolic syndrome and any disorder associated therewith selected from diabetes type 2, insulin resistance, obesity and overweight.

In another embodiment the pathologic disorder is metabolic syndrome or non-alcoholic steatohepatitis or both.

In another embodiment, the pathologic disorder is diabetes. In another embodiment, the pathologic disorder is impaired glucose tolerance.

In another embodiment, the method decreases glucose tolerance, decreases serum insulin levels, decreases hepatic triglyceride levels, or decreases cholesterol levels.

In another embodiment, the method modulates the Th1/Th2, Tr1/Th3 cell balance toward a pro-inflammatory Th1/Th2 immune response thereby enhancing an immune response specifically directed toward said disorder, and wherein said composition is for the treatment of infectious diseases, and proliferative disorders, In another embodiment, the composition further comprises non-hyperimmune colostrum and/or a therapeutic agent, carrier or adjuvant.

The composition may be administered orally, by inhalation as an aerosol, or by parenteral, intravaginal, intranasal, mucosal, sublingual, topical, or rectal administration, or any combination thereof.

In another embodiment, the immunoglobulin preparation or any fractions thereof recognizes and binds LPS or any fragments thereof.

In another embodiment, the method reduces or inhibits mucosal microbial translocation. In another embodiment, the method reduces or inhibits mucosal microbial translocation and thereby modulates immune activation.

In another aspect, the present invention provides a method for modulating immune tolerance in a subject comprising the step of administering to a subject in need thereof a therapeutically effective amount of a composition comprising a mammalian anti-LPS enriched colostrum-derived immunoglobulin preparation. Alternatively, the method may be for modulating oral tolerance.

A method for inducing CD4+ CD25+ T cells in the liver of a subject comprising the step of administering to a subject in need thereof a therapeutically effective amount of a composition comprising a mammalian anti-LPS enriched colostrum-derived immunoglobulin preparation. In another embodiment, the method may be for inducing CD4+ CD25+ LAP− T cells in the liver, CD45+ LAP+ T cells in the liver, inducing CD3+ LAP+ T cells in the liver, inducing CD45+ LAP+ T cells in the spleen, inducing CD8+ LAP+ T cells in the spleen, inducing CD3+ LAP+ T cells in the spleen, inducing CD8+ CD25+ T cells in the spleen, inducing CD4+ CD25+ T cells in adipose tissue, inducing CD3+ LAP+ T cells in adipose tissue, inducing CD4+ CD25+ T cells in stromal vascular cells, inducing CD4+ CD25+ LAP+ T cells in stromal vascular cells, decreasing CD3+ NK1.1+ cells in the liver, decreasing CD25+ LAP− T cells in the liver, decreasing CD25+ LAP+ T cells in the liver, inducing CD4+ CD25+ LAP− T cells in the spleen, or inducing CD4+ CD25+ LAP− T cells in adipose tissue.

In a further aspect, the present invention provides a method for the treatment and/or prophylaxis of a pathologic disorder. The method of the invention comprises the step of administering to a subject in need thereof a therapeutically effective amount of a mammalian colostrum-derived anti-LPS enriched immunoglobulin preparation or of a composition comprising the same. It should be noted that the immunoglobulin preparation or any fractions thereof recognizes and binds LPS and any fragments thereof. According to an optional embodiment, the method of the invention comprises the step of administering a combined composition of anti-LPS enriched immunoglobulin preparation of the invention with at least one immunoglobulin preparation comprising immunoglobulins recognizing at least one antigen specific for said disorder, thereby activating or inhibiting an immune response specifically directed toward said disorder.

According to one embodiment, the colostrum-derived, milk or milk product/s-derived anti-LPS enriched immunoglobulin preparation or any fragment or mixture, combination, or any composition thereof, used by the method of the invention comprises a monomeric, dimeric and multimeric immunoglobulin selected from the group consisting of IgG, IgA and IgM and any fragments thereof, preparations, mixtures and compositions thereof. More specifically, the immunoglobulin preparation used by the method of the invention may specifically comprise IgG, particularly, IgG1 and/or IgG2 and any fragments thereof. Alternatively or additionally, the immunoglobulin preparation used by the method of the invention may specifically comprise secretory dimeric IgA.

According to another embodiment, the method of the invention may use a composition or combined composition comprising colostrum-derived anti-LPS enriched immunoglobulin preparation. Such composition optionally further comprises colostrum component/s, preferably, alarmins, defenensins, colostrinin, or any glycolipids, carbohydrates or any preparations, mixtures and combinations thereof, or any other adjuvant/s. It should be noted that the present invention further provides the use of colostrum or any colostrum-derived preparations for enhancing an immunomodulatory effect of an immunomodulatory therapeutic agent. In one specific embodiment, the composition or combined composition used by the method of the invention may comprise any additional adjuvant. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner.

In yet another embodiment, the anti-LPS enriched immunoglobulin preparation or any other immunoglobulin preparation used by the invention may be obtained from a mammal, preferably a cow, immunized with LPS and optionally, in addition, with at least one antigen or a mixture of at least two antigens specific for a disorder to be treated.

According to one embodiment, the method of the invention comprises the step of administering to said subject a therapeutically effective amount of a mammalian anti-lipopolysaccharide (LPS) colostrum-derived immunoglobulin preparation or any composition comprising the same. It should be noted that such method may be particularly applicable for the treatment, prevention and prophylaxis of acute or chronic liver disease, cirrhosis and any disease or complication associated therewith.

More specifically, acute or chronic liver disease, cirrhosis and any disease or complication associated therewith is at least one of hepatic encephalopathy, spontaneous bacterial peritonitis (SBP), ascitess, cirrhosis associated hyperdynamic circulation, hepatorenal syndrome, hepatopulmonary syndrome, portopulmonary hypertension, variceal bleeding, adrenal insufficiency and altered level of consciousness.

It should be noted that these complications may results from chronic HCV infection, alcoholic hepatitis, chronic HBV, non-alcoholic steatoheaptitis, drug induced liver injury, or any other cause of acute or chronic liver disease.

According to one optional embodiment, the invention provides a method for treating immune-related disorders.

According to this specific embodiment, the method of the invention comprises the step of administering to said subject a therapeutically effective amount of a combination of anti-LPS enriched immunoglobulin preparation with at least one colostrum-derived immunoglobulin preparation comprising immunoglobulins that recognize and bind at least one antigen specific for said pathologic disorder, or of a combined composition comprising the same and optionally an additional therapeutic agent or any carrier and adjuvant.

According to this embodiment, the combination used by the invention modulates regulatory T cells leading to modulation of the Th1/Th2, Tr1/Th3 cell balance toward an anti-inflammatory Th2, Tr1/Th3 immune response or a pro-inflammatory Th1 immune response thereby inhibiting or activating an immune response specifically directed toward said disorder.

According to another embodiment, the method of the invention may be particularly applicable or treating an immune-related disorder, for example, autoimmune disease, non-alcoholic steatohepatitis, fatty liver, metabolic syndrome and any disorder associated therewith, infectious disease, and proliferative disorder.

In another embodiment, the present invention provides a method of treating impaired glucose tolerance.

In another embodiment, the present invention provides a method of decreasing glucose tolerance.

In another embodiment, the present invention provides a method of decreasing serum insulin levels In another embodiment, the present invention provides a method of decreasing hepatic triglyceride levels.

In another embodiment, the present invention provides a method of decreasing cholesterol levels.

It should be noted that the method of the invention is for treatment of acute complications, for preventing the development and/or the recurrence of these complications.

According to one embodiment, the combined composition used by the method of the invention leads to modulation of the Th1/Th2, Tr1/Th3 cell balance toward an anti-inflammatory Th2, Tr1/Th3 immune response thereby inhibiting an immune response specifically directed toward said disorder. According to this specific embodiment, such composition may be applicable in the treatment of any one of an autoimmune disease, non-alcoholic steatohepatitis, fatty liver, atherosclerosis, metabolic syndrome and any disorder associated therewith for example, diabetes type 2, insulin resistance, obesity and overweight.

Alternatively, the combined composition used by the method of the invention may lead to modulation of the Th1/Th2, Tr1/Th3 cell balance toward a pro-inflammatory Th1/Th2 immune response thereby enhancing an immune response specifically directed toward said disorder. According to this specific embodiment, such composition may be applicable in the treatment of infectious disease, and proliferative disorder.

According to one embodiment, the method of the invention may be specifically applicable for treating viral disease including HCV, HBV, CMV, and EBV.

In an even further embodiment of said method of the invention, the anti-LPS-enriched immunoglobulin preparation, or any composition comprising the same, is to be administered orally or by inhalation as an aerosol, or by intravenous, intramuscular, subcutaneous, intraperitoneal, parenteral, transdermal, intravaginal, intranasal, mucosal, sublingual, topical, rectal or subcutaneous administration, or any combination thereof.

According to a specifically preferred embodiment, the method of the invention is specifically suitable for the treatment of a mammalian subject. "Mammal" or "mammalian" for purposes of treatment refers to any animal classified as a mammal including, human, research animals, domestic and farm animals, and zoo, sports, or pet animals, such as dogs, horses, cats, cows, etc. In a particular embodiment said mammalian subject is a human subject.

"Treatment" refers to therapeutic treatment. Those in need of treatment are mammalian subjects suffering from an immune-related disease. By "patient" or "subject in need" is meant any mammal for which administration of the immuno-modulatory composition of the invention is desired, in order to prevent, overcome or slow down such infliction.

The terms "effective amount" or "sufficient amount" mean an amount necessary to achieve a selected result. The "effective treatment amount" is determined by the severity of the disease in conjunction with the preventive or therapeutic objectives, the route of administration and the patient's general condition (age, sex, weight and other considerations known to the attending physician).

As indicated above, generally, the dosage of needed to achieve a therapeutic effect will depend not only on such factors as the age, weight and sex of the patient and mode of administration, but also on the degree of disease progression and the potency of the particular derivative being utilized for the particular disorder of disease concerned.

It should be appreciated that the prevention or reduction of the risk of developing an immune-related disease is also encompassed within the scope of the invention. Such method may comprise the administration of a prophylactically effective amount of the composition of the invention or of the active ingredients comprised within such composition, to a person at risk of developing a disease.

The term "prophylactically effective amount" is intended to mean that amount of a pharmaceutical combined composition that will prevent or reduce the risk of occurrence of the biological or medical event that is sought to be prevented in a tissue, a system, animal or human by a researcher, veterinarian, medical doctor or other clinician.

It should be noted that for the method of treatment and prevention provided in the present invention, said therapeutic effective amount, or dosage, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the composition of the invention in bodily fluids or tissues. Following successful treatment, it may be desirable to have the patient undergo maintenance therapy to prevent the recurrence of the disease state, wherein the composition of the invention is administered in maintenance doses, once or more daily.

In another aspect the present invention provides a method for treating a human subject with a condition selected from the group consisting of hypertension, increase in body mass index (BMI), increase in waist circumference, dyslipidemia, insulin resistance, elevated liver enzymes, and fatty liver comprising administering to the subject an effective amount of a composition comprising an anti-LPS immunoglobulin preparation.

In another aspect the present invention provides a composition comprising an anti-LPS immunoglobulin preparation for use in treatment and/or prophylaxis of a human subject with a condition selected from the group consisting of hypertension, increase in body mass index (BMI), increase in waist circumference, dyslipidemia, insulin resistance, elevated liver enzymes, and fatty liver.

In another aspect the present invention provides a use of an anti-LPS immunoglobulin preparation in the manufacture of a medicament for the treatment and/or prophylaxis of a human subject with a condition selected from the group consisting of hypertension, increase in body mass index (BMI), increase in waist circumference, dyslipidemia, insulin resistance, elevated liver enzymes, and fatty liver.

The term "hypertension" encompasses high blood pressure, in which both the systolic and diastolic pressure levels are elevated (e.g. >140 mmHg/>90 mmHg), and isolated systolic hypertension, in which only the systolic pressure is elevated, for example elevated to greater than or equal to 140 mm Hg, while the diastolic pressure is less than 90 mm Hg, and isolated diastolic hypertension, in which only the diastolic pressure is elevated, for example elevated to greater than or equal to 90 mmHg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure.

The hypertension may characterized by a blood pressure of >120 mmHg/80 mmHg, a blood pressure of >130 mmHg/90 mmHg or a blood pressure of >140 mmHg/90 mmHg.

Treatment of hypertension using the compositions of the present invention may result in a decrease in blood pressure of about 1, 2, 3, 5, 10, 15, 20, 25, 30, 35, 40, 45, 50, 55, 60, 65, 70, 75, 80, 85, 90, 95 and over 99% relative to untreated control, or levels prior to the treatment.

The term "obesity" as used herein is a condition in which there is an excess of body fat. An operational definition of obesity is based on the Body Mass Index (BMI), which is calculated as body weight per height in meters squared (kg/m2). "Obesity" refers to a condition whereby an otherwise healthy subject has a Body Mass Index (BMI) greater than or equal to 30 kg/m2, or a condition whereby a subject with at least one co-morbidity has a BMI greater than or equal to 27 kg/m2. An "obese subject" is an otherwise healthy subject with a Body Mass Index (BMI) greater than or equal to 30 kg/m2 or a subject with at least one co-morbidity with a BMI greater than or equal to 27 kg/m2. A "subject at risk of obesity" also referred to as "overweight" or "pre-obese" is an otherwise healthy subject with a BMI of 25 kg/m2 to less than 30 kg/m2 or a subject with at least one co-morbidity with a BMI of 25 kg/m2 to less than 27 kg/m2. A "normal" BMI is 18.5 to 24.9 kg/m2. The increased risks associated with obesity occur at a lower Body Mass Index (BMI) in other populations, e.g. Asians. Exemplary measurements cutoffs for different populations are well known, for example, those in discussed in the WHO publication "Redefining obesity and its treatment", World Health Organization Western Pacific Region, International Association for the Study of Obesity, International Obesity Task Force (2000)

Obesity-induced or obesity-related co-morbidities include, but are not limited to, diabetes, non-insulin dependent diabetes mellitus-type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity related conditions.

Treatment of increase in BMI or prevention of increase in BMI includes the treatment of increases in BMI, for example from normal to pre-obese, normal to obese, or pre-obese to obese.

The increased BMI may be a BMI of at least 25 kg/m2 to less than 30 kg/m2 or a BMI of at least 30 kg/m2. The increased waist circumference may be a waist circumference of at least 102 cm in men or a waist circumference of at least 88 cm in women. A 'abdominal obesity' is defined by a waist circumference greater than 102 cm (40 inches) in men or 88 cm (35 inches) in women according to NCEP ATP III.

Treatment of increased BMI or waist circumference using the compositions of the present invention may result in a decrease in BMI, or waist circumference, respectively, of about 1, 2, 3, 5, 10, 15, 20, 25, 30, 35, 40, 45, 50, 55, 60, 65, 70, 75, 80, 85, 90, 95 and over 99% relative to untreated control, or levels prior to the treatment.

"Metabolic syndrome" or "syndrome X" is defined here on the basis of NCEP ATP III criteria, which are the presence of three or more of the following factors: 1) increased waist circumference (>102 cm (>40 in) for men, >88 cm (>35 in) for women); 2) elevated triglycerides (>150 mg/dl); 3) low HDL cholesterol (<40 mg/dl in men, <50 mg/dl in women); 4) non-optimal blood pressure (>130 mmHg systolic or ˆ5 mmHg diastolic); and 5) impaired fasting glucose (>110 mg/dl).

Dyslipidemias or disorders of lipid metabolism, include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

Guidelines for lipid-lowering therapy were established in 2001 by Adult Treatment Panel III (ATP III) of the National Cholesterol Education Program (NCEP), and updated in 2004 (Grundy et al., Circulation, 2004, 110, 227-239). The guidelines include obtaining a complete lipoprotein profile, typically after a 9 to 12 hour fast, for determination of LDL-C, total cholesterol, and HDL-C levels. According to the most recently established guidelines, LDL-C levels of 130-159 mg/dL, 160-189 mg/dL, and greater than or equal to 190 mg/dL are considered borderline high, high, and very high, respectively. Total cholesterol levels of 200-239 and greater than or equal to 240 mg/dL are considered borderline high and high, respectively. HDL-C levels of less than 40 mg/dL are considered low.

In certain embodiments, the patient has been identified as in need of lipid-lowering therapy. In certain such embodiments, the individual has been identified as in need of lipid-lowering therapy according to the guidelines established in 2001 by Adult Treatment Panel III (ATP III) of the National Cholesterol Education Program (NCEP), and updated in 2004 (Grundy et al., Circulation, 2004, 110, 227-239).

In certain embodiments, the invention provides methods for reducing LDL-C in an individual. In certain embodiments, the invention provides methods for reducing VLDL-C in an individual. In certain embodiments, the invention provides methods for reducing IDL-C in an individual. In certain embodiments, the invention provides methods for reducing non-HDL-C in an individual. In certain embodiments the invention provides methods for reducing Lp(a) in an individual. In certain embodiments, the invention provides methods for reducing serum triglyceride in an individual. In certain embodiments, the invention provides methods for reducing liver triglyceride in an individual. In certain embodiments, the invention provides methods for reducing Ox-LDL-C in an individual. In certain embodiments, the invention provides methods for reducing small LDL particles in an individual. In certain embodiments, the invention provides methods for reducing small VLDL particles in an individual. In certain embodiments, the invention provides methods for reducing phospholipids in an individual. In certain embodiments, the invention provides methods for reducing oxidized phospholipids in an individual.

An individual's response to administration of the ant-LPS immunoglobulin preparation is used by a physician to determine the amount and duration of therapeutic intervention.

An individual having elevated LDL-C levels may also exhibit reduced HDL-C levels and/or elevated total cholesterol levels. Individuals having elevated LDL-C levels may also exhibit elevated triglyceride levels.

In some embodiments, the dyslipidemia may be characterized by a LDL cholesterol of at least 160 mg/dL, a LDL cholesterol of at least 190 mg/dL, a Total Cholesterol of at least 200 mg/dL, a Total Cholesterol of at least 240 mg/dL, a HDL Cholesterol of less than 60 mg/dL, a HDL Cholesterol of less than 40 mg/dL, serum triglycerides of between 150 and 199 mg/dL, serum triglycerides of between 200 and 499 mg/dL, or serum triglycerides of at least 500 mg/dL.

Treatment of dyslipidemia using the compositions of the present invention may result in a decrease in total cholesterol, LDL, or serum triglycerides, respectively, of about 1, 2, 3, 5, 10, 15, 20, 25, 30, 35, 40, 45, 50, 55, 60, 65, 70, 75, 80, 85, 90, 95 and over 99% relative to untreated control, or levels prior to the treatment.

Measurements of cholesterol, lipoproteins and triglycerides are obtained using serum or plasma collected from an individual. Methods of obtaining serum or plasma samples are routine, as are methods of preparation of the serum samples for analysis of cholesterol, triglycerides, and other serum markers. A physician may determine the need for therapeutic intervention for individuals in cases where more or less aggressive LDL-lowering therapy is needed. The practice of the methods herein may be applied to any altered guidelines provided by the NCEP, or other entities that establish guidelines for physicians used in treating any of the diseases or conditions listed herein, for determining coronary heart disease risk and diagnosing metabolic syndrome.

The term "insulin resistance" refers to a state in which a given concentration of insulin is associated with a subnormal glucose response. Insulin resistance is a component of a number of states which include, but are not limited to, the following:

insulin resistance associated with obesity, stress, infection, acromegaly, Cushings Syndrome or Disease, the polycystic ovary syndrome, ovarian hyperthecosis;

insulin resistance unassociated with other pathological states;

extreme insulin resistance syndromes such as the type B syndrome which have autoantibodies associated with the insulin receptor, leprechaunism with insulin receptor mutations and the lipodystrophic states;

insulin resistance associated with intake of pharmacologic protease inhibitor drugs, valproic acid, olanzapine, clozapine and psychoactive agents;

resistance to endogenous insulin as defined by a high serum insulin concentration in association with blood glucose concentrations that are normal or high;

resistance to exogenous insulin as evident in patients treated with either insulin or the oral hypoglycemic agents and/or insulin sensitizing agents described herein who require either abnormally high doses of insulin or the specified oral hypoglycemic agent and/or insulin sensitizing agent to prevent or treat hyperglycemia.

Insulin resistance can be defined as an abnormal value according to e.g. generally known and/or accepted methods/procedures of determining insulin resistance and/or sensitivity. Those skilled in the art are well aware of certain methods/procedures of determining such insulin resistance and/or sensitivity values, including but not limited to, the homeostasis model assessment-insulin resistance (HOMA or HOMAIR), whole body insulin sensitivity index (WBISI), insulin sensitivity index (ISI), euglycemic-hyperinsulinemic clamp measure, and others.

Homeostasis model assessment-insulin resistance (HOMA or HOMAIR) can be calculated using the equation: (HOMAIR)=(FI×FG)/22.5, wherein FI is the fasting insulin concentration (in microunits per milliliter) and FG is the fasting glucose lever (in millimoles per liter). Accordingly, relatively lower HOMA-IR values correspond to relatively greater insulin sensitivity, whereas relatively higher HOMA-IR values correspond to relatively lower insulin sensitivity.

Whole body insulin sensitivity index (WBISI) can be calculated using parameters obtained from a standard oral glucose tolerance test (OGTT) (1.75 g/kg body weight (up to 75 g)), and using the equation: WBISI=10,000/square root of ((fasting glucose×fasting insulin)×(mean (OGTT) glucose×mean (OGTT) insulin)).

As used herein, the term "insulin resistance" includes impaired glucose tolerance, impaired fasting glucose and diabetes. The definition of the terms "Impaired glucose tolerance", "impaired fasting glucose" and "diabetes" can include the clinical diagnosis definitions of the WHO, such as those published in "Definition and diagnosis of diabetes mellitus and intermediate hyperglycemia: report of a WHO/IDF consultation", (2006). The term "Impaired glucose tolerance" (IGT) refers to a fasting plasma glucose of less than 7.0 mmol/l (126 mg/dl) and a 2-h plasma glucose of between 7.8 mmol/l (140 mg/dl). to less than 11.1 mmol/l (200 mg/dl). The term "a 2-hour plasma glucose" refers to venous plasma glucose 2 hours after ingestion of 75 g oral glucose load (Oral Glucose Tolerance Test; OGTT). The term "Impaired Fasting Glucose" refers to a fasting plasma glucose of between 6.1 mmol/l (110 mg/dl) to 6.9 mmol/l (125 mg/dl), or a fasting glucose of between 6.1 mmol/l (110 mg/dl) to 6.9 mmol/l (125 mg/dl) and a 2-h plasma glucose of less than 7.8 mmol/l (140 mg/dl). The term "diabetes" refers to a fasting plasma glucose of >7.0 mmol/l (126 mg/dl) or a 2-h plasma glucose of >11.1 mmol/l (200 mg/dl).

Insulin sensitivity index (ISI) can be calculated using parameters obtained from a standard oral glucose tolerance test (OGTT) (1.75 g/kg body weight (up to 75 g)), and using the equation: ISIOGTT=(1.9/6×body weight (kg)×fasting plasma glucose (mmol/liter)+520-1.9/18×body weight×area under the glucose curve (mmol/h-liter)−urinary glucose (mmol)/1.8)/(area under the insulin curve (pmol/h-liter)×body weight).

In some embodiments, the insulin resistance may be characterized by a fasting plasma glucose of less than 7.0 mmol/l (126 mg/dl) and a 2-h plasma glucose of between 7.8 mmol/l (140 mg/dl) to less than 11.1 mmol/l (200 mg/dl), a fasting plasma glucose of between 6.1 mmol/l (110 mg/dl) to 6.9 mmol/l (125 mg/dl), a fasting plasma glucose of between 6.1 mmol/l (110 mg/dl) to 6.9 mmol/l (125 mg/dl) and a 2-h plasma glucose of less than 7.8 mmol/l (140 mg/dl), or a fasting plasma glucose of ≥7.0 mmol/l (126 mg/dl) or a 2-h plasma glucose of ≥11.1 mmol/l (200 mg/dl).

Assessment of improvement in glycemic control may be assessed, for example, based on a change in hemoglobin A1c (HbA1c, see for example Reynolds et al., BMJ, 333(7568): 586-589, 2006). Improvements (e.g., decrease) in HbA1c that are indicative of therapeutic efficacy may vary depending on the initial baseline measurement in a patient, with a larger decrease often corresponding to a higher initial baseline and a smaller decrease often corresponding to a lower initial baseline. In one aspect of the invention, the method should result in an HbA1c decrease of at least about 0.5% (e.g., at least about 0.5%, at least about 1%, at least about 1.5%, at least about 2%, at least about 2.5%, at least about 3%, at least about 3.5%, at least about 4% or more) compared with pre-dose levels. An A1C of ≥6.5% is indicative of diabetes.

GLP-I is a neuroendocrine hormone of the distal gut with a strong insulinotropic action that is synthesized and secreted from L-cells in the intestine in response to meal ingestion (Kieffer T J, Habener J F 1999. Endocr Rev 20: 876-913). Importantly, the action of GLP-I is glucose-dependent, avoiding the occurrence of hypoglycemia. The intracellular precursor to GLP-I, GLP-1-(1-37), is cleaved from proglucagon, and the first six aminoacids are subsequently removed from the N terminus to form bioactive peptides. About 80% of truncated GLP-I is amidated to form GLP-1(7-36) amide; the predominant secreted form of GLP-I, whereas the remainder is released as GLP-1-(7-37) (Orskov C. et al; Diabetes 43:535-539, 1994). Both GLP-1(7-36) NH2 and GLP-1(7-37) interact with a specific GLP-I receptor (GLP-Ir) that is expressed on the pancreatic β-cell, and in other tissues such as the gastrointestinal tract and central nervous system. In vivo, GLP-1(7-36) NH2 and GLP-1(7-37) have equipotent effects to stimulate glucose-stimulated insulin release, (Orskov C. et al; Diabetes 43:535-539, 1994), and a physiological role for these hormones in the incretin response has been established in several animal models. Numerous effects other than stimulation of insulin release have been ascribed to GLP-I. In pancreas, it stimulates insulin biosynthesis, restoration of glucose sensitivity to the islets and stimulates increased expression of the glucose transporter GLUT-2 and glucokinase. GLP-I regulates β cell mass by stimulating replication and growth and also inhibits apoptosis of existing β cells and neogenesis of new β-cells from duct precursor cells. GLP-I inhibits glucagon secretion and leads to reduced hepatic glucose output. In the gut GLP-I is a potent inhibitor of motility and gastric emptying and also inhibits gastric acid secretion. This leads to decreased food intake and reduced body weight (Stoffers, D. A. et al; Diabetes 2000, 49, 741-748. Drucker D J Diabetes Care 26:2929-2940, 2003).

GLP-I acts through a G protein-coupled receptor to exert its functions. This receptor is expressed in many tissues, including pancreatic islets, the central nervous system, lung, kidney, heart, and the gut. GLP-I is coupled to its receptor through stimulatory Ga and adenylyl cyclase to increase intracellular cAMP. GLP-I can induce other intracellular signals as well, including increases in intracellular calcium, phosphoinositol 3-kinase (PI3K) activity, and mitogen-activated protein kinase activity (Buteau J. et al; Diabetologia 42:856-864, 1999; Bullock B P. et al; Endocrinology 137: 2968-2978, 1996).

The plasma level of bioactive GLP-1 is 5-10 pmol/L in normal fasting humans, however is significantly decreased in diabetic patients.

Adiponectin is secreted into the bloodsteam where it accounts for approximately 0.01% of all plasma protein, at around 5-10 μg/mL. Adiponectin levels are significantly lower in the diabetic than the lean subjects, and serum adiponectin levels were statistically significantly lower in patients with NAFLD than controls.

Accordingly, treatment of insulin resistance using the compositions of the present invention may result in an increase in early peak of insulin secretion, adiponectin and GLP-1, of about 1, 2, 3, 5, 10, 15, 20, 25, 30, 35, 40, 45, 50, 55, 60, 65, 70, 75, 80, 85, 90, 95 and over 99% relative to untreated control, or levels prior to the treatment.

Treatment of insulin resistance using the compositions of the present invention may result in a decrease in fasting plasma glucose, HBA1c, HOMA score, and OGTT of about 1, 2, 3, 5, 10, 15, 20, 25, 30, 35, 40, 45, 50, 55, 60, 65, 70, 75, 80, 85, 90, 95 and over 99% relative to untreated control, or levels prior to the treatment.

Treatment of insulin resistance using the compositions of the present invention may result in an increase in early peak of insulin secretion, adiponectin and GLP-1, of about 1, 2, 3, 5, 10, 15, 20, 25, 30, 35, 40, 45, 50, 55, 60, 65, 70, 75, 80, 85, 90, 95 and over 99% relative to untreated control, or levels prior to the treatment.

Nonalcoholic fatty liver disease (NAFLD) describes a spectrum of liver diseases ranging from simple fatty liver (steatosis) to nonalcoholic steatohepatitis (NASH) with progressive fibrosis and liver failure. Hyperglycemia with or without evidence of hyperlipidemia is commonly associated with NAFLD. The disease exhibits the histological features of alcohol-induced liver disease in patients who do not consume significant amounts of alcohol. All of the stages of NAFLD have in common the accumulation of fat in the liver cells. Farrell and Larter in Hepatology, 243:899 S112 (2006) describe NASH as "the lynchpin" between hepatic steatosis and cirrhosis in the spectrum of NAFLD. See also, Palekar, et al., Liver Int., 26(2): 151-6 (2006). In NASH, the fat accumulation of associated with varying degrees of inflammation and fibrosis. Conditions most commonly associated with NAFLD are obesity, type 2 diabetes and metabolic syndrome.

Alcoholic hepatitis is a precursor to cirrhosis and is caused by alcohol. The typical histologic picture includes hepatocellular necrosis and ballooning degeneration, and alcoholic Mallory's hyaline bodies (abnormal aggregations of cellular intermediate filament proteins indicative of fibrosis). Cholestasis is prominent. Alcoholic hepatitis can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma. Alcoholic hepatitis is reversible if the patient stops drinking, but it usually takes several months to resolve. Alcoholic hepatitis can lead to liver scarring and cirrhosis. If the liver abnormalities last less than about six months, the disease will be considered acute hepatitis; if the disease course becomes longer than about six months, the hepatitis is considered chronic. In one embodiment the present invention provides methods of treatment and/or prophylaxis of alcoholic hepatitis.

In patients with histologically proven NAFLD, serum hepatic aminotransferases, specifically alanine aminotransferase (ALT), levels are elevated from the upper limit of normal to 10 times this level (Schwimmer et al., J Pediatr 2003; 143 (4): 500-5; Rashid et al., J Pediatr Gastroenterol Nutr 2000; 30 (1): 48-53). The ratio of ALT/AST (aspartate aminotransferase) is >1 (range 1.5-1.7) which differs from alcoholic steatohepatitis where the ratio is generally <1. Other abnormal serologic tests that may be abnormally elevated in NASH include gamma-glutamyltransferase (gamma-GT) and fasting levels of plasma insulin, cholesterol and triglyceride.

Accordingly, a human subject in need of treatment may also be presumptively diagnosed by serum tests of liver enzymes. For example, steatosis may be indicated by elevated serum levels (often moderately elevated, e.g., elevated approximately 2, 3, 4, 5, 6, 7, 9, 10, 11, or 12-fold above normal levels) of liver enzymes (such as, e.g., alanine aminotransferase, aspartate aminotransferase, γ-glutamyltransferase, alkaline phosphatase) when other causes (such as, e.g., acute hepatitis, autoimmune disease, chronic hepatitis, cirrhosis, fulminant hepatitis, hepatocellular carcinoma, metastatic carcinoma, right heart failure, and viral hepatitis) have been eliminated. For example, alanine aminotransferase (ALT or SGPT) values greater than 32, 24, or 56 units per liter of serum or at least 2, 3, 4, 5, 6, 7, 8, 9, 10, 11, 12, or more times normal values may be indicative of a disorder associated with hepatic lipid deposits, or by aspartate aminotransferase (AST or SGOT) values greater than 40 units per liter of serum or at least 2, 3, 4, 5, 6, 7, 8, 9, 10, 11, 12, or more times normal values. The ratio of AST to ALT is often less than one in NAFLD, but may be greater than one in patients with alcoholic liver disease or advanced liver disease. In addition, γ-glutamyltransferase levels may be significantly elevated, e.g., at least 2, 3, 4, 5, 6, 7, 8, 9, 10, 11, 12, or more times normal values. The mean corpuscular volume (MPV) may be greater than, e.g., 86, 98, 100, or 110 femtoliters.

The term elevated liver enzymes relates to elevated levels of liver enzymes such as Alanine transaminase (ALT) g-glutamyl-transferase (GGT), Aspartate transaminase (AST), and Alkaline phosphatase (ALP). The degree of enzyme elevation may be between 1 and 4 times the upper limit of normal values.

In some embodiments, the elevated liver enzymes may be characterized by an AST of greater than 40 IU/L, ALT of greater than 30 IU/L, and ALT of greater than 56 IU/L, an ALP of greater than 115 IU/L, or a GGT of greater than 80 IU/L.

In addition to being presumptively diagnosed by serum tests of liver enzymes, a subject in need of treatment may also be presumptively diagnosed by noninvasive imaging techniques (e.g., ultrasonography, computed tomography, and magnetic resonance imaging) when steatosis is greater than, e.g., 25% or 30%. In general, it may be difficult to distinguish between NAFLD and NASH to detect fibrosis, or to determine the progression of disease, by such imaging methods. NAFLD may present as a focal or diffuse accumulation of lipid, but in NASH the lipid is generally diffuse. NAFLD may also be detected by magnetic resonance spectroscopy, a technique which may be of value for quantitative determination of hepatic lipid levels. For example, determination of hepatic triglyceride levels by MRI has been demonstrated to correlate with histologic biopsy results. See, e.g., Kawamitsu et al., Magn. Reson. Med. Sci. 2:47-50 (2003).

A subject in need of treatment may be definitively diagnosed by liver biopsy. A liver is considered to be steatotic when a biopsy reveals at least 5-10% w/w fatty deposits (in practice, this is value may be determined microscopically as the fraction of lipid-filled hepatocytes). See, e.g., Clark et al., J. Am. Med. Assoc. 289:3000-3004 (2003) and Adams et al., Can. Med. Assoc. J. 172:899-905 (2005). A liver with fatty deposits comprising up to 25% w/w may be considered mildly steatotic, and a liver with fatty deposits comprising greater than 25% w/w may be considered severely steatotic. Histological findings indicative of NASH include steatosis, hepatocyte ballooning, lobular inflammation, Mallory hyaline bodies, mixed inflammatory infiltrate, pericellular fibrosis, and perisinusoidal fibrosis. Additional information may be found in, e.g., Neuschwander-Tetri et al., Hepatology 37:1202-1219 (2003).

Disease progression in NAFLD/NASH, as assessed by fibrosis in liver histology, has been reported to correlate with the degree of insulin resistance and other features of metabolic syndrome. Ryan et al., Diabetes Care, 28:1222-1224 (2005). Elevated levels of serum immunoglobulin A have also been associated with disease progression. Neuschwander-Tetri et al., Hepatology 37: 1202-1219. Other markers proposed to be related to fibrosis in NAFLD patients include laminin, hyaluronan, type IV collagen, and aspartate aminotransferase. Dos Santos et al., Braz. J. Med. Biol. Res. 38:747-753 (2005). Female gender is also associated with more rapid disease progression.

The fatty liver may be characterized by macrovesicular steatosis, macrovesicular steatosis and necroinflammatory activity, or a NAS score of at least 4.

Efficacy of treatment may also be determined by detection of a reduction in one or more symptoms or clinical manifestations of a disease as well as any of the tests described above for diagnosis.

Treatment of liver damage/fatty liver using the compositions of the present invention may result in a decrease AST, ALT, AP, GGT about 1, 2, 3, 5, 10, 15, 20, 25, 30, 35, 40, 45, 50, 55, 60, 65, 70, 75, 80, 85, 90, 95 and over 99% relative to untreated control, or levels prior to the treatment.

One or more of the following secondary endpoints also may be determined in order to assess efficacy of the treatment, such as for example fasting blood sugar (e.g., glucose) levels (e.g., decrease to <130, <125, <120, <115, <110, <105, <100; alternatively decrease of >20%, >30%, >40%, >50%, >60%, >70%, >80%, >90%, >95% compared to pre-dose levels), 120 minute oral glucose tolerance test (OGTT) (e.g., <200, <190, <180, <170, <160, <150, <140), glucose/insulin C-peptide AUC (e.g., >25%, >50%, >60%, >70%, >80%, >90%, >100% increase from pre-treatment), reduction in diabetes medication (e.g., insulin, oral hypoglycemic agent), improvement in insulin sensitivity, serum cytokine levels (e.g., normalization), CRP levels (e.g., decrease of >0.2, >0.4, >0.6, >0.8, >1.0, >1.4, >1.8, >2.2, >2.6, >3.0 mg/L; alternatively a decrease of >20%, >30%, >40%, >50%, >60%, >70%, >80%, >90%, >95% from pre-treatment) quality of life measurements, BMI improvement (reduction of 1%, 3%, 5%), pharmacokinetics, and the like (Saudek, et al., JAMA, 295:1688-97, 2006; Pfutzner et al., Diabetes Technol Ther. 8:28-36, 2006; Norberg, et al., J Intern Med. 260:263-71, 2006).

Similarly, assessment of efficacy for other diseases or conditions may use one or more of the aforementioned endpoints and/or others known in the art. For example, the effect on hyperglycemia can be assessed by measuring fasting blood sugar (i.e., glucose) levels, the effect on hyperinsulinemia may be assessed by measuring insulin levels and/or C-peptide levels, the effect on obesity may be assessed by measuring weight and/or BMI, and the effect on insulin resistance may be assessed by OGTT.

Alternatively, or in addition, subjects treated in accordance with the present disclosure may experience a decrease in a cardiovascular risk indicator(s) and/or a decrease in serum lipids with improvement in the lipid profile. Such measurements of serum lipids and/or lipid profile may include, for example a decrease in cholesterol, a decrease in low-density lipoprotein cholesterol (LDL), a decrease in very-low-density lipoprotein cholesterol (VLDL), a decrease in triglycerides, a decrease in free fatty acids, a decrease in apolipoprotein B (Apo B), an increase in high-density lipoprotein cholesterol (HDL), maintaining the level of high-density lipoprotein cholesterol (HDL) compared to pre-treatment level, and/or an increase in apolipoprotein A (Apo A). For example, a decrease in the level of cholesterol (e.g., total cholesterol) may be a decrease of at least 5%, 10%, 15%, 20%, 25%, 30%, 35%, 40%, 45%, 50%, 55%, 60%, or more from the pre-treatment level. A decrease in the level of low-density lipoprotein cholesterol may be a decrease of at least 5%, 10%, 15%, 20%, 25%, 30%, 35%, 40%, 45%, 50%, 55%, 60%, or more from the pre-treatment level. A decrease in the triglyceride level in the blood of the subject may be a decrease of at least 5%, 10%, 15%, 20%, 25%, 30%, 35%, 40%, 45%, 50%, 55%, 60%, 65%, 70%, or more from the pre-treatment level. A decrease in the level of free fatty acids may be a decrease of at least 5%, 10%, 15%, 20%, 25%, 30%, 35%, 40%, 45%, 50%, 55%, 60%, or more from the pre-treatment level. An increase in the level of high-density lipoprotein cholesterol may be an increase of at least 1%, 2%, 3%, 4%, 5%, 6%, 8%, 10%, 12%, 14%, 16%, or more from the pre-treatment level.

Similarly, subjects treated in accordance with the present disclosure may experience a decrease in insulin resistance. Such decrease in insulin resistance may be measured by an improvement in a homeostasis model assessment (HOMA), an insulin tolerance test, an insulin suppression test, a steady-state plasma glucose method, or any of the other assay methods know in the art (see for example Matthews et al, 1985, Diabetologia 28:412-419; Odegaard et al., 2007, Nature 447:1116-1121; Emoto et al., 1999, Diabetes Care 22:818-822). Other of the aforementioned measurements may be made using any of a variety of standard assays known in the art, for example assays published in Chemecky C C, Berger B J, eds. (2004). Laboratory Tests and Diagnostic Procedures, 4th ed. Philadelphia: Saunders; Fischbach F T, Dunning M B III, eds. (2004). Manual of Laboratory and Diagnostic Tests, 7th ed. Philadelphia: Lippincott Williams and Wilkins; Genest J, et al. (2003). Recommendations for the management of dyslipidemia and the prevention of cardiovascular disease: Summary of the 2003 update. Canadian Medical Association Journal, 169(9): 921-924. Also available online: http://www.cmaj.ca/cgi/content/full/169/9/921/DC1; Handbook of Diagnostic Tests (2003). 3rd ed. Philadelphia: Lippincott Williams and Wilkins; and Pagana K D, Pagana T J (2002). Mosby's Manual of Diagnostic and Laboratory Tests, 2nd ed. St. Louis: Mosby.

The anti-LPS immunoglobulin preparation may be derived from colostrum or avian eggs.

The administration of the composition of the present invention in order to practice the present methods of therapy is carried out by administering a therapeutically effective amount of the compounds in the composition to a subject in need of such treatment or prophylaxis. The need for a prophylactic administration according to the methods of the present invention is determined via the use of the well known risk factors as described herein.

Each oral dose form may, for example, comprise the colostrum equivalent of less than 1200 mg (dry weight basis), preferably 800 mg, preferably less than 400 mg, more preferably less than 200 mg. By colostrum equivalent we mean the amount of raw colostrum, howsoever purified, which is processed to provide the contents of a dose form.

For oral administration, the oral dose form may comprise 5 mg to 500 mg bovine colostrum powder (BCP) (dry weight basis), e.g. 5, 10, 15, 20, 25, 30, 35, 40, 45, 50, 55, 60, 70, 80, 90, 100, 125, 150, 175, 200, 225, 250, or 500 mg.

The oral dose form may comprise 500 mg to 5000 mg bovine colostrum powder (dry weight basis), e.g. 500, 750, 1000, 1250, 1500, 1750, 2000, 2250, 2500, 2750, 3000, 3250, 3500, 3750, 4000, 4250, 4500, 4750 or 5000 mg.

Suitable dosage ranges are, e.g. from about 5 mg to about 5000 mg/day, preferably 50 mg to about 5000 mg/day, more preferably 500 mg to about 5000 mg/day, or most preferably 1500 mg to about 2000 mg/day BCP (dry weight basis). In one preferred embodiment, the dose is 1800 mg/day BCP (dry weight basis).

In one embodiment the antibodies are present in the composition for oral administration in an amount sufficient to provide from at least 7% by dry weight of the composition of IgG.

In another embodiment the antibodies are present in the composition for oral administration in an amount sufficient to provide from at least 40% by weight of the composition of IgG.

Accordingly, for oral administration, the oral dose form may comprise 2 mg to 200 mg IgG, e.g. 2, 4, 6, 8, 10, 12, 14, 16, 18, 20, 25, 30, 35, 40 45, 50, 55, 60, 65, 70, 75, 80, 85, 90, 95, 100, 110, 125, 150, 175, or 200 mg IgG.

The oral dose form may comprise 200 mg to 2000 mg IgG e.g. 200, 300, 400, 500, 600, 700, 800, 900, 1000, 1100, 1200, 1300, 1400, 1500, 1600, 1700, 1800, 1900 or 2000 mg IgG.

In one embodiment antibodies specific to the antigen are present in the composition for oral administration in an amount sufficient to provide from at least 10% specific IgG of the weight of IgG.

Accordingly, for oral administration, the oral dose form may comprise 0.2 mg to 20 mg specific IgG, e.g. 0.2, 0.4, 0.6, 0.8, 1, 1.2, 1.4, 1.6, 1.8, 2.0, 2.5, 3.0, 3.5, 4.0, 4.5, 5.0, 5.5, 6.0, 6.5, 7.0, 7.5, 8.0, 8.5, 9.0, 9.5, 10.0, 11.0, 12.5, 15.0, 17.5, or 20.0 mg specific IgG.

Suitable dosage ranges are, e.g. from about 2 to about 200 mg/day, preferably 20 to about 2000 mg/day, more preferably 200 to about 2000 mg/day, or most preferably 600 mg to about 800 mg/day IgG. In one preferred embodiment, the dose is 720 mg/day IgG.

In one embodiment, the anti-LPS immunoglobulin preparation is not administered at a dose of about 600 mg per day (dry weight volume).

The oral dose form may be administered for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days.

In one embodiment, the oral dose form is administered for 30 days.

In one embodiment, the anti-LPS immunoglobulin preparation is administered for 30 days at dose of 1.8 g/day. In one embodiment, the anti-insulin immunoglobulin preparation is administered for 30 days at dose of 1.2 g/day.

The oral dose form preferably comprises colostrum derived from the hyperimmune colostrum and/or colostrum which has been added to the polyclonal antibodies in accordance with the teaching of PCT/AU03/00348 (Pub. No.: WO/2003/080082). The oral dosage form may also comprise a buffer system such as that disclosed in PCT/AU2005/001746 (Pub. No.: WO/2006/053383). The contents of these patents are incorporated by reference.

The term "therapeutically effective amount" as used herein means the amount of the active compounds in the composition that will elicit the biological or medical response in a tissue, system, subject, or human that is being sought by the researcher, veterinarian, medical doctor or other clinician, which includes alleviation of the symptoms of the disorder being treated. The novel methods of treatment of this invention are for disorders known to those skilled in the art.

The term "prophylactically effective amount" as used herein means the amount of the active compounds in the composition that will elicit the biological or medical response in a tissue, system, subject, or human that is being sought by the researcher, veterinarian, medical doctor or other clinician, to prevent the onset of the symptoms of the disorder in a subject at risk of developing the disorder.

The magnitude of prophylactic or therapeutic dose of the active ingredients can, of course, vary with the nature of the severity of the condition to be treated. It can also vary according to the age, weight and response of the individual patient, and may be administered in subject in single or divided doses. On the other hand, it may be necessary to use dosages outside the ranges provided herein in some cases.

The anti-LPS immunoglobulin preparation may be administered at a dose of about 5 mg to about 25000 mg per day, 10 mg to about 20000 mg per day, 25 mg to about 15000 mg per day, 100 mg to about 2000 mg per day, or about 1800 mg per day. In one embodiment, the anti-LPS immunoglobulin preparation is not administered at a dose of about 600 mg per day.

The anti-LPS immunoglobulin preparation may be formulated for administration at a dose of about 5 mg to about 25000 mg per day, about 10 mg to about 20000 mg per day, about 25 mg to about 15000 mg per day, about 100 mg to about 2000 mg per day or about 1800 mg per day.

In one embodiment, the anti-LPS immunoglobulin preparation is not formulated for administration at a dose of about 600 mg per day.

It is preferred the bacteria from which each type of O antigen is isolated are grown in separate bacterial culture systems, and after separation of the O antigen from the bacteria, the component antigens are added together to form a component of the vaccine.

Methods of preparing LPS/O antigen are known in the art and described in WO/2004/078209, which is incorporated herein by reference. Methods of preparing hyperimmune bovine colostrum (HIBC) are also described in WO/2004/078209.

The anti-LPS immunoglobulin preparation may be prepared by immunizing a mammal or avian with LPS from multiple *E. coli* strains. The mammal or avian may be immunized with LPS selected from the group consisting of O6, O8, O15, O25, O27, O63, O78, O114, O115, O128, O148, O153, O159, and other LPS associated with enterotoxigenic *E. coli*.

The mammal or avian may be immunized with LPS selected from the group consisting of O78, O6, O8, O129 and O153 LPS. The LPS may comprise O78 LPS.

In another embodiment, composition further comprises an anti-insulin immunoglobulin preparation.

The anti-insulin immunoglobulin preparation is administered at a dose of about 5 mg to about 25000 mg per day, about 10 mg to about 20000 mg per day, about 25 mg to about 15000 mg per day, about 50 mg to about 10000 mg per day, about 50 mg to about 4000 mg per day, about 500 mg to about 3000 mg per day, about 1000 mg to about 1400 mg per day, or about 1200 mg per day.

The anti-insulin immunoglobulin preparation may be formulated for administration at a dose of about 5 mg to about 25000 mg per day, about 10 mg to about 20000 mg per day, about 25 mg to about 15000 mg per day, about 50 mg to about 10000 mg per day, about 50 mg to about 4000 mg per day, about 500 mg to about 3000 mg per day, about 1000 mg to about 1400 mg per day or of about 1200 mg per day.

For oral administration, the oral dose form may comprise 5 mg to 500 mg bovine colostrum powder (BCP) (dry weight basis), e.g. 5, 10, 15, 20, 25, 30, 35, 40, 45, 50, 55, 60, 70, 80, 90, 100, 125, 150, 175, 200, 225, 250, or 500 mg.

The oral dose form may comprise 500 mg to 5000 mg bovine colostrum powder (dry weight basis), e.g. 500, 750, 1000, 1250, 1500, 1750, 2000, 2250, 2500, 2750, 3000, 3250, 3500, 3750, 4000, 4250, 4500, 4750 or 5000 mg.

In one embodiment the antibodies are present in the composition for oral administration in an amount sufficient to provide from at least 7% by dry weight of the composition of IgG.

In another embodiment the antibodies are present in the composition for oral administration in an amount sufficient to provide from at least 40% by weight of the composition of IgG.

Accordingly, for oral administration, the oral dose form may comprise 2 mg to 200 mg IgG, e.g. 2, 4, 6, 8, 10, 12, 14, 16, 18, 20, 25, 30, 35, 40 45, 50, 55, 60, 65, 70, 75, 80, 85, 90, 95, 100, 110, 125, 150, 175, or 200 mg IgG.

The oral dose form may comprise 200 mg to 2000 mg IgG e.g. 200, 300, 400, 500, 600, 700, 800, 900, 1000, 1100, 1200, 1300, 1400, 1500, 1600, 1700, 1800, 1900 or 2000 mg IgG.

In one embodiment antibodies specific to the antigen are present in the composition for oral administration in an amount sufficient to provide from at least 10% specific IgG of the weight of IgG.

Accordingly, for oral administration, the oral dose form may comprise 0.2 mg to 20 mg specific IgG, e.g. 0.2, 0.4, 0.6, 0.8, 1, 1.2, 1.4, 1.6, 1.8, 2.0, 2.5, 3.0, 3.5, 4.0, 4.5, 5.0, 5.5, 6.0, 6.5, 7.0, 7.5, 8.0, 8.5, 9.0, 9.5, 10.0, 11.0, 12.5, 15.0, 17.5, or 20.0 mg specific IgG.

The oral dose form may be administered for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days.

The anti-insulin immunoglobulin preparation may be prepared by immunizing a mammal or avian with insulin conjugated to a protein. Insulin may be conjugated to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysien residues), glutaraldehyde, succinic anhydride, SOCl2, or R1N=C=NR, where R and R1 are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The anti-insulin immunoglobulin preparation may be prepared by immunizing a mammal or avian with insulin conjugated to keyhole limpet hemocyanin (KLH).

In another aspect, the present invention provides a method for reducing fasting glucose levels in a human patient in need thereof, comprising administering to said patient a therapeutically effective amount a composition comprising an anti-LPS immunoglobulin preparation.

In another aspect, the present invention provides a method for increasing the early peak of insulin secretion in a human patient in need thereof, comprising administering to said patient a therapeutically effective amount a composition comprising an anti-LPS immunoglobulin preparation.

In another aspect, the present invention provides a method for decreasing oral glucose tolerance in a human patient in need thereof, comprising administering to said patient a therapeutically effective amount a composition comprising an anti-LPS immunoglobulin preparation.

In another aspect, the present invention provides a method for increasing insulin secretion in a human patient in need thereof, comprising administering to said patient a therapeutically effective amount a composition comprising an anti-LPS immunoglobulin preparation.

In another aspect, the present invention provides a method for decreasing HBA1C levels in a human patient in need thereof, comprising administering to said patient a therapeutically effective amount a composition comprising an anti-LPS immunoglobulin preparation.

In another aspect, the present invention provides a method for decreasing triglyceride levels in a human patient in need thereof, comprising administering to said patient a therapeutically effective amount a composition comprising an anti-LPS immunoglobulin preparation.

In another aspect, the present invention provides a method for decreasing total cholesterol levels in a human patient in need thereof, comprising administering to said patient a therapeutically effective amount a composition comprising an anti-LPS immunoglobulin preparation.

In another aspect, the present invention provides a method for decreasing LDL cholesterol levels in a human patient in need thereof, comprising administering to said patient a therapeutically effective amount a composition comprising an anti-LPS immunoglobulin preparation.

In another aspect, the present invention provides a method for decreasing ALT levels in a human patient in need thereof, comprising administering to said patient a therapeutically effective amount a composition comprising an anti-LPS immunoglobulin preparation.

In another aspect, the present invention provides a method for decreasing AST levels in a human patient in need thereof, comprising administering to said patient a therapeutically effective amount a composition comprising an anti-LPS immunoglobulin preparation.

In another aspect, the present invention provides a method for decreasing ALP levels in a human patient in need thereof, comprising administering to said patient a therapeutically effective amount a composition comprising an anti-LPS immunoglobulin preparation.

In another aspect, the present invention provides a method for decreasing GGT levels in a human patient in need thereof, comprising administering to said patient a therapeutically effective amount a composition comprising an anti-LPS immunoglobulin preparation.

In another aspect, the present invention provides a method for increasing GLP-1 levels in a human patient in need thereof, comprising administering to said patient a therapeutically effective amount a composition comprising an anti-LPS immunoglobulin preparation.

In another aspect, the present invention provides a method for increasing Adiponectin levels in a human patient in need thereof, comprising administering to said patient a therapeutically effective amount a composition comprising an anti-LPS immunoglobulin preparation.

In another aspect, the present invention provides a method for increasing the Adiponectin/IL-6 ratio in a human patient in need thereof, comprising administering to said patient a therapeutically effective amount a composition comprising an anti-LPS immunoglobulin preparation.

In another aspect, the present invention provides a method for increasing the CD25+ T regulatory cells in a human patient in need thereof, comprising administering to said patient a therapeutically effective amount a composition comprising an anti-LPS immunoglobulin preparation.

In another aspect, the present invention provides a method for decreasing body weight in a human patient in need thereof, comprising administering to said patient a therapeutically effective amount a composition comprising an anti-LPS immunoglobulin preparation.

In another aspect, the present invention provides a method for decreasing waist circumference or arm circumference in a human patient in need thereof, comprising administering to said patient a therapeutically effective amount a composition comprising an anti-LPS immunoglobulin preparation.

In another aspect, the present invention provides a composition comprising an anti-LPS immunoglobulin preparation for use in reducing fasting glucose levels in a human patient in need thereof.

In another aspect, the present invention provides a composition comprising an anti-LPS immunoglobulin preparation for use in increasing the early peak of insulin secretion in a human patient in need thereof.

In another aspect, the present invention provides a composition comprising an anti-LPS immunoglobulin preparation for use in decreasing oral glucose tolerance in a human patient in need thereof.

In another aspect, the present invention provides a composition comprising an anti-LPS immunoglobulin preparation for use in increasing insulin secretion in a human patient in need thereof.

In another aspect, the present invention provides a composition comprising an anti-LPS immunoglobulin preparation for use in decreasing HBA1C levels in a human patient in need thereof.

In another aspect, the present invention provides a composition comprising an anti-LPS immunoglobulin preparation for use in decreasing triglyceride levels in a human patient in need thereof.

In another aspect, the present invention provides a composition comprising an anti-LPS immunoglobulin preparation for use in decreasing total cholesterol levels in a human patient in need thereof.

In another aspect, the present invention provides a composition comprising an anti-LPS immunoglobulin preparation for use in decreasing LDL cholesterol levels in a human patient in need thereof.

In another aspect, the present invention provides a composition comprising an anti-LPS immunoglobulin preparation for use in decreasing ALT levels in a human patient in need thereof.

In another aspect, the present invention provides a composition comprising an anti-LPS immunoglobulin preparation for use in decreasing AST levels in a human patient in need thereof.

In another aspect, the present invention provides a composition comprising an anti-LPS immunoglobulin preparation for use in decreasing ALP levels in a human patient in need thereof.

In another aspect, the present invention provides a composition comprising an anti-LPS immunoglobulin preparation for use in decreasing GGT levels in a human patient in need thereof.

In another aspect, the present invention provides a composition comprising an anti-LPS immunoglobulin preparation for use in increasing GLP-1 levels in a human patient in need thereof.

In another aspect, the present invention provides a composition comprising an anti-LPS immunoglobulin preparation for use in increasing Adiponectin levels in a human patient in need thereof.

In another aspect, the present invention provides a composition comprising an anti-LPS immunoglobulin preparation for use in increasing the Adiponectin/IL-6 ratio in a human patient in need thereof.

In another aspect, the present invention provides a composition comprising an anti-LPS immunoglobulin preparation for use in increasing the CD25+ T regulatory cells in a human patient in need thereof.

In another aspect, the present invention provides a composition comprising an anti-LPS immunoglobulin preparation for use in decreasing body weight in a human patient in need thereof.

In another aspect, the present invention provides a composition comprising an anti-LPS immunoglobulin preparation for use in decreasing waist circumference or arm circumference in a human patient in need thereof.

In another aspect, the present invention provides a use of an anti-LPS immunoglobulin preparation in the manufacture of a medicament for reducing fasting glucose levels in a human patient in need thereof.

In another aspect, the present invention provides a use of an anti-LPS immunoglobulin preparation in the manufacture of a medicament for increasing the early peak of insulin secretion in a human patient in need thereof.

In another aspect, the present invention provides a use of an anti-LPS immunoglobulin preparation in the manufacture of a medicament for decreasing oral glucose tolerance in a human patient in need thereof.

In another aspect, the present invention provides a use of an anti-LPS immunoglobulin preparation in the manufacture of a medicament for increasing insulin secretion in a human patient in need thereof.

In another aspect, the present invention provides a use of an anti-LPS immunoglobulin preparation in the manufacture of a medicament for decreasing HBA1C levels in a human patient in need thereof.

In another aspect, the present invention provides a use of an anti-LPS immunoglobulin preparation in the manufacture of a medicament for decreasing triglyceride levels in a human patient in need thereof.

In another aspect, the present invention provides a use of an anti-LPS immunoglobulin preparation in the manufacture of a medicament for decreasing total cholesterol levels in a human patient in need thereof.

In another aspect, the present invention provides a use of an anti-LPS immunoglobulin preparation in the manufacture of a medicament for decreasing LDL cholesterol levels in a human patient in need thereof.

In another aspect, the present invention provides a use of an anti-LPS immunoglobulin preparation in the manufacture of a medicament for decreasing ALT levels in a human patient in need thereof.

In another aspect, the present invention provides a use of an anti-LPS immunoglobulin preparation in the manufacture of a medicament for decreasing AST levels in a human patient in need thereof.

In another aspect, the present invention provides a use of an anti-LPS immunoglobulin preparation in the manufacture of a medicament for decreasing ALP levels in a human patient in need thereof.

In another aspect, the present invention provides a use of an anti-LPS immunoglobulin preparation in the manufacture of a medicament for decreasing GGT levels in a human patient in need thereof.

In another aspect, the present invention provides a use of an anti-LPS immunoglobulin preparation in the manufacture of a medicament for increasing GLP-1 levels in a human patient in need thereof.

In another aspect, the present invention provides a use of an anti-LPS immunoglobulin preparation in the manufacture of a medicament for increasing Adiponectin levels in a human patient in need thereof.

In another aspect, the present invention provides a use of an anti-LPS immunoglobulin preparation in the manufacture of a medicament for increasing the Adiponectin/IL-6 ratio in a human patient in need thereof.

In another aspect, the present invention provides a use of an anti-LPS immunoglobulin preparation in the manufacture of a medicament for increasing the CD25+ T regulatory cells in a human patient in need thereof.

Treatment using the compositions of the present invention may result in an increase in T regulatory cells, of about 1, 2, 3, 5, 10, 15, 20, 25, 30, 35, 40, 45, 50, 55, 60, 65, 70, 75, 80, 85, 90, 95 and over 99% relative to untreated control, or levels prior to the treatment.

T cell responses may be quantified using methods known in the art, for example ELISPOT assays, flow cytometry or useful immunodetection methods described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed T regulatory cells.

Examples of immunoassays are enzyme linked immunosorbent assays (ELISAs), enzyme linked immunospot assay (ELISPOT), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP)

In another aspect, the present invention provides a use of an anti-LPS immunoglobulin preparation in the manufacture of a medicament for decreasing body weight in a human patient in need thereof.

In another aspect, the present invention provides a use of an anti-LPS immunoglobulin preparation in the manufacture of a medicament for decreasing waist circumference or arm circumference in a human patient in need thereof.

In another aspect, the present invention provides a method of treating a human suffering a T-cell mediated disease comprising administering to the human an effective amount of a composition comprising an anti-LPS immunoglobulin preparation.

As used herein, the term "T cell mediated disease" is intended to mean a condition in which an inappropriate T cell response is a component of the pathology. The term is intended to include both diseases directly mediated by T cells and those indirectly mediated by T cells such as diseases in which an inappropriate T cell response contributes to damage resulting from the production of autoimmune antibodies. The term is intended to encompass both T cell mediated autoimmune diseases and unregulated clonal T cell replication. Therefore, a T cell mediated disease includes T cell mediated conditions exhibiting clinically recognizable symptoms as well as T cell mediated dysfunctions. Specific examples of T cell mediated diseases include type 1 diabetes, insulitis, Graves' disease, rheumatoid arthritis (RA), multiple sclerosis (MS), systemic lupus erythematosus, myasthenia gravis, pemphigus vulgaris, Hashimoto's Thyroditis, Autoimmune Uveitis, Sjogren's syndrome, Dermamyositis and Addison's disease.

As used herein, "Th1-mediated" in reference to a disease, disorder, or condition is one that has been associated with increased cytokine production from Th1 cells, including IFN-Y, IL-2, GM-CSF, TNF-alpha and IL-3. Specific examples include multiple sclerosis, insulindependent diabetes mellitus, Crohn's disease, uveitis, chronic rheumatism, and systemic lupus erythematosus.

As used herein, "Th2 mediated" in reference to a disease, disorder, or condition is one that has not been associated with increased cytokine production from Th1 cells. Specific examples include scleroderma, multiple myositis, vasculitis syndrome, mixed connective tissue disease, Sjogren's syndrome, hyperthyroidism, Hashimoto's disease, myasthenia gravis, Guillain-Barre syndrome, autoimmune hepatopathy, ulcerative colitis, autoimmune nephropathy, autoimmune hematopathy, idiopathic interstitial pneumonia, hypersensitivity pneumonitis, autoimmune dermatosis, autoimmune cardiopathy, autoimmune infertility, and Behcet's disease.

All references to a disease or condition are contemplated to encompass other diseases, conditions, and/or symptoms associated with the referenced disease or condition by the medical community. For instance, the phrase "autoimmune disease(s)" is used herein to refer to a large group of illnesses, some with ill-defined causes, thought to be associated with abnormalities in immunoregulation. Therefore, the term as used herein is intended to include, but is not limited to, diseases such as rheumatoid arthritis, lupus, graft versus host disease, host versus graft disease, insulindependent diabetes, autoimmune enchephlomyelitis, autoimmune hepatitis, Crohn's disease, and multiple sclerosis. Additionally, the term "allergy" is meant to encompass allergic disease(s) including, but not limited to, chronic bronchitis, atopic dermatitis, pollinosis (allergic rhinitis), allergic angiitis, allergic conjunctivitis, allergic gastroenteritis, allergic hepatopathy, allergic cystitis, and allergic purpura.

In another aspect, the present invention provides a composition comprising an anti-LPS immunoglobulin preparation for use in treating a human suffering a T-cell mediated disease In another aspect, the present invention provides a use of an anti-LPS immunoglobulin preparation in the manufacture of a medicament for the treatment and/or prophylaxis of a human subject suffering a T-cell mediated disease The T-cell mediated disease may be insulin resistance, impaired glucose tolerance, diabetes, metabolic syndrome, or a disease associated therewith, or non-alcoholic steatohepatitis (NASH).

In another aspect, the present invention provides a method of treatment of a human suffering a disease selected from insulin resistance or associated disorders comprising administering an effective amount of a composition comprising an anti-LPS immunoglobulin preparation.

In another aspect, the present invention provides a composition comprising an anti-LPS immunoglobulin preparation for use in treatment of a human suffering a disease selected from insulin resistance or associated disorders.

In another aspect, the present invention provides a use of an anti-LPS immunoglobulin preparation in the manufacture of a medicament treatment of a human suffering a disease selected from insulin resistance or associated disorders.

The insulin resistance or an associated disorder may be diabetes, metabolic syndrome or non-alcoholic steatohepatitis (NASH).

Reference is also made to PCT/IL2009/000273 (WO/2009/113065) and PCT/IL2010/000339, the disclosures of which are incorporated herein in their entirety by reference.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

Example 1: Preparation of Anti-LPS Immunoglobulin Preparations

The product 'BioGARD' is a colostrum preparation supplied by Immuron Limited.

Each Immuron BioGARD tablet is an uncoated 1.2 g oral tablet, which contains 600 mg of freeze-dried Bovine Colostrum Powder, in combination with excipients. The active substance in BioGARD tablets is freeze-dried bovine colostrum powder milked from commercial dairy cowherds. The cows in these herds, as well as being vaccinated for routine cattle pathogens, have been vaccinated with a vaccine against the outer cell wall antigens of multiple strains of *E. coli* bacteria, a major organism in human gut microflora. Immuron BCP (bovine colostrum powder) is a high-protein (>80%), lactose- and fat-reduced natural product derived from the first milking of commercial dairy cows collected after calving. It is presented before tableting as a concentrated, freeze dried powder.

Immuron BCP contains approximately 40% antibodies (immunoglobulins) in the dry powder. The immunoglobulins in BioGARD's BCP have high binding activity against the Lipopolysaccharide (LPS) of Gram-negative bacteria. Binding of LPS is assayed by Immuron using a standardized ELISA and immuno-blotting detection systems.

BioGARD was produced as follows. Dairy cows were immunized with a mixture of LPS antigens. For example, dairy cows were immunized with LPS O78, or a mixture of O6, O8, O15, O25, O27, O63, O78, O114, O115, O128, O148, O153, O159, and other LPS associated with enterotoxigenic *E. coli*. The antigen vaccine was administered during the last eight weeks of gestation. Colostral milk was collected during the first two days of lactation. The milk fat was removed and skim milk was pasteurized at 56° C. for 30 minutes and then coagulated by renetting as in Hilpert, Human Milk Banking 1984. After removal of milk curd containing casein, the whey was centrifuged and the fine precipitate was discarded. An equal volume of saturated ammonium sulfate solution was slowly added to the supernatant with continuous mixing as in Brandon et al. (Brandon et al., Aust. J. Exp. Biol. Med. Sci. 49:613 (1971)). After centrifugation the resulting precipitate was saved and the supernatant containing lactose and salts was discarded.

The precipitate was dissolved in 0.01M TRIS-HCl buffer pH 8 containing 0.32M NaCl (30% of original volume). This solution was extensively dialyzed against five volumes of the same buffer using an Amicon spiral membrane SIY30 cartridge. The antibody solution was then concentrated to 10%, snap frozen and freeze dried.

Production of Antibody Fragments from Colostrum.

Antibody fragments are prepared according to modified method based on the methods described by Jones R. G. A. and Landon J. (Jones R. G. A. and Landon J. J. Immunol. Methods 263: 57-74 (2002)). Briefly, an equal volume of 0.2M Sodium Acetate buffer pH 4.0, is added to a colostrum pool obtained from immunized animals as described above.

The pH of the diluted colostrum pool has been adjusted to 4.6 and incubated at 37° C. for two hours to precipitate caseins. Subsequently, colostrum is centrifuged and filtered (0.45 μm) to remove casein. The pH of the resultant colostral whey has been adjusted to pH 4.0, followed by addition of Pepsin (Enzyme Solutions with 1:15,000 activity) at 5.0% w/w and incubation for twenty hours at 45° C. Pepsin digestion has been stopped by addition of 0.5 vol. of 1M Tris pH8 and cooling the reaction mix to 4° C. The pH of the reaction is adjusted to pH to 7.0 and the F(ab')2 mix is concentrated using 30 kD ultra-filtration membrane and dia-filtrate vs. >50 volumes of 20 mM sodium phosphate/ 150 mM NaCl pH 6.0 buffer. Small peptides are then removed and the resulting solution containing F(ab')2, Pepsin and Large Peptides was then subjected to Q Sepharose Anion Exchange column that Binds Pepsin and acidic aggregates. To obtain purified F(ab')2, the remaining Fc and undigested Ig are removed from the F(ab')2 (mixed with remaining large Peptides and undigested Ig), by Protein G or by Prometic Mabsorbent AlP chromatography.

Preparation of Fab' by 2-mercaptoethylamine (MEA). To prepare Fab$^1$, 50 ul (1/9 vol.) of 0.1M 2-mercaptoethylamine (MEA) in 0.1M sodium phosphate buffer pH 6.0, containing freshly prepared 5 mM EDTA-disodium, are added to 0.1- 3.0 mg of F(ab')2 in 0.45 ml of 0.1 M sodium phosphate buffer, pH 6.0. The mixture is then incubated at 37° C. for 90 mins. Subsequently, the reaction mixture is applied on a PD-10 column, or a suitable G25 column, to remove the excess MEA. 0.1M sodium phosphate (pH 6.0, with 5 mM EDTA-disodium) is used as the running buffer. The first protein peak which contains Fab', is collected and used for treating the corresponding different indications as indicated herein below.

For preparation of the anti-LPS enriched immunoglobulin preparation, colostrum was collected from approximately 200 commercial dairy cowherds, The cows in these herds, as well as being vaccinated for routine cattle pathogens, have been vaccinated with a vaccine against the outer cell wall antigens of multiple strains of *E. coli* bacteria, a major organism in human gut microflora. The obtained colostrum was frozen in individual bags for testing. For processing, colostrum was thawed, pooled and fat was removed. Each batch was pasteurized. Colostrum was concentrated by ultra-filtration to reduce volume before freeze drying. The ultra-filtration step reduced lactose in the final powder to less than 7% (from about 50%).

Example 2: Use of Colostrum-Derived Anti-LPS Enriched Immunoglobulin Preparations in the Treatment of Hepatitis For immune mediated hepatitis model, eleven to twelve weeks old male C57/bl mice are tail vein injected with a dose of 500 g/mouse (approximately 15 mg/kg) of Con A (MP Biornedicals, USA) which is dissolved in 50 mM Trig pH 7, 150 mM NaCl, 4 mM $CaCl_2$, known to induce hepatitis. Animals of all tested groups are orally administered using different concentrations and preparations of specific antibodies, or the BioGARD preparation described in experimental procedures, as compared to untreated controls. Animals of all tested groups are followed for the following parameters: serum aspartate aminotransferase (AST) and alanine aminotransferase (ALT) levels, histological examination of liver specimens, FACS analysis of intra-hepatic and intrasplenic lymphocytes for NKT markers, measurement of serum cytokine levels and Western blot analysis for the expression of the transcription factors STAT 1, 4 and 6 and NFκB and are compared to control groups.

Example 3: Oral Administration of Colostrum Enriched with Anti LPS Antibodies For preparation of the anti-LPS immunoglobulin preparations, colostrum was collected from approximately 200 commercial dairy cowherds, The cows in these herds, as well as being vaccinated for routine cattle pathogens, have been vaccinated with a vaccine against the outer cell wall antigens of multiple strains of *E. coli* bacteria, a major organism in human gut microflora. The obtained colostrum was frozen in individual bags for testing. For processing, colostrum was thawed, pooled and fat was removed. Each batch was pasteurized. Colostrum was concentrated by ultra-filtration to reduce volume before freeze drying. The ultra-filtration step reduced lactose in the final powder to less than 7% (from about 50%).

Two compositions comprising anti-LPS immunoglobulin preparations (hyperimmune bovine colostrum) were prepared by vaccinating pregnant cows with bacterial cell wall antigens (e.g. LPS) prepared from a number of *E. coli* strains to produce highly concentrated antibodies (including IgG) to LPS in colostrum. In the following examples, this anti-LPS immunoglobulin preparation is denoted by 'HIBC'.

A second preparation was prepared by vaccinating pregnant cows with a vaccine comprising a number of *E. coli* strains, and also enriched for LPS and other surface antigens, to produce highly concentrated antibodies (including IgG) to LPS in colostrum. IgG was then purified from this colostrum preparation. In the following examples, this composition is denoted by 'T-IgG'

Methods of preparing LPS/O antigen are known in the art and described in WO/2004/078209, which is incorporated herein by reference. Methods of preparing hyperimmune bovine colostrum (HIBC) are also described in WO/2004/078209.

TABLE 1

Experimental design

| Group | DDW | Colostrum preparation (3 mg) | Administration |
|---|---|---|---|
| A N = 10 | 30 ml | — | PO |
| B N = 10 | — | 30 ml | PO |

Experimental Groups.

Two groups of mice (Table 1) were studied. Mice (10 per group) were fed (perorally) daily for 7 days with 30 ul of water (control, group A) or 30 ul (approximately 3 mg) of anti-LPS enriched colostrum-derived immunoglobulin preparation (group B) which was dissolved in water. After 7 days mice were sacrificed. On sacrifice day, cardiac blood was collected by standard techniques then serum was obtained for future purposes.

Animals.

Naïve C57Bl/6 mice (age 11-12 weeks) were used. Mice were obtained from Harlan Laboratories (Jerusalem, Israel) and were maintained in the Animal Core of the Hadassah-Hebrew University Medical School. Mice were administered standard laboratory chow and water ad libitum and kept in a 12-hour light/dark cycle. The animal experiments were carried out according to the guidelines of the Hebrew University-Hadassah Institutional Committee for Care and Use of Laboratory Animals and with the committee's approval.

Liver:

After harvesting the livers are transferred to ice cold PBS cut, minced and homogenized using a dounce homogenizer with 9 ml of sterile cold lysis buffer 1, divided into eppendorff tubes (1.5 ml in each tube), and kept on ice for 30 minutes, followed by sonication (five cycles of 25 seconds) and centrifugation (at 4° C., 14,000 RPM for 15 minutes). The supernatants are collected into one tube, sampled for protein quantification using the Bradford technique and stored at −20° C.

Spleen.

Following excision the spleens are minced on cells dissociation grids (60 mesh) in RPMI 1640 medium, centrifuged (at 4° C., 1,400 RPM for 10 minutes) and the supernatant discarded; Red blood cells are lysed by adding 1 ml of cold RBC lysis buffer (155 mM ammonium chloride), followed by rinsing three times with cold PBS and centrifugation.

Preparation of Cytosolic Fraction of Spleen.

Cold buffer 1 was added to the pellet of spleen cells (in a 6:1 ratio of buffer to pellet) and the cells are divided into 2 ml vials, kept on ice for 30 minutes, sonicated five times (25 seconds each time), and centrifuged (at 4° C., 14,000 RPM for 15 minutes); Supernatants are then collected from all vials, sampled for protein quantification, and kept at −20° C.

Preparation of Membranal Fraction of Spleen.

The remaining pellet from the above mentioned centrifugation step of the cytosolic fractionation is added with 100-250 ml of buffer 2, agitated for 30 minutes at 4° C., and centrifuged (at 4° C., 14,000 RPM for 15 minutes). The supernatants are then collected from all vials, sampled for protein quantification and kept at −20° C.

Isolation of Splenic and Hepatic Lymphocytes for Determination of T Cell Subpopulations.

Mice of different experimental models are sacrificed on the days indicated. Splenic lymphocytes and NKT cells are isolated and red blood cells removed. Intrahepatic lymphocytes are isolated as follows: After cutting the inferior vena cava above the diaphragm, the liver is flushed with cold PBS until it become pale, followed by removal of connective tissue and gall bladder. Livers and spleens were kept in RPMI-1640+FCS. Then spleens were crushed through a 70 m nylon cell strainer (Falcon) and centrifuged (1250 rpm for 7 min) for the removal of cell debris. Red blood cells were lysed with 1 ml of cold 155 mM ammonium chloride lysis buffer and immediately centrifuged (1250 rpm for 3 min). Splenocytes were then washed and resuspended with ImI RPMI+FCS. Remains of connective tissue were removed. The viability by trypan blue staining was above 90%. For intrahepatic lymphocytes, livers were first crushed through a stainless mesh (size 60, Sigma) and the cell suspension was placed in a 50-ml tube for 5 min to enable cell debris to descend. 10 ml of Lymphoprep (Ficoll, Axis-Shield PoC AS, Oslo, Norway) was slowly placed under the same volume of cell suspension in 50-ml tubes. The tubes were then centrifuged at 1800 rpm for 18 min. Cells in the interface were collected and moved to new tubes which were centrifuged again at 1800 rpm for 10 min, to obtain a pellet of cells depleted of hepatocytes to a final volume of 2501. Approximately $1 \times 10^6$ cells/mouse liver, were recovered. Cells viability was detected by trypan blue staining.

Isolation of Adipocytes.

Adipose tissue (visceral fat pads) was minced and incubated in Krebs-Ringer bicarbonate buffer (3 mL/g adipose tissue) containing 10 mM glucose and 2.5% bovine serum albumin, incubated with 840 U/g collagenase type I (Sigma, Rehovot, Israel) at 37° C. with gentle agitation for 1 hour. Then filtered twice through chiffon mesh (100 µm) and centrifuged 50×g for 5 minutes. Floating adipocytes were then separated from the pellet of stromal vasculature (SV) fraction. The lower fraction was removed and centrifuged at 200×g for 5 min to pellet the SV cells. Cell number was then counted.

Flow Cytometery Analysis (FACs) for Determination of Different Subsets of Lymphocytes.

Following lymphocyte isolation from blood, spleen or any organ, triplicates of $2-5 \times 10^5$ cells/500 µL PBS are placed in Falcon 2052 tubes, incubated with 4 mL of 1% BSA for 10 minutes, and centrifuged at 1400 rpm for 5 minutes. Cells are re-suspended in 10 µL FCS with 1:20 labeled (FITC, APC or PE-labeled) primary antibodies directed to the following lymphocyte markers: CD3, CD4, CD8, NK1.1, CD25, FOX p3, LAP cells, IL-17, Annexiin and surface markers for T cell activation. Cells-antibody mixtures are mixed every 10 minutes for 30 minutes. Cells are isolated using anti-CD3 and anti-CD4, anti-CD8, and anti-NK1.1, respectively. Cells are washed twice in 1% BSA and kept at 4° C. until reading. For the control group, only 5 µL of 1% BSA are added. Surface staining was performed by incubating cells with antibodies and anti-CD 16/32 (blocks Fc, eBioscience) at 4° C. in FACS buffer containing PBS and 0.5% BSA, for 30 min. Cells were further washed twice with FACS buffer, resuspended in FACS buffer, and analyzed by flow cytometry. Analytical cell sorting is performed on $1 \times 10^4$ cells from each group with a fluorescence-activated cell sorter (FACStar Plus, Becton Dickinson). Appropriate isotype controls were used in all experiments. Analysis was performed using a FACSCalibur instrument (Becton Dickinson, San Jose, Calif.). Only live cells were counted, and background fluorescence from non-antibody-treated lymphocytes was subtracted. Gates were set on forward- and side-scatters to exclude dead cells and red blood cells. Data was analyzed by the Consort 30 two-color contour plot (Becton Dickinson, Oxnard, Calif., USA) or Cell Quest programs.

FACS Analysis for Determination of NKT Lymphocyte Percentage.

Immediately after lymphocyte isolation, triplicates of $2-5 \times 10^4$ cells/500 µl PBS are placed into Falcon 2052 tubes, incubated with 4 ml of 1% BSA for 10 minutes, and centrifuged at 350 g for 5 minutes. For determination of the percentage of NKT lymphocytes, anti-CD3 and anti DX5 antibodies are used (Pharmingen, USA). Analytical cell sorting is performed on $1 \times 10^4$ cells from each group with a fluorescence-activated cell sorter (FACSTAE plus, Becton Dickinson). Only live cells are counted, and background fluorescence from non-antibody-treated lymphocytes is subtracted. Gates are set on forward- and side-scatters to exclude dead cells and red blood cells. Data is analyzed with the Consort 30 two-color contour plot program (Becton Dickinson, Oxnard, Calif.), or the CELLQuest 25 program.

Isolation of NKT Lymphocytes.

Cell separation is performed using Magnetic Cell Sorting (MACS, Miltenyi Biotec, Germany) according to the manufacturer's instructions. Anti-CD 3 and anti-DX5 magnetic beads are used for separation of NKT lymphocytes. Beads are removed between the two steps according to the manufacturer's instructions. Above 95% accuracy is achieved by FACS analysis of cells.

Hepaotcellular Damage.

Liver injury was evaluated by serum aspartic transaminase (AST) and alanine aminotransferase (ALT) activities, which were determined with an automatic analyzer.

Measurements.

The following parameters were measured: blood glucose, total cholesterol and triglyceride. Blood glucose values were measured with a standard glucometer. Plasma triglyceride and total cholesterol values were measured by a clinical chemistry analyzer Reflovet Plus machine (Roche Diagnostics, GmbH, Mannheim, Germany).

Glucose Tolerance Test.

Mice were subjected to a glucose tolerance test (GTT) on day 30 after overnight fasting. Glucose was administered orally (1.25 g per kg). Serum glucose measurements were performed on tail-vein blood every 15 minutes for 3 hours. Glucose levels were measured by a standard glucometer.

Glucose Morning Levels.

Study groups were also evaluated by resting (non-fasting) morning glucose levels.

Cytokine Determination.

IFN-γ and TGF-β levels were determined on serum by "sandwich" ELISA, using commercial kits (Quantikine, R&D Systems, Minneapolis, Minn., USA). Serum insulin was also determined by "sandwich" ELISA, using the commercial kit of Mercodia AB (Uppsala, Sweden) according to the manufacturer's instructions.

Statistics.

Statistical significance was determined by unpaired, two-tailed Student's t test and only values of $p<0.05$ are shown.

Triglyceride Measurement.

On the day indicated, serum triglyceride levels are measured using a spectrophotometer (Cobas DP-25P).

Liver Steatohepatitis Score.

A liver segment from each mouse was fixed in 10% formaldehyde and embedded in paraffin for histological analysis. Five sections (5 μm) are stained with hematoxylin/eosin and reviewed by two pathologists in a blinded fashion. Histological examination and the steatohepatitis grade scoring (NASH score) are performed using the steatohepatitis scoring system.

Histological Examination.

Hematoxylin/eosin staining of paraffin-embedded liver sections is performed. Sections are examined by two experienced pathologists (VD, YS) that are blinded to the experiment conditions.

Example 4: Oral Administration of Anti-LPS Enriched Colostrum-Derived Immunoglobulin Preparation Decreases Liver Enzymes The inventors evaluated whether the liver enzyme levels, which indicate liver injury, of animals orally administered with anti-LPS enriched colostrum-derived immunoglobulin preparation are improved due to the treatment. Levels of aspartyl transaminase (AST) and alanine aminotransferase (ALT) activities were determined by a clinical chemistry analyzer, Reflovet Plus (Roche Diagnostics, GmbH, Mannheim, Germany). FIG. 1 demonstrates the decrease was significant for AST group A versus B (*$p<0.001$). This demonstrates amelioration of liver injury, as manifested by a clear and significant decrease in ALT and AST serum levels vs. the control group.

Example 5: Oral Anti-LPS Enriched Colostrum-Derived Immunoglobulin Preparation Increases the Expression of CD4+CD25+ Regulatory T Cells in the Liver Isolation of intrahepatic lymphocytes. Intrahepatic lymphocytes were isolated after mice were sacrificed, as follows: After the removal of livers, they were kept in medium (RPMI-1640+FCS). Then, livers were crushed through a stainless mesh (size 60, Sigma) and the cell suspension was placed in a 50-ml tube for 5 min. Lymphoprep (10 ml, Ficoll, Axis-Shield PoC AS, Oslo, Norway) was placed under similar volume of cell suspension in 50-ml tubes. Tubes were centrifuged at 1800 rpm for 18 min. Cells in the interface were collected and centrifuged at 1800 rpm for 10 min, to obtain a pellet of cells depleted of hepatocytes to a final volume of 250 ul. Approximately $1\times10^6$ cells/mouse liver, were recovered and analyzed by flow cytometry.

Flow Cytometry.

Surface two to three color staining of cells were done with the following surface antibodies: anti-CD4-FITC and anti-CD25-PE. (Antibodies were purchased from eBioscience, San Diego, Calif.). Surface staining was performed by incubating freshly isolated cells with antibodies and anti-CD16/32 (blocks Fc, eBioscience) at 4° C. in FACS buffer containing PBS and 0.5% BSA, for 30 min. Cells were washed twice with FACS buffer, resuspended in FACS buffer, and analyzed by flow cytometry. Appropriate isotype controls were used in all experiments. Analysis was performed using a FACSCalibur instrument (Becton Dickinson, San Jose, Calif.) with FCS express V.3 software (DeNovo software, Los Angeles, Calif.).

Statistical Analysis.

Statistical analysis was performed using the student t test. $P<0.05$ was considered significant.

Figure 2A:
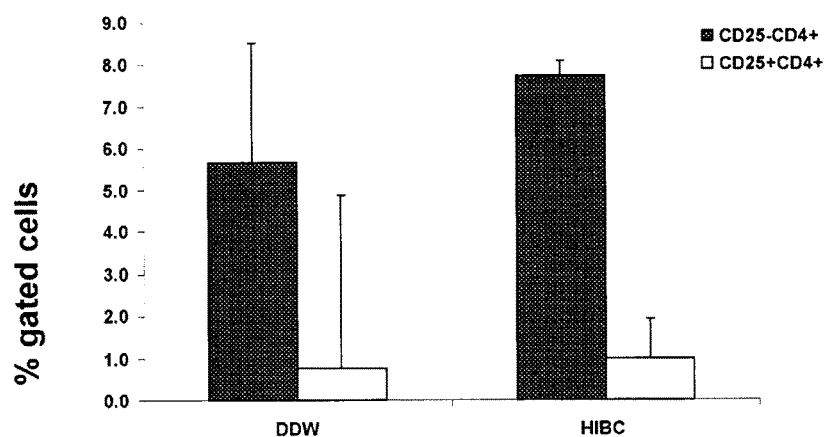
FIG. 2A-B: Oral anti-LPS enriched colostrum-derived immunoglobulin preparation increases the expression of CD4+CD25+ regulatory T cells in the liver. A; average surface expression of markers on lymphocytes. Values are mean±SD. B; A representative dot blot derived from FACS analysis.

To determine the specificity of the increase in regulatory T cells in the liver, the average surface expression of markers (CD4+CD25+) on hepatic lymphocytes was measured using flow cytometry on day 7 (sacrifice day) in all mice treated with 3.0 mg anti-LPS enriched colostrum-derived immunoglobulin preparation. FIG. 2A demonstrates oral anti-LPS enriched colostrum-derived immunoglobulin preparation increases the expression of CD4+CD25+ regulatory T cells in the liver. Gating was on CD4 and values are mean±SD.

Figure 2B:
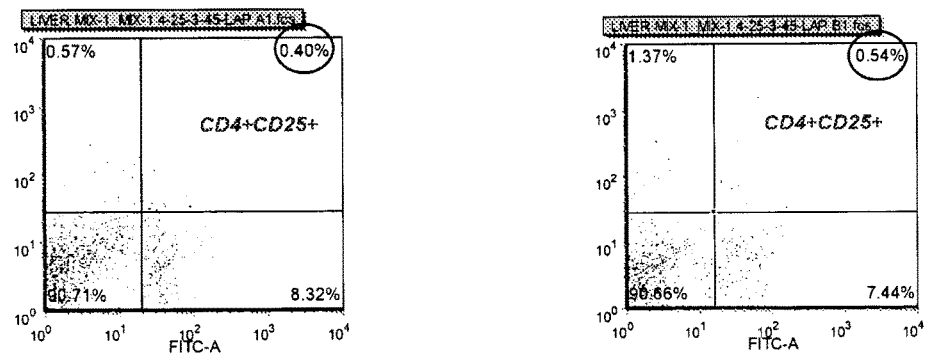

A representative dot blot derived from FACS performed on lymphocytes isolated from the livers of mice treated with anti-LPS enriched colostrum-derived immunoglobulin preparation (group B) or from untreated controls (group A) is shown in FIG. 2B which shows oral anti-LPS enriched colostrum-derived immunoglobulin preparation increases the expression of CD4+CD25+ regulatory T cells in the liver.

Example 6: Oral Anti-LPS Enriched Colostrum-Derived Immunoglobulin Preparation Increases the Expression of CD25+CD4+LAP−, CD45+LAP+ and CD3+LAP+ Regulatory T Cells in the Liver Isolation of intrahepatic lymphocytes and FACS analysis was performed as described above.

Flow Cytometry.

For LAP staining the following antibodies were used: anti-CD3-Alexa-fluor 405, anti-CD45-PerCP-Cy5.5 and anti-LAP-APC. Affinity-purified biotinylated goat anti-LAP specific polyclonal antibody was purchased from R&D Systems (Minneapolis, Minn., USA), and strepavidin-APC was used as secondary reagent for detecting the biotinylated primary antibody (R&D). For LAP staining cells were preincubated with LAP/control antibody for 20 min, and stained with CD3-Alexa-fluor 405 or CD45-PerCP-Cy5.5, followed by strepavidin-APC staining.

Figure 3A:
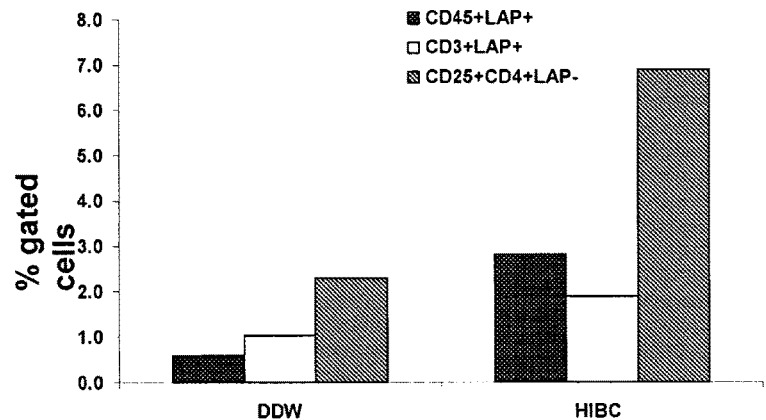
FIG. 3A-B: Oral anti-LPS enriched colostrum-derived immunoglobulin preparation increases the expression of CD25+CD4+LAP−, CD45+LAP+ and CD3+LAP+ regulatory T cells in the liver. Values are means. A; average surface expression of markers on lymphocytes. B; A representative dot blot derived from FACS analysis.
Figure 3B:
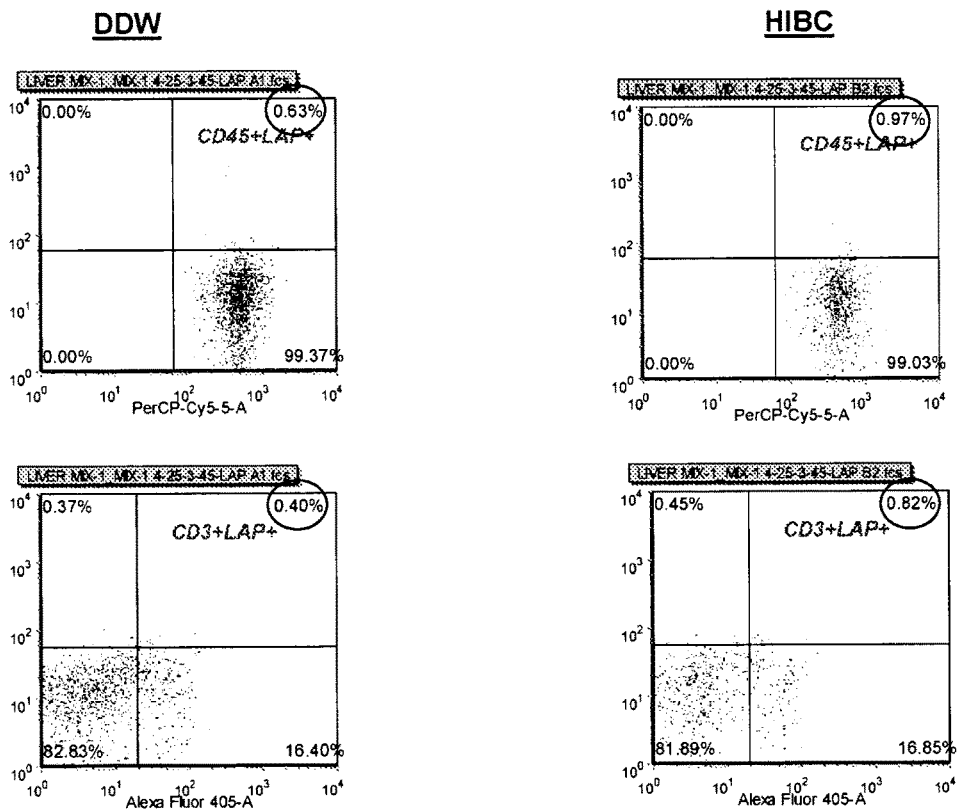

In order to determine whether oral anti-LPS enriched colostrum-derived immunoglobulin preparation promotes Tregs, the inventors examined the effect of oral administration on the tissue derived subsets of regulatory T cells. FIG. 3 shows the average surface expression of markers (CD25+CD4+LAP−, CD45+LAP+ and CD3+LAP+) on hepatic lymphocytes measured using flow cytometry on day 7 (sacrifice day) in all mice treated with 3.0 mg. Values are means. FIGS. 3A and B demonstrate oral administration of anti-LPS enriched colostrum-derived immunoglobulin preparation increased a subset of CD25+CD4+LAP−, CD45+LAP+ and CD3+LAP+ regulatory T cells in the liver.

Figure 4A:
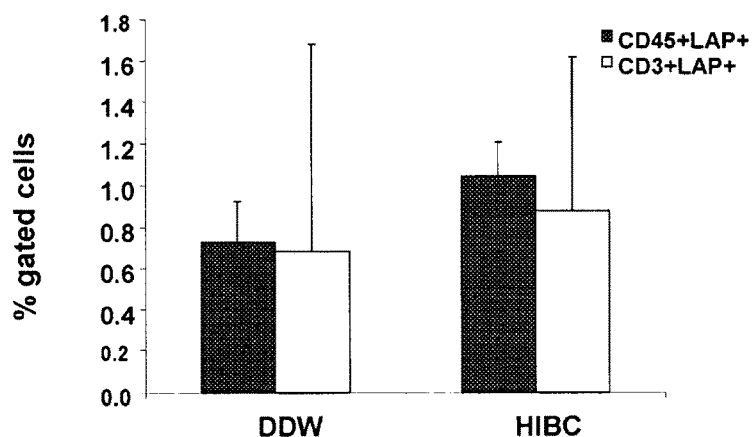
FIG. 4A-B: Oral anti-LPS enriched colostrum-derived immunoglobulin preparation increases the expression of CD45+LAP+ and CD8+LAP+ regulatory T cells in the spleen. A; average surface expression of markers on lymphocytes. Values are mean±SD. B; A representative dot blot derived from FACS analysis.
Figure 4B:
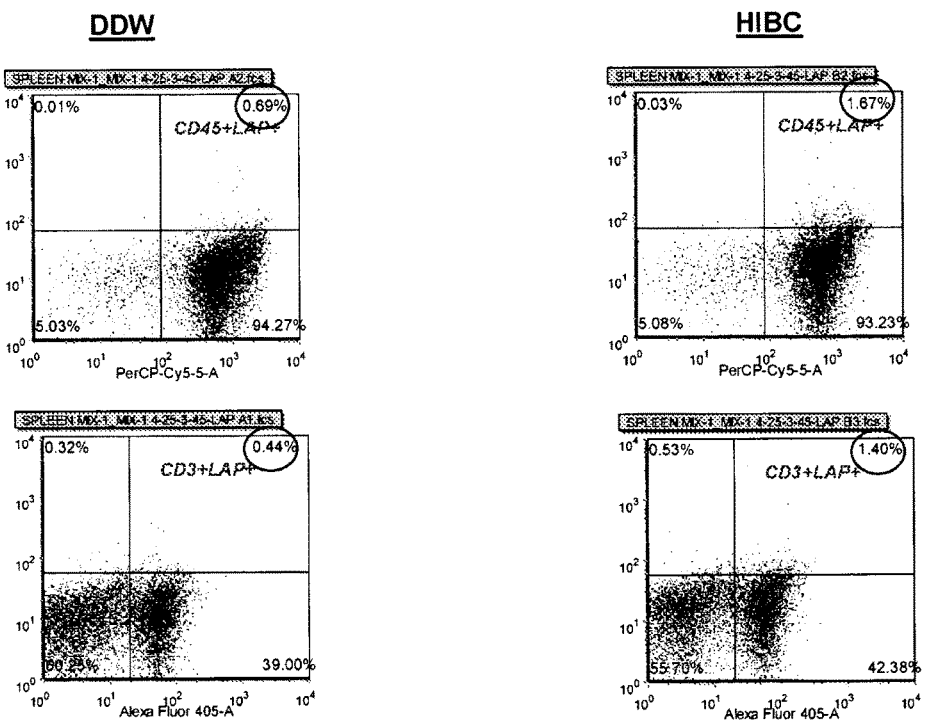

Example 7: Oral Anti-LPS Enriched Colostrum-Derived Immunoglobulin Preparation Increases the Expression of CD45+LAP+ and CD8+LAP+ Regulatory T Cells in the Spleen In order to determine whether oral anti-LPS enriched colostrum-derived immunoglobulin preparation promotes Tregs, the inventors examined the effect of oral administration on the tissue derived subsets of regulatory T cells in the spleen. FIG. 4 shows the average surface expression of markers (CD45+LAP+ and CD8+LAP+) on splenic lymphocytes measured using flow cytometry on day 7 (sacrifice day) in all mice treated with 3.0 mg. Values are mean±SD. FIGS. 4A and B demonstrate oral administration of anti-LPS enriched colostrum-derived immunoglobulin preparation increases a subset of CD45+LAP+ and CD8+LAP+ regulatory T cells in the spleen.

Example 8: Oral Administration of Colostrum Enriched with Anti LPS Antibodies to Ob/Ob Mice Experimental Groups.

Three groups of mice (Table 2) were studied. Ob/Ob mice (4 per group) were fed (PO) daily for 25 days (5 days a week) with 30 ul of PBS (control, group A) or 30 ul (=100 ug) of T-IgG colostrum (group B) which was dissolved in water, or with or 30 ul (=100 ug) of anti-LPS enriched colostrum-derived immunoglobulin preparation (group C). After 4 weeks mice were sacrificed. On sacrifice day, cardiac blood was collected by standard techniques then serum was obtained.

TABLE 2

| Experimental design | | | |
|---|---|---|---|
| Group | PBS | T-IgG | HIBC |
| A<br>N = 4 | 30 ul | — | — |
| B<br>N = 4 | — | 100 ug/ml | — |
| C<br>N = 4 | — | — | 100 ug/ml |

Animals.

For the Ob/Ob model, we used young (age 6-7 weeks) male C57BL/6 Ob/Ob mice which were purchased from Harlan Laboratories (USA). All mice were maintained in the Animal Core of the Hadassah-Hebrew University Medical School. Mice were administered standard laboratory chow and water ad libitum and kept in a 12-hour light/dark cycle. The animal experiments were carried out according to the guidelines of the Hebrew University-Hadassah Institutional Committee for Care and Use of Laboratory Animals and with the committee's approval.

Example 9: Oral T-IgG Decreases Serum Insulin in Ob/Ob Mice

Figure 5:
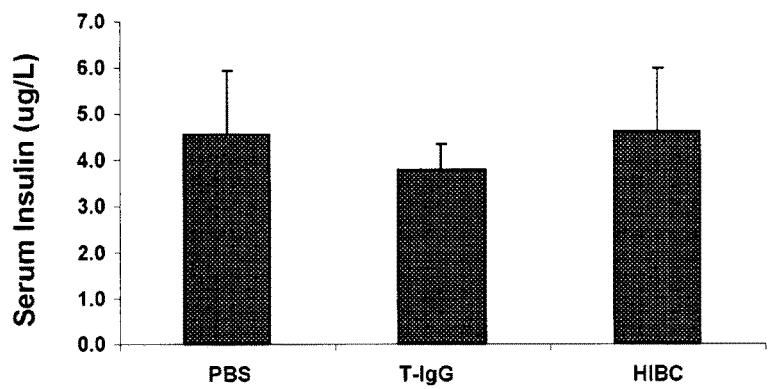
FIG. 5: Oral T-IgG-Colostrum decreases serum insulin in Ob/Ob mice. Values are mean±SD.

To further assess the effect of oral anti-LPS enriched colostrum-derived immunoglobulin preparation, levels of fasting serum insulin were determined in mice of groups A-C following four weeks of T-IgG or HIBC administered orally. Serum insulin was determined by "sandwich" ELISA, using the commercial kit of Mercodia AB (Uppsala, Sweden) according to the manufacturer's instructions. Sera were collected from Ob/Ob mice on day 30 after sacrificing the mice. FIG. 5 demonstrates mice administered T-IgG exhibited a decrease in serum insulin levels, indicating the beneficial impact of the anti LPS antibodies on insulin resistance. Moreover, the decrease observed in provides data in support of an important role for the colostrum derived adjuvants in the metabolic effect.

Example 10: Oral Anti-LPS Enriched Colostrum-Derived Immunoglobulin Preparation Decreases Glucose Tolerance in Ob/Ob Mice In order to examine whether oral anti-LPS enriched colostrum-derived immunoglobulin preparation can decrease in serum glucose levels, Ob/Ob mice underwent a glucose tolerance test (GTT) on day 30 after overnight fasting. Glucose was administered orally (1.25 g per kg). Serum glucose measurements were performed on tail-vein blood every 15 min for 3 h. Glucose levels were measured by a standard glucometer.

Figure 6:
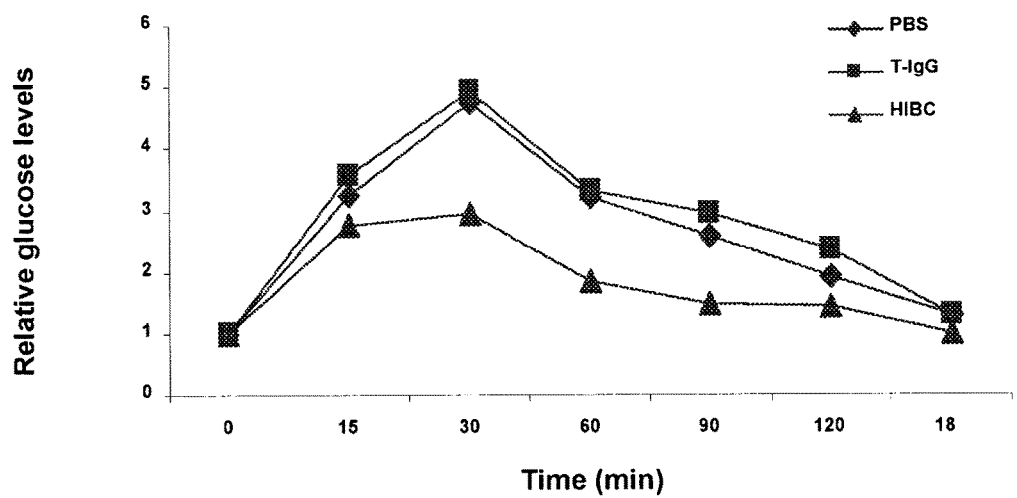
FIG. 6: Oral anti-LPS enriched colostrum-derived immunoglobulin preparation decreases glucose tolerance in Ob/Ob mice.

As shown in FIG. 6, mice administered HIBC improved glucose tolerance demonstrated by lower glucose values at glucose tolerance test with a decrease in the area under the curve as compared to the control group. Taken together, the data obtained in Examples 9 and 10 supports the importance of HIBC according to the present invention in the improvement of the metabolic syndrome.

Figure 7:
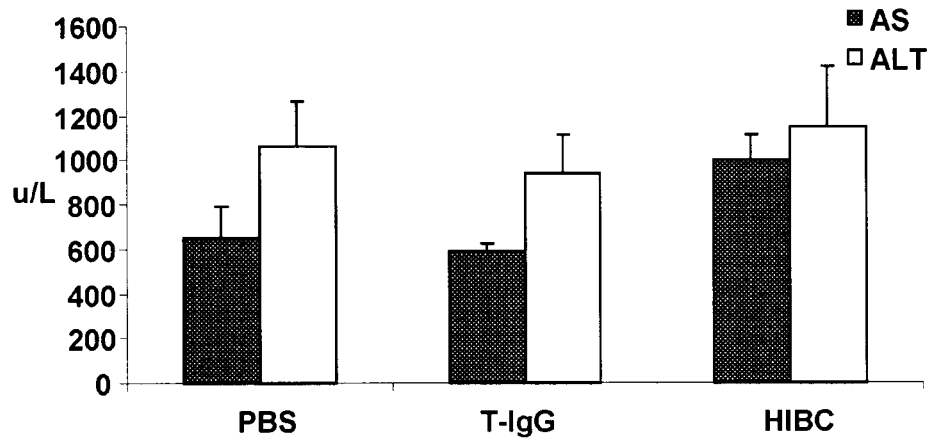
FIG. 7: Oral administration of anti-LPS enriched colostrum-derived immunoglobulin preparation decreases liver injury in Ob/Ob mice. Values are mean±SD. AST; aspartic transaminase, and ALT; alanine aminotransferase.

Example 11: Oral Administration of Anti-LPS Enriched Colostrum-Derived Immunoglobulin Preparation Decreases Liver Injury in Ob/Ob Mice Having shown that oral administration of anti-LPS enriched colostrum-derived immunoglobulin preparation improves various metabolic syndrome markers, such as decreasing glucose tolerance and decreasing serum insulin, the inventors next evaluated whether the liver enzyme levels, which indicate liver injury, of animals fed with the preparation have also improved due to the treatment. Levels of AST and ALT activities were determined by a clinical chemistry analyzer, Reflovet Plus (Roche Diagnostics, GmbH, Mannheim, Germany). FIG. 7 demonstrates a decrease of AST and ALT levels in T-IgG-colostrum-treated mice.

Example 12: Oral Administration of Anti-LPS Enriched Colostrum-Derived Immunoglobulin Preparation Decreases Hepatic TGs in Ob/Ob Mice Having shown that oral administration of anti-LPS enriched colostrum-derived immunoglobulin preparation improves various metabolic syndrome markers, the effect of oral administration of anti-LPS enriched colostrum-derived immunoglobulin preparation and T-IgG colostrums on hepatic triglycerides accumulation was determined at the end of the study, after sacrificing the mice. Accumulation of intracellular triglycerides (TGs) within the liver was quantified using a modification of the Folch method. TGs were extracted from aliquots of snap-frozen livers and then assayed spectrophotometrically using the GPO-Trinder kit (Sigma, Rehovot, Israel) and were normalized to the protein content in the homogenate. Heaptic triglyceride content was calculated on all treated and control groups.

Figure 8:
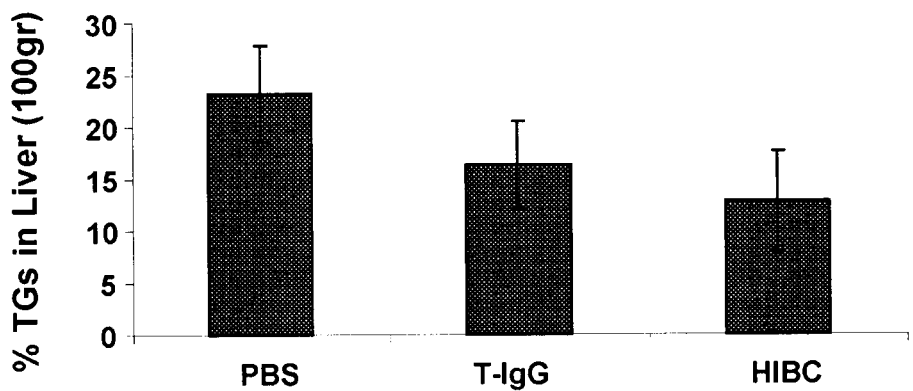
FIG. 8: Oral administration of anti-LPS enriched colostrum-derived immunoglobulin preparation decreases hepatic triglycerides (TGs) in Ob/Ob mice. Values are mean±SD

FIG. 8 demonstrates that oral administration anti-LPS enriched colostrum-derived immunoglobulin preparation decreased hepatic triglyceride content compared to mice in the control group. The decrease was significant for HIBC relative to controls (*P<0.04).

Figure 9A:
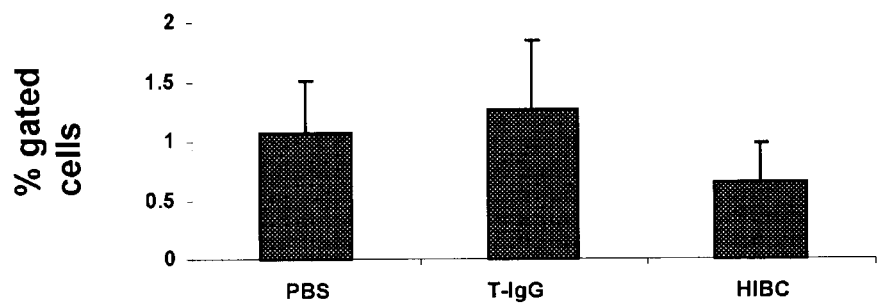
FIG. 9A-B: Oral administration of anti-LPS enriched colostrum-derived immunoglobulin preparation increases the expression of CD3+LAP+ regulatory T cells in the spleen. A; average surface expression of markers on lymphocytes. Values are mean±SD. B; A representative dot blot derived from FACS analysis.
Figure 9B:
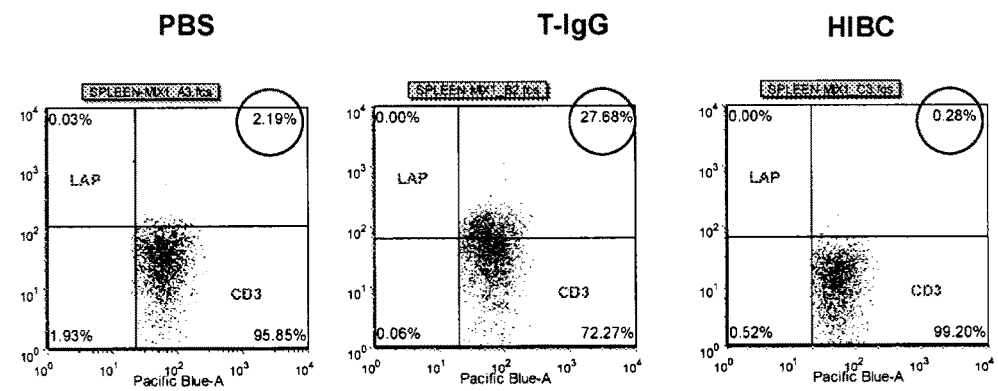

Example 13: Oral Administration of Anti-LPS Enriched Colostrum-Derived Immunoglobulin Preparation Increases the Expression of CD3+LAP+ Regulatory T Cells in the Spleen In order to determine whether oral anti-LPS enriched colostrum-derived immunoglobulin preparation promotes Tregs, the inventors examined the effect of oral administration on the tissue derived subsets of regulatory T cells in the spleen. FIG. 9 shows the average surface expression of markers (CD3+LAP+) on splenic lymphocytes measured using flow cytometry on day 25 (sacrifice day) in all Ob/Ob mice. Values are mean±SD. FIGS. 9A and B demonstrate oral administration of T-IgG increases a subset of CD3+LAP+ regulatory T cells in the spleen.

Figure 10:
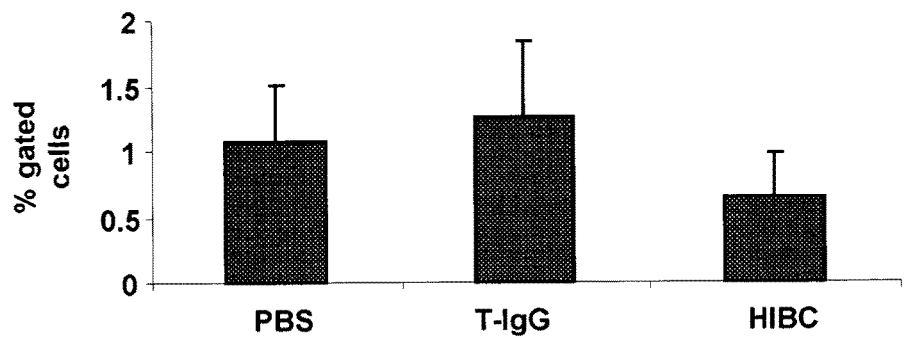
FIG. 10: Oral administration of anti-LPS enriched colostrum-derived immunoglobulin preparation increases the expression of CD8+CD25+ regulatory T cells in the spleen. Values are mean±SD
Figure 11:
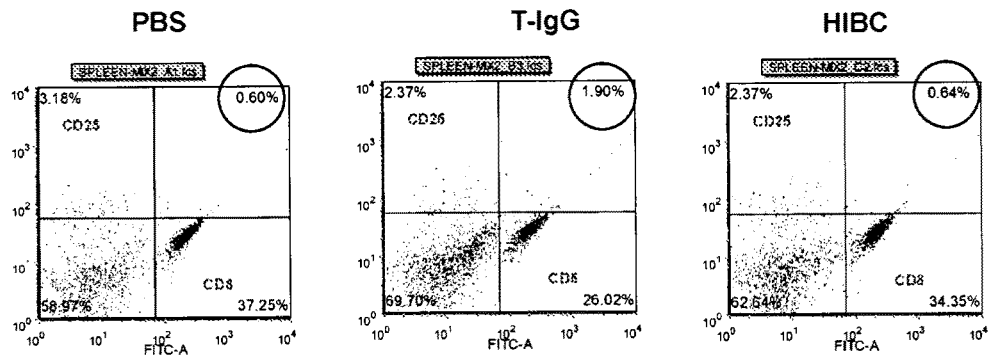
FIG. 11: Oral administration of anti-LPS enriched colostrum-derived immunoglobulin preparation increases the expression of CD8+CD25+ regulatory T cells in the spleen. Shown is a representative dot blot derived from FACS analysis.

Example 14: Oral Administration of Anti-LPS Enriched Colostrum-Derived Immunoglobulin Preparation Increases the Expression of CD8+CD25+ Regulatory T Cells in the Spleen In order to determine whether oral anti-LPS enriched colostrum-derived immunoglobulin preparation promotes Tregs, the inventors examined the effect of oral administration on the tissue derived subsets of regulatory T cells in the spleen. Isolation of splenic lymphocytes, flow cytometry procedures and analysis and staining antibodies, are the same as described above. FIGS. 10 and 11 show the average surface expression of markers (CD8+CD25+) on splenic lymphocytes measured using flow cytometry on day 25 (sacrifice day) in all Ob/Ob mice. Values are mean±SD.

FIGS. 10 and 11 demonstrate oral administration of T-IgG increases a subset of CD8+CD25+ regulatory T cells in the spleen.

Figure 12A:
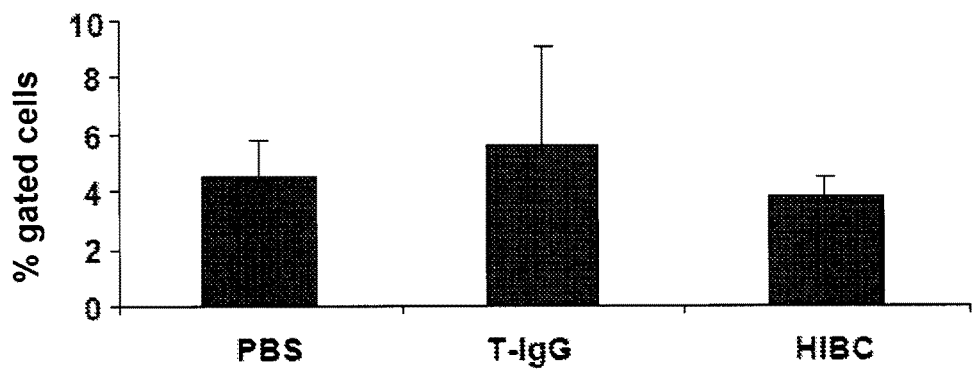
FIG. 12A-B: Oral anti-LPS enriched colostrum-derived immunoglobulin preparation increases the expression of CD4+CD25+ regulatory T cells in adipose tissue. A; average surface expression of markers on lymphocytes. Values are mean±SD. B; A representative dot blot derived from FACS analysis.
Figure 12B:
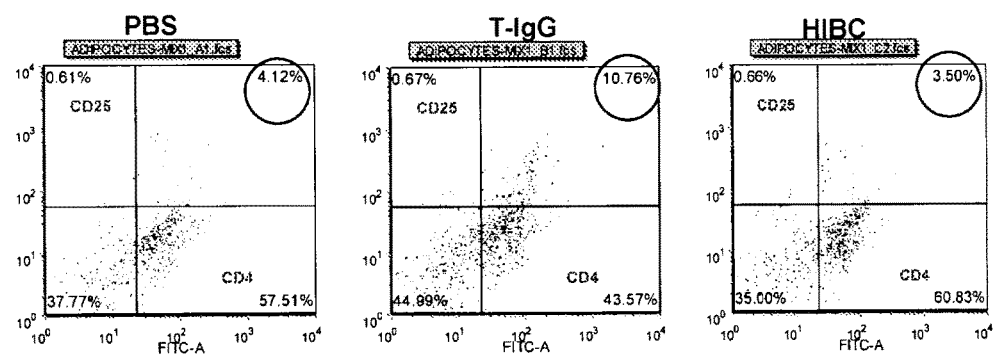

Example 15: Oral Anti-LPS Enriched Colostrum-Derived Immunoglobulin Preparation Increases the Expression of CD4+CD25+ Regulatory T Cells in Adipose Tissue In order to determine whether oral anti-LPS enriched colostrum-derived immunoglobulin preparation promotes Tregs in adipose tissue, the inventors examined the effect of oral administration on the tissue derived subsets of regulatory T cells. FACS analysis was performed on lymphocytes isolated from adipose tissue. Adipose tissue was isolated from Ob/Ob mice immediately after sacrifice. Tissues (visceral fat pads) were minced into fine pieces. Minced samples were placed in Krebs-Ringer bicarbonate buffer (3 mL/g adipose tissue) containing 10 mM glucose and 2.5% bovine serum albumin, incubated with 840 U/g collagenase type I (Sigma, Rehovot, Israel) at 37° C. for 1 hour. Cells were filtered twice through chiffon mesh (100 um) and centrifuged 50 g for 5 min. Floating adipocytes were separated from pelleted adipose tissue-associated stromal-vascular (S/V) cells. fraction: The infranatant fraction was removed and centrifuged at 200 g for 5 min to pellet the S/V cells. FIGS. 12A and 12B show the average surface expression of markers (CD4+CD25+) on adipose tissue lymphocytes measured using flow cytometry on day 25 (sacrifice day) in all Ob/Ob mice.

FIG. 12 demonstrates oral administration of T-IgG increases a subset of CD4+CD25+ regulatory T cells in adipose tissue.

Figure 13A:
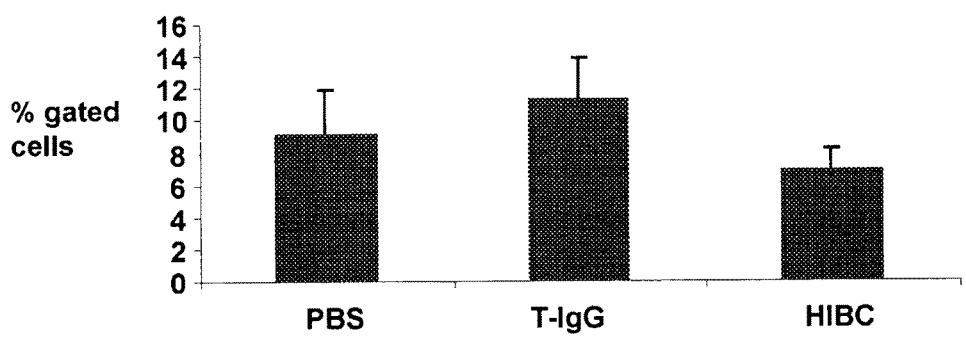
FIG. 13A-B. Oral anti-LPS enriched colostrum-derived immunoglobulin preparation increases the expression of CD3+LAP+ regulatory T cells in adipose tissue. A; average surface expression of markers on lymphocytes. Values are mean±SD. B; A representative dot blot derived from FACS analysis.
Figure 13B:
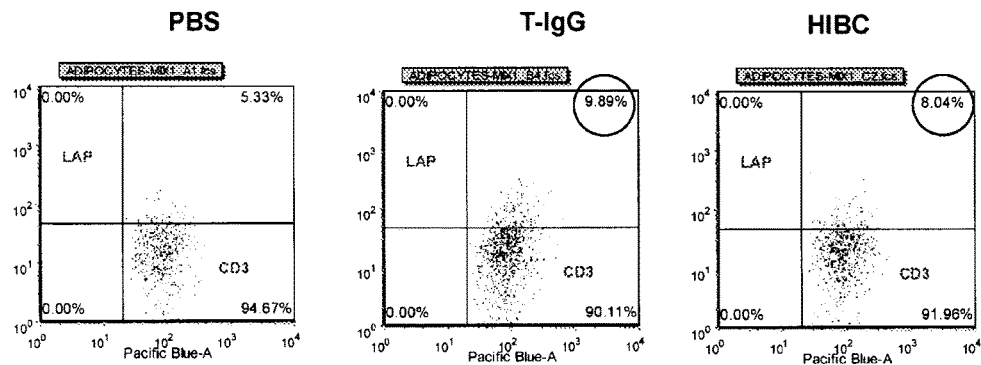

Example 16: Oral Anti-LPS Enriched Colostrum-Derived Immunoglobulin Preparation Increases the Expression of CD3+LAP+ Regulatory T Cells in Adipose Tissue In order to determine whether oral anti-LPS enriched colostrum-derived immunoglobulin preparation promotes Tregs in adipose tissue, the inventors examined the effect of oral administration on the tissue derived subsets of regulatory T cells. FACS analysis was performed on lymphocytes isolated from adipose tissue isolated according to the method discussed above. FIGS. 13A and 13B show the average surface expression of markers (CD3+LAP+) on adipose tissue lymphocytes measured using flow cytometry on day (sacrifice day) in all Ob/Ob mice.

FIG. 13 demonstrates oral administration of T-IgG increases a subset of CD3+LAP+ regulatory T cells in adipose tissue.

Example 17: Oral Anti-LPS Enriched Colostrum-Derived Immunoglobulin Preparation Increases the Expression of CD4+CD25+ Regulatory T Cells in Stromal Vascular Cells (Containing Preadipocytes)

In order to determine whether oral anti-LPS enriched colostrum-derived immunoglobulin preparation promotes Tregs in adipose tissue, the inventors examined the effect of oral administration on the tissue derived subsets of regulatory T cells. FACS analysis was performed on lymphocytes isolated from Stromal Vascular Cells containing preadipocytes isolated according to the method discussed above.

Figure 14A:
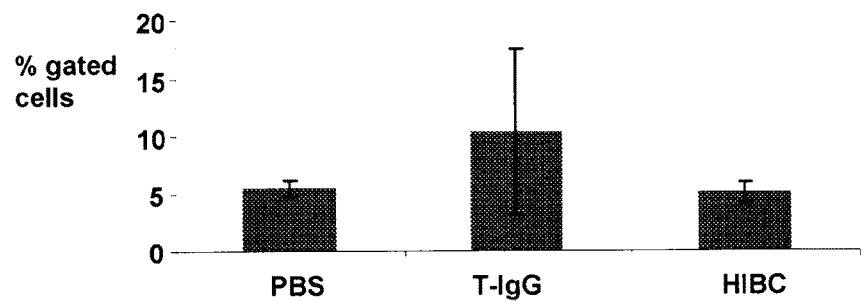
FIG. 14A-B: Oral anti-LPS enriched colostrum-derived immunoglobulin preparation increases the expression of CD4+CD25+ regulatory T cells in Stromal Vascular Cells (containing preadipocytes). A; average surface expression of markers on lymphocytes. Values are mean±SD. B; A representative dot blot derived from FACS analysis.
Figure 14B:
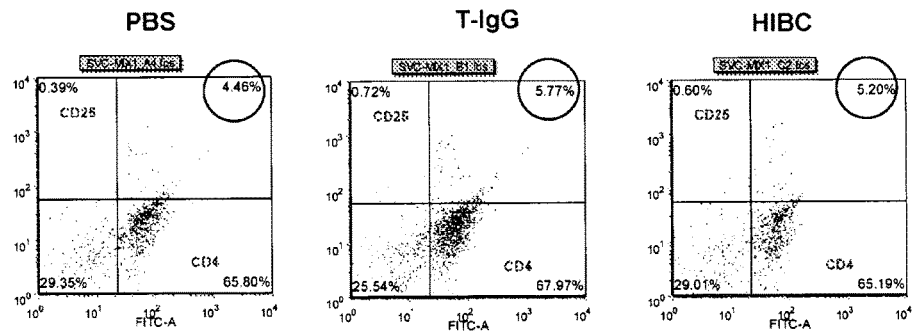

FIGS. 14A and 14B show the average surface expression of markers (CD4+CD25+) on adipose tissue lymphocytes measured using flow cytometry on day 25 (sacrifice day) in all Ob/Ob mice.

FIG. 14 demonstrates oral administration of T-IgG increases a subset of CD4+CD25+ regulatory T cells in the Stromal Vascular Cells containing preadipocytes.

To further investigate this population of cells, FACS analysis was performed on lymphocytes isolated from Stromal Vascular Cells to examine the expression of markers (CD4+CD25+LAP+) (on day 25 (sacrifice day) in all ob/ob mice.)

Figure 15A:
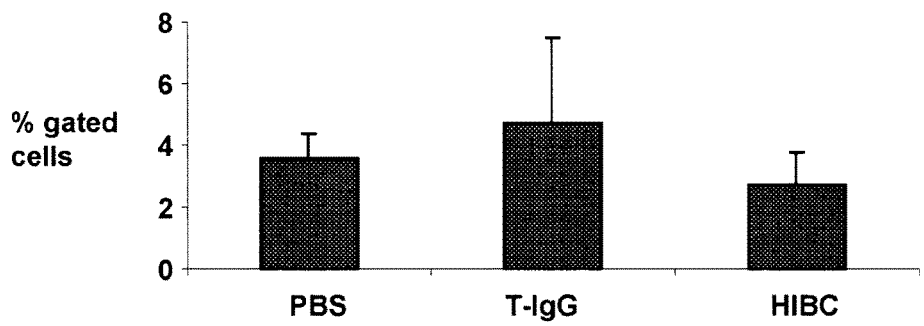
FIG. 15A-B: Oral anti-LPS enriched colostrum-derived immunoglobulin preparation increases the expression of CD4+CD25+LAP+ lymphocytes in Stromal Vascular Cells (containing preadipocytes). A; average surface expression of markers on lymphocytes. Values are mean±SD. B; A representative dot blot derived from FACS analysis.
Figure 15B:
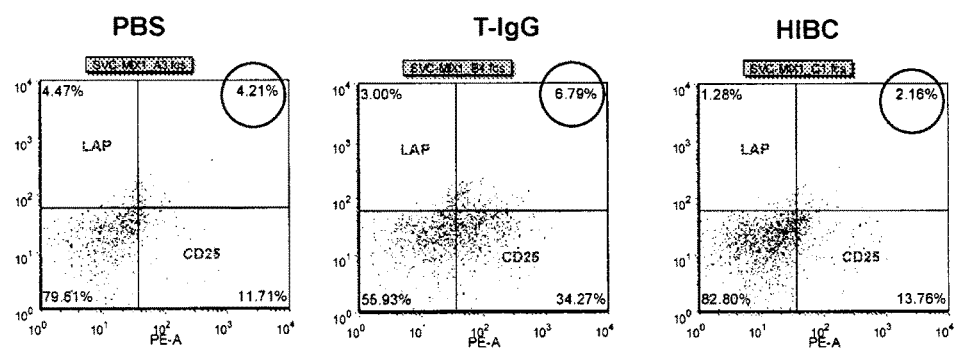

FIGS. 15A and 15B show the average surface expression of markers (CD4+CD25+LAP+) on adipose tissue lymphocytes measured using flow cytometry on day (sacrifice day) in all Ob/Ob mice.

FIG. 15 demonstrates oral administration of T-IgG increases a subset of CD4+CD25+ regulatory T cells in the Stromal Vascular Cells containing preadipocytes.

Example 18: Dosage Studies of Anti-LPS Enriched Colostrum-Derived Immunoglobulin Preparation in Ob/Ob Mice

TABLE 3

Experimental design

| Group | PBS | T-IgG | T-IgG | T-IgG | T-IgG | HIBC |
|---|---|---|---|---|---|---|
| A<br>N = 5 | 30 ul | — | — | — | — | — |
| B<br>N = 5 | — | 1 ug | — | — | — | — |
| C<br>N = 5 | — | — | 100 ug | — | — | — |
| D<br>N = 5 | — | — | — | 1 mg | — | — |
| E<br>N = 5 | — | — | — | — | 3 mg | — |
| F<br>N = 5 | — | — | — | — | — | 100 ug |

Experimental Groups.

Six groups of mice (Table 3) were studied. Ob/Ob mice (5 per group) were fed (PO) daily for 25 days (5 days a week) with 30 ul of PBS (control, group A) or 30 ul (=1 ug) of T-IgG colostrum (group B), or 30 ul (=100 ug) of T-IgG colostrum (group C) or 30 ul (=1 mg) of T-IgG colostrum (group D) or 30 ul (=3 mg) of T-IgG colostrum (group E) or 30 ul (=100 ug) of HIBC colostrum (group F). Both colostrum preparations were dissolved in water.

After 4 weeks mice were sacrificed. On sacrifice day, cardiac blood was collected by standard techniques then serum was obtained for future purposes.

Animals.

For the Ob/Ob model, we used young (age 6-7 weeks) male C57BL/6 Ob/Ob mice which were purchased from Harlan Laboratories (USA). All mice were maintained in the Animal Core of the Hadassah-Hebrew University Medical School. Mice were administered standard laboratory chow and water ad libitum and kept in a 12-hour light/dark cycle. The animal experiments were carried out according to the guidelines of the Hebrew University-Hadassah Institutional Committee for Care and Use of Laboratory Animals and with the committee's approval.

Figure 16:
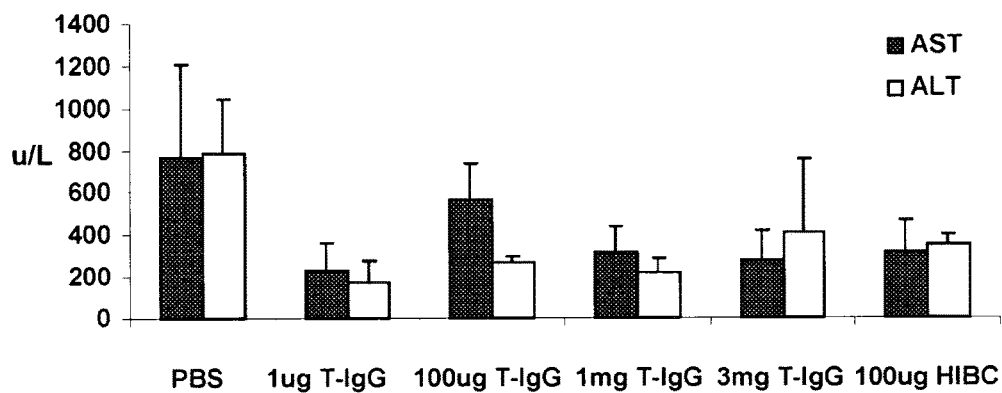
FIG. 16: Oral anti-LPS enriched colostrum-derived immunoglobulin preparation decreases liver enzymes in Ob/Ob mice. Values are mean±SD. AST; aspartic transaminase, and ALT; alanine aminotransferase.

Example 19: Oral Administration of Anti-LPS Enriched Colostrum-Derived Immunoglobulin Decreases Liver Enzymes in Ob/Ob Mice Levels of AST and ALT activities were determined by a clinical chemistry analyzer, as described above. FIG. 16 demonstrates 1 mg of T-IgG was the most effective dose in decreasing liver enzymes.

Figure 17:
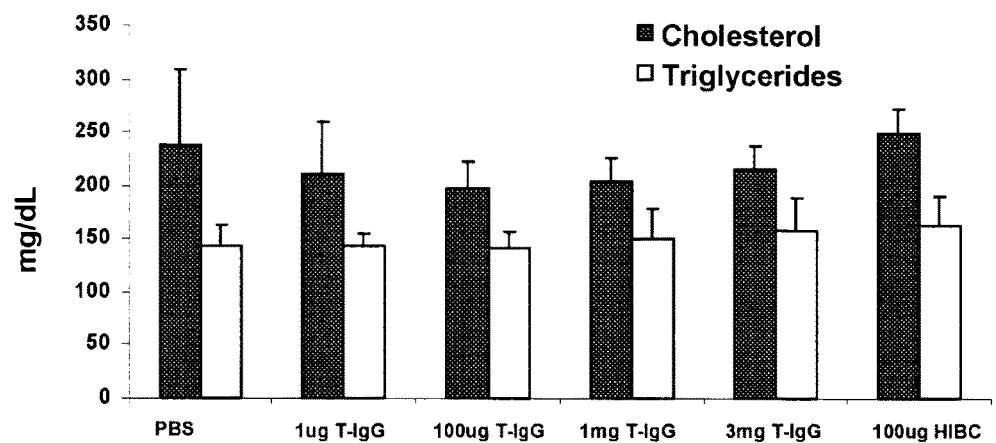
FIG. 17: Oral anti-LPS enriched colostrum-derived immunoglobulin preparation decreases total cholesterol in Ob/Ob mice. Values are mean±SD.

Example 20: Oral Administration of Anti-LPS Enriched Colostrum-Derived Immunoglobulin Decreases Total Cholesterol in Ob/Ob Mice Plasma triglycerides and total cholesterol were determined by a clinical chemistry analyzer, Reflovet Plus (Roche Diagnostics, GmbH, Mannheim, Germany) as described above. FIG. 17 demonstrates 100 ug of T-IgG was the most effective dose in decreasing total cholesterol.

Example 21: Oral Administration of Anti-LPS Enriched Colostrum-Derived Immunoglobulin Decreases Hepatic TGs in Ob/Ob Mice Accumulation of intracellular triglycerides (TGs) within the liver was quantified using a modification of the Folch method. TGs were extracted from aliquots of snap-frozen livers and then assayed spectrophotometrically using the GPO-Trinder kit (Sigma, Rehovot, Israel) and were normalized to the protein content in the homogenate.

Figure 18:
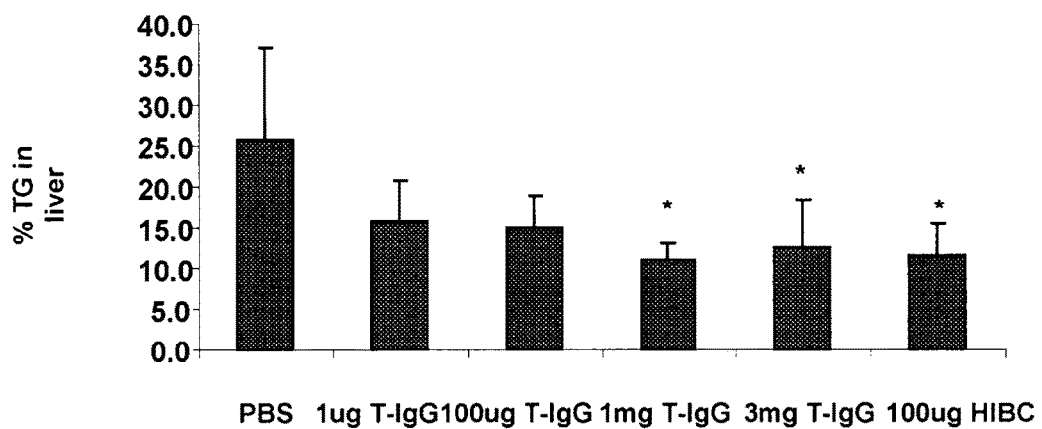
FIG. 18: Oral anti-LPS enriched colostrum-derived immunoglobulin preparation decreases hepatic TGs in Ob/Ob mice. Oral administration of T-IgG and anti-LPS immunoglobulin preparation (denoted HIBC) colostrums decreases hepatic TGs in Ob/Ob mice. Values are mean±SD. The decrease was significant for group A versus D, E, F (* p<0.05).

FIG. 18 demonstrates 100 ug of 1 mg, 3 mg and 100 ug of T-IgG were the most effective doses in decreasing hepatic triglycerides. The decrease was statistically significant for group A versus D, E, F (*$p<0.05$).

Example 22: Oral Administration of 1 Ug, 1 Mg, 3 Mg of T-IgG, Along with 100 Ug HIBC, Decreased CD3+NK1.1+ Cells in the Livers of Ob/Ob Mice FACS analysis was performed on lymphocytes isolated from livers of Ob/Ob mice. Average of expression of markers (CD3+NK1.1+) on hepatic lymphocytes was measured using flow cytometry on day 25 (sacrifice day) in all ob/ob mice. For flow cytometry, the following antibodies were used: anti-CD3–FITC and anti NK1.1– PE. Surface staining and FACS analysis was performed as described above.

Figure 19A:
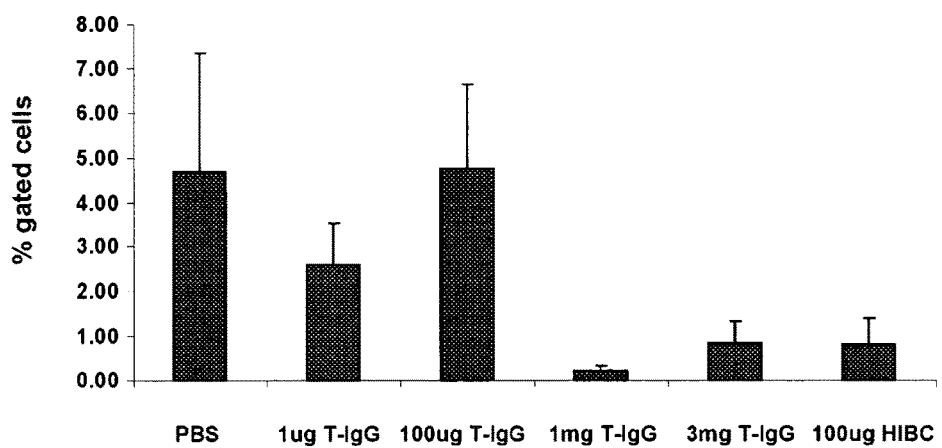
FIG. 19A-B: Oral anti-LPS enriched colostrum-derived immunoglobulin preparation decreased CD3+NK1.1+ cells in the livers of Ob/Ob mice. A. Oral administration of 1 ug, 1 mg, 3 mg of T-IgG, along with 100 ug HIBC, decreased CD3+NK1.1+ cells in the livers of Ob/Ob mice. Average surface expression of markers on lymphocytes. Values are mean±SD. B: Oral administration of 1 ug and 100 ug of T-IgG, decreased CD3+NK1.1+ cells in the livers of Ob/Ob mice. A representative dot blot derived from FACS analysis.
Figure 19B:
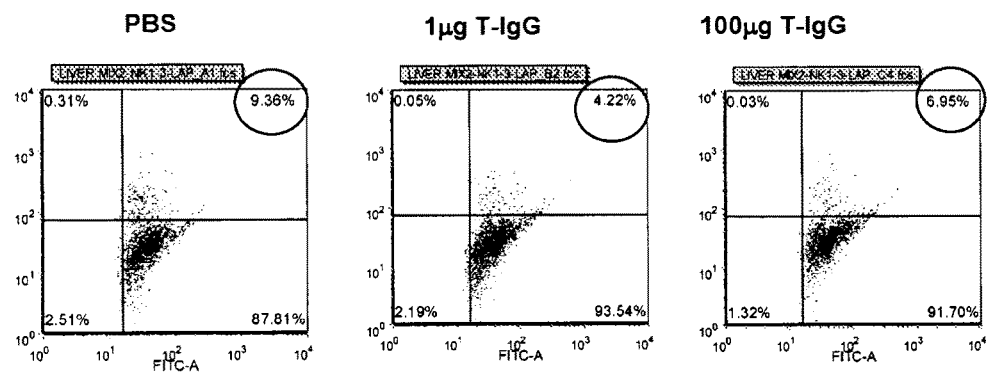

FIG. 19A demonstrates oral administration of 1 ug, 1 mg, 3 mg of T-IgG, along with 100 ug HIBC, decreased CD3+NK1.1+ cells in the livers of Ob/Ob mice. Furthermore, FIG. 19B demonstrates oral administration of 1 ug and 100 ug of T-IgG, decreased CD3+NK1.1+ cells in the livers of Ob/Ob mice Example 23: Oral Administration of T-IgG and HIBC Colostrums, Increases CD4+CD25+LAP−/LAP+ Cells in the Livers of Ob/Ob Mice In order to determine dosages of oral anti-LPS enriched colostrum-derived immunoglobulin preparation that promotes Tregs in livers, the inventors examined the effect of oral administration on the tissue derived subsets of regulatory T cells. FACS analysis was performed on lymphocytes isolated from livers according to the method discussed above. FACS analysis was performed on lymphocytes isolated from livers of Ob/Ob mice. FIG. 20 shows the average of expression of markers (on hepatic lymphocytes was measured using flow cytometry on day 25 (sacrifice day) in all ob/ob mice.

Figure 20A:
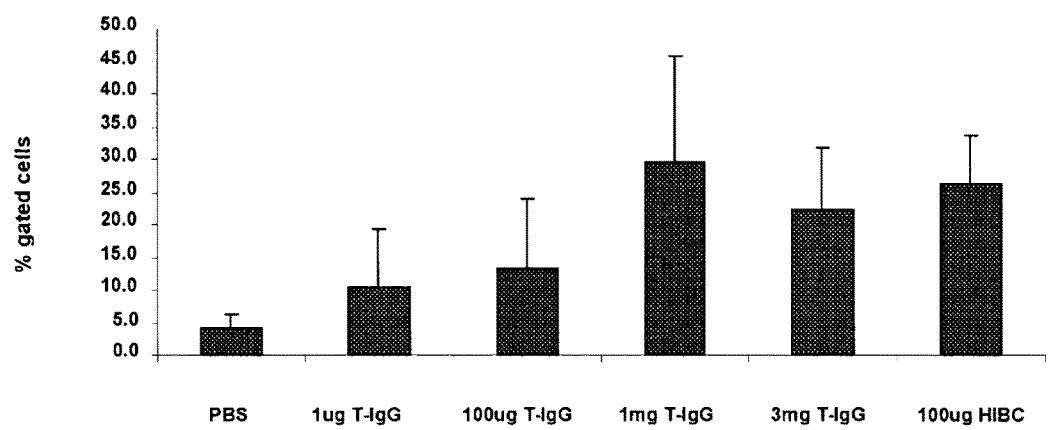
FIG. 20A-B: Oral anti-LPS enriched colostrum-derived immunoglobulin preparation increases CD4+CD25+LAP−/LAP+ cells in the livers of Ob/Ob mice. A; average surface expression of markers on lymphocytes. Values are mean±SD. B; A representative dot blot derived from FACS analysis.
Figure 20A:
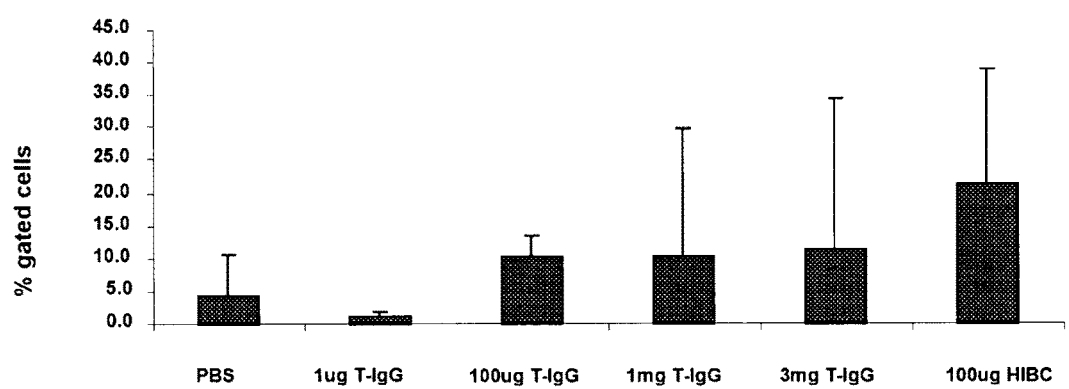
Figure 20B:
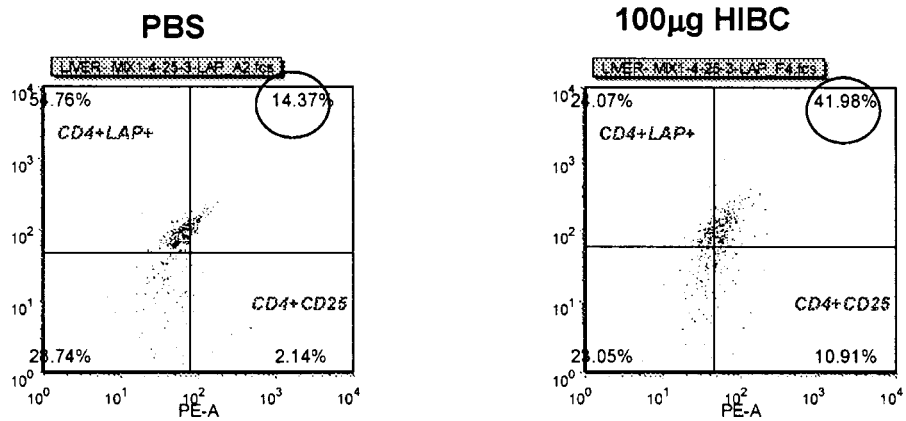

FIG. 20A demonstrates oral administration of T-IgG and HIBC colostrums, increases CD4+CD25+LAP−/LAP+ cells in the livers of Ob/Ob mice. FIG. 20B demonstrates oral administration of 100 ug of HIBC colostrum, increases CD4+CD25+LAP+ cells in the livers of Ob/Ob mice.

Figure 21:
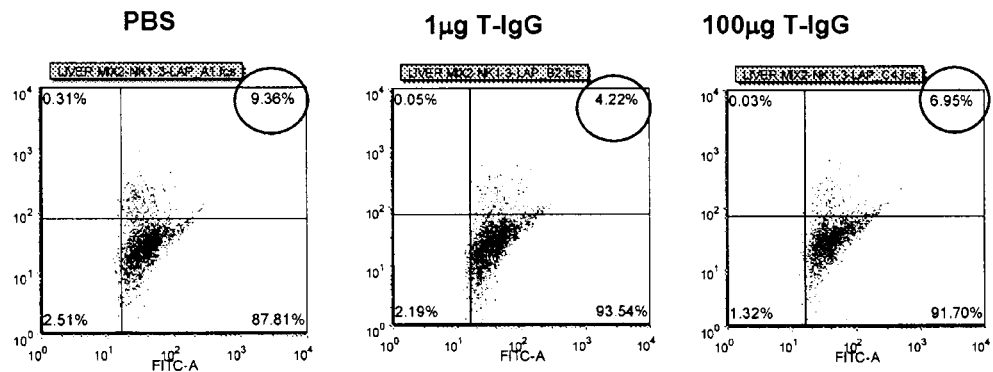
FIG. 21: Oral anti-LPS enriched colostrum-derived immunoglobulin preparation induces changes in CD25+LAP− hepatic lymphocytes. Oral administration of T-IgG and of HIBC-colostrums, induces changes in CD25+LAP− hepatic lymphocytes. A representative dot blot derived from FACS analysis.
Figure 21:
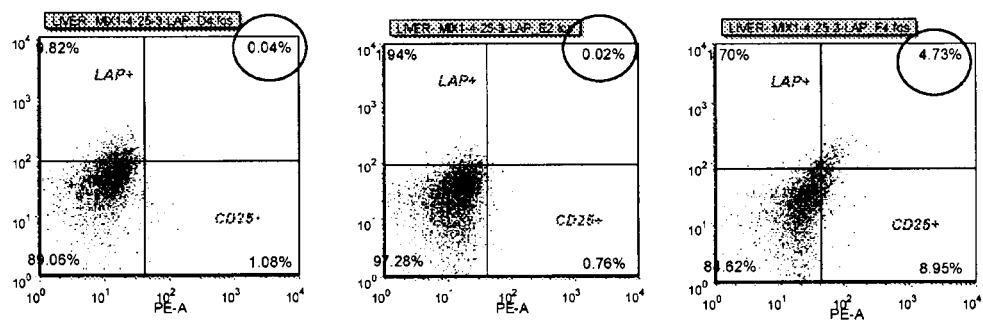

Example 24: Oral Administration of T-IgG and of HIBC-Colostrums, Induces Changes in CD25+LAP− Hepatic Lymphocytes FIG. 21 demonstrates oral administration of 1 ug, 1 mg, 3 mg of T-IgG, along with 100 ug HIBC, induces changes in CD25+LAP− lymphocytes in the livers of Ob/Ob mice.

Figure 22A:
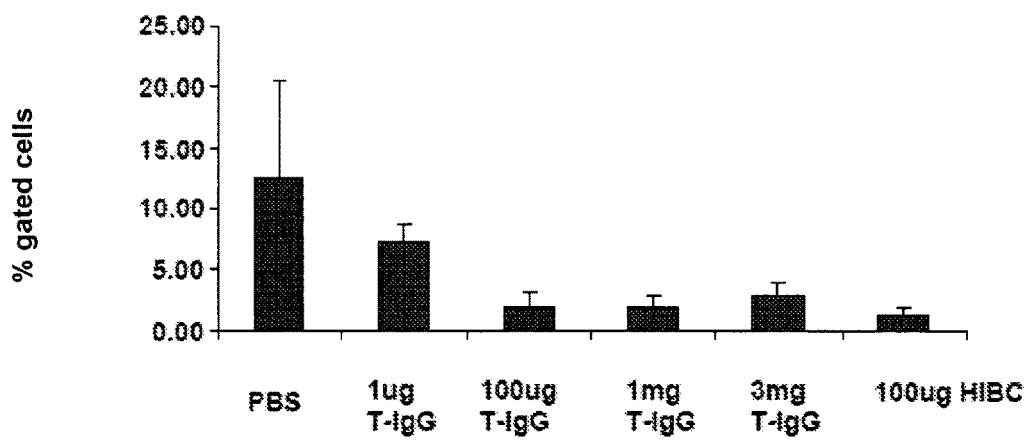
FIG. 22A-B: Oral anti-LPS enriched colostrum-derived immunoglobulin preparation decreases CD25+LAP+ splenic lymphocytes. A. Oral administration of T-IgG and of HIBC-colostrums, decreases CD25+LAP+ splenic lymphocytes. Average surface expression of markers on lymphocytes. Values are mean±SD. B: A representative dot blot derived from FACS analysis.
Figure 22B:
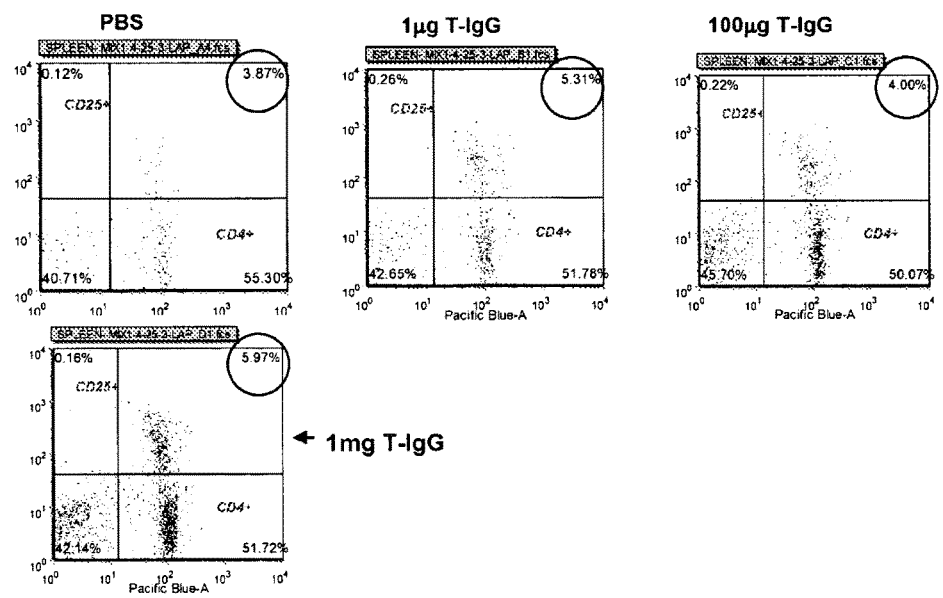

Example 25: Oral Administration of T-IgG and of HIBC-Colostrums Induces Changes in CD25+LAP+ Splenic Lymphocytes FIG. 22A demonstrates administration of T-IgG and of HIBC-colostrums, decreases CD25+LAP+ splenic lymphocytes. FIG. 22B demonstrates oral administration of T-IgG-colostrums increases CD25+LAP+ splenic lymphocytes.

Figure 23:
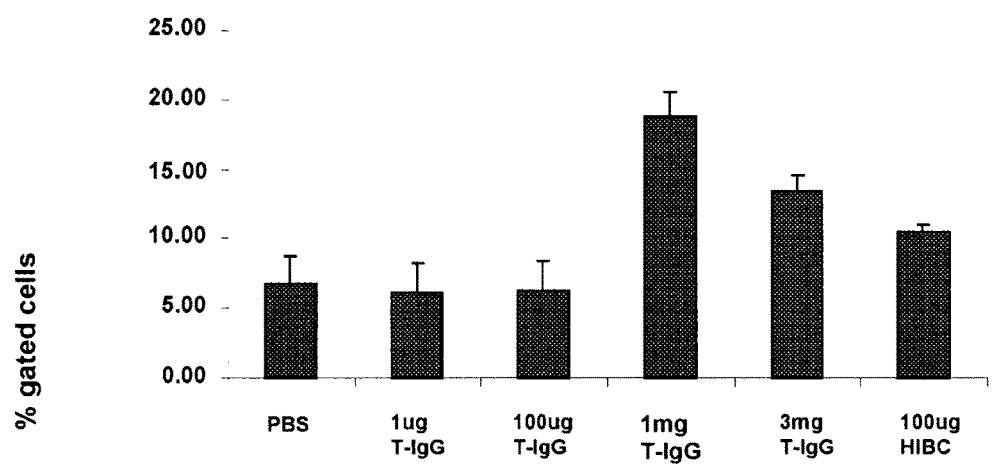
FIG. 23: Oral anti-LPS enriched colostrum-derived immunoglobulin preparation increases CD4+CD25+LAP− splenic lymphocytes. Oral administration of 1 and 3 mg of T-IgG and of 100 mg of HIBC-colostrums, increases CD4+CD25+LAP− splenic lymphocytes.

Example 26: Oral Administration of 1 and 3 mg of T-IgG and of 100 Ug of HIBC-Colostrums, Increases CD4+CD25+LAP− Splenic Lymphocytes FACS analysis was performed on lymphocytes isolated from livers of Ob/Ob mice. FIG. 23 shows the average of expression of markers (CD4+CD25+LAP−) on splenic lymphocytes was measured using flow cytometry on day 25 (sacrifice day) in all ob/ob mice. FIG. 23 demonstrates oral administration of 1 and 3 mg of T-IgG and of 100 ug of HIBC-colostrums, increases CD4+CD25+LAP− splenic lymphocytes

Figure 24:
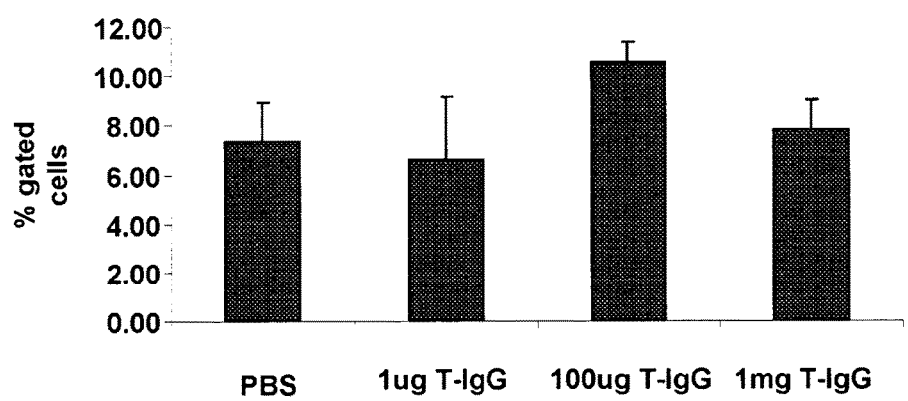
FIG. 24: Oral anti-LPS enriched colostrum-derived immunoglobulin preparation increases CD4+CD25+ in adipose tissue. A. Oral administration of T-IgG-colostrums, increases CD4+CD25+ in adipose tissue. Average surface expression of markers on lymphocytes. Values are mean±SD.

Example 27: Oral Administration of T-IgG-Colostrums, Increases CD4+CD25+ in Adipose Tissue FACS analysis was performed on lymphocytes isolated from adipose tissues of Ob/Ob mice, as described above. FIG. 24 shows Average of expression of markers (CD4+CD25+) on adipose tissue cells was measured using flow cytometry on day 25 (sacrifice day) in all ob/ob mice. FIG. 24 demonstrates oral administration of T-IgG-colostrums, increases CD4+CD25+ lymphocytes in adipose tissue.

Figure 25A:
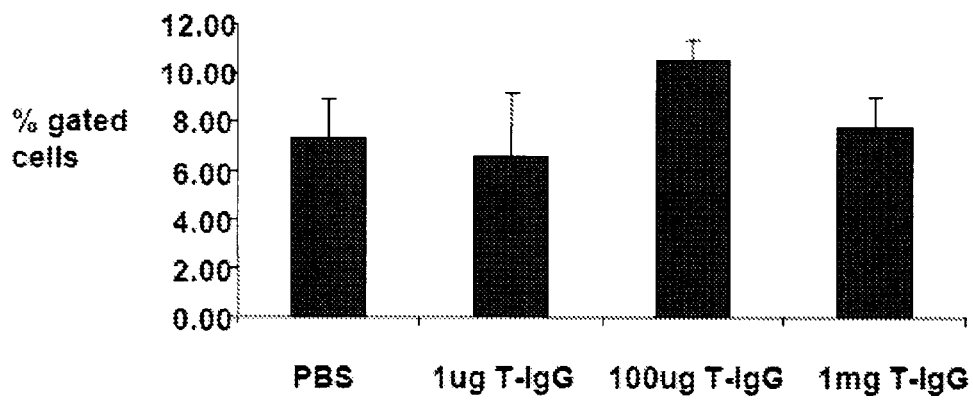
FIG. 25A-B: Oral anti-LPS enriched colostrum-derived immunoglobulin preparation increases CD4+CD25+ in adipocytes. A. Oral administration of 100 mg of T-IgG-colostrum, increases CD4+CD25+ in adipocytes. Average surface expression of markers on lymphocytes. Values are mean±SD. B. Oral administration of 1 ug, 100 mg and 1 mg of T-IgG-colostrum, increases CD4+CD25+ in adipocytes. A representative dot blot derived from FACS analysis.
Figure 25B:
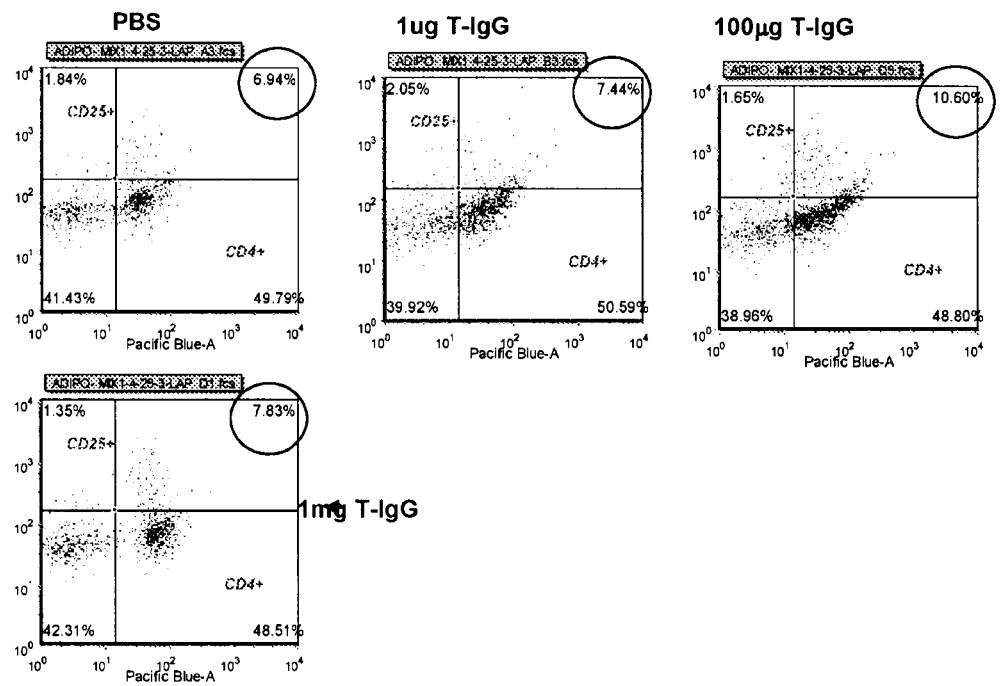

Example 28: Oral Administration of 100 Ug of T-IgG-Colostrum, Increases CD4+CD25+ in Adipocytes FACS analysis was performed on adipocytes isolated from adipose tissues of Ob/Ob mice, as described above. FIG. 25A demonstrates the average of expression of markers (CD4+CD25+) on adipocytes was measured using flow cytometry on day 25 (sacrifice day) in all ob/ob mice. FIG. 25A demonstrates administration of 100 ug of T-IgG-colostrum, increases CD4+CD25+ in adipocytes. FIG. 25B demonstrates oral administration of 100 ug of T-IgG-colostrum, increases CD4+CD25+ in adipocytes.

Figure 26A:
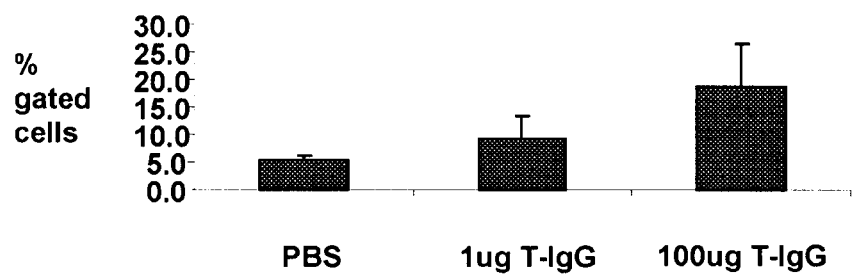
FIG. 26A-B: Oral anti-LPS enriched colostrum-derived immunoglobulin preparation increases CD3+LAP+ in adipocytes. A. Oral administration of T-IgG-colostrum, increases CD3+LAP+ in adipocytes. Average surface expression of markers on lymphocytes. Values are mean±SD. B: A representative dot blot derived from FACS analysis.
Figure 26B:
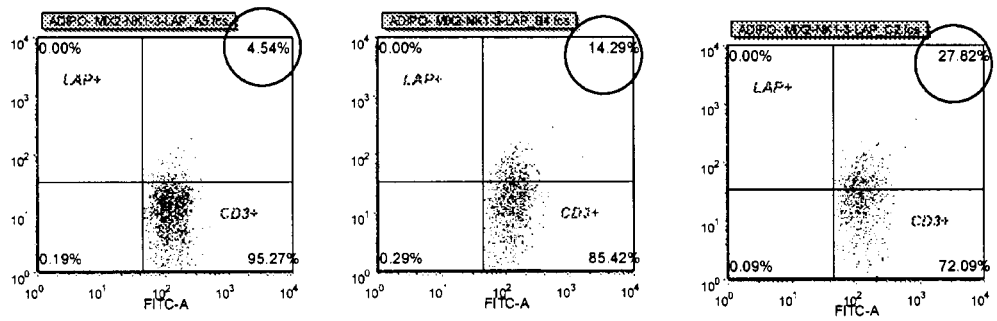

Example 29: Oral Administration of T-IgG-Colostrum, Increases CD3+LAP+ in Adipocytes FACS analysis was performed on adipocytes isolated from adipose tissues of Ob/Ob mice, as described above. FIG. 26 shows the average of expression of markers (CD3+LAP+) on adipocytes was measured using flow cytometry on day 25 (sacrifice day) in all ob/ob mice. FIG. 26A demonstrates oral administration of T-IgG-colostrum, increases CD3+LAP+ in adipocytes. FIG. 26B demonstrates oral administration of T-IgG-colostrum, increases CD3+LAP+ in adipocytes.

Figure 27A:
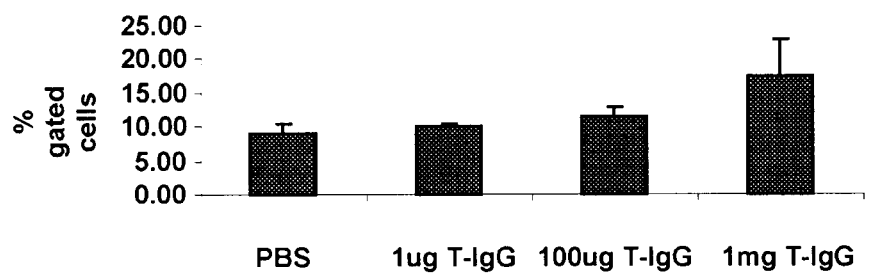
FIG. 27A-B: Oral anti-LPS enriched colostrum-derived immunoglobulin preparation increases CD4+CD25+ in adipocytes. A. Oral administration of T-IgG-colostrum, increases CD3+LAP+ in adipocytes. Average surface expression of markers on lymphocytes. Values are mean±SD. B: A representative dot blot derived from FACS analysis.
Figure 27B:
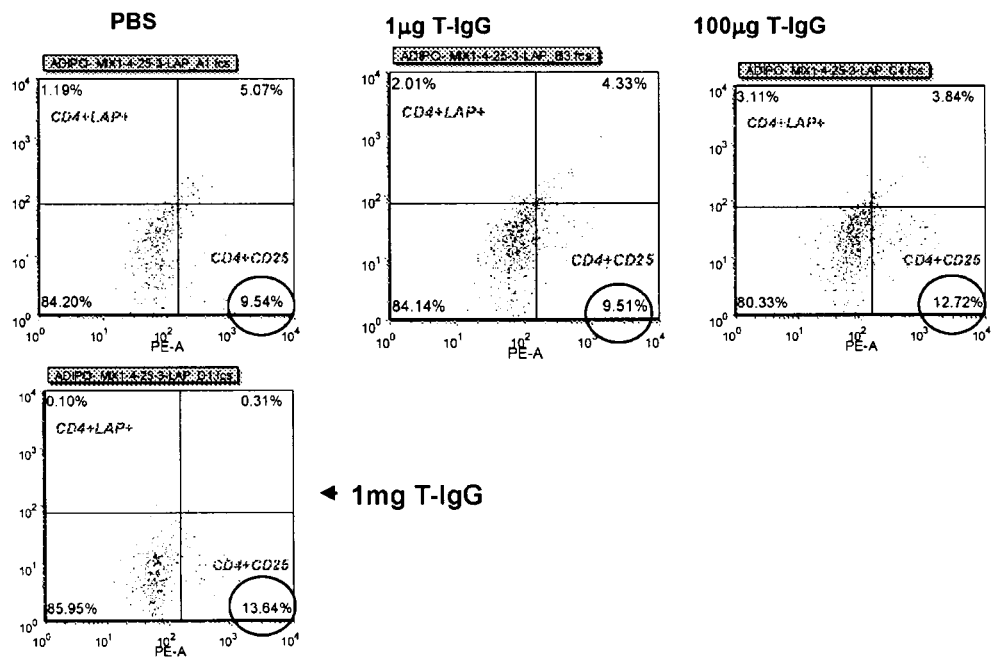

Example 30: Oral Administration of T-IgG-Colostrum, Increases CD4+CD25+LAP− in Adipocytes FIG. 27A demonstrates administration of T-IgG-colostrum, increases CD4+CD25+LAP− in adipocytes.

Example 31: Oral Administration of Anti LPS Enriched Colostrum Decreases Bacterial Translocation in a Model of Hepatitis To examine bacterial translocation and hepatitis, groups of mice were treated as follows: Group A: Treated with BCP antibody free colostrum; Group B: anti LPS containing colostrum. Mice were fed with colostrum for 4 days prior to induction of Con A hepatitis.

Administration of Con A and Measurement of Serum Transaminase Activities.

Con A was purchased from MP Biomedicals (Ohio, USA). Con A (0.5 mg, 20 mg/kg) was dissolved in 200 uL of 50 mM Tris (pH 7), 150 mM NaCl, 4 mM CaCl$_2$, and injected intravenously into mice. Sera from individual mice were obtained 8 or 20 h after Con A injection. Serum activities of alanine aminotransferase (ALT) and aspartate aminotransferase (AST) were measured using an automatic analyzer.

To assess bacterial translocation, lipopolysaccharide (LPS) levels were measured using the using the *limulus amebocyte* lysate (LAL) chromogenic assay; LAL is a measure for degree of bacterial translocation. Table 4 demonstrates oral administration of anti LPS colostrum decreased bacterial translocation, as shown by a decrease in average LAL levels.

TABLE 4

| | | average | std. dev. | P value |
|---|---|---|---|---|
| Group A | ConA + BCP | 1.52 | 0.75 | 0.37 |
| Group B | ConA + LPS Colostrum | 1.18 | 0.30 | |

Importantly, the reduced bacterial translocation was associated with improved in liver enzyme ALT which is a marker of liver damage, as shown in Table 5

TABLE 5

| | | ALT | average | STD. DEV. |
|---|---|---|---|---|
| Group A | A1 | 28170 | | |
| ConA + BCP | A2 | 857.6 | | |
| | A3 | 1356.8 | | |
| | A4 | 340.8 | | |
| | A5 | 26340 | | |
| | | | 11413.04 | 14480.59 |
| Group B | B1 | 10992 | | |
| ConA + T- | B2 | 796.8 | | |
| IgG | B3 | 187.2 | | |
| | B4 | 2816 | | |
| | B5 | 12672 | | |
| | | | 5492.8 | 5898.076 |

Example 32: Preparation of Compositions Containing Colostrum-Derived Anti-LPS Enriched Preparations and Anti-Insulin Antibodies For preparation of the anti-LPS enriched immunoglobulin preparation, colostrum was collected from approximately 200 commercial dairy cowherds. The cows in these herds, as well as being vaccinated for routine cattle pathogens, have been vaccinated with a vaccine against the outer cell wall antigens of multiple strains of *E. coli* bacteria, a major organism in human gut microflora. For preparation of the anti-insulin enriched immunoglobulin preparation, three dairy cows are immunized with insulin conjugated to KLH as an antigen. The antigen vaccines are administered during the last eight weeks of gestation. Colostral milk is collected during the first two days of lactation. The obtained colostrum was frozen in individual bags for testing. For processing, colostrum was thawed, pooled and fat was removed. Each batch was pasteurized. Colostrum was concentrated by ultra-filtration to reduce volume before freeze drying. The ultra-filtration step reduced lactose in the final powder to less than 7% (from about 50%).

The anti-LPS enriched immunoglobulin preparation and the anti-insulin enriched immunoglobulin preparation are mixed to form a composition for use as described below. For immune mediated hepatitis model, eleven to twelve weeks old male C57/bl mice are tail vein injected with a dose of 500 g linouse (approximately 15 mg/kg) of Con A (MP Biornedicals, USA) which is dissolved in 50 mM Trig pH 7, 150 mM NaCl, 4 mM $CaCl_2$, known to induce hepatitis. Animals of all tested groups are orally administered (e.g. by gavage) using different concentrations of the composition containing the anti-LPS and anti-insulin enriched immunoglobulin preparations and compared to untreated controls. Animals of all tested groups are followed for the following parameters: serum aspartate aminotransferase (AST) and alanine aminotransferase (ALT) levels, histological examination of liver specimens, FACS analysis of intrahepatic and intrasplenic lymphocytes for NKT markers, measurement of TGs, total cholesterol, glucose tolerance, serum insulin, serum glucose, cytokine levels and Western blot analysis for the expression of the transcription factors STAT 1, 4 and 6 and NFκB and are compared to control groups.

Example 33: Phase I/II Clinical Trial

As disclosed herein, anti-LPS immunoglobulin preparation can exert an immunomodulatory effect and alleviate target organ damage in animal models. A study was performed to determine the safety and efficacy of oral administration of anti-LPS immunoglobulin preparation to patients with insulin resistance and NASH.

Study Design

A double-arm, open label, before-and-after exploratory trial has been performed to evaluate the effect of 4 weeks of control BCP (CBCP) or anti-LPS immunoglobulin preparation or anti-insulin immunoglobulin preparation (HIBC preparations) administration on serum liver enzymes and metabolic syndrome in patients with NASH. Candidates were identified from among the patients treated in the department of medicine and liver unit of the Hadassah Hebrew University Medical Center and signed an approved informed consent from before the study activities were initiated. Participants were be randomized to receive either control bovine (CBCP) (30 patients) or anti-LPS immunoglobulin preparation (20 patients). Patients were followed on study with weekly visits as well as for an additional 4 weeks after concluding treatment to assess safety.

1. Selection and Enrollment of Subjects
1.1. Inclusion Criteria
1.1.1. Biopsy proven NASH (NAS Score ≥4)
1.1.2. Serum ALT levels ≥30 (U/L)
1.1.3. Age 18-80
1.1.4. Treatment of diabetes by up to 2 oral medications, with stable doses for 2 months.
1.1.5. If participating in sexual activity that could lead to pregnancy, the study volunteer must agree that two reliable methods of contraception will be used simultaneously while receiving the protocol-specified medication and for 1 month after stopping the medication.

NOTE: Hormonal-based methods alone are not sufficient. At least two of the following methods MUST be used appropriately unless documentation of menopause, sterilization, or azoospermia is present:

Condoms (male or female) with or without a spermicidal agent.—Condoms are recommended because their appropriate use is the only contraception method effective for preventing HIV transmission Diaphragm or cervical cap with spermicide
IUD
Hormonal-based contraception Study subjects who are not of reproductive potential (girls who have not reached menarche or women who have been post-menopausal for at least 24 consecutive months or have undergone hysterectomy and/or bilateral oophorectomy are eligible without requiring the use of contraceptives. Written or oral documentation communicated by clinician or clinician's staff is required by one of the following:

Physician report/letter
Operative report or other source documentation in the patient record (a laboratory report of azoospermia is required to document successful vasectomy)
Discharge summary
Laboratory report of azoospermia
FSH measurement elevated into the menopausal range as established by the reporting laboratory.

1.1.6. Ability and willingness of subject or legal guardian/representative to provide informed consent.
a. EXCLUSION CRITERIA
i. Pregnancy or Breast-Feeding
ii. Continuous use of the following medications for more than 3 days within 30 days of study entry:
1. Immunosuppressives
2. Immune modulators
3. Systemic glucocorticoids
4. Anti-neoplastic agents
iii. Active drug or alcohol use or dependence that, in the opinion of the site investigator, would interfere with adherence to study requirements.
iv. Serious illness requiring systemic treatment and/or hospitalization within 30 days prior to entry.
v. Operation within the previous 3 months.
vi. A serious infectious, cardiac, pulmonary, or nephrological disease
vii. Allergic to cow milk or lactose intolerant.
2. Study Treatment
a. Regimen, Administration and Duration
i. Per-Protocol Treatment Regimen Subjects received treatment with control BCP 1.8 grams (3×200 mg capsules), anti-LPS immunoglobulin preparation (HIBC) 1.8 g daily (3×200 mg capsules, three times daily) or anti-insulin immunoglobulin preparation 600 mg per day (2×100 mg capsules, three times daily), for 4 weeks and then monitored off study treatment for an additional 4 weeks.
ii. Study Treatment Modifications Dose reductions were not allowed. All study drug modifications were documented and recorded.
b. STUDY PRODUCT FORMULATION AND PREPARATION The study medication was supplied at tablets packaged individually in blister packs.

For anti-LPS immunoglobulin preparation, each 200 mg tablet contains 200 mg of freeze-dried BCP from cows immunized with LPS as the only active component in combination with excipients including silica colloidal anhydrous, magnesium stearate, microcrystalline cellulose and calcium carbonate. The product can be stored at room temperature and has a shelf life of 5 years.

For anti-insulin immunoglobulin preparation, each 100 mg tablet contains 100 mg of freeze-dried BCP from cows immunized with insulin as the only active component in combination with excipients including silica colloidal anhydrous, magnesium stearate, microcrystalline cellulose and calcium carbonate. The product can be stored at room temperature and has a shelf life of 5 years.

c. Pharmacy: Product Supply, Distribution, and Accountability i. Study Product Acquisition/Distribution Compositions were stored and dispensed by the research pharmacies at the Hadassah Hebrew University Medical Center.

ii. Study Product Accountability

The site pharmacist is required to maintain complete records of all study products.

d. Concomitant Medications i. General Guidelines

There are no specific protocol-imposed restrictions on concomitant medications, other than stipulated in the inclusion/exclusion criteria. Nonetheless, whenever a concomitant medication or study agent is initiated or a dose changed, investigators reviewed the concomitant medications' and study agents' most recent package inserts, investigator's brochures, or updated information from on-line sources to obtain the most current information on drug interactions, contraindications, and precautions.

ii. Prohibited Medications

Use of the following medications for more than 3 days within 30 days of study entry: Insulin, immunosuppressives, immune modulators, anti-neoplastic agents, glucocorticoids.

e. Adherence Assessment

At each visit, participants were queried about the number of doses of study medication missed since the last visit.

3. Clinical and Laboratory Evaluations a. Schedule of Events

See Table 6

Pre-Trial Subject Assessment: Consent and Pre-Trial Evaluation (Screening)

Each candidate subject was scheduled for a screening visit. At the screening visit the study investigator(s) explained the study in detail, answered any questions the candidate may have had, and gave the candidate a consent form to read and sign. After signing the consent form, the candidate subject was asked to provide a complete medical history and undergo a physical examination, including measurement of blood pressure, pulse, temperature, body weight and height. Blood was drawn for a complete blood count (CBC) and other laboratory analyses. (See Table 6). Serum was collected and archived for use in the development of surrogate markers. Women of childbearing potential underwent a pregnancy test. The subjects' medication history was evaluated to determine that both the medication itself and the dose regimen of the medication fall within the inclusion criteria. Patients were randomized to the different treatment arm (CBCP, anti-LPS immunoglobulin preparation or anti-insulin immunoglobulin preparation).

Results of routine diagnostic tests obtained during pretreatment evaluation or during the course of research project will be made available to the subject's primary care physician upon receipt by the principal investigator of a signed written consent from the candidate subject.

Trial Entry and Enrollment: Medication Schedule

At the initial visit following a determination that a subject is eligible for entry into the trial (day zero), the subject was instructed concerning the manner in which the study drug components must be taken. Thereafter, the subject visited the clinic on days 7, 14, 21, 30 and 60.

The CBCP, anti-LPS immunoglobulin preparation, and anti-insulin immunoglobulin preparation were taken every day for 30 days.

Subjects took the drug (CBCP or immunoglobulin preparations) in the morning before breakfast and were required not to eat for 2 hours after taking the drug.

If a subject forgets to take the drug in the morning, he/she can take the drug during the day. He/she is required not to ingest food for 2 hours before and 2 hours after taking the drug. Subjects were treated on an outpatient basis and were monitored during a 30 day, treatment period and a 30 days follow-up after completion of the study.

Clinical and Laboratory Follow Up a. Subjects were followed through regularly scheduled visits that will include physical examination, on-going medical history review, and laboratory tests as described in Table 6.

b. Safety was assessed by monitoring the subjects for adverse events. The subjects were requested to keep a diary detailing any adverse events that may occur during the time period between visits.

c. Evaluation of the effect of oral administration of the study was assessed by determining the clinical and laboratory tests as exemplified and summarized below.

Assessment of Treatment a. The safety and tolerability of oral administration of the study drug cocktail was evaluated at days 7, 14, 21 and 30 by physical examinations and through medical history and laboratory evaluations as described below and by the subject in his/her diary entries. The study monitor, study director and principal investigator continually monitored the subjects by reviewing adverse events, laboratory data and the clinical status of the subject.

b. Data collection was undertaken at each of the visits; the following tests (also described supra) were performed.

Dose Modifications

There will be no dose modifications in this protocol.

Visit 1:

Visit 1 will took place up to 14 days after the screening visit. In case of a delay, the screening visit was repeated.

Prior to engaging in any study procedures, the subject must meet the inclusion/exclusion criteria by history (which includes a signed declination), and review and sign an informed consent form.

At this screening visit there was a review of the subject's demographic information, medical history, and past and current medications. The subjects underwent a complete physical (including vital signs), height and weight, physical examination and will have the following laboratory tests performed:

CBC with differential.

Chemistry tests: total protein, albumin, ALT, AST, ALP, GGTP, LDH, cholesterol, uric acid, creatinine, urea (BUN), Na, K, glucose, total bilirubin FACS, ELISA and Bacterial Translocation Test Glucose tolerance test HOMA/HOMAIR score Visit 2-5: Days 7, 14, 21, 30

The subjects underwent vital signs assessment, evaluation for AE, weight and height measurement and blood samples were collected for biochemistry and CBC. On days 14 and HbA1C, Insulin, FACS and ELISA and Bacterial Translocation Test were performed as well.

Visit 6: Day 60:

The subjects underwent AE assessment, physical exam and vital signs, BMI and blood collected for: biochemistry, CBC, CRP, HbA1C, Insulin.

b. Definitions and Procedures for Clinical and Laboratory Evaluations
i. Recording and Grading of Laboratory Evaluations
At screening and entry all laboratory values were recorded. For post-entry assessments, all laboratory values were recorded. All laboratory toxicities that lead to a change in treatment, regardless of grade, were recorded.
ii. Hematology
Including hemoglobin, hematocrit, mean corpuscular volume (MCV), white blood cell count (WBC), differential, absolute neutrophil count (ANC), and platelets.
iii. Liver Function Tests
Include total bilirubin, AST (SGOT), ALT (SGPT), alkaline phosphatase, total protein, and albumin.
iv. Blood Chemistries
Include glucose, creatinine, BUN, cholesterol, LDL, HDL, TG, Uric acid, albumin, ALP, GGTP, LDH, Na, K.
v. Pregnancy Test
To be done in women of reproductive potential. (Approved urine β-HCG test with a sensitivity of 25-50 mIU/mL)
vi. Immunologic Studies
FACS analysis done for: Anti CD3, anti CD4, anti CD8, anti CD25+, FoxP3+, anti CD56, CD62L+HLA-DR
ELISA done for: IL6, TNFα, adiponectin, GLP-1
Bacterial Translocation Test done as well
vii. Evaluations Of Cell Counts And Percentages Were Performed At The Same Laboratory, If possible, for screening and throughout the course of the study.
Because of the diurnal variation in cell counts, determinations for individual participants obtained consistently in either the morning or the afternoon throughout the study, if possible.
All advanced flow cytometric studies, including immune activation assays, done according to ACTG consensus methods. Activated T cells defined as those coexpressing CD38 and HLA-DR.
viii. Medical History
The medical history included, at a minimum, duration of known HCV infection, previous hospitalizations and diagnoses, with a special emphasis on liver related complications and other HCV-related conditions, exposure to antiviral medications, and any pre-existing medical conditions that may interfere with the conduction of the study.
ix. Complete Physical Exam
A complete physical examination is to include at a minimum an examination of the skin, head, mouth, and neck; auscultation of the chest; cardiac exam; abdominal exam; examination of the lower extremities for edema. The complete physical exam also includes signs and symptoms, diagnoses, and vital signs (temperature, pulse, respiration rate, and blood pressure).
x. Targeted Physical Exam
A targeted physical examination includes vital signs (temperature, pulse, respiration rate, and blood pressure) and is to be driven by any previously identified or new symptoms that the subject has experienced or diagnoses that have been made on the subject since the last visit.
7.0 Clinical Management Issues
7.1 Pregnancy
Women who become pregnant during the study will discontinue study treatment, i.e. will not receive any further doses of colostrum, and report pregnancy-related information (e.g., complications, births, fetal loss/abnormalities). These subjects were encouraged to remain in the study to be followed off study treatment/on study, for safety evaluations (clinical assessment, targeted exam) per protocol until study completion and will be followed by telephone contact thereafter to determine the pregnancy outcome. Outcomes (health of the infant) and any pregnancy-related complications must also be recorded.
8.0 Criteria for Discontinuation
8.1 Permanent Treatment Discontinuation
Drug-related toxicity.
Pregnancy or breast-feeding.
Completion of treatment as defined in the protocol.
Request by subject to terminate treatment.
Clinical reasons believed life threatening by the physician, even if not addressed in the toxicity section of the protocol.
8.2 Premature Study Discontinuation
Failure by the subject to attend 2 consecutive clinic visits.
Subject repeatedly noncompliant with study medications as prescribed.
Request by the subject to withdraw.
Request of the primary care provider if s/he thinks the study is no longer in the best interest of the subject.
Subject judged by the investigator to be at significant risk of failing to comply with the provisions of the protocol as to cause harm to self or seriously interfere with the validity of the study results.
At the discretion of the IRB, Ministry of Health, investigator, or pharmaceutical sponsor.
9.0 Statistical Considerations
9.1 General Design Issues
The hypothesis that the administration of HIBC reduces the levels of plasma microbial products in the study population after a 4-week administration period was tested using the Wilcoxon signed-rank test to compare the average of the pre-treatment values to the values observed at the end of the 4-week treatment period and the value 4 weeks after discontinuation of therapy.
The baseline value (defined as the average of 2 observations prior to study treatment) was compared to each of the on-treatment measurements and each of the post-treatment observations, and the values at the end of the treatment period to the post-treatment values. A similar approach was used to test the secondary hypothesis of a decrease in immune activation after the administration of study treatment.
To test the hypothesis of an association between on-treatment levels of plasma levels of microbial products and levels of cellular immune activation, we will explore the data graphically, and fit a repeated-measures regression model, using the frequency of activated T cells as the dependent variable and both the level of microbial products in plasma and the study phase (pre-, on- or post-treatment) as the explanatory variables. This allows both obtaining an estimate of the treatment effect on immune activation (if any), and whether the effect is entirely dependent on the intermediary effect on levels of microbial products.
Given the exploratory nature of this preliminary study, no correction for multiple comparisons will be initially applied.
10.0 Data Collection and Monitoring and Adverse Event Reporting
10.1 RECORDS TO BE KEPT Case report forms (CRF) will be provided for each subject. Subjects must not be identified by name on any CRFs. Subjects will be identified by the patient identification number (PID) and study identification number (SID) provided upon randomization.
11.0 Human Subjects
11.1 INSTITUTIONAL REVIEW BOARD (IRB) REVIEW AND INFORMED CONSENT The protocol and the informed consent document and any subsequent modifications were reviewed and approved by the IRB or ethics committee responsible for oversight of the study. A signed consent form was obtained from the subject (or parent, legal guardian, or person with power of attorney for subjects who cannot consent for themselves). The consent form describes the purpose of the study, the procedures to be followed, and the risks and benefits of participation. A copy of the consent form was given to the subject, parent, or legal guardian, and this fact documented in the subject's record.

11.2 SUBJECT CONFIDENTIALITY All laboratory specimens, evaluation forms, reports, and other records that leave the site will be identified by coded number only to maintain subject confidentiality. All records will be kept locked. All computer entry and networking programs will be done with coded numbers only. Clinical information will not be released without written permission of the subject, except as necessary for monitoring by IRB, the Ministry of Health, or the pharmaceutical supporter(s) or designee.

11.3 Study Monitoring

Although this was an exploratory trial assessing a nutritional supplement only, without any approved or experimental drugs, patients will be followed for any expected and unexpected side effects.

12.0 Biohazard Containment

Appropriate blood and secretion precautions were employed by all personnel in the drawing of blood and shipping and handling of all specimens for this study, as currently recommended by the Centers for Disease Control and Prevention and the National Institutes of Health.

All dangerous goods materials, including diagnostic specimens and infectious substances, were transported using packaging as mandated by law.

TABLE 6

| | Visit | | | | | | |
|---|---|---|---|---|---|---|---|
| | −1 | 1 | 2 | 3 | 4 | 5 | 6 |
| | | | | Day | | | |
| | Screen | 1 | 7 | 14 | 21 | 30 | 60 |
| Treatment (daily for days 1-30) | | X | X | X | X | X | |
| Informed Consent | X | | | | | | |
| Medical History | X | | | | | | |
| Medication History | X | | | | | | |
| AE Assessment | | X | X | X | X | X | X |
| Physical Exam | X | X | | | | X | X |
| Vital Signs | X | X | X | X | X | X | X |
| BMI | X | X | X | X | X | X | X |
| SMA[1] | X | X | X | X | X | X | X |
| CRP | X | | | | | X | X |
| CBC/differential | X | X | X | X | X | X | X |
| ESR | X | | | | | X | |
| HbA1C | X | | X | | | X | X |
| Insulin | | X | X | | | X | X |
| Pregnancy (beta HCG) | X | | | | | | |
| FACS[2] | | X | | X | | X | |
| ELISA | | X | | X | | X | |
| Bacterial Translocation Test | | X | | X | | X | |
| HOMA score | | X | | X | | X | X |
| Glucose tolerance test | | X | | | | X | |
| Randomization | X | | | | | | |
| Study medication intake | | X | X | X | X | X | |

[1]SMA includes: Total protein, albumin, ALT, AST, ALP, GGTP, LDH, cholesterol, LDL, HDL, TG, uric acid, creatinine, urea (BUN), Na, K, glucose, total bilirubin
[2]FACS analysis includes but not limited to: Anti CD3, anti CD4, anti CD8, anti CD25+, FoxP3+, anti CD56, CD62L + HLA-DR
[3]ELISA:IL6, TNFα, adiponectin, GLP-1
* Visits 2-6 may be done within a time window of 3 days of the appointed date.

Example 34: Alleviation of Insulin Resistance and Liver Damage by Oral Administration of Anti-LPS Immunoglobulin Enriched Colostrum Preparation is Mediated by Increased Tregs and Associated with Increased Serum GLP-1 and Adiponectin: Results of a Phase I/II Clinical Trial in NASH In an open-label trial ten patients with biopsy proven NASH and insulin resistance were orally treated for 30 days with an anti-LPS immunoglobulin enriched colostrum preparation (Immuron, Australia) prepared as described herein in Example 47. Patients were monitored for safety, insulin resistance, regulatory T cells (Tregs), serum IL-6 adiponectin and GLP-1. The clinical effect was determined by glycated haemoglobin A1c (HbA1c), oral glucose tolerance test (OGTT), HOMA score, liver enzyme and lipid profile. The comparison was done between day 1 and day 30 for each patient.

Inclusion Criteria.

Ten patients were enrolled in an open-label trial. Participants (men and women between 18 and 60 years old) were evaluated for eligibility after they signed a written informed consent form. The diagnosis of NASH was based on a liver biopsy score of 4 or above and altered glucose metabolism, including diabetes (non-treated or treated with up to two drugs, without any change in medication two months prior to enrollment), impaired fasting glucose or impaired glucose tolerance and HbA1C between 5.5 and 14%. Impaired fasting glucose was defined as >100 mg/dl. Impaired glucose tolerance was defined as a blood sugar level >140 mg/dl two hours post-glucose load and an HBA1C between 5.5 and 8%. No evidence of other viral or immune-mediated liver disease was present.

Exclusion Criteria.

Patients meeting any of the following criteria were excluded: active co-infection with hepatitis A, B, or C viruses; the presence of human immunodeficiency virus (HIV) infection, hepatocellular carcinoma, fulminant liver failure, severe deteriorating synthetic liver functions or a clinically significant infectious, immune-mediated or malignant disease; any history of treatment with immunomodulatory drugs, including steroids and NSAID, at any time within the last four weeks; a history of coagulopathy; women with childbearing potential unless surgically sterile or using adequate contraception (i.e., IUD, oral or Depo-Provera contraceptive or barrier plus spermicide); anemia (Hb <10.5 gm/dl), thrombocytopenia (platelets <100 k/µl) or lymphopenia (absolute lymphocyte count <0.7) or Allergy to cow milk or lactose intolerant.

Therapy and Laboratory Follow-Up.

After complete medical evaluation and liver biopsy, patients who qualified for therapy were given an anti-LPS immunoglobulin enriched colostrum preparation in a dose of 600 mg three times daily (total of 1800 mg). Patients were followed for 60 days through regular weekly scheduled visits, which included physical examination, on-going medical history review, and laboratory tests. Safety was assessed by monitoring the patients for adverse events. Blood was drawn at each visit for determination of complete blood counts (CBC), sedimentation rate (ESR) and standard chemistries, including liver enzymes, INR, lipid profile, CRP, HbA1C, and serum insulin level. All patients underwent a repeat oral glucose tolerance test and a HOMA score evaluation at the end of the study.

Summary of Results.

Oral administration of anti-LPS immunoglobulin preparation was safe and no side effects were noted in any of the treated subjects. Alleviation of insulin resistance, was determined by the following measures: A decrease in fasting glucose levels (6.9 vs. 6.05 mmol/L p<0.03); Elevation in the early peak of insulin secretion following glucose administration (278 vs. 470 pmol/L, p<0.03); Improved OGTT (AUC of 2492 vs. 2252, p<0.08); Improved insulin secretion during the OGTT (AUC of 99177 vs. 117784 and p<0.08); Improved HOMA score (6.71 vs. 4.82 p<0.06). Treated patients showed a decrease in serum levels of triglycerides (1.88 vs. 1.32 µmol/L, p<0.05), total cholesterol (5.28 vs. 4.44 µmol/L, p<0.04), and LDL. cholesterol (3.7 vs. 2.49 µmol/L, p<0.05). A decrease in liver enzymes was noted in most treated patients (ALT: 54.5 vs. 43.16, u/l, p<0.04; AST: 50.58 vs. 45.5 u/l, p<0.05; Alkaline phosphatase: 82.1 vs. 72.4 u/l, p<0.001; GGT: 84.3 vs. 58.6 u/l, p<0.05). A weight loss of at least 10% of the original body weight was observed in 90% of treated subjects, with mean weight loss of 3 kg within the study period of 30 days (100.25 vs. 97.23 kg, p<0.05) along with a reduction in arm, abdomen and waist circumference. These effects were mediated by increased serum levels of GLP-1 and adiponectin noted in 60% and 80% of treated patients respectively (58816 vs. 62828, for GLP1, p<0.04; and 6181 vs. 7068, UNITS, for adiponectin, p<0.01). An increased in CD25+ and CD4+ CD25+Foxp3+ Tregs (5.24% vs. 7.12% and 2% vs. 2.26% respectively, p<0.002), and in CD4+CD62+ subsets of cells (34.41 vs. 38.44, p<0.01) was noted in treated subjects. Conclusion: Oral administration of anti-LPS immunoglobulin preparation is safe and exerts an immunomodulatory effect in patients with type 2 diabetes, hyperlipidemia and NASH. The anti-inflammatory effect and the promotion of Tregs are associated with alleviation of insulin resistance, hyperlipidemia, and liver damage in these patients.

Example 35: Oral Administration of Anti-LPS Immunoglobulin Preparation Decreases Liver Injury in Humans The levels of liver enzymes (AST and ALT, AP and GGT), serum fasting glucose, insulin, and plasma lipids (cholesterol and triglycerides) were determined using standard methods.

The results demonstrate oral administration of anti-LPS immunoglobulin preparation (HIBC) decreases liver injury in humans.

FIGS. 28A-B, 29, 30 and 31 show the effect of oral administration of anti-LPS immunoglobulin preparation (HIBC) at a dose of 1.8 g/day on serum levels of ALT, AST, Alkaline phosphatase (AP) and γ-GGT, respectively. ALT levels were decreased in five patients (57.4 vs. 48.6 u/L, for day 1 vs. day 30; P<0.04). AST levels were decreased in five treated subjects (51.2 vs. 44.6 u/L, for day 1 vs. day 30; P=0.013). AP levels were improved in eight treated patients (83.1 vs. 73.9 u/L, for day 1 vs. day 30; P<0.002) and γ-GGT levels were decreased in five treated patients (88.2 vs. 73.2 u/L, for day 1 vs. day 30; P<0.05).

Figure 28A:
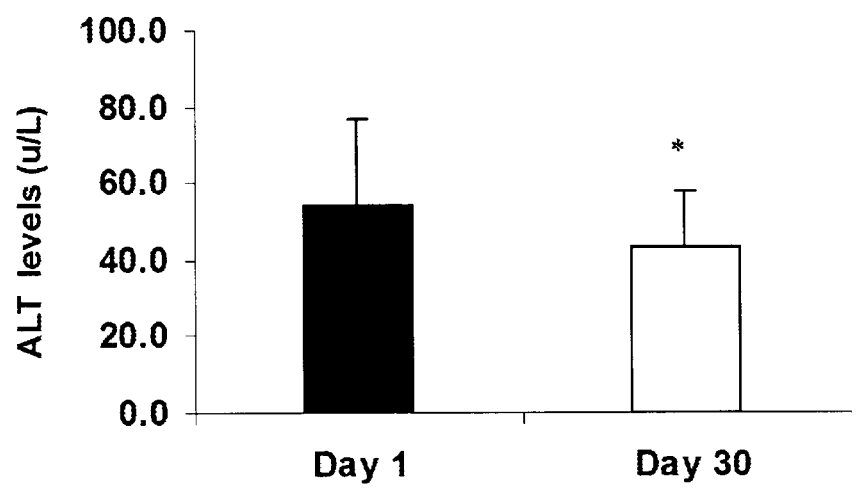
FIG. 28A-B: Oral anti-LPS immunoglobulin preparation decreases liver injury in humans. Oral administration of anti-LPS immunoglobulin preparation (HIBC) decreases ALT; 54.5 vs. 43.16, u/L, (p<0.04).
Figure 28B:
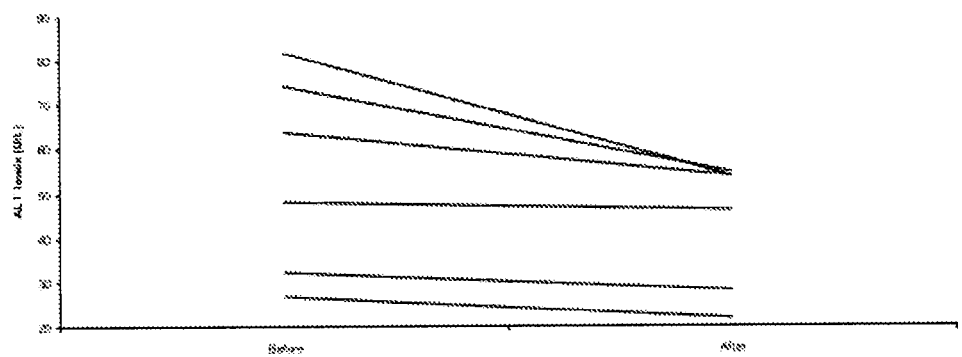

As can be seen in FIG. 28B, a greater decrease in ALT levels was seen in those subjects with higher baseline levels of ALT. Thus, the methods can include identifying a subject with a level of ALT above a given level, e.g., 50 U/L, and administering the anti-LPS enriched colostrum as described herein.

Figure 29A:
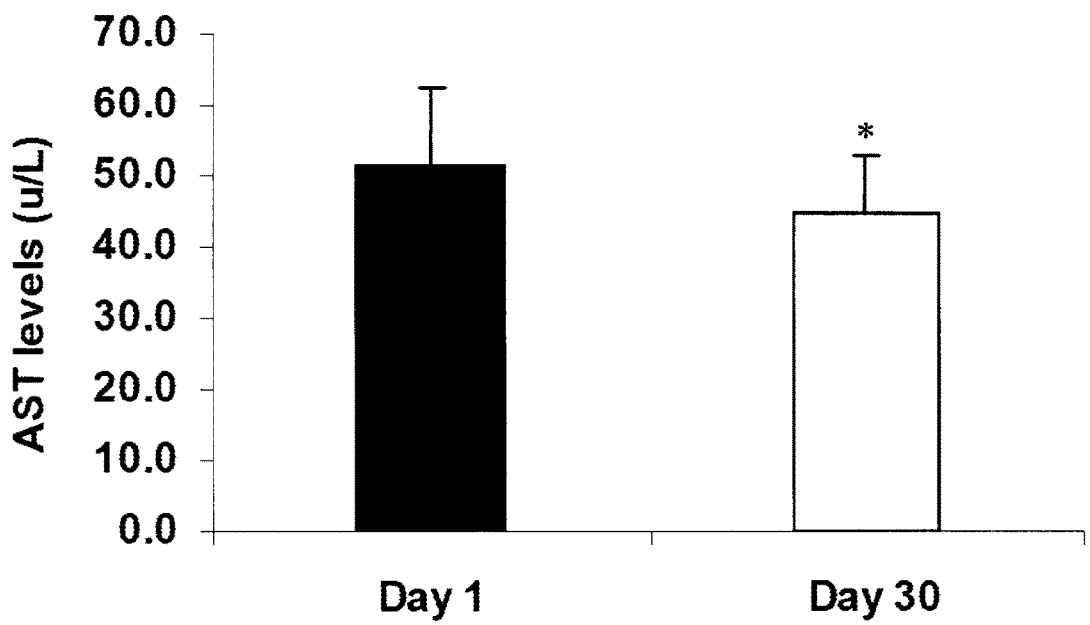
FIG. 29A-B: Oral anti-LPS immunoglobulin preparation decreases liver injury in humans. Oral administration of anti-LPS immunoglobulin preparation (HIBC) decreases AST-50.58 vs. 45.5 u/L, (p<0.05).
Figure 29B:
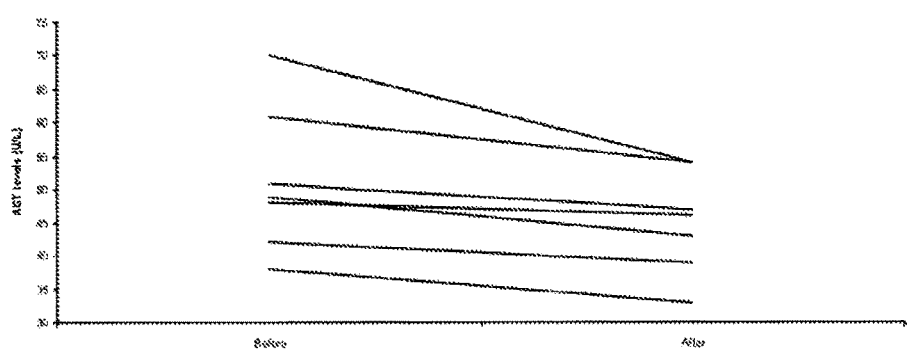

In addition, as can be seen in FIG. 29B, a greater decrease in AST levels was seen in those subjects with higher baseline levels of AST. Thus, the methods can include identifying a subject with a level of AST above a given level, e.g., 50 U/L, and administering the anti-LPS enriched colostrum as described herein.

Figure 30A:
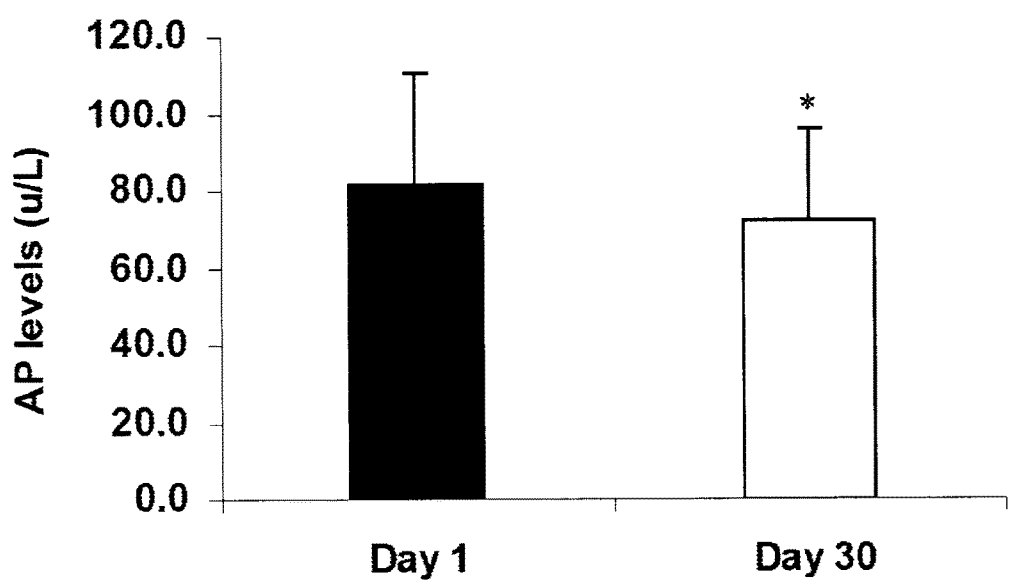
FIG. 30A-B: Oral anti-LPS immunoglobulin preparation decreases liver injury in humans. Oral administration of anti-LPS immunoglobulin preparation (HIBC) decreases Alkaline phosphatase (AP/ALP): 82.1 vs. 72.4 u/L, (p<0.001).
Figure 30B:
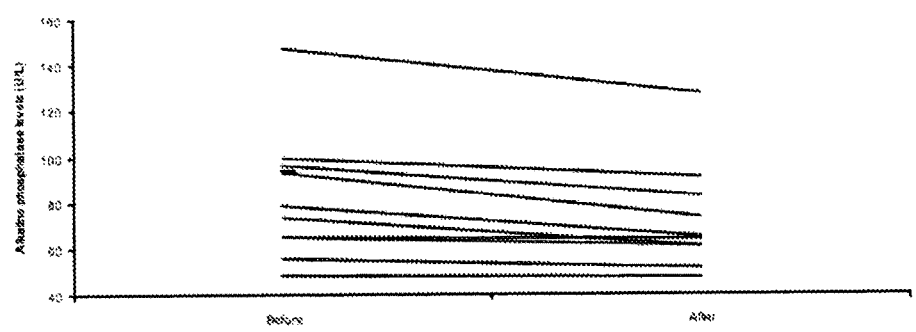

In addition, as can be seen in FIG. 30B, a greater decrease in AP levels was seen in those subjects with higher baseline levels of AP. Thus, the methods can include identifying a subject with a level of AP above a given level, e.g., 70 U/L, and administering the anti-LPS enriched colostrum as described herein.

Figure 31A:
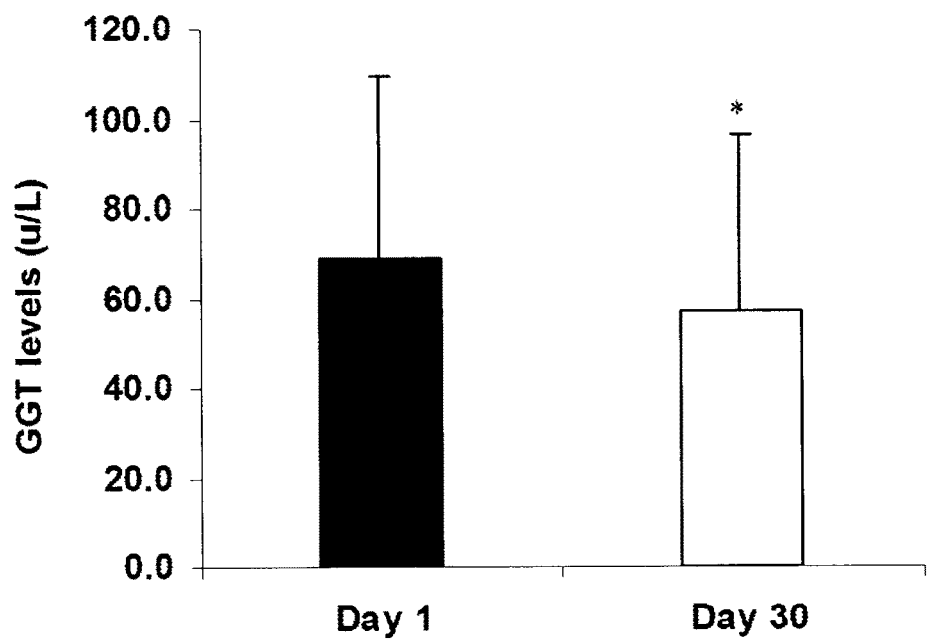
FIG. 31A-B: Oral anti-LPS immunoglobulin preparation decreases liver injury in humans. Oral administration of anti-LPS immunoglobulin preparation (HIBC) decreases GGT 84.3 vs. 58.6 u/L, (p<0.05).
Figure 31B:
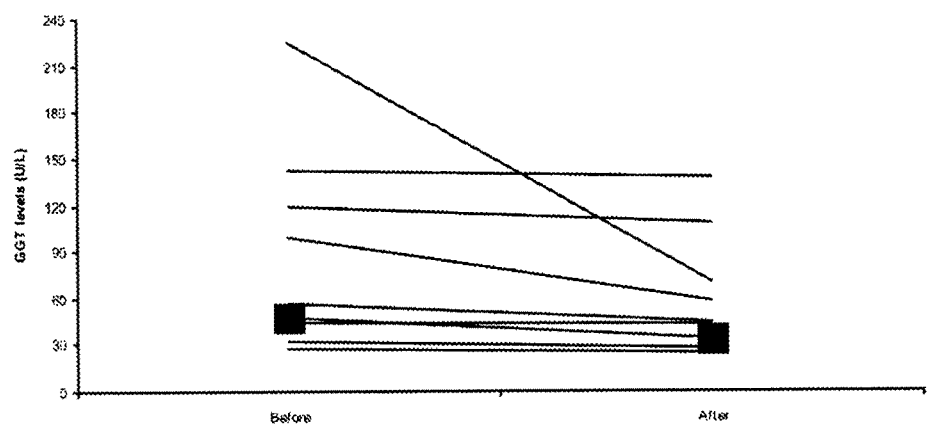

In addition, as can be seen in FIG. 31B, a greater decrease in GGT levels was seen in those subjects with higher baseline levels of GGT. Thus, the methods can include identifying a subject with a level of GGT above a given level, e.g., 60 U/L, and administering the anti-LPS enriched colostrum as described herein.

Example 36: Oral Administration of Anti-LPS Immunoglobulin Preparation Decreases Fasting Glucose Levels, Increases Early Peak Insulin Secretion, Improves Oral Glucose Tolerance and Improves HB1Ac Levels, HOMA Scores, GLP-1 Levels in Humans To determine the effect of anti-LPS enriched immunoglobulin on the glycemic control in NASH patients, especially in the diabetic patients with impaired glucose tolerance, several parameters were tested. A recommended target of HbA1c in clinical trials is a decrease between 6.5% and 7.0% (DeFronzo et al., Diabet Med 27, 309-317 (2010)).

Figure 35A:
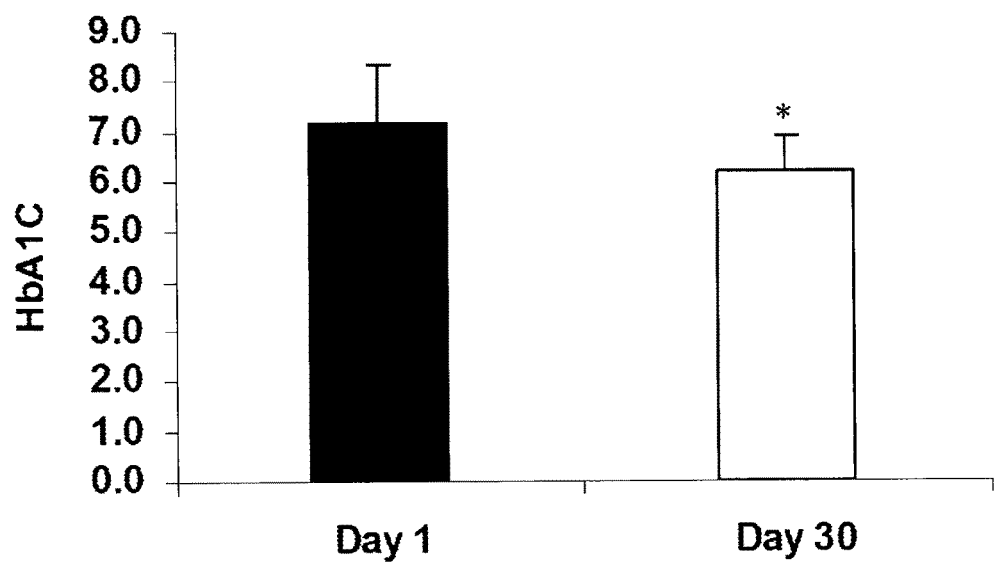
FIG. 35A-B: Oral anti-LPS immunoglobulin preparation increases improves HB1Ac levels in humans. Oral administration of anti-LPS immunoglobulin preparation (HIBC) results in improved HBA1C levels (7.19 vs. 6.20, p<0.001).
Figure 35B:
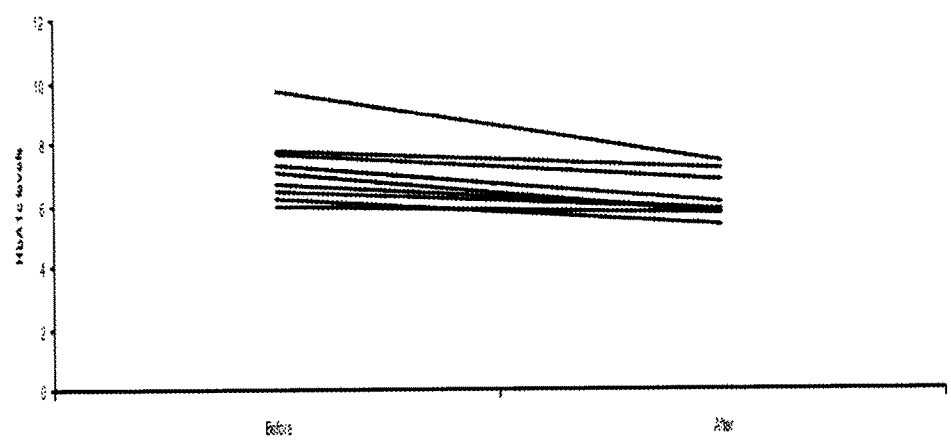

FIGS. 35A-B show a significant improvement in HbA1c values in all treated patients (7.49 vs. 6.38%, for day 1 vs. day 30, respectively, for ten patients; P<0.001). The treatment with an anti-LPS immunoglobulin enriched colostrum preparation for 30 days caused a 14.8% decrease in HbA1c values in all ten patients. As can be seen in FIG. 35B, the greatest decrease occurred in patients with higher baseline HbA1c values. Thus, the methods can include identifying a subject with a level of HbA1c above a given level, e.g., over 7 or 8, and administering the anti-LPS enriched colostrum as described herein.

Figure 33A:
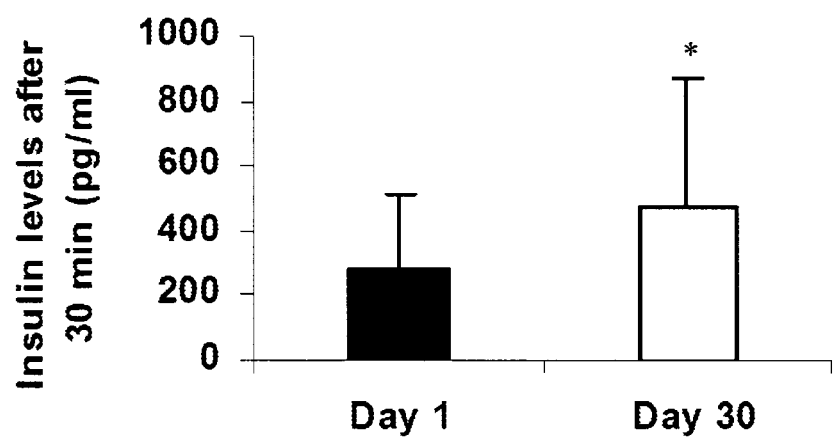
FIG. 33A-B: Oral anti-LPS immunoglobulin preparation increases early peak insulin secretion in humans. Oral administration of anti-LPS immunoglobulin preparation (HIBC) results in an elevation in the early peak of insulin secretion following glucose administration (278 vs. 470 pmol/L, p<0.03).
Figure 33B:
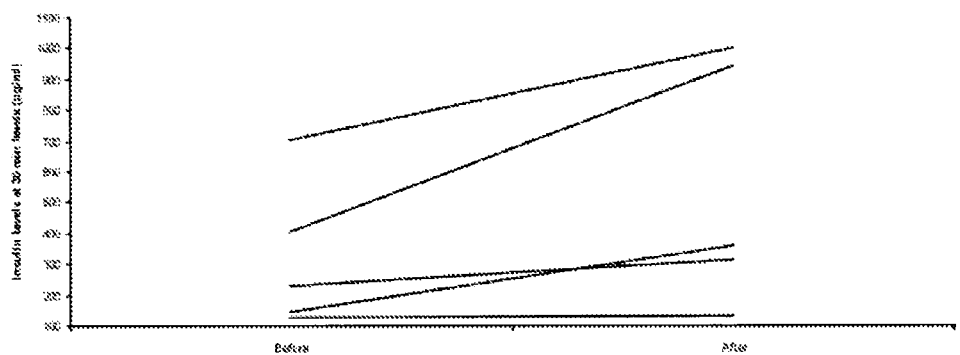

FIGS. 33A-B show that anti-LPS enriched immunoglobulin also exerted a beneficial effect on insulin resistance as assessed by measuring the early peak of insulin secretion at 30 minutes after glucose administration (OGTT of 75 g of glucose). Insulin secretion increased after 30 min from 310 to 538.4 pmol/L for day 1 vs. day 30, respectively, for five treated patients (P=0.083). As shown in FIG. 33B, the greatest increases occurred in those subjects with the highest levels of baseline insulin secretion, thus, the methods can include selecting subjects who have a level of insulin secretion above a threshold level, e.g., above 300 pg/ml, and administering the anti-LPS enriched colostrum as described herein.

Figure 32A:
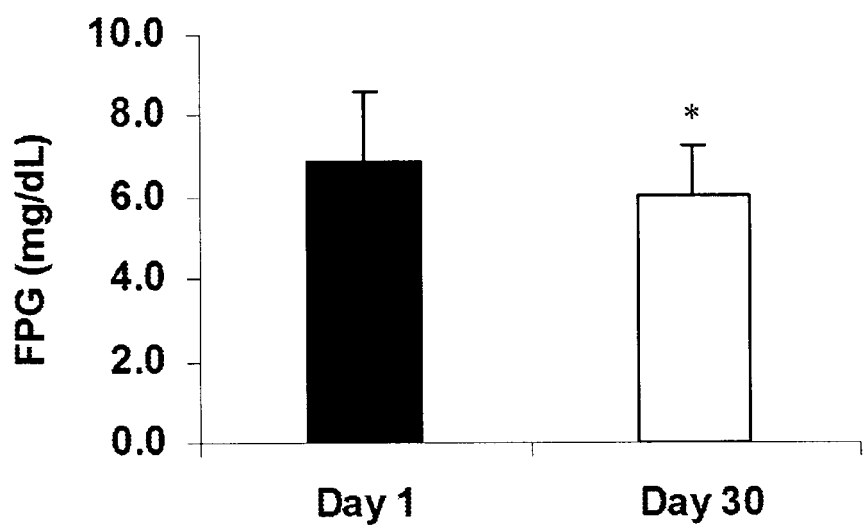
FIG. 32A-B: Oral anti-LPS immunoglobulin preparation decreases fasting glucose levels in humans. Oral administration of anti-LPS immunoglobulin preparation (HIBC) decreases fasting (serum) glucose levels (6.9 vs. 6.05 mmol/L, p<0.03).
Figure 32B:
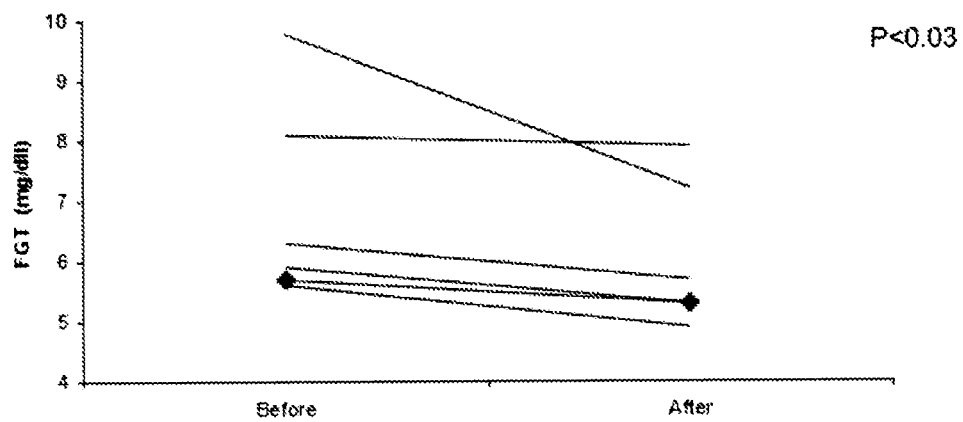

FIGS. 32A-B show a significant (p<0.01) reduction in fasting plasma glucose levels of treated patients (6.3 vs. 5.8 mmol/L, for day 1 vs. day 30, respectively, for five patients; P=0.063).

Figure 34A:
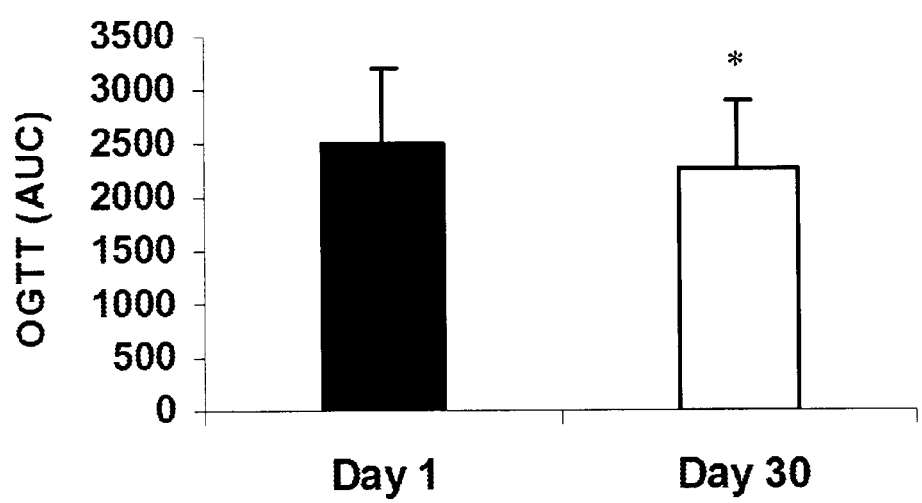
FIG. 34A-B: Oral anti-LPS immunoglobulin preparation increases improves oral glucose tolerance in humans. Oral administration of anti-LPS immunoglobulin preparation (HIBC) results in an improved OGTT (area under the curve (AUC) of 2492 vs. 2252, p<0.05).
Figure 34B:
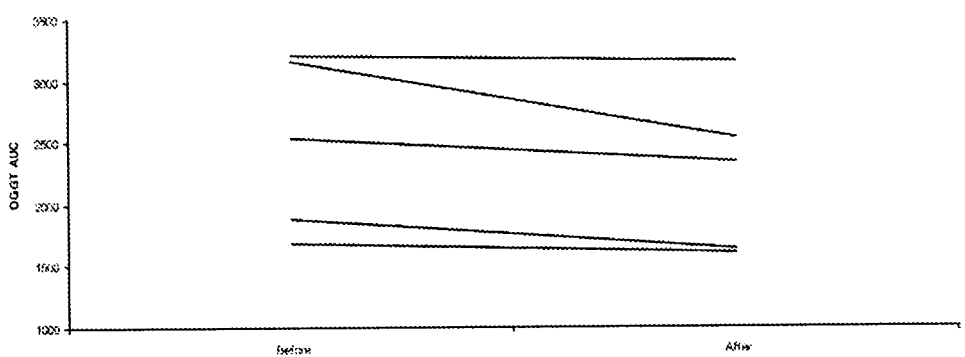

FIG. 34A-B show an improvement (p=0.08) in the results of oral glucose tolerance test (OGTT), as indicated by the area under the curve (2492 vs. 2252 for day 1 vs. day 30, respectively, for five patients).

Figure 36A:
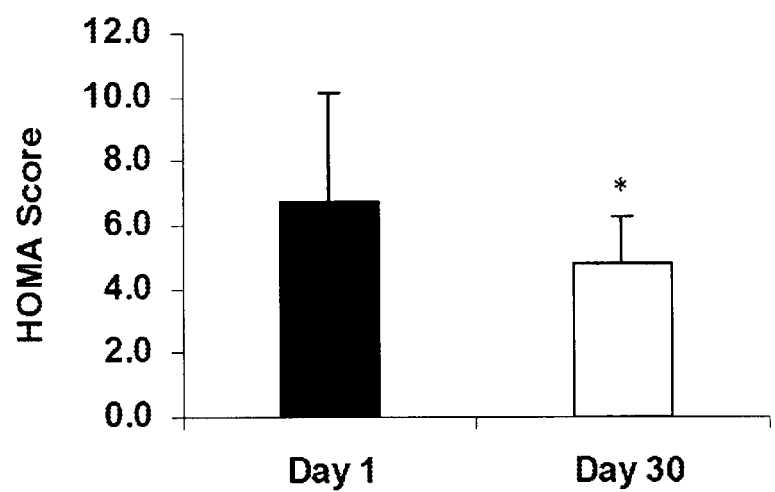
FIG. 36A-B: Oral anti-LPS immunoglobulin preparation improves HOMA scores in humans. Oral administration of anti-LPS immunoglobulin preparation (HIBC) results in improved HOMA scores (6.71 vs. 4.82, p<0.06)
Figure 36B:
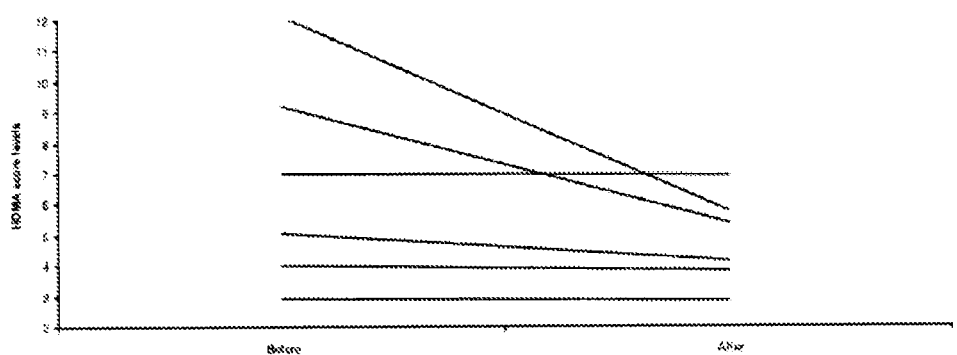

FIG. 36A-B show the improved HOMA scores (6.7 vs. 4.8, for day 1 vs. day 30, respectively, for six patients). As shown in FIG. 36B, the greatest decreases occurred in those subjects with the highest baseline HOMA scores, thus, the methods can include selecting subjects who have a HOMA score above a threshold, e.g., above 7 or 8, and administering the anti-LPS enriched colostrum as described herein.

Taking together these results show a clear improvement in insulin resistance in patients treated with oral anti-LPS immunoglobulin preparation at a dose of 1.8 g/day.

The central role of GLP-1 in glucose tolerance has raised questions about the possible involvement of this peptide in the pathogenesis of diabetes. A recent study found that the sensitivity of diabetic patients to GLP-1 was significantly reduced relative to nondiabetic individuals (Kjems et al., Diabetes 52, 380-386 (2003)).

Measurements of circulating cytokines and adiponectin were made as follows. Blood was drawn from all patients on day 1 and on day 30 of the study. Serum levels of IL-6 were determined using a "sandwich" ELISA using commercial kits (Quantikine, R&D Systems, Minneapolis, Minn., USA), according to the manufacturer's instructions. Glucagon-Like Peptide-1 (GLP-1) was tested by the following method: Blood was collected from all patients after a 12-hour overnight fasting at 180 min time point of OGTT. Blood was collected in ice-cooled EDTA tubes and immediately (<30 seconds) after collection, 20 µl of DPP-IV inhibitor was added to 2 ml of plasma, according to manufacturer's directions. Tubes were inverted and were then centrifuged immediately at 1000×g for 10 min in refrigerated centrifuge. After plasma separation, specimens were stored at −70° C. until running the ELISA assay. The circulating level of human GLP-1 was quantified using a commercial ELISA kit from Millipore (MA, USA) according to the manufacturer's instructions. Serum levels of human adiponectin were determined using a commercial ELISA kit from Linco Research (Missouri, USA). Serum was diluted 500 fold before the assay, and 20 µl of diluted serum, standard samples and controls were plated in duplicate on a mouse anti-human adiponectin-coated plate and examined using an ELISA reader at 450 nm, according to the manufacturer's instructions.

Figure 37A:
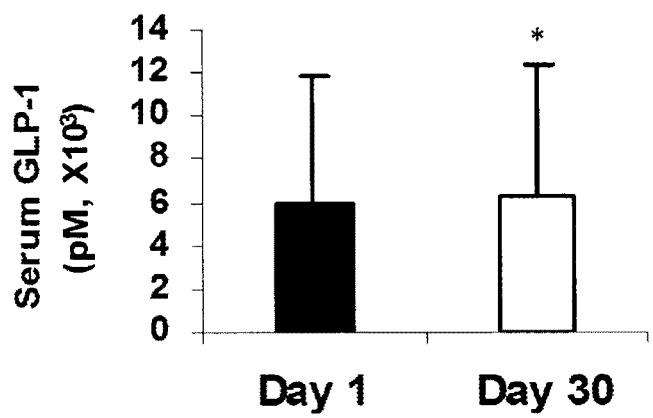
FIG. 37A-B: Oral anti-LPS immunoglobulin preparation increases GLP-1 levels in humans. Oral administration of anti-LPS immunoglobulin preparation (HIBC) results in increased GLP-1 levels in 60% of treated patients, (58.816 vs. 62.828 pM, p<0.04).
Figure 37B:
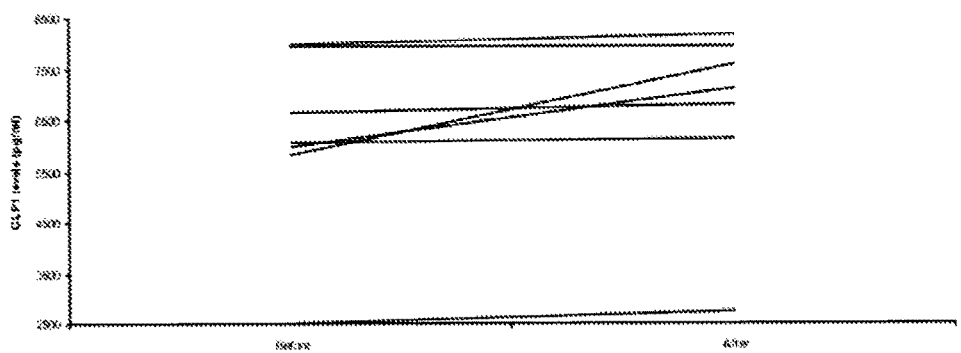
Figure 38A:
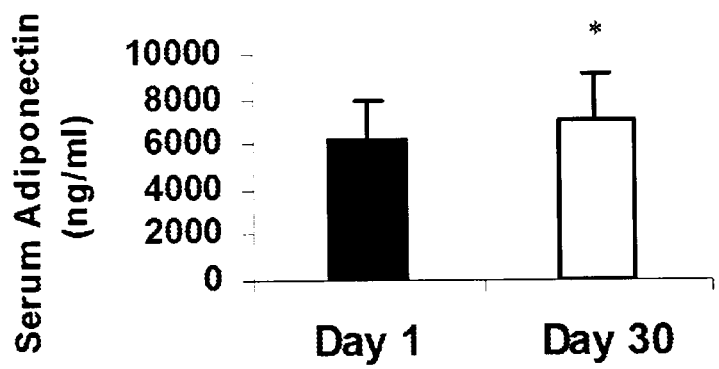
FIG. 38A-B: Oral anti-LPS immunoglobulin preparation increases adiponectin1 levels in humans. Oral administration of anti-LPS immunoglobulin preparation (HIBC) results in increased Adiponectin levels in 80% of treated patients, (6181 vs. 7068, ng/ml, p<0.01).
Figure 38B:
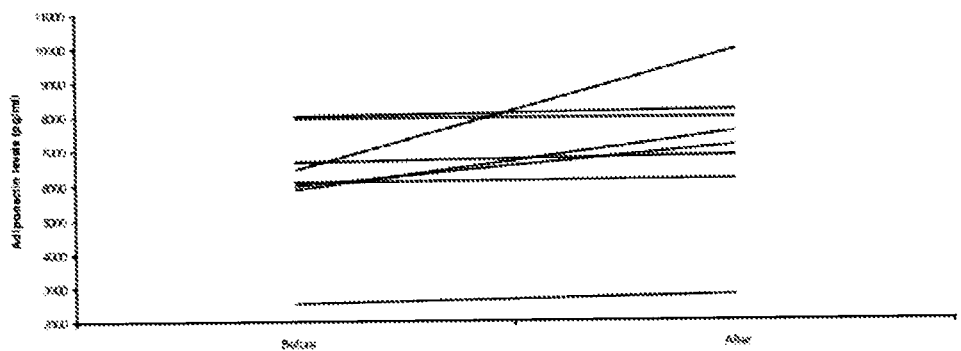

The circulating levels of serum GLP-1 were compared before and after carrying OGTT on day 1 and on day 30. FIGS. 37A-B show that treatment for 30 days increased serum levels of GLP-1 post-OGTT in five treated patients (6.31 vs. 6.78×10$^4$ pM, in responders). FIGS. 38A-B show the serum levels of adiponectin, which were increased in eight patients (6181 vs. 7069 ng/ml). Thus, oral anti-LPS immunoglobulin preparation at a dose of 1.8 g/day increases GLP-1 levels and adiponectin1 levels in humans.

Figure 39A:
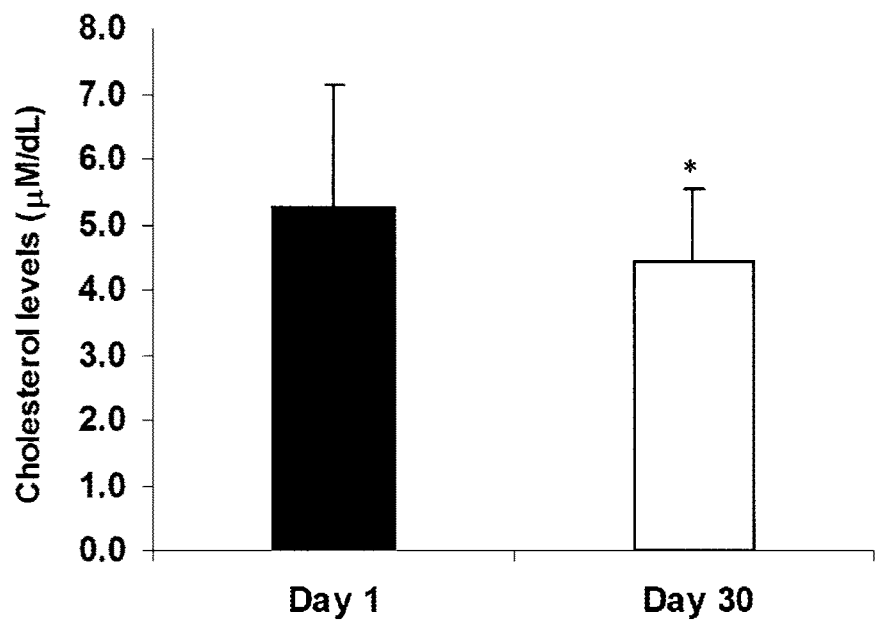
FIG. 39A-B: Oral anti-LPS immunoglobulin preparation decreases total cholesterol levels in humans. Oral administration of anti-LPS immunoglobulin preparation (HIBC) results in decreased Total cholesterol levels (5.28 vs. 4.44 µmol/L, p<0.04).
Figure 39B:
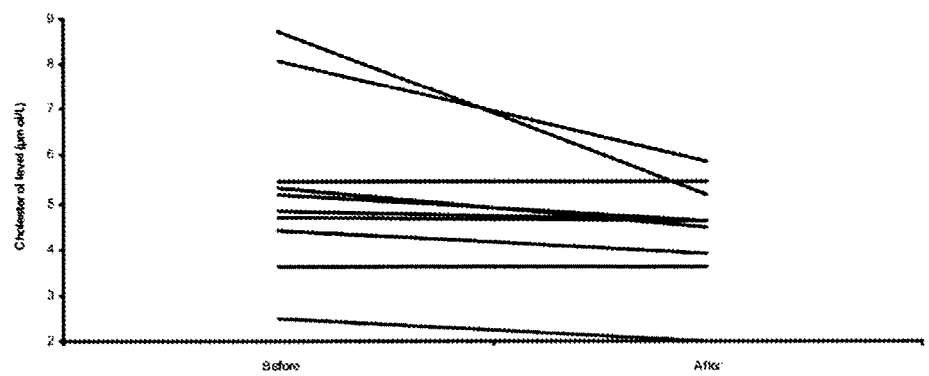
Figure 40A:
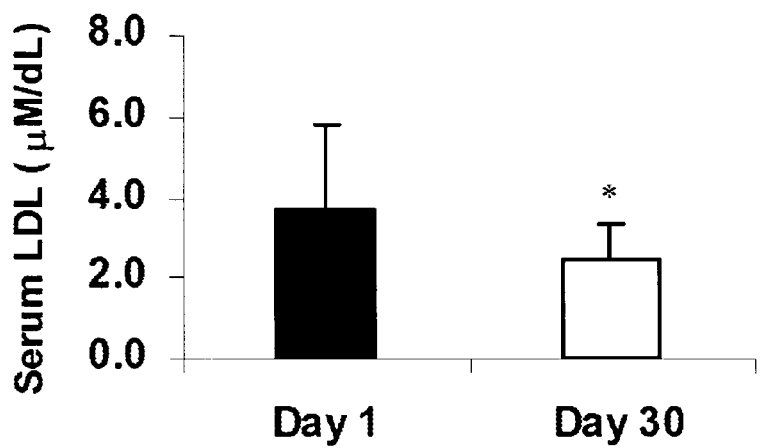
FIG. 40A-B: Oral anti-LPS immunoglobulin preparation decreases LDL cholesterol levels in humans. Oral administration of anti-LPS immunoglobulin preparation (HIBC) results in decreased LDL cholesterol (3.7 vs. 2.49 µmol/L, p<0.05).
Figure 40B:
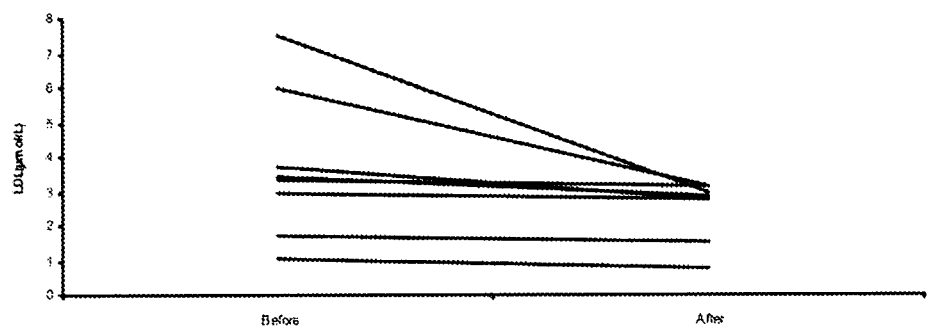
Figure 41A:
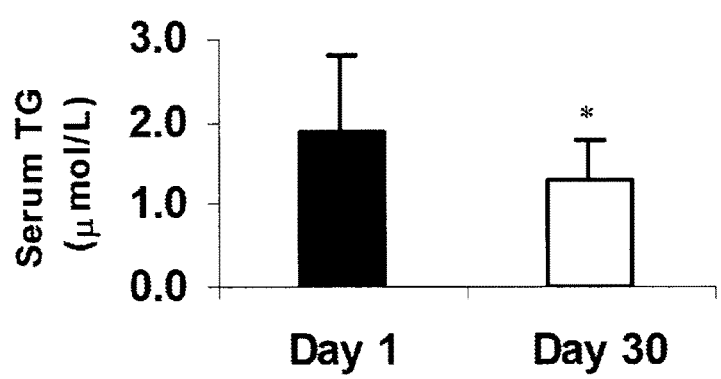
FIG. 41A-B: Oral anti-LPS immunoglobulin preparation decreases triglyceride levels in humans. Oral administration of anti-LPS immunoglobulin preparation (HIBC) results in decreased Triglycerides (1.88 vs. 1.32 µmol/L, p<0.05).
Figure 41B:
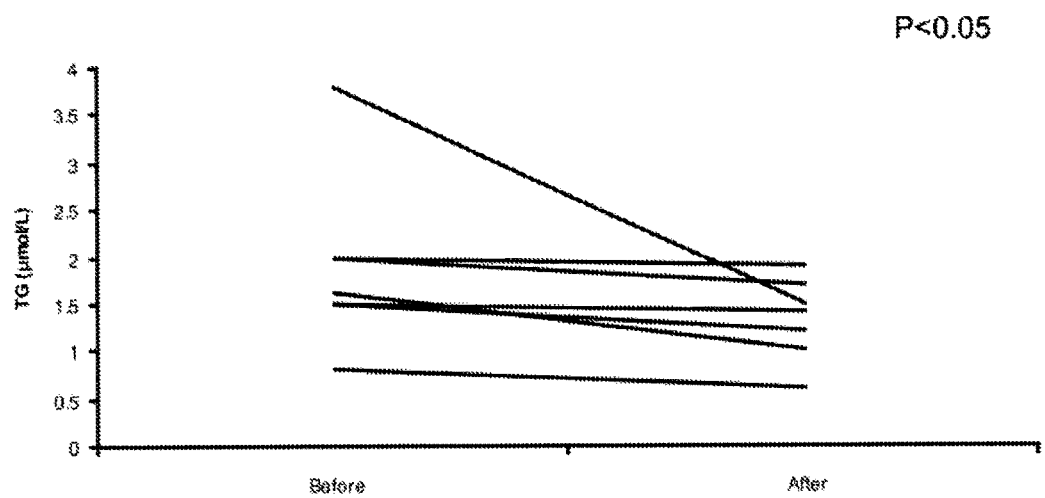

Example 37: Oral Administration of Anti-LPS Immunoglobulin Preparation Decreases Total Cholesterol Levels, LDL Cholesterol Levels and Triglyceride Levels in Humans FIGS. 39A-B show a beneficial effect of the anti-LPS immunoglobulin preparation on serum levels of total cholesterol in five treated patients (5.8 vs. 4.5 µmol/L, for day 1 vs. day 30, respectively). Similar results were obtained with serum LDL measurements (3.8 vs. 2.7 µmol/L, for day 1 vs. day 30, respectively, FIGS. 40A-B). A slight improvement in serum triglycerides levels was noted in five patients (FIGS. 41A-B). As shown in FIGS. 39B, 40B, and 41B, the greatest effects were seen in subjects with the highest levels of cholesterol, LDL, and trigylcerides; thus, the methods can include selecting subjects who have a level of total serum cholesterol above a threshold, e.g., above 6 uM/dL; a level of serum LDL above a threshold, e.g., 4 uM/dL, and/or a level of serum triglycerides above a threshold, e.g., above 2 or 2.5 uM/dL, and administering the anti-LPS enriched colostrum as described herein.

The data presented here suggest that oral administration of anti-LPS enriched colostrum has an ameliorating effect on the lipid profile, e.g., in NASH patients.

Example 38: Oral Administration of Anti-LPS Immunoglobulin Preparation Decreases Increases CD4+ CD25+ and CD4+ CD25+ Foxp3+ T Regulatory Cells in Humans In obesity-related disorders, such as NASH, chronic local inflammation is present in adipose tissue, and cells of the innate immune system are crucially involved in adipose inflammation and systemic metabolic abnormalities (Ilan et al., Proc Natl Acad Sci USA 107, 9765-9770 (2010)). Several subsets of peripheral T cells from PBMCs were characterized using flow cytometry. PBMCs from blood samples collected at day 0 and day were isolated using a Ficoll-Hypaque gradient. Cells were re-suspended in PBS containing 1% BSA. For surface staining, PBMCs were incubated with either fluorochrome-conjugated antibodies against the indicated cell surface markers (eBioscience, San Diego, Calif., USA) at the recommended dilution or with isotype control antibodies for 30 minutes at 4° C. We used the following cell surface antibodies: CD4−FITC, CD25−PE, CD8−FITC, CD56−FITC, CD69−PE, CD3−APC, CD62−PE and HLA-DR-APC. Cells were then washed in PBS containing 1% BSA and fixed with fixation buffer (eBiosciences) for another 50 minutes. For intracellular staining of Foxp3, cells were permeabilized with Foxp3 staining buffer (eBioscience) after fixation and stained with APC-conjugated antibodies against Foxp3 (eBioscience). The stained cells were then washed twice and resuspended in 250 µl of PBS containing 1% BSA and kept at 4° C. A total of 10$^6$ stained cells in 250 µl of PBS containing 1% BSA were subsequently analyzed using a FACS LSR II instrument (Becton Dickinson, San Jose, Calif.) with the FCS express V.3 software (DeNovo software, CA, USA). Only live cells were counted, and the background fluorescence from non-antibody-treated lymphocytes was subtracted.

Figure 42A:
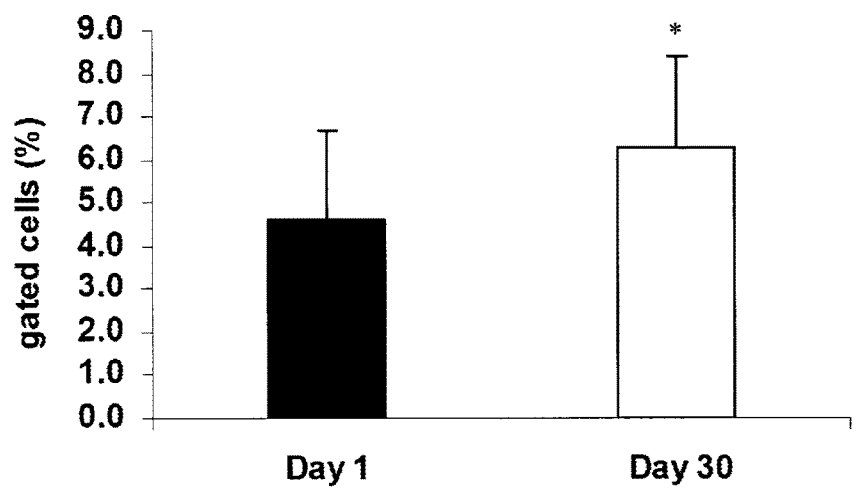
FIG. 42A-D: Oral anti-LPS immunoglobulin preparation increases CD4+ CD25+ T regulatory cell levels in humans. Oral administration of anti-LPS immunoglobulin preparation (HIBC) results in increased levels of CD25+ Tregs (5.24% vs. 7.12%), as shown in 42A-B. A significant (p=0.002) increase in CD4+CD25+ HLA-DR cells is shown in 42C.
Figure 42B:
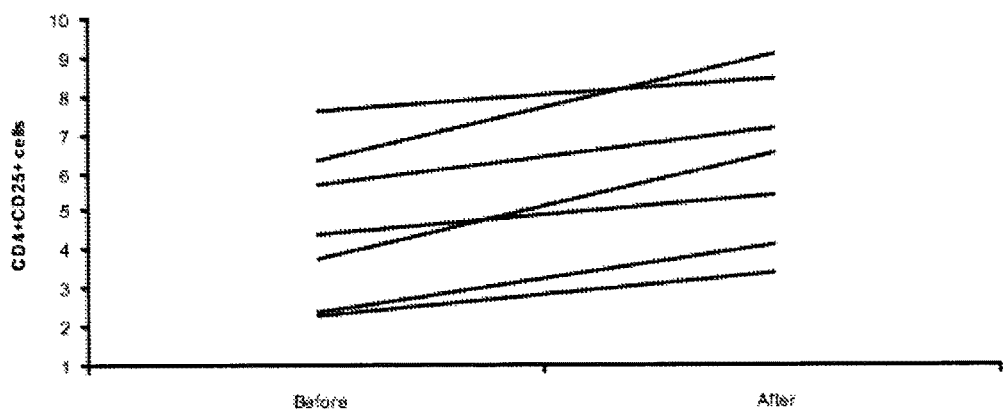
Figure 42C:
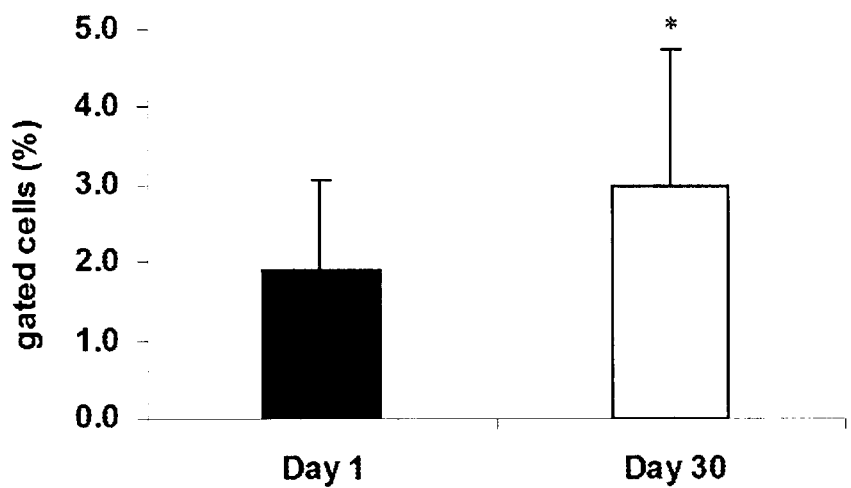
Figure 42D:
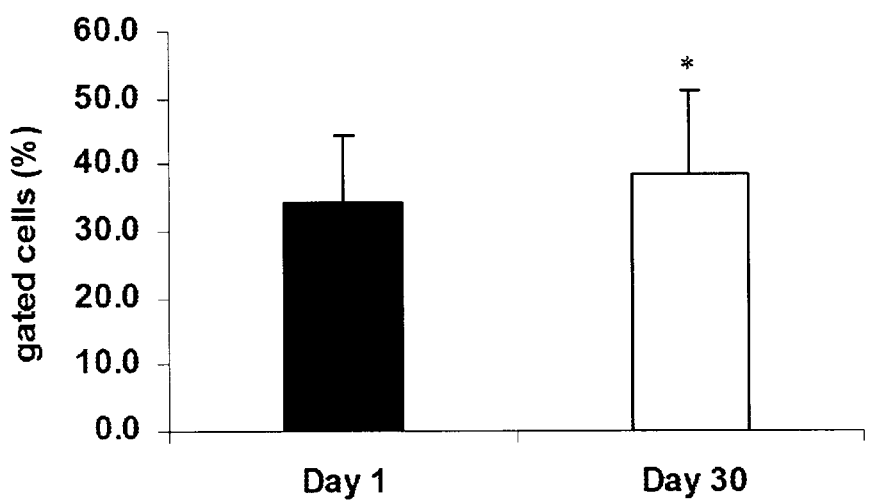
Figure 43A:
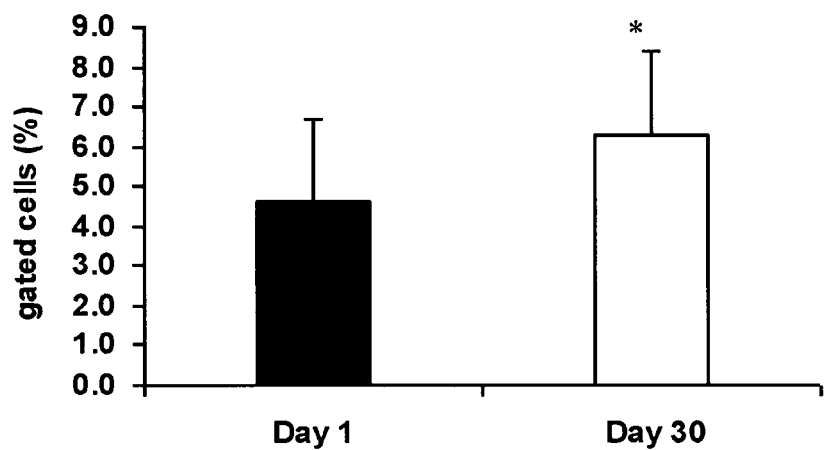
FIG. 43A-B: Oral anti-LPS immunoglobulin preparation increases CD4+ CD25+ T regulatory cell levels in humans. Oral administration of anti-LPS immunoglobulin preparation (HIBC) results in increased levels of CD4+CD25+ Foxp3+ Tregs (2% vs. 2.26% respectively, p<0.002).
Figure 43B:
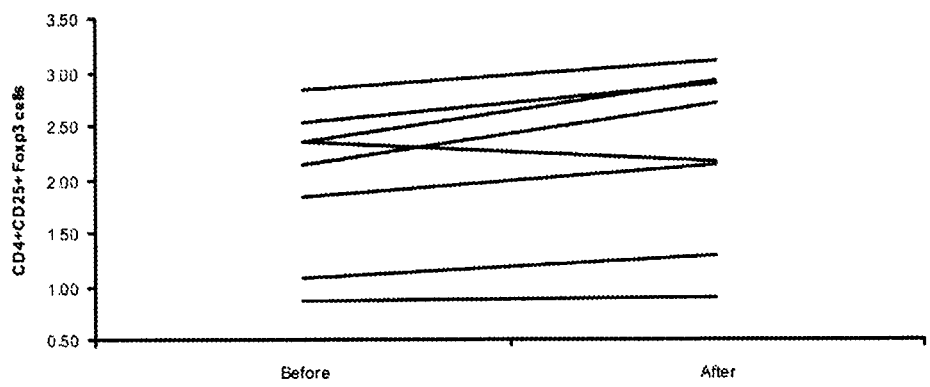
Figure 44:
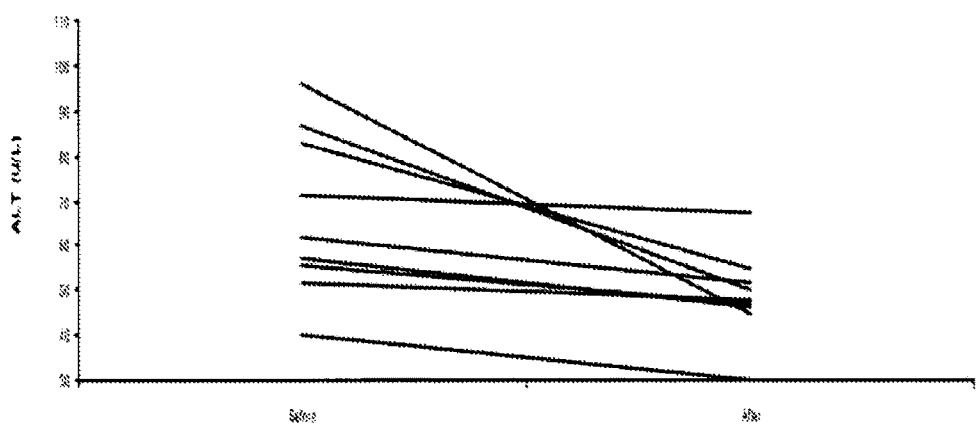
FIG. 44: Oral anti-insulin immunoglobulin decreases liver injury in humans. Oral administration of anti-insulin immunoglobulin preparation (HIBC) decreases ALT serum levels in 90% of patients (67 vs. 48 u/L, (p<0.01)).
Figure 45:
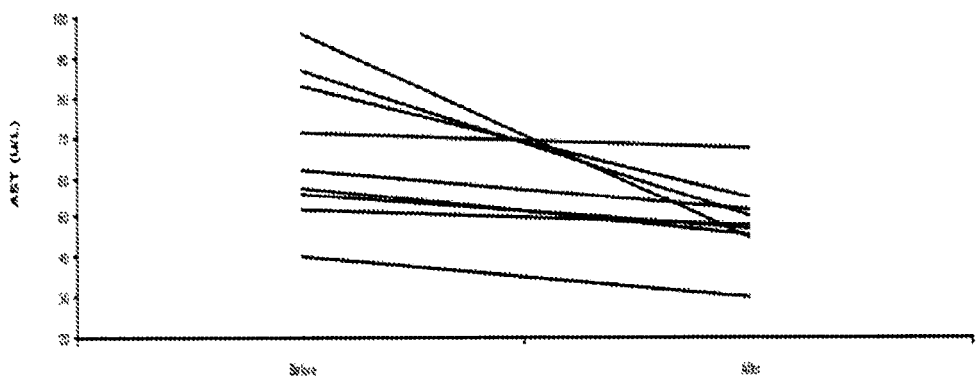
FIG. 45; Oral anti-insulin immunoglobulin decreases liver injury in humans. Oral administration of anti-LPS immunoglobulin preparation (HIBC) decreases AST serum levels in 80% of patients (59 vs. 48 u/L, (p<0.05)).
Figure 46:
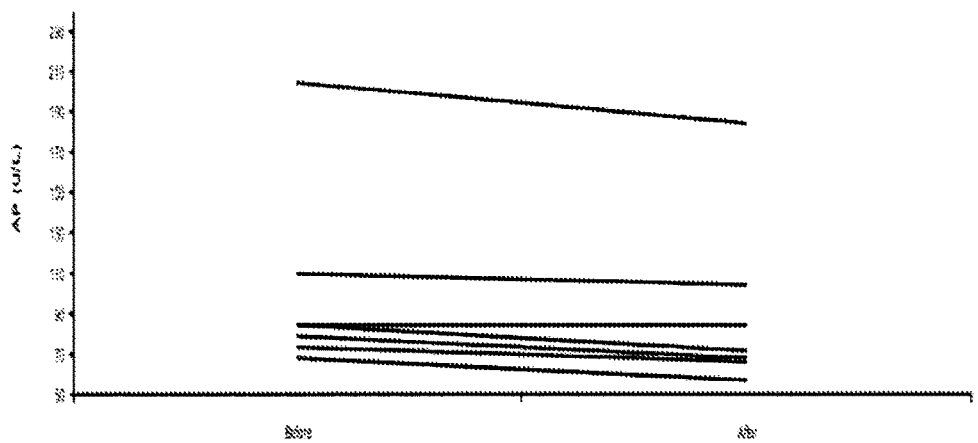
FIG. 46: Oral anti-insulin immunoglobulin decreases liver injury in humans. Oral administration of anti-insulin immunoglobulin preparation (HIBC) decreases AP serum levels in 70% of patients (101 vs. 91 u/L, (p<0.004)).
Figure 47:
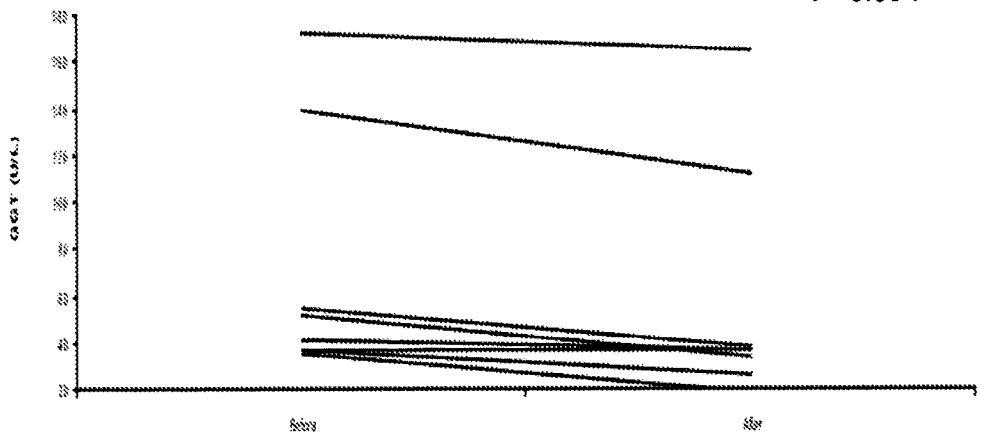
FIG. 47: Oral anti-insulin immunoglobulin decreases liver injury in humans. Oral administration of anti-insulin immunoglobulin preparation (HIBC) decreases GGT serum levels in 80% of patients (70 vs. 58 u/L, (p<0.004)).

FIGS. 42A-B show that CD4+CD25+ cells were elevated 30 days after oral treatment with an anti-LPS immunoglobulin enriched colostrum preparation in 7 out of the 10 patients (4.63 vs. 6.28%). A significant (p=0.002) increase in CD4+ CD25+ HLA-DR cells was noted in PBMCs (2.3 vs. 3.8% gated on CD4, for day 1 vs. day 30) of seven treated patients, as presented in FIG. 42C. FIG. 42D shows an increase in CD4+CD62+ cells which was noted in six patients (36.5 vs. 41% in responders, gated for CD4 cells). An increase in CD4+CD25+Foxp3+ cells was noted in seven out often treated patients (FIGS. 43A-B, 1.7 vs. 2.2% in responders). Taking together, the data presented here shows that oral administration of anti-LPS immunoglobulin preparation is associated with alterations of regulatory T lymphocytes, which may contribute to some of its anti-inflammatory effects.

Example 40: Oral Administration of Anti-LPS Immunoglobulin Preparation in Mice

Introduction: The metabolic syndrome is a chronic inflammatory condition. Regulatory T cells (Tregs) are essential for maintaining peripheral tolerance and limiting chronic inflammatory diseases. Tregs were shown to alleviate the pathological and metabolic abnormalities accompanied NASH in ob/ob mice.

Aim: To assess the effects of the induction of Tregs on hepatic injury and insulin resistance in NASH.

Methods: Leptin deficient Ob/Ob mice were fed for 6 weeks with bovine colostrum powder (BCP) prepared from cows that were not immunized or with colostrum from cows that were "hyper immunized" with LPS (Enterotoxigenic *E. coli*, 0.1 mg per dose), or with IgG-enhanced fraction of anti-LPS immunoglobulin preparation ('T-IgG') in three dosages, 0.001, 0.1 and 1 mg. Hepatic injury and insulin resistance were measured by fasting glucose levels, glucose tolerance tests (GTT) and liver enzymes. Fat accumulation in the liver and plasma lipids were measured. Serum TNF-alpha was determined by ELISA and the staining of Tregs in the spleen and liver was performed by flow cytometry.

Results: Oral administration of high dose (1 mg) of anti-LPS immunoglobulin preparation decreased ALT levels (P<0.05) and serum and hepatic triglycerides (P<0.009 and P<0.05, respectively), compared with control animals. Glucose intolerance measured by GTT, was alleviated after 90 and 120 min (P<0.05). Low and high doses of anti-LPS immunoglobulin preparation and T-IgG colostrums lowered glucose levels after 3 weeks of treatment. Serum TNF-alpha levels decreased by oral treatment of 0.1 and 1 mg of anti-LPS immunoglobulin preparation. The beneficial effect of anti-LPS immunoglobulin preparation and T-IgG was associated with an increase in the number of CD4+CD25+ cells (P<0.01, P<0.05, for 0.001, 0.1 and 1 mg anti-LPS immunoglobulin preparation, and T-IgG, respectively), CD4+CD25+Foxp3 cells (P<0.001, P<0.05 for 0.001 mg of anti-LPS immunoglobulin preparation, and 0.1 mg of T-IgG, respectively) and CD3+NK1.1 cells (P<0.05 for 0.1 mg of anti-LPS immunoglobulin preparation, and 0.1 mg of T-IgG).

Conclusions: Oral administration of IgG-enhanced fraction of ETEC colostrum induces Tregs and alleviates the chronic inflammatory state in the metabolic syndrome, alleviating insulin resistance and liver injury.

Example 41: Oral Administration of Anti-Insulin Immunoglobulin Preparation in Humans Metabolic syndrome is a chronic inflammatory disorder associated with insulin resistance and hepatic steatosis. Anti insulin (AI) colostrum ('anti-insulin immunoglobulin preparation' as described herein) can exert an immunomodulatory effect and alleviate target organ damage in animal models.

Aim: To determine the safety and efficacy of oral administration of anti-insulin immunoglobulin preparation to patients with insulin resistance and NASH.

Methods: In an open-label trial subjects with biopsy proven NASH and insulin resistance were orally treated for 30 days with 1.2 g/day (based on BCP dry weight) anti-insulin immunoglobulin preparation which was raised against Human insulin. Subjects were monitored for safety, serum levels of adiponectin, and GLP-1, and regulatory T cells (Tregs). The clinical effect was determined by OGTT, liver enzyme tests, and lipid profile, the comparison was done between day 30 and day 0 for each patient.

Results: Oral administration of anti-insulin immunoglobulin preparation was safe and no side effects were noted in any of the treated subjects. Alleviation of insulin resistance was determined by the following measures: A decrease in fasting glucose levels (6.01 vs. 5.55 mmol/L, p<0.008); Elevation in the early peak of insulin secretion following glucose administration was noted in 70% of treated patients (541 vs. 679 pmol/L, p<0.02); Improved OGTT (AUC of 1515 vs. 1420, p<0.002); and improved in HBA1C levels in 50% of treated patients (5.8 vs. 5.54, p<0.05). Treated patients (70%) showed a decrease in serum levels of triglycerides (2.62 vs. 1.72 μmol/L, p<0.06), total cholesterol (4.9 vs. 4.47 μmol/L, p<0.04), and LDL cholesterol (3.59 vs. 2.97 μmol/L, p<0.04). A decrease in liver enzymes was noted in most treated patients (ALT: 67 vs. 48, u/L, p<0.01; AST: 59 vs. 40 u/L, p<0.05; Alkaline phosphatase: 101 vs. 91 u/L, p<0.004; GGT: 70 vs. 58 u/L, p<0.004). A weight loss of at least 15% of the original body weight was observed in 90% of treated subjects (80.5 vs. 79.2 Kg, p<0.05), also noted a net reduction in waist circumference (99.6 vs. 95.6 cm, p<0.001), These effects were associated with increased serum levels of IL-6 90% of treated patients, (4.29 vs. 6.61 pM p<0.05). The Adiponectin/IL-6 ratio decreased in 90% of patients (2410 vs. 1970 p<0.03). An increased in CD25+ in 70% of treated patients and CD4+ CD25+Foxp3+ Tregs (3.38% vs. 6.61% and 2.95% vs. 4.27% respectively, p<0.002).

Conclusion: Oral administration of anti-insulin immunoglobulin preparation is safe and exerts an immunomodulatory effect in patients with type 2 diabetes, hyperlipidemia and NASH. The anti-inflammatory effect and the promotion of Tregs are associated with alleviation of insulin resistance, hyperlipidemia, and liver damage in these patients.

Example 42: Oral Administration of Anti-Insulin Immunoglobulin Preparation Decreases Liver Injury in Humans FIGS. 44, 45, 46 and 47 demonstrate oral administration of anti-insulin immunoglobulin preparation (anti-insulin HIBC) at a dose of 1.2 g/day decreases liver injury in humans.

Figure 48:
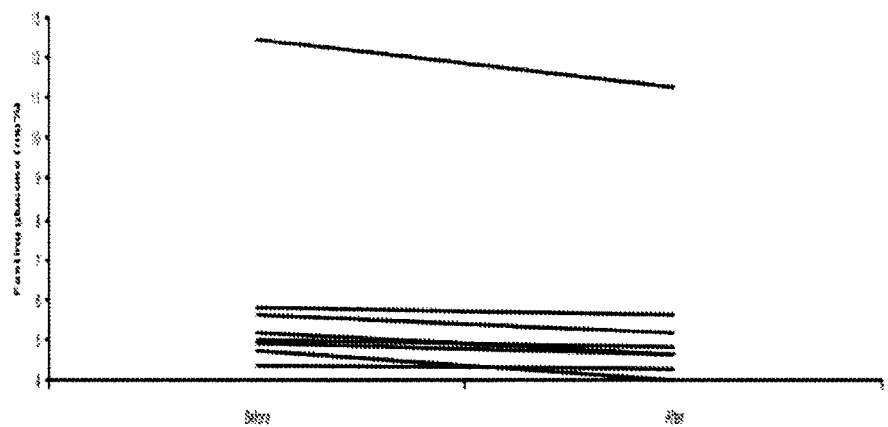
FIG. 48: Oral anti-insulin immunoglobulin decreases fasting glucose levels in humans. Oral administration of anti-insulin immunoglobulin preparation (HIBC) decreases fasting (serum) glucose levels in 80% of patients (6.01 vs. 5.55 u/L, (p<0.008)).
Figure 49:
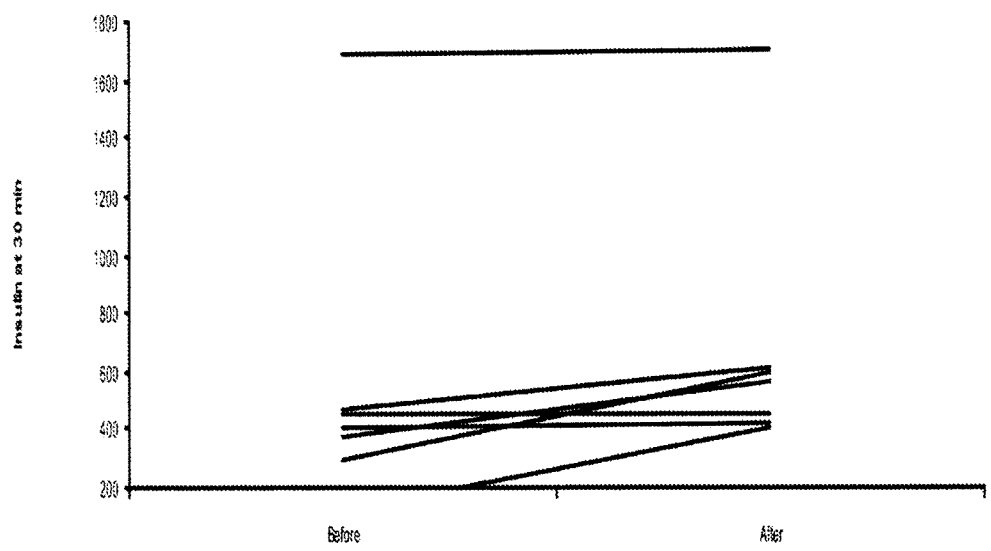
FIG. 49: Oral anti-insulin immunoglobulin preparation increases early peak insulin secretion in humans. Oral administration of anti-insulin immunoglobulin preparation (HIBC) results in an elevation in the early peak of insulin secretion following glucose administration in 70% of patients (541 vs. 679 pmol/L, p<0.02).
Figure 50:
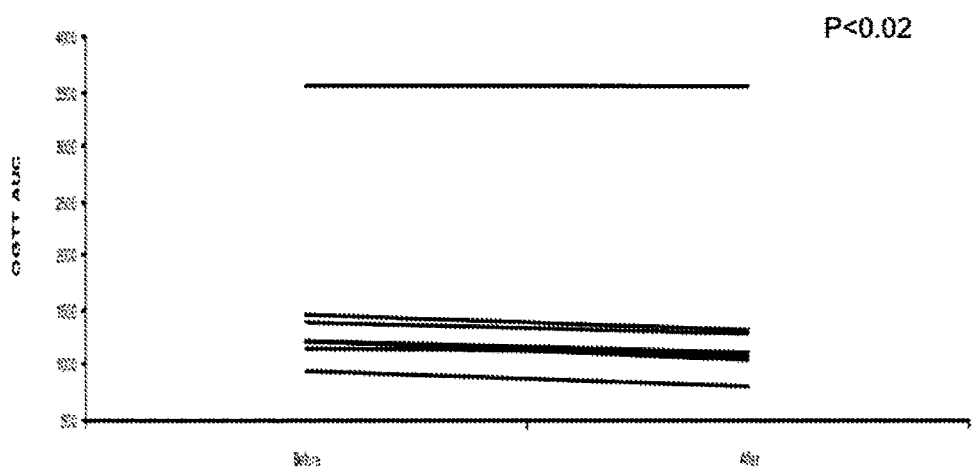
FIG. 50: Oral anti-insulin immunoglobulin preparation increases improves oral glucose tolerance in humans. Oral administration of anti-insulin immunoglobulin preparation (HIBC) results in an improved OGTT (area under the curve (AUC)) in 80% of patients of 1515 vs. 1420, p<0.02).

Example 43: Oral Administration of Anti-Insulin Immunoglobulin Preparation Decreases Fasting Glucose Levels, Increases Early Peak Insulin Secretion, Improves Oral Glucose Tolerance and Improves HB1Ac Levels, Improves HOMA Scores, GLP-1 Levels in Humans FIG. 48 demonstrates oral anti-insulin immunoglobulin preparation at a dose of 1.2 g/day decreases fasting glucose levels in humans. FIG. 49 demonstrates anti-insulin immunoglobulin preparation at a dose of 1.2 g/day increases early peak insulin secretion in humans. FIG. 50 demonstrates oral anti-insulin immunoglobulin preparation at a dose of 1.2 g/day improves oral glucose tolerance in humans.

Figure 51:
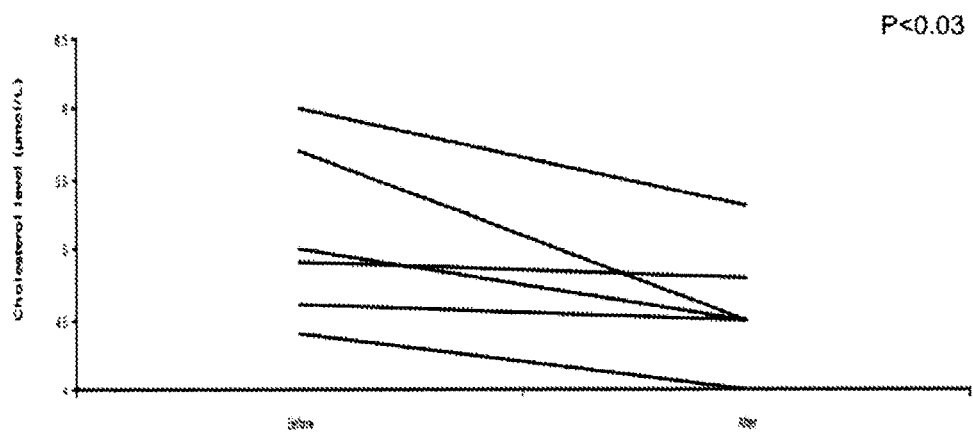
FIG. 51: Oral anti-insulin immunoglobulin preparation decreases total cholesterol levels in humans. Oral administration of anti-insulin immunoglobulin preparation (HIBC) results in decreased total cholesterol levels in serum in 70% of treated patients (4.9 vs. 4.47, p<0.03).

Example 44: Oral Administration of Anti-Insulin Immunoglobulin Preparation Decreases Total Cholesterol Levels, LDL Cholesterol Levels and Triglyceride Levels in Humans FIG. 51 demonstrates oral anti-insulin immunoglobulin preparation at a dose of 1.2 g/day decreases total cholesterol levels in humans. An anti-insulin immunoglobulin preparation at a dose of 1.2 g/day decreases body weight in humans.

Figure 52:
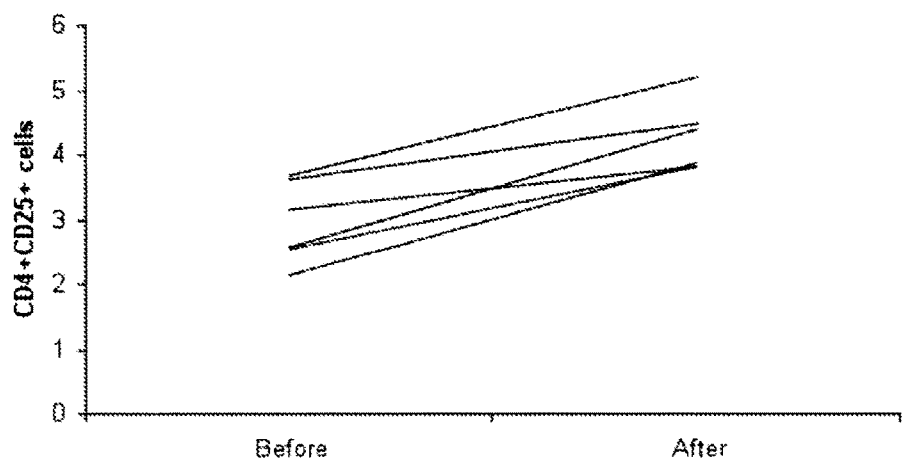
FIG. 52: Oral anti-insulin immunoglobulin preparation increases CD4+ CD25+ T regulatory cell levels in humans. Oral administration of anti-insulin immunoglobulin preparation (HIBC) results in increased CD4+CD25+ Tregs in 60% of patients (2.95% vs. 4.27%, p<0.003).

Example 45: Oral Administration of Anti-Insulin Immunoglobulin Preparation Decreases Increases CD4+ CD25+ T Regulatory Cells in Humans FIG. 52 demonstrates oral administration of anti-insulin immunoglobulin preparation (HIBC) at a dose of 1.2 g/day results in increased CD4+CD25+ Tregs in 60% of patients (2.95% vs. 4.27%, p<0.003).

Example 46: Oral Administration of Anti-Insulin Immunoglobulin Preparation Decreases Waist and Arm Circumference in Humans Oral administration of anti-insulin immunoglobulin preparation (HIBC) at a dose of 1.2 g/day results in decreased waist and arm circumference in humans.

Example 47: Preparation of Anti-LPS Immunoglobulin Enriched Colostrum Preparation Dairy cows at commercial dairy farms are immunized with either a killed single strain ETEC vaccine (O78 serotype) or a killed multivalent ETEC vaccine in adjuvant (combined O6, O8, O15, O25, O27, O63, O114, O115, O128, O148, O153 and O159 serotypes). The single strain vaccine is used to immunize approximately one third of the cows against one of the most common ETEC strains (serotype O78) and the multi-strain vaccine is used to immunize the other two-thirds of the cows in the immunization program.

Single Strain and Multi-Strain *E. coli* Vaccine Production Process

Strain Rejuvenation—The O78 single strain, H10407, to be rejuvenated is streaked on 2 CFA media plates. These "rejuvenation plates" are placed in the 37° C. incubator overnight under aerobic conditions.

Inoculation of "starter suspension"—Each "rejuvenation plate" is examined for pure growth. If growth is absent or non-pure, the production is restarted from the beginning. If growth is pure, several colonies from one rejuvenation plate are removed with a sterile loop and are used to inoculate a starter suspension in a McCartney bottle containing 20 mL of phosphate buffered saline (PBS) pH 7.2.

Inoculation of vaccine plates—starter suspension is inoculated onto multiple CFA plates. These vaccine plates are incubated at 37° C. for 18-24 hrs under aerobic conditions.

A haemagglutination test is carried out on one of the vaccine plates to confirm pilus production.

Washing of "vaccine plates"—The bacterial growth from the surfaces of the vaccine plates are washed with cooled, sterile 0.1M sodium phosphate buffer (pH 7.2) into a sterile Schott bottle. The vaccine washings are cooled on ice for at least 30 minutes before commencing homogenization.

Enumeration of Vaccine Washings—The "vaccine washings" step is enumerated. The material should be thoroughly agitated to disperse all clumps and ensure that the dilutions chosen are appropriate to the degree of concentration of bacterial cells in the washings for the batch being manufactured.

Purity sampling—Several different plates (HBA, TSA and MAC) are assembled for purity testing of each "vaccine washing." Single colonies are cultured on media and placed in the 37° C. incubator under aerobic conditions. Process is continued only if plates contain only pure colonies of *E. coli*.

Homogenization of vaccine washing—The "vaccine washing" is homogenized using a sterilized probe with a homogenizer for a total of 15 minutes at one minute intervals, with one minute of cooling in an ice-bath between each interval.

Separation and dialysis of Pilus/LPS fraction—The "homogenized vaccine washing" is centrifuged at 12,000 g for 20 minutes at 4° C. and the supernatant is kept. Sterile saturated ammonium sulphate solution is added slowly to the supernatant until 20% saturation is reached. Recentrifuge the mixture and again keep the supernatant. Add further saturated ammonium sulphate solution until 40% saturation is reached and then recentrifuged again. The "Pilus/LPS" fraction is located in the pellet. The "Pilus/LPS" fraction is resuspended and then dialyzed, using a 3,500 MW cut-off membrane, for 24-48 hours at 4° C. against 250-1,000 volumes of cold 0.05M sodium phosphate buffer pH 7.2.

Assaying protein content of "Pilus/LPS dialysate"—The protein content of each "Pilus/LPS dialysate" is measured using a Pearce protein assay and the concentration is adjusted to 1 mg/ml.

Inactivation of vaccine—Formaldehyde is added to each "Pilus/LPS dialysate" so that the final concentration of formalin is 0.3% and stored at 4° C. for three days. Then the vaccine is tested for sterility.

Storage of formalinized Pilus/LPS dialysate—The "formalinized Pilus/LPS dialysate", is stored at minus 20° C.

Equal quantities of thawed "formalinized Pilus/LPS dialysate" and Seppic Montanide ISA 206 adjuvant are warmed to 30° C. and then mixed together gradually while stirring. After overnight storage at 4° C., vaccine is re-mixed and then filled into sterile pillow packs.

Final QC of the vaccine before release includes testing for sterility, free formalin level and safety test for one week at 2×normal dose in 3 cows.

The Immuron Multi Strain *E. coli* Vaccine is derived from the equivalent cell mass as the Single Strain *E. coli* Vaccine, with each strain contributing an equal share of the total. Each of the 12 strains are prepared using the above process and then pooled before final formulation with adjuvant. The 12 strains are shown in Table 7A.

TABLE 7A

Enterotoxigenic *E. coli* Strains in Immuron's Killed ETEC Vaccines

| Serotype | Strain no. | Source | Date of Isolation[ref] |
|---|---|---|---|
| ETEC O6: H16 | B2C | USA | pre-1971[1] |
| ETEC O8: H19 | C55 3/3c3 | USA | mid-1980's |
| ETEC O15: H4 | PE 595 | IMVS, Adelaide | Aust. source |
| ETEC O25: H42 | E11881A | USA | 1986 |
| ETEC O27: HR | C1067-77 | USA | 1985 |
| ETEC O63: H- | PE 673 | IMVS, Adelaide | Aust. source |
| ETEC O78: H11 | H10407 | USA | pre-1973[2] |
| ETEC O114: H21 | E20738/0 | UK | 1980[3] |
| ETEC O115: H- | PE 724 | IMVS, Adelaide | Aust. source |
| ETEC O128: H21 | EI 37-2 | USA | 1985 |
| ETEC O148: H28 | B7A | USA | pre-1971[1] |
| ETEC O153: H12 | E8772/0 | UK | pre-1980 |
| ETEC O159: H- | PE 768 | IMVS, Adelaide | Aust. source |

References quoted in table:

[1]DuPont, H. L. et al., (1971) Pathogenesis of *Escherichia coli* diarrhea. New England J. of Medicine, 285: 1-9.

[2]Evans, DJ, Jr. and Evans, DG (1973) Three characteristics associated with enterotoxigenic *Escherichia coli* isolated from man. Infect. Immunity 8: 322-328.

[3]McConnell MM, Hibberd M, Field AM, Chart H and Rowe B (1990) Characterization of a new putative colonization factor (CS17) from a human enterotoxigenic *Escherichia coli* of serotype O114:H21 which produces only heat-labile enterotoxin. J. Infect. Dis. 161(2): 343-347.

The following Table 7B describes the vaccine composition.

TABLE 7B

ETEC Vaccine Composition

| Constituent | Manufacturing Specification | Concentration | Purpose in Formulation |
|---|---|---|---|
| A. Each 2 ml of Single Strain *E. coli* Vaccine contains: | | | |
| 1 ml of "Formalised Pilus/LPS Dialysate" from O78 *E. coli* serotype | Prepared as described in Allied Biotech Doc. No. S04gs | Final conc. of "Pilus/LPS" immunogen is min. of 1.0 mg/ml | Immunogen |
| Containing 0.05M sodium phosphate buffer Ph 7.2 | | | Buffer |
| Free Formalin | | <0.002% w/v in final emulsion | Inactivates vaccine |
| Plus 1 ml of Seppic Montanide ISA206 Adjuvant | | | Adjuvant |
| B. Each 2 ml of Multi Strain *E. coli* Vaccine contains: | | | |
| 1 ml of "Formalised Pilus/LPS Dialysate" from the following *E. coli* serotypes: O6, O8, O15, O25, O27, O63, O114, O115, O128, O148, O153 and O159. | Prepared as described in Allied Biotech Doc. No. S04gm | Each strain contributing an equal share (1/12) of the total minimum equivalent cell mass needed to produce the 1.0 mg/ml final concentration of the Immuron Single Strain *E. coli* vaccine | Immunogen |
| Containing 0.05M sodium phosphate buffer Ph 7.2 | | | Buffer |
| Free Formalin | | | Inactivates vaccine |
| Plus 1 ml of Seppic Montanide ISA206 Adjuvant | | | Adjuvant |

Hyper-Immunization of Dairy Cows

All immunizations are administered using clean handling procedures in order to maximize immune response to the antigens, and to minimize any reaction to the injection. Starting preferably 2 to 4 months pre partum, the selected cows are yarded and a sub-cutaneous injection is administered. The cows are immunized a further 2 times leading up to calving at 2-4 week intervals, ceasing at least 1 month before calving. Injections are given by the sub-cutaneous route after thoroughly disinfecting site by scrubbing with an iodine preparation.

A hygienic, food grade polyethylene bag is used to collect and store the colostrum at each farm. The colostrum is filtered as it enters the bag using a 200 micron filter, to remove gross matter.

The colostrum is harvested from Holstein Friesian and Jersey cows. They are all government registered and at the time of harvesting are free from antibiotics. They are not given steroids at any stage of the process. Colostrum is harvested at the first milking which will be within twelve hours of calving. Each cow produces approximately 8 liters of colostrum. New born calves are given a portion of the harvested colostrum to ensure they receive the necessary nutrients. After the colostrum is harvested it is rapidly cooled in water before being stored in the freezer at −20° C.

Preparation of Drug Substance

Frozen blocks of colostrum are chipped into the raw colostrum tank, using a modified "Butcher Boy" milling machine. Milled colostrum is thawed and recirculated at 7° C. and then heated to 30° C., before being diluted by the addition of similar volume of microfiltered water. At this stage, the pH is confirmed to be in the 6.4-6.6 range.

The diluted colostrum is heated to 55° C. before centrifugation for 1 hr, using a Westfalia milk separator with an automatic desludger, to remove fat, somatic cells, cell debris and some bacteria.

Colostrum skim is collected into the water-jacketed, pasteurization tank where the product is pasteurized to destroy the pathogenic bacteria. The maximum temperature it is exposed to is 65° C., which ensures that the immunoglobulin remains active. Colostrum is pasteurized at a minimum temperature of 63° C. for 30 minutes, cooled to 5° C. and then subjected to membrane ultra-filtration, removing much of the water, ions and lactose.

The ultra-filtration step, using an APV spiral wound ultrafiltration unit with 100 kD membranes, results in the production of a finished product with high protein (over 80% protein) and over 35% IgG, the key component of the product. Ultrafiltration produces a concentrate with about half of the initial volume of the colostrum, by removing water and lactose and concentrates the protein content to around 18% and total solids content to approximately 20%. In general, an amount of IgG of not less than 7% is desirable.

The colostrum wet concentrate at 4° C. is transferred into freeze-drying trays and lyophilized at −20° C. to produce a powder, which is milled to 200 microns.

Determination of Anti LPS Antibodies in Anti-LPS Immunoglobulin Enriched Colostrum Preparation The immunization of cows with several strains of enteropathogenic *E. coli* boosts the concentration of specific antibodies against these microbes in the blood and colostrum. For immunization, a patented killed vaccine was used to produce very high levels of specific antibodies against selected surface antigens from 13 of the most common strains of *E. coli*. The resulting antibodies were enriched with anti-LPS antibodies. The specific antibody titers in an anti-LPS immunoglobulin enriched colostrum preparation hyperimmune BC was analyzed by a validated in-house ELISA against a pool of antigens from both the multiple *E. coli* strain vaccine (O6, O8, O15, O25, O27, O63, O114, O115, O128, O148, O153 and O159 serotypes) and the single-strain (O78) vaccine antigens.

ELISA methods were as follows. First an anti-LPS immunoglobulin enriched colostrum preparation colostrum powders were weighed and resuspended vigorously in PBS-T at 40 mg/ml. Suspensions were vortexed repeatedly over 2-3 hrs at room temperature and un-dissolved components were removed by centrifugation. Supernatant was then collected into fresh tubes for further dilution. Diluted samples in 0.5% casein-PBS-T were made by serial four-fold steps, to give dilutions of 1/250, 1/1000, 1/4000 and 1/16,000, prior to assay. 100 µl of coating antigen (described above) was dispensed into a flat-bottomed 96 well plate (Nunc-Immuno, Nunc, Denmark) and then incubated overnight at 4° C. One ELISA plate was coated with single strain antigen at $1\times10^{-3}$ mg/ml and another plate was coated with multi-strain antigen at $1\times10^{-2}$ mg/ml. Following incubation, plates were washed five times with PBS-T and then tapped dry on paper towel. 200 µl of blocking solution (5% casein-PBS) was added and the plates were incubated for 2 hr at 37° C. to reduce non-specific binding. After washing, four-fold dilutions (1/250, 1/1000, 1/4000, 1/16,000, 1/64,000 and 1/256,000) of each sample and controls were prepared in an uncoated 96-well plate, using 0.5% casein-PBS-T as the diluent. 100 µl of each dilution was removed from the dilution tray and transferred into the wells of the ELISA plate and incubated at 37° C. for 2 hrs. All samples were tested at least twice to ensure accurate results. Positive and negative (no antibody) controls were included in each plate. Plates were washed 5 times with PBS-T and tapped dry. Then 100 µl of a 1/4000 final concentration of HRP conjugated rabbit anti-bovine secondary antibody (Sigma) was dispensed into 96 well plate and then incubated for 1 hr at 37° C. Plates were washed again 5 times and 100 µl of substrate reagent (KPL SureBlue TMB peroxidase substrate) was dispensed into the plates, which were then mixed and incubated at room temperature, with gentle shaking. The substrate reaction was then stopped by the addition of 100 µl of 1M HCl. The optical density (OD) of each well was read at 450 nm on a plate reader (Labsystems "Multiskan Ascent" ELISA) and analysed using Ascent software version 2.4.

Figure 53:
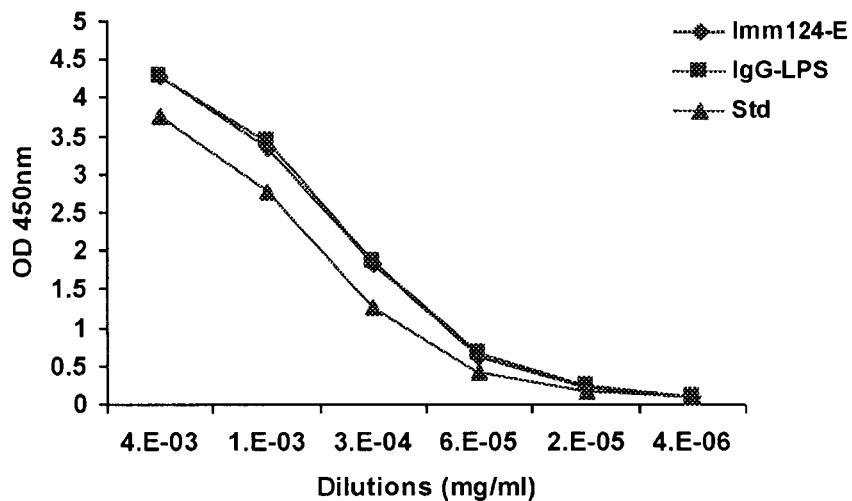
FIGS. 53 and 54: Results of ELISA for determining specific anti LPS antibodies titer in single-strain (53) and the multi-strain (54) vaccines.
Figure 54:
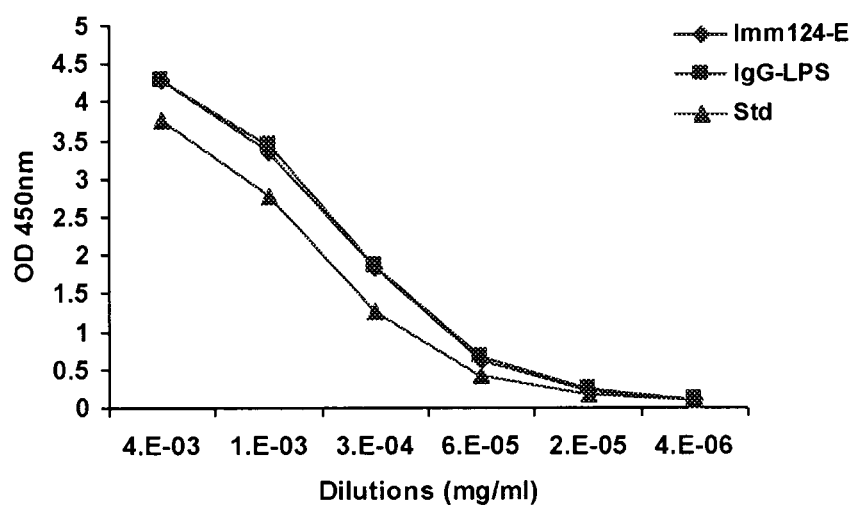

The titer of anti-LPS antibodies was compared to control. FIGS. 53 and 54 show the results of this assay, which clearly demonstrates the high content of anti LPS antibodies in an anti-LPS immunoglobulin enriched colostrum preparation.

Example 48: Anti-LPS Enriched Immunoglobulin Preparation Ameliorates Inflammatory Bowel Disease The effect of an anti LPS enriched immunoglobulin preparation on the immune system was assessed in an animal model of inflammatory bowel disease.

To investigate the immunopathogenesis of inflammatory bowel disease (IBD), murine models of experimental colitis have been developed that frequently are used to evaluate new anti-inflammatory strategies. One of the most widely used models is colitis induced by the haptinizing agent 2,4,6-trinitrobenzene sulfonic acid (TNBS). It is thought that this model resembles Crohn's disease because of the resulting mucosal inflammation mediated by a Th1 response with excessive proinflammatory cytokine production.

TNBS colitis generally is induced by intrarectal application of TNBS in ethanol. In the development of a delayed-type hypersensitivity (DTH) reaction, the first period is the sensitization phase. The application of the hapten in TNBS results in modification of autologous molecules in the mucosa, leading to priming of antigen-specific T cells. The initial sensitization phase is about 7 days. The animals were sensitized for TNBS using another site, e.g., the skin. The TNBS-induced colitis was scored on day +4, which reflects this acute local reaction representing the initial sensitizing phase. The efferent or elicitation phase, the DTH reaction, can be studied only after reapplication of the initiating agents.

Male, Balb-c, 7-8 weeks old nice were maintained on standard laboratory chow and kept in 12-h light/dark cycles. The mice were moved to an SPF-free environment (laboratory) 3 days before commencing the experiment. To induce hapten-mediated colitis, the mice were sensitized with 160 mL of the haptenizing agent TNBS (Sigma-Aldrich, Rhovot, Israel) at a concentration of 2.5% in 50% ethanol by skin painting on day −7. On day 0, 120 mL of 2.5% TNBS in 50% ethanol was administered intrarectally via a 3.5-French catheter which was carefully inserted into the colon such that the tip was 4 cm proximal to the anus. Animals were then kept in a vertical position for 30 seconds and returned to their cages. Animals were treated orally (see tables 8 and 9) by various treatments during and after the senstization phase, and then sacrificed on day +4 (four days after the intrarectal TNBS installation.

TABLE 8

| | Days | | | | | | | | |
|---|---|---|---|---|---|---|---|---|---|
| | −7 | −6 | −5 | −4 3− | 0 | 1+ | +2 | 3+ | 4+ |
| Group A: | S | TNBS | Sacrifice | | | | | | |
| Group B: | S | B | B | B B | TNBS | B | B | B | Sacrifice |
| Group C: | S | I | I | I I | TNBS | I | I | I | Sacrifice |
| Group D: | S | I | I | I I | TNBS | I | I | I | Sacrifice |

S—Sensitization (skin painting);
TNBS—Intra rectal TNBS;
B—BCP;
I—anti LPS

TABLE 9

| Group | Treatment | Ligand | Administration |
|---|---|---|---|
| A<br>N = 4 | TNBS | water | PO (30 ml) |
| B<br>N = 4 | TNBS | 100 mg BCP* | PO (30 ml) |
| C<br>N = 4 | TNBS | 50 mg anti LPS** | PO (30 ml) |
| D<br>N = 4 | TNBS | 500 mg anti LPS | PO (30 ml) |

Figure 55:
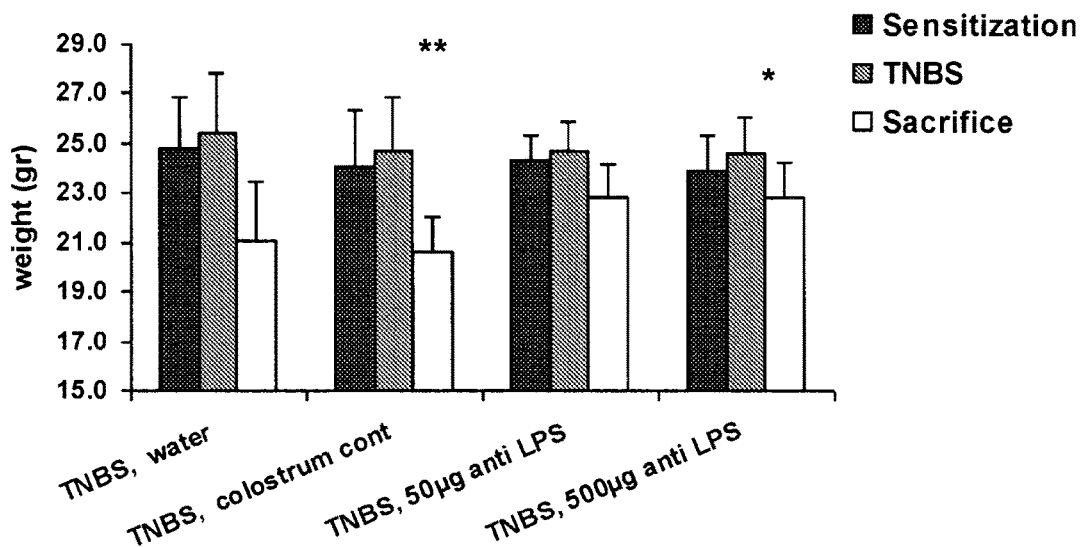
FIG. 55 is a graph showing weight loss (% of weight loss from their starting weight) in an animal model of Inflammatory Bowel Disease.

*BCP—Colostrum control (colostrum that was collected from non-immunized cows), dissolved in water
**anti-LPS—Hyper immunized Enterotoxigenic *E. coli* colostrum, dissolved in water Weight is one of the key parameters in the TNBS-model. In order to assess weight loss, all mice were weighed on day −7 (beginning of experiment), on day 0 (intrarectal TNBS) and on the sacrifice day. The graphs shown in FIG. 55 represent weight loss (% of weight loss from their starting weight). The data is shown in Table 10.

TABLE 10

| Treatment | Average Weight (gr) | | |
| --- | --- | --- | --- |
| | Sensitization | TNBS | Sacrifice |
| TNBS - water | 24.82 | 25.44 | 21.04 |
| TNBS - colostrum cont | 24.07 | 24.76 | 20.60 |
| TNBS - 50 μg anti LPS | 24.33 | 24.75 | 22.87 |
| TNBS - 500 μg anti LPS | 23.91 | 24.64 | 22.88 |

The results showed that untreated mice or colostrum control-treated mice lost significantly more weight during the experiment, then mice that were treated with anti-LPS (both dosages).

Figure 56:
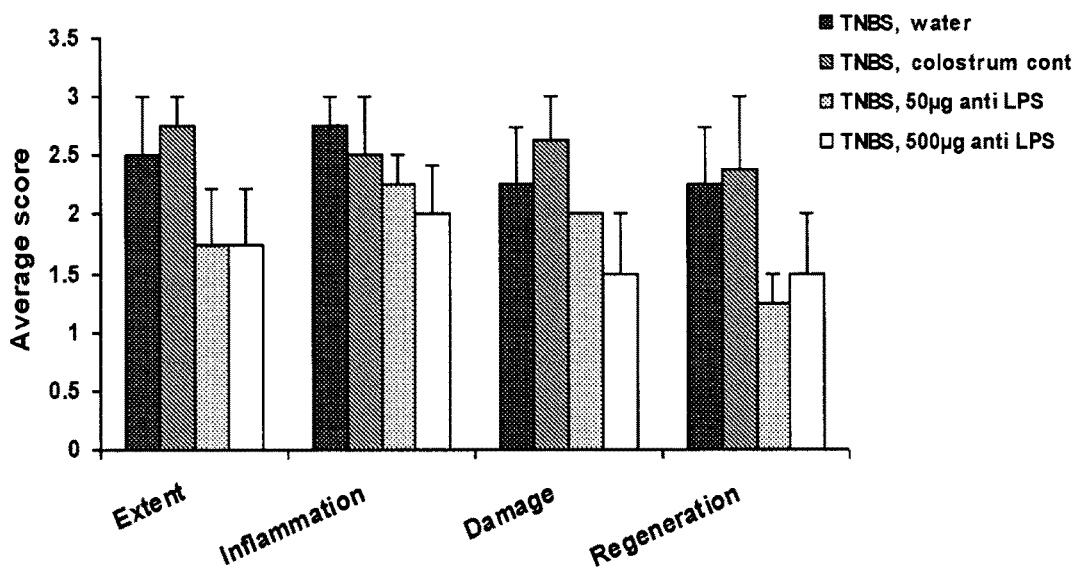
FIG. 56 is a graph showing that mice that in an animal model of Inflammatory Bowel Disease treatment with anti LPS Ig-enriched colostrum preparation, in the two examined dosages, improved colon histological grading in all four tested parameters.

Grading of colon histology was performed as follows. For histological evaluation of inflammation, distal colonic tissue (last 10 cm) was removed after mice were sacrificed, and then fixed in 10% formaldehyde. Paraffin sections from each animal were then stained with hematoxylin-eosin according to standard techniques. The degree of inflammation, extent, damage and regeneration on microscopic cross sections of the colon was graded from 0 to 3 as grade 0 was considered normal. Grading was performed by an experienced blinded pathologist. The results, shown in FIG. 56, demonstrate that mice that were treated with anti LPS, in the two examined dosages, exhibited improved colon histological grading in all four tested parameters.

As TNBS-colitis is resulting from mucosal inflammation mediated by a Th1 response, many components of the immune system are involved. Changes in the distribution of regulatory T cells in the spleen and liver of treated mice were examined by flow cytometry after sacrificing the animals. Isolation of splenocytes and intrahepatic lymphocytes was performed as follows. Livers and spleens were kept in RPMI-1640 supplemented with FCS. Spleens were crushed through a 70-mm nylon cell strainer 26 and centrifuged (1250 rpm for 7 min). Red blood cells were lysed in 1 ml of cold 155 mM ammonium chloride lysis buffer. Splenocytes were washed and resuspended in 1 ml of RPMI supplemented with FCS. Viability assessed by trypan blue exclusion was above 90%. For intrahepatic lymphocytes, livers were crushed through a stainless mesh (size 60, Sigma). 10 ml of Lymphoprep (Ficoll, Axis-Shield PoC AS, Oslo, Norway) was loaded with a similar volume of cell suspension in 50 ml tubes. The tubes were centrifuged at 1800 rpm for 18 min. Cells present in the interface were collected and centrifuged again at 1800 rpm for 10 min to obtain a pellet of cells depleted of hepatocytes. Approximately $1\times10^6$ cells/ mouse liver, were recovered. Flow cytometry for lymphocyte subsets was performed as follows. Flow cytometry was performed following splenocyte and hepatic lymphocyte isolation using $1\times10^6$ lymphocytes in 100 ml PBS with 0.1% BSA. For surface staining, cells were incubated with fluorochrome-conjugated antibodies to the indicated cell-surface markers (eBioscience, San Diego, Calif., USA) at the recommended dilution or with isotype control antibodies for 30 minutes at 4° C. The following cell surface anti-mouse antibodies were used: CD4–eFluoro 450, CD8– FITC and CD25– PE. Cells were then washed in PBS containing 1% BSA and fixed with fixation buffer (eBioscience) for another 50 minutes. For intracellular staining of Foxp3, cells after fixation were permeabilized with Foxp3 staining buffer (eBioscience). Resulting cells were stained with PE-Cy7-conjugated antibodies to Foxp3 (eBiosciences). Cells were then washed twice and resuspended in 250 μl of PBS containing 1% BSA and kept at 4° C. $1\times10^6$ stained cells in 250 μl of PBS containing 1% BSA were analyzed subsequently using a FACS LSR II instrument (Becton Dickinson, San Jose, Calif.) with FCS express V.3 software (DeNovo software, CA, USA). Only live cells were counted, and background fluorescence from non-antibody-treated lymphocytes was subtracted.

Figure 57:
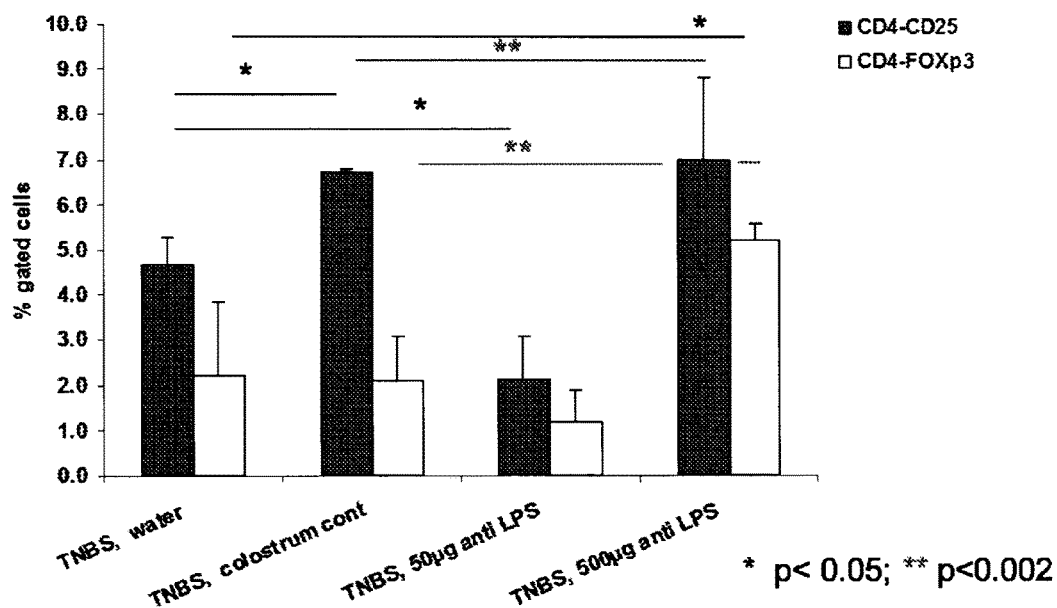
FIG. 57 shows the effects observed on populations of T regulatory cells in the spleen in an animal model of Inflammatory Bowel Disease after treatment with anti LPS Ig-enriched colostrum preparation. CD4+CD25+ cells were augmented by treatment of colostrum control and 500 mg dose of anti LPS, however, the 50 mg dose of anti LPS caused a significant decrease in the expression of this marker in the spleen. CD4+FOXP3+ cells were increased by the higher dose of anti LPS Ig-enriched colostrum preparation, when compared to colostrum control.
Figure 58:
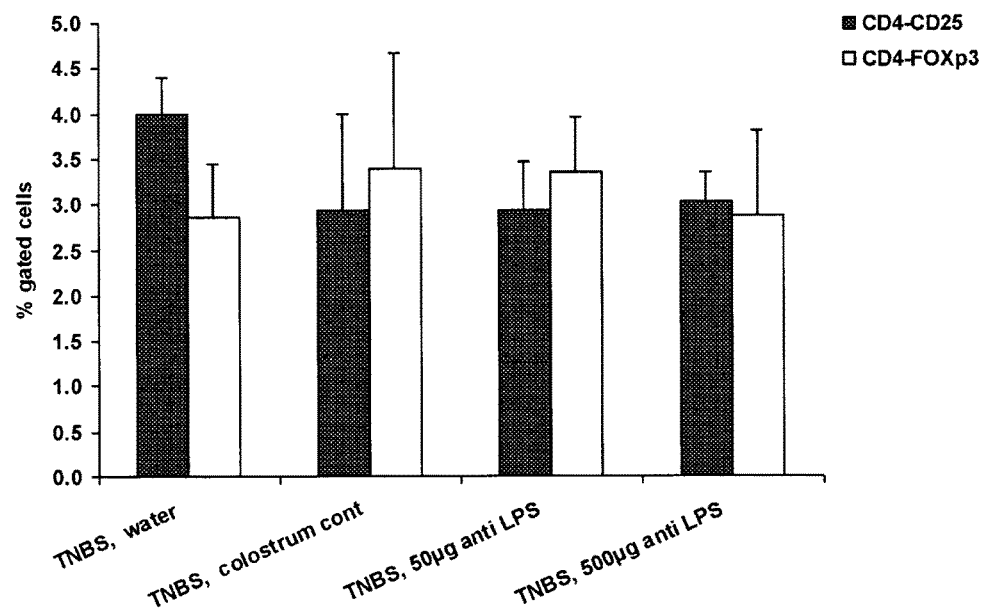
FIG. 58 shows that, in the same animal model described in FIG. 58, in the liver, no significant changes were seen after treatment with anti LPS Ig-enriched colostrum preparation.
Figure 59:
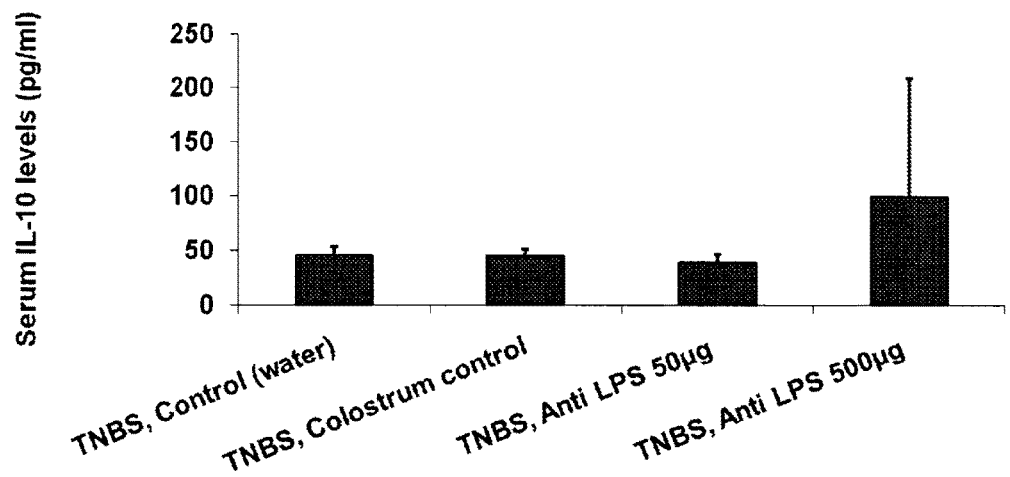
FIG. 59 is a bar graph showing that, in the same animal model described in FIG. 58, the higher dose (500 ug) of anti LPS Ig-enriched colostrum preparation induced an increase in serum levels of serum IL-10, an anti-inflammatory cytokine.
Figure 60:
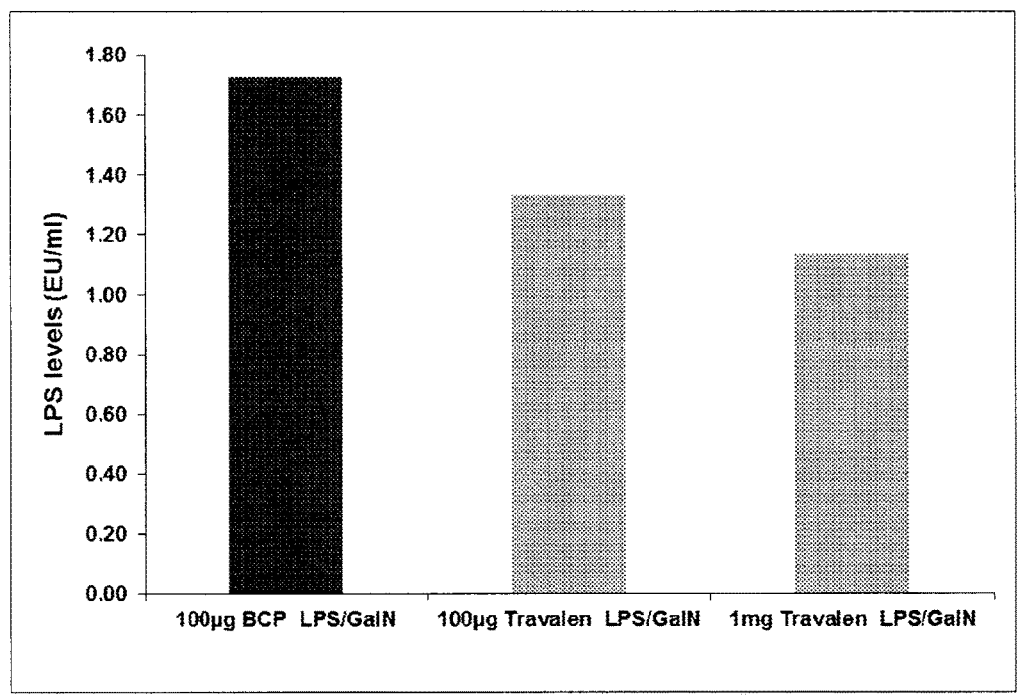
FIG. 60 shows the results of a *Limulus amebocyte* lysate (LAL) assay that demonstrate a dose-dependent decrease in bacterial translocation in a sepsis model after treatment with the anti-LPS enriched immunoglobulin colostrum preparation for 10 days. Sepsis was induced by IP injection of 1 mg LPS and 20 mg of Gal/N on the last day of the experiment, 5 hours before sacrificing the mice.

As shown in FIG. 57, several effects were observed on populations of T regulatory cells in the spleen. CD4+CD25+ cells were augmented by treatment of colostrum control and 500 mg dose of anti LPS, however, the 50 mg dose of anti LPS caused a significant decrease in the expression of this marker in the spleen. CD4+FOXP3+ cells were increased by the higher dose of anti LPS, when compared to colostrum control. Interestingly, in the liver, no significant changes were seen (FIG. 58). Serum IL-10 levels were also determined, and the higher dose (500 ug) induced an increase in serum levels of this anti-inflammatory cytokine (FIG. 59).

Example 49: Anti-LPS Enriched Immunoglobulin Preparation Ameliorates Symptoms of Infection To evaluate the effect of the Anti-LPS enriched immunoglobulin preparation on symptoms of infection, the preparation was tested in a sepsis model. C57Bl/6, 11-12 weeks old (25 gr) mice were fed with BCP control or Anti-LPS enriched immunoglobulin colostrum preparation for 10 days. Sepsis was induced by IP injection of 1 mg LPS and 20 mg of Gal/N on the last day of the experiment, 5 hours before sacrificing the mice.

Figure 61:
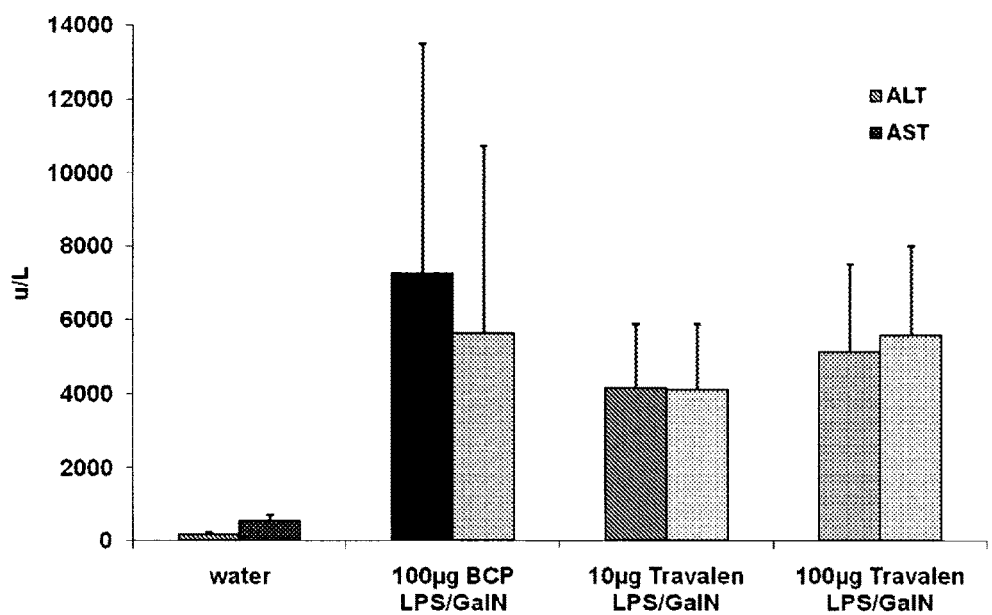
FIG. 61 shows that, in the same model as FIG. 61, both doses improved liver function as compared to the control colostrum (BCP).

A *Limulus amebocyte* lysate (LAL) assay was performed; the results, shown in FIG. 61, demonstrate a dose-dependent decrease in bacterial translocation. In addition, as shown in FIG. 61, both doses improved liver function as compared to the control colostrum (BCP).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating non-alcoholic steatohepatitis (NASH) in a subject who has one or more of:
   an alanine aminotransferase (ALT) level above 50 IU/dL,
   an aspartate aminotransferase (AST) level above 50 IU/dL,
   an alkaline phosphatase (AP) of greater than 70 U/L, or
   a γ-glutamyl transferase (GGT) of greater than 60 U/L,
   the method comprising:
   selecting a subject on the basis that they have NASH and one or more of:
   an ALT level above 50 IU/dL,
   an AST level above 50 IU/dL,
   an AP of greater than 70 U/L, or
   a GGT of greater than 60 U/L, and
   orally administering to the subject who has NASH a therapeutically effective amount of a composition comprising an anti-LPS immunoglobulin-enriched colostrum preparation for at least 14 days.

2. The method of claim 1, wherein the anti-LPS immunoglobulin preparation is prepared by immunizing a cow with LPS comprising O6, O8, O15, O25, O27, O63, O78, O114, O115, O128, O148, O153, and O159.

3. The method of claim 1 wherein the anti-LPS immunoglobulin preparation is administered at a dose of about 100 mg to about 2000 mg per day.

4. The method of claim 1, wherein the anti-LPS immunoglobulin preparation is administered at a dose of about 1800 mg per day.

5. The method of claim 1, wherein the subject has:
an ALT level above 50 IU/dL,
an AST level above 50 IU/dL,
an AP of greater than 70 U/L, and
a GGT of greater than 60 U/L,
the method comprising:
selecting a subject on the basis that they have NASH and:
an ALT level above 50 IU/dL,
an AST level above 50 IU/dL,
an AP of greater than 70 U/L, and
a GGT of greater than 60 U/L, and
orally administering to the subject who has NASH a therapeutically effective amount of a composition comprising an anti-LPS immunoglobulin-enriched colostrum preparation for at least 14 days.

6. The method of claim 1, wherein the method comprises orally administering to the subject a therapeutically effective amount of a composition comprising an anti-LPS immunoglobulin-enriched colostrum preparation for at least 21 days.

7. The method of claim 1, wherein the method comprises orally administering to the subject a therapeutically effective amount of a composition comprising an anti-LPS immunoglobulin-enriched colostrum preparation for at least 28 days.

8. The method of claim 1, wherein the method comprises orally administering to the subject a therapeutically effective amount of a composition comprising an anti-LPS immunoglobulin-enriched colostrum preparation for at least 31 days.

9. The method of claim 1, wherein the method comprises orally administering to the subject a therapeutically effective amount of a composition comprising an anti-LPS immunoglobulin-enriched colostrum preparation over several months.

10. The method of claim 1, wherein the method comprises orally administering to the subject a therapeutically effective amount of a composition comprising an anti-LPS immunoglobulin-enriched colostrum preparation once or more monthly.

* * * * *

UNITED STATES PATENT AND TRADEMARK OFFICE
CERTIFICATE OF CORRECTION

PATENT NO. : 9,943,597 B2
APPLICATION NO. : 13/817414
DATED : April 17, 2018
INVENTOR(S) : Yaron Ilan et al.

Page 1 of 1

It is certified that error appears in the above-identified patent and that said Letters Patent is hereby corrected as shown below:

On the Title Page

In item (73), in Column 1, in "Assignee", Lines 1-2, delete "Blackburn Nortth, VIC (AU)" and insert -- Blackburn North, VIC (AU) --, therefor.

Signed and Sealed this
Twenty-fourth Day of July, 2018

Andrei Iancu
*Director of the United States Patent and Trademark Office*